(12) United States Patent
Alvarez et al.

(10) Patent No.: US 7,135,457 B1
(45) Date of Patent: Nov. 14, 2006

(54) RANDOM PEPTIDES THAT BIND TO GASTRO-INTESTINAL TRACT (GIT) TRANSPORT RECEPTORS AND RELATED METHODS

(75) Inventors: Vernon L. Alvarez, Morrisville, PA (US); Daniel J. O'Mahony, Dublin (IE); Imelda J. Lambkin, Dublin (IE); Catherine A. Patterson, Dublin (IE); Judith Singleton, Rocky Hill, NJ (US); Benjamin A. Belinka, Jr., Kendall Park, NJ (US); John M. Carter, Trenton, NJ (US); Gerard M. Cagney, Seattle, WA (US)

(73) Assignees: Cytogen Corporation, Princeton, NJ (US); Elan Corporation, PLC, Dublin (IE)

(*) Notice: Subject to any disclaimer, the term of this patent is extended or adjusted under 35 U.S.C. 154(b) by 0 days.

(21) Appl. No.: 09/079,819

(22) Filed: May 15, 1998

Related U.S. Application Data
(60) Provisional application No. 60/046,595, filed on May 15, 1997.

(51) Int. Cl.
| | |
|---|---|
| *A61K 38/00* | (2006.01) |
| *A61K 39/00* | (2006.01) |
| *C07K 5/00* | (2006.01) |
| *C07K 7/00* | (2006.01) |

(52) U.S. Cl. ............................ 514/12; 514/15; 514/21; 530/350; 530/324; 530/327; 424/185.1
(58) Field of Classification Search .............. 424/184.1, 424/185.1; 514/12, 21, 15; 530/350, 300, 530/327, 324
See application file for complete search history.

(56) References Cited

U.S. PATENT DOCUMENTS

| | | | | |
|---|---|---|---|---|
| 5,338,665 | A | | 8/1994 | Schatz et al. |
| 5,498,538 | A | | 3/1996 | Kay et al. |
| 5,620,855 | A | * | 4/1997 | Dantzig .......................... 435/6 |
| 5,710,018 | A | * | 1/1998 | Dantzig ..................... 435/69.1 |
| 6,117,632 | A | * | 9/2000 | O'Mahony ...................... 435/6 |
| 6,271,362 | B1 | * | 8/2001 | Morikawa ................... 536/23.5 |

FOREIGN PATENT DOCUMENTS

| | | |
|---|---|---|
| JP | WO 94/07530 | 4/1994 |
| WO | WO 91/19818 | 12/1991 |
| WO | WO 94/18318 | 8/1994 |
| WO | WO 95/29938 | 11/1995 |

OTHER PUBLICATIONS

Balass et al., 1993, "Identification of a hexapeptide that mimics a conformation–dependent binding site of acetylcholine receptor by use of a phage–epitope library", Proc. Natl. Acad. Sci. USA 90:10638–10642.
Bass et al., 1990, "Hormone phage: an enrichment method for variant proteins with altered binding properties", Proteins: Struct. Func. Genet. 8:309–314.
Cesareni, 1992, "Peptide display on filamentous phage capsids", FEBS Lett. 307:66–70.
Christian et al., 1992, "Simplified methods for construction, assessment and rapid screening of peptide libraries in bacteriophage", J. Mol. Biol. 227:711–718.
Cwirla et al., 1990, "Peptides on phage: A vast library of peptides for identifying ligands", Proc. Natl. Acad. Sci. USA 87:6378–6382.
Davis and Jllum, 1994, "Particulate systems for site specific drug delivery", In: Targeting of Drugs 4 (Eds), Gregoriadis, McCormack and Poste, 183–194.
De la Cruz et al., 1988, "Immunogenicity and epitope mapping of foreign sequences via genetically engineered filamentous phage", J. Biol. Chem. 263:4318–4322.
Devlin et al., 1990, "Random peptide libraries: a source of specific protein binding molecules", Science 249:404–406.
Evers, 1995, Developments in Drug Delivery: Technology and Markets, Financial Times Management Report, p. 1–26.
Fix, 1996, "Strategies for delivery of peptides utilizing absorption–enhancing agents", J. Pharmac. Sci. 85:1282–1285.
Fodor et al., 1991, "Light–directed, spatially addressable parallel chemical synthesis", Science 251:767–773.
Fong et al., 1994, "Scanning whole cells with phage–display libraries: identification of peptide ligands that modulate cell function", Drug Development Reseach 33:64–70.
Gallop et al., 1994, "Applications of combinatorial technologies to drug discovery. 1. Background and peptide combinatorial libraries", J. Med. Chem. 37:1233–1251.
Greenwood et al., 1991, "Multiple display of foreign peptides on a filamentous bacteriophage", J. Mol. Biol. 220:821–827.
Houghton et al., 1991, "Generation and use of synthetic peptide combinatorial libraries for basic research and drug discovery", Nature 354:84–86.

(Continued)

*Primary Examiner*—Christopher R. Tate
*Assistant Examiner*—Roy Teller
(74) *Attorney, Agent, or Firm*—Pennie & Edmonds LLP

(57) ABSTRACT

This invention relates to proteins (e.g., peptides) that are capable of facilitating transport of an active agent through a human or animal gastro-intestinal tissue, and derivatives (e.g., fragments) and analogs thereof, and nucleotide sequences coding for said proteins and derivatives. The proteins of the invention have use in facilitating transport of active agents from the lumenal side of the GIT into the systemic blood system, and/or in targeting active agents to the GIT. Thus, for example, by binding (covalently or noncovalently) a protein of the invention to an orally administered drug, the drug can be targeted to specific receptor sites or transport pathways which are known to operate in the human gastrointestinal tract, thus facilitating its absorption into the systemic system.

45 Claims, 48 Drawing Sheets

OTHER PUBLICATIONS

Figure 5A:
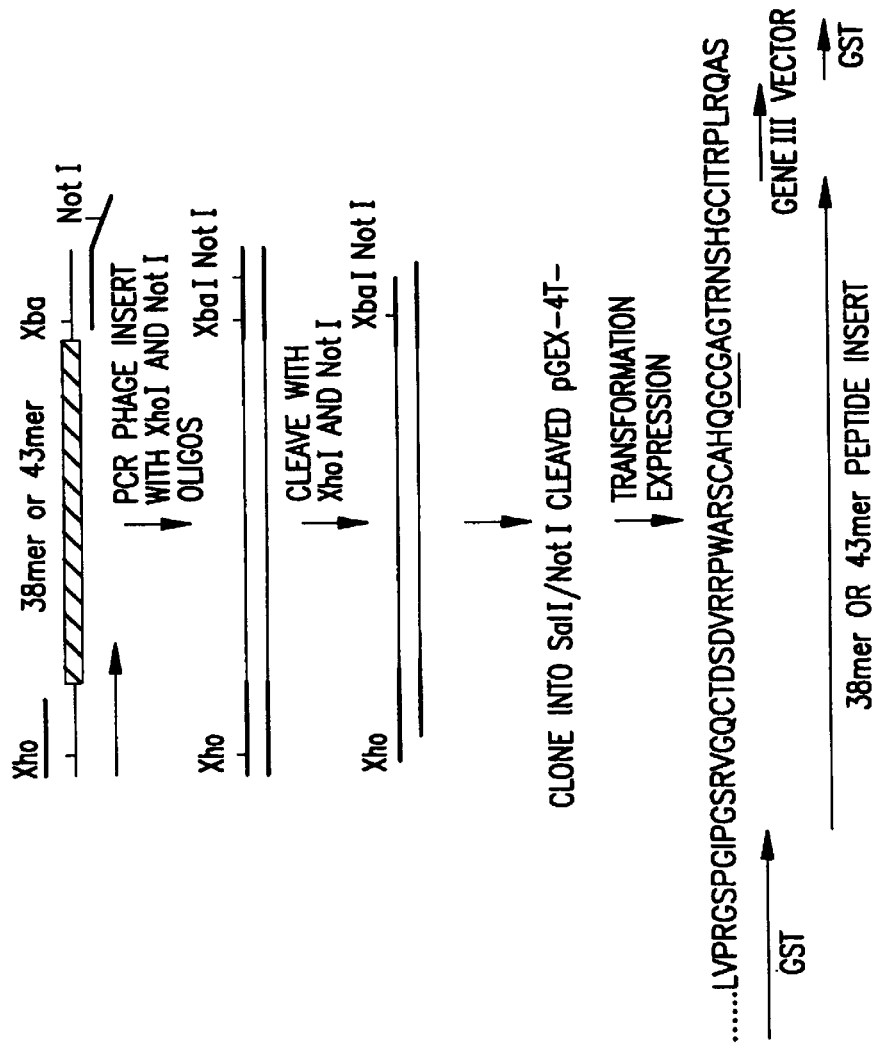

Hoogenboom et al., 1991, "Multi-subunit proteins on the surface of filamentous phage: methodologies for displaying antibody (Fab) heavy and light chains", Nucleic Acids Res. 19:4133–4137.

Kang et al., 1991, "Linkage of recognition and replication functions by assembling combinatorial antibody Fab libraries along phage sufaces", Proc. Natl. Acad. Sci. USA 88:4363–4366.

Kay et al., 1993, "An M13 phage library displaying random 38-amino-acid peptides as a source of novel sequences with affinity to select targets", Gene 128:59–65.

Lam et al, 1991, "A new type of synthetic peptide library for identifying ligand-binding activity", Nature 354:82–84.

Liang et al., 1995, "Human intestinal $H^+$/peptide cotransporter: cloning, functional expression, and chromosomal localization," J. Biol. Chem. 270:6456–6463.

Lowman et al., 1991, "Selecting high-affinity binding proteins by monovalent phage display", Biochemistry 30:10832–10838.

Marks et al., "By-passing immunization: human antibodies from V-gene libraries displayed on phage", J. Mol. Biol. 222:581–597.

McCafferty et al., 1990, "Phage antibodies: filamentous phage displaying antibody variable domains", Nature 348:552–554.

Parmley and Smith, 1988, "Antibody-selectable filamentous fd phage vectors: affinity purification of target genes", Gene 73:305–318.

Parmley and Smith, 1989, "Filamentous fusion phage cloning vectors for the study of epitopes and design of vaccines", Adv. Exp. Med. Biol. 251:215–218.

Peterson and Mooseker, 1992, "Characterization of the enterocyte-like brush border cytoskeleton of the $C2_{BBe}$ clones of the human intestinal cell line, Caco-2", J. Cell Science 102:581–600.

Pietersz, 1990, "The linkage of cytotoxic drugs to monoclonal antibodies for the treatment of cancer", Bioconjugate Chem. 1:89–95.

Saito et al., 1997, "Cloning and characterization of a pH-sensing regulatory factor that modulates transport activity of the human H+/peptide cotransporter, PEPT1," Biochem. and Biophys. Res. Commun. 237:577–582.

Scott and Smith, 1990, "Searching for peptide ligands with an epitope library", Science 249:386–390.

Smith, 1985, "Filamentous fusion phage: Novel expression vectors that display cloned antigens on the virion surface", Science 228:1315–1317.

Stevenson et al., 1995, "Permeability screen for synthetic peptide combinatorial libraries using CACO-2 cell monolayers and LC/MS/MS", Pharmaceutical Res. 12(9), S94.

Yayon et al., 1993, "Isolation of peptides that inhibit binding of basic fibroblast growth factor to its receptor from a random phage-epitope library", Proc. Natl. Acad. Sci. USA 90:10643–10647.

* cited by examiner

```
                    20                      40                      60
MGMSKSHSFFGYPLSIFFIV    VNEFCERFSYYGMRAILILY    FTNFISWDDNLSTAIYHTFV 80                     100                     120
ALCYLTPILGALIADSWLGK    FKTIVSLSIVYTIGQAVTSV    SSINDLTDHNHDGTPDSLPV 140                     160                     180
HVVLSLIGLALIALGTGGIK    PCVSAFGGDQFEEGQEKQRN    RFFSIFYLAINAGSLLSTII 200                     220                     240
TPMLRVQQCGIHSKQACYPL    AFGVPAALMAVALIVFVLGS    GMYKKFKPQGNIMGKVAKCI 260                     280                     300
GFAIKNRFRHRSKAFPKREH    WLDWAKEKYDERLISQIKMV    TRVMFLYIPLPMFWALFDQQ 320                     340                     360
GSRWTLQATTMSGKIGALEI    QPDQMQTVNAILIVIMVPIF    DAVLYPLIAKCGFNFTSLKK 380                     400                     420
MAVGMVLASMAFVVAAIVQV    EIDKTLPVFPKGNEVQIKVL    NIGNNTMNISLPGEMVTLGP 440                     460                     480
MSQTNAFMTFDVNKLTRINI    SSPGSPVTAVTDDFKQGQRH    TLLVWAPNHYQVVKDGLNQK 500                     520                     540
PEKGENGIRFVNTFNELITI    TMSGKVYANISSYNASTYQF    FPSGIKGFTISSTEIPPQCQ 560                     580                     600
PNFNTFYLEFGSAYTYIVQR    KNDSCPEVKVFEDISANTVN    MALQIPQYFLLTCGEVVFSV 620                     640                     660
TGLEFSYSQAPSNMKSVLQA    GWLLTVAVGNIIVLIVAGAG    QFSKQWAEYILFAALLLVVC 680                     700          708
VIFAIMARFYTYINPAEIEA    QFDEDEKKNRLEKSNPYFMS    GANSQKQM
```

FIG.1

```
   1 gaattccgtc tcgaccactg aatggaagaa aaggactttt aaccaccatt ttgtgactta
  61 cagaaaggaa tttgaataaa gaaaactatg atacttcagg cccatcttca ctccctgtgt
                              M  I  L  Q  A  H  L  H  S  L  C
 121 cttcttatgc tttatttggc aactggatat ggccaagagg ggaagtttag tggacccctg
      L  L  M  L  Y  L  A  T  G  Y  G  Q  E  G  K  F  S  G  P  L
 181 aaacccatga catttctat ttatgaaggc caagaaccga gtcaaattat attccagttt
      K  P  M  T  F  S  I  Y  E  G  Q  E  P  S  Q  I  I  F  Q  F
 241 aaggccaatc ctcctgctgt gactttgaa ctaactgggg agacagacaa catatttgtg
      K  A  N  P  P  A  V  T  F  E  L  T  G  E  T  D  N  I  F  V
 301 atagaacggg agggacttct gtattacaac agagccttgg acagggaaac aagatctact
      I  E  R  E  G  L  L  Y  Y  N  R  A  L  D  R  E  T  R  S  T
 361 cacaatctcc aggttgcagc cctggacgct aatggaatta tagtggaggg tccagtccct
      H  N  L  Q  V  A  A  L  D  A  N  G  I  I  V  E  G  P  V  P
 421 atcaccatag aagtgaagga catcaacgac aatcgaccca cgtttctcca gtcaaagtac
      I  T  I  E  V  K  D  I  N  D  N  R  P  T  F  L  Q  S  K  Y
 481 gaaggctcag taaggcagaa ctctcgccca ggaaagccct tcttgtatgt caatgccaca
      E  G  S  V  R  Q  N  S  R  P  G  K  P  F  L  Y  V  N  A  T
 541 gacctggatg atccggccac tcccaatggc cagctttatt accagattgt catccagctt
      D  L  D  D  P  A  T  P  N  G  Q  L  Y  Y  Q  I  V  I  Q  L
 601 cccatgatca acaatgtcat gtactttcag atcaacaaca aaacgggagc catctctctt
      P  M  I  N  N  V  M  Y  F  Q  I  N  N  K  T  G  A  I  S  L
 661 acccgagagg gatctcagga attgaatcct gctaagaatc cttcctataa tctggtgatc
      T  R  E  G  S  Q  E  L  N  P  A  K  N  P  S  Y  N  L  V  I
 721 tcagtgaagg acatgggagg ccagagtgag aattccttca gtgataccac atctgtggat
      S  V  K  D  M  G  G  Q  S  E  N  S  F  S  D  T  T  S  V  D
 781 atcatagtga cagagaatat ttggaaagca ccaaaacctg tggagatggt ggaaaactca
      I  I  V  T  E  N  I  W  K  A  P  K  P  V  E  M  V  E  N  S
 841 actgatcctc accccatcaa aatcactcag gtgcggtgga atgatcccgg tgcacaatat
      T  D  P  H  P  I  K  I  T  Q  V  R  W  N  D  P  G  A  Q  Y
 901 tccttagttg acaaagagaa gctgccaaga ttcccatttt caattgacca ggaaggagat
      S  L  V  D  K  E  K  L  P  R  F  P  F  S  I  D  Q  E  G  D
 961 atttacgtga ctcagccctt ggaccgagaa gaaaaggatg catatgtttt ttatgcagtt
      I  Y  V  T  Q  P  L  D  R  E  E  K  D  A  Y  V  F  Y  A  V
1021 gcaaaggatg agtacggaaa accactttca tatccgctgg aaattcatgt aaaagttaaa
      A  K  D  E  Y  G  K  P  L  S  Y  P  L  E  I  H  V  K  V  K
1081 gatattaatg ataatccacc tacatgtccg tcaccagtaa ccgtatttga ggtccaggag
      D  I  N  D  N  P  P  T  C  P  S  P  V  T  V  F  E  V  Q  E
1141 aatgaacgac tgggtaacag tatcgggacc cttactgcac atgacaggga tgaagaaaat
      N  E  R  L  G  N  S  I  G  T  L  T  A  H  D  R  D  E  E  N
1201 actgccaaca gttttctaaa ctacaggatt gtggagcaaa ctcccaaact tcccatggat
      T  A  N  S  F  L  N  Y  R  I  V  E  Q  T  P  K  L  P  M  D
```

FIG.2A

```
1261 ggactcttcc taatccaaac ctatgctgga atgttacagt tagctaaaca gtccttgaag
      G  L  F    L  I  Q    T  Y  A  G  M  L  Q    L  A  K    Q  S  L  K
1321 aagcaagata ctcctcagta caacttaacg atagaggtgt ctgacaaaga tttcaagacc
      K  Q  D   T  P  Q    Y  N  L  T  I  E  V    S  D  K    D  F  K  T
1381 ctttgttttg tgcaaatcaa cgttattgat atcaatgatc agatccccat ctttgaaaaa
      L  C  F   V  Q  I  N  V  I  D  I  N  D    Q  I  P    I  F  E  K
1441 tcagattatg gaaacctgac tcttgctgaa gacacaaaca ttgggtccac catcttaacc
      S  D  Y   G  N  L    T  L  A  E  D  T  N   I  G  S    T  I  L  T
1501 atccaggcca ctgatgctga tgagccattt actgggagtt ctaaaattct gtatcatatc
      I  Q  A   T  D  A    D  E  P  F  T  G  S    S  K  I  L  Y  H  I
1561 ataaagggag acagtgaggg acgcctgggg gttgacacag atccccatac caacaccgga
      I  K  G   D  S  E   G  R  L  G  V  D  T   D  P  H   T  N  T  G
1621 tatgtcataa ttaaaaagcc tcttgatttt gaaacagcag ctgtttccaa cattgtgttc
      Y  V  I  I  K  K    P  L  D  F  E  T  A    A  V  S  N  I  V  F
1681 aaagcagaaa atcctgagcc tctagtgttt ggtgtgaagt acaatgcaag ttcttttgcc
      K  A  E  N  P  E    P  L  V  F  G  V  K    Y  N  A  S  S  F  A
1741 aagttcacgc ttattgtgac agatgtgaat gaagcacctc aattttccca acacgtattc
      K  F  T   L  I  V   T  D  V  N  E  A  P   Q  F  S    Q  H  V  F
1801 caagcgaaag tcagtgagga tgtagctata ggcactaaag tgggcaatgt gactgccaag
      Q  A  K   V  S  E   D  V  A  I  G  T  K    V  G  N  V  T  A  K
1861 gatccagaag gtctggacat aagctattca ctgaggggag acacaagagg ttggcttaaa
      D  P  E   G  L  D   I  S  Y  S  L  R  G   D  T  R   G  W  L  K
1921 attgaccacg tgactggtga gatctttagt gtggctccat tggacagaga agccggaagt
      I  D  H   V  T  G   E  I  F  S  V  A  P    L  D  R   E  A  G  S
1981 ccatatcggg tacaagtggt ggccacagaa gtagggggt cttccttaag ctctgtgtca
      P  Y  R   V  Q  V   V  A  T  E  V  G  G   S  S  L   S  S  V  S
2041 gagttccacc tgatccttat ggatgtgaat gacaaccctc ccaggctagc caaggactac
      E  F  H   L  I  L   M  D  V  N  D  N  P    P  R  L   A  K  D  Y
2101 acgggcttgt tcttctgcca tccccctcagt gcacctggaa gtctcatttt cgaggctact
      T  G  L   F  F  C   H  P  L  S  A  P  G    S  L  I   F  E  A  T
2161 gatgatgatc agcacttatt tcggggtccc cattttacat tttccctcgg cagtggaagc
      D  D  D   Q  H  L   F  R  G  P  H  F  T    F  S  L   G  S  G  S
2221 ttacaaaacg actgggaagt ttccaaaatc aatggtactc atgcccgact gtctaccagg
      L  Q  N   D  W  E   V  S  K  I  N  G  T    H  A  R   L  S  T  R
2281 cacacagact tgaggagag ggcgtatgtc gtcttgatcc gcatcaatga tgggggtcgg
      H  T  D   F  E  E   R  A  Y  V  V  L  I    R  I  N  D  G  G  R
2341 ccacccttgg aaggcattgt ttctttacca gttacattct gcagttgtgt ggaaggaagt
      P  P  L   E  G  I   V  S  L  P  V  T  F    C  S  C   V  E  G  S
2401 tgtttccggc cagcaggtca ccagactggg atacccactg tgggcatggc agttggtata
      C  F  R   P  A  G   H  Q  T  G  I  P  T    V  G  M   A  V  G  I
```

FIG.2B

```
2461 ctgctgacca cccttctggt gattggtata attttagcag ttgtgtttat ccgcataaag
      L  L  T    T  L  L    V  I  G  I    I  L  A    V  V  F    I  R  I  K
2521 aaggataaag gcaaagataa tgttgaaagt gctcaagcat ctgaagtcaa acctctgaga
      K  D  K    G  K  D    N  V  E  S   A  Q  A    S  E  V    K  P  L  R
2581 agctgaattt gaaaaggaat gtttgcattt atatagcaag tgctatttca gcaacaacca
      S
2641 tctcatccta ttacttttca tctaacgtgc attataattt tttaaacaga tattccctct
2701 tgtcctttaa tatttgctaa atatttcttt tttgaggtgg agtcttgctc tgtcgcccag
2761 gctggagtac agtggtgtga tcccagctca ctgcaacctc cgcctcctgg gttcacatga
2821 ttctcctgcc tcagcttcct aagtagctgg gtttacaggc acccaccacc atgcccagct
2881 aattttttgta tttttaatag agacggggtt tcgccatttg gccaggatgg tcttgcactc
2941 ctgacgtcaa gtgatctgcc tgccttggtc tcccaataca ggcatgaacc actgcaccca
3001 cctacttaga tatttcatgt gctatagaca ttagagagat ttttcatttt tccatgacat
3061 ttttcctctc tgcaaatggc ttagctactt gtgtttttcc cttttggggc aagacagact
3121 cattaaatat tctgtacatt ttttctttat caaggagata tatcagtgtt gtctcataga
3181 actgcctgga ttccatttat gttttttctg attccatcct gtgtccccctt catccttgac
3241 tcctttggta tttcactgaa tttcaaacat ttgtcagaga agaaaaaagt gaggactcag
3301 gaaaaataaa taaataaaag aacagccttt tgcggccgcg aattc
```

FIG.2C

```
                    20                        40                        60
MARKKFSGLEISLIVLFVIV    TIIAIALIVVLATKTPAVDE    ISDSTSTPATTRVTTNPSDS
                    80                       100                       120
GKCPNVLNDPVNVRINCIPE    QFPTEGICAQRGCCWRPWND    SLIPWCFFVDNHGYNVQDMT
                   140                       160                       180
TTSIGVEAKLNRIPSPTLFG    NDINSVLFTTQNQTPNRFRF    KITDPNNRRYEVPHQYVKEF
                   200                       220                       240
TGPTVSDTLYDVKVAQNPFS    IQVIRKSNGKTLFDTSIGPL    VYSDQYLQISARLPSDYIYG
                   260                       280                       300
IGEQVHKRFRHDLSWKTWPI    FTRDQLPGDNNNNLYGHQTF    FMCIEDTSGKSFGVFLMNSN
                   320                       340                       360
AMEIFIQPTPIVTYRVTGGI    LDFYILLGDTPEQVVQQYQQ    LVGLPAMPAYWNLGFQLSRW
                   380                       400                       420
NYKSLDVVKEVVRRNREAGI    PFDTQVTDIDYMEDKKDFTY    DQVAFNGLPQFVQDLHDHGQ
                   440                       460                       480
KYVIILDPAISIGRRANGTT    YATYERGNTQHVWINESDGS    TPIIGEVWPGLTVYPDFTNP
                   500                       520                       540
NCIDWWANECSIFHQEVQYD    GLWIDMNEVSSFIQGSTKGC    NVNKLNYPPFTPDILDKLMY
                   560                       580                       600
SKTICMDAVQNWGKQYDVHS    LYGYSMAIATEQAVQKVFPN    KRSFILTRSTFAGSGRHAAH
                   620                       640                       660
WLGDNTASWEQMEWSITGML    EFSLFGIPLVGADICGFVAE    TTEELCRRWMQLGAFYPFSR
                   680                       700                       720
NHNSDGYEHQDPAFFGQNSL    LVKSSRQYLTIRYTLLPFLY    TLFYKAHVFGETVARPVLHE
                   740                       760                       780
FYEDTNSWIEDTEFLWGPAL    LITPVLKQGADTVSAYIPDA    IWYDYESGAKRPWRKQRVDM
                   800                       820                       840
YLPADKIGLHLRGGYIIPIQ    EPDVTTTASRKNPLGLIVAL    GENNTAKGDFFWDDGETKDT
                   860                       880                       900
IQNGNYILYTFSVSNNTLDI    VCTHSSYQEGTTLAFQTVKI    LGLTDSVTEVRVAENNQPMN
                   920                       940                       960
AHSNFTYDASNQVLLIADLK    LNLGRNFSVQWNQIFSENER    FNCYPDADLATEQKCTQRGC
                   980                      1000                      1020
VWRTGSSLSKAPECYFPRQD    NSYSVNSARYSSMGITADLQ    LNTANARIKLPSDPISTLRV
                  1040                      1060                      1080
EVKYHKNDMLQFKIYDPQKK    RYEVPVPLNIPTTPISTYED    RLYDVEIKENPFGIQIRRRS
                  1100                      1120                      1140
SGRVIWDSWLPGFAFNDQFI    QISTRLPSEYIYGFGEVEHT    AFKRDLNWNTWGMFTRDQPP
                  1160                      1180                      1200
GYKLNSYGFHPYYMALEEEG    NAHGVFLLNSNAMDVTFQPT    PALTYRTVGGILDFYMFLGP
                  1220                      1240                      1260
TPQVATKQYHEVIGHPVMPA    YWALGFQLCRYGYANTSEVR    ELYDAMVAANIPYDVQYTDI
```

FIG.3A

```
                    1280                 1300                 1320
DYMERQLDFTIGEAFQDLPQ FVDKIRGEGMRYIIILDPAI SGNETKTYPAFERGQQNDVF
                    1340                 1360                 1380
VKWPNTNDICWAKVWPDLPN ITIDKTLTEDEAVNASRAHV AFPDFFRTSTAEWWAREIVD
                    1400                 1420                 1440
FYNEKMKFDGLWIDMNEPSS FVNGTTTNQCRNDELNYPPY FPELTKRTDGLHFRTICMEA
                    1460                 1480                 1500
EQILSDGTSVLHYDVHNLYG WSQMKPTHDALQKTTGKRGI VISRSTYPTSGRWGGHWLGD
                    1520                 1540                 1560
NYARWDNMDKSIIGMMEFSL FGISYTGADICGFFNNSEYH LCTRWMQLGAFYPYSRNHNI
                    1580                 1600                 1620
ANTRRQDPASWNETFAEMSR NILNIRYTLLPYFYTQMHEI HANGGTVIRPLLHEFFDEKP
                    1640                 1660                 1680
TWDIFKQFLWGPAFMVTPVL EPYVQTVNAYVPNARWFDYH TGKDIGVRGQFQTFNASYDT
                    1700                 1720                 1740
INLHVRGGHILPCQEPAQNT FYSRQKHMKLIVAADDNQMA QGSLFWDDGESIDTYERDLY
                    1760                 1780                 1800
LSVQFNLNQTTLTSTILKRG YINKSETRLGSLHVWGKGTT PVNAVTLTYNGNKNSLPFNE
                    1820  1827
DTTNMILRIDLTTHNVTLEE PIEINWS
```

FIG.3B

```
  1 gccttactgc aggaaggcac tccgaagaca taagtcggtg agacatggct gaagataaaa
                                                        M  A   E  D  K
 61 gcaagagaga ctccatcgag atgagtatga agggatgcca gacaaacaac gggtttgtcc
     S  K  R   D  S  I  E   M  S  M   K  G  C   Q  T  N  N   G  F  V
121 ataatgaaga cattctggag cagaccccgg atccaggcag ctcaacagac aacctgaagc
     H  N  E   D  I  L  E   Q  T  P   D  P  G   S  S  T  D   N  L  K
181 acagcaccag gggcatcctt ggctcccagg agcccgactt caagggcgtc cagccctatg
     H  S  T   R  G  I  L   G  S  Q   E  P  D   F  K  G  V   Q  P  Y
241 cggggatgcc caaggaggtg ctgttccagt tctctggcca ggcccgctac cgcatacctc
     A  G  M   P  K  E  V   L  F  Q   F  S  G   Q  A  R  Y   R  I  P
301 gggagatcct cttctggctc acagtggctt ctgtgctggt gctcatcgcg gccaccatag
     R  E  I   L  F  W  L   T  V  A   S  V  L   V  L  I  A   A  T  I
361 ccatcattgc cctctctcca aagtgcctag actggtggca ggaggggccc atgtaccaga
     A  I  I   A  L  S  P   K  C  L   D  W  W   Q  E  G  P   M  Y  Q
421 tctacccaag gtctttcaag gacagtaaca aggatgggaa cggagatctg aaaggtattc
     I  Y  P   R  S  F  K   D  S  N   K  D  G   N  G  D  L   K  G  I
481 aagataaact ggactacatc acagctttaa atataaaaac tgtttggatt acttcatttt
     Q  D  K   L  D  Y  I   T  A  L   N  I  K   T  V  W  I   T  S  F
541 ataaatcgtc ccttaaagat ttcagatatg gtgttgaaga tttccgggaa gttgatccca
     Y  K  S   L  K  D   F  R  Y   G  V  E   D  F  R  E   V  D  P
601 tttttggaac gatggaagat tttgagaatc tggttgcagc catacatgat aaaggtttaa
     I  F  G   T  M  E  D   F  E  N   L  V  A   A  I  H  D   K  G  L
661 aattaatcat cgatttcata ccaaaccaca cgagtgataa acatatttgg tttcaattga
     K  L  I   I  D  F  I   P  N  H   T  S  D   K  H  I  W   F  Q  L
721 gtcggacacg gacaggaaaa tatactgatt attatatctg gcatgactgt acccatgaaa
     S  R  T   R  T  G  K   Y  T  D   Y  Y  I   W  H  D  C   T  H  E
781 atggcaaaac cattccaccc aacaactggt taagtgtgta tggaaactcc agttggcact
     N  G  K   T  I  P  P   N  N  W   L  S  V   Y  G  N  S   S  W  H
841 ttgacgaagt gcgaaaccaa tgttattttc atcagtttat gaaagagcaa cctgatttaa
     F  D  E   V  R  N  Q   C  Y  F   H  Q  F   M  K  E  Q   P  D  L
901 atttccgcaa tcctgatgtt caagaagaaa taaaagaaat tttacggttc tggctcacaa
     N  F  R   N  P  D  V   Q  E  E   I  K  E   I  L  R  F   W  L  T
961 agggtgttga tggttttagt ttggatgctg ttaaattcct cctagaagca aagcacctga
     K  G  V   D  G  F  S   L  D  A   V  K  F   L  L  E  A   K  H  L
```

FIG.4A

```
1021 gagatgagat ccaagtaaat aagacccaaa tcccggacac ggtcacacaa tactcggagc
      R  D  E    I  Q  V  N    K  T  Q    I  P  D    T  V  T  Q    Y  S  E
1081 tgtaccatga cttcaccacc acgcaggtgg gaatgcacga cattgtccgc agcttccggc
      L  Y  H  D  F  T  T    T  Q  V    G  M  H  D  I  V  R    S  F  R
1141 agaccatgga ccaatacagc acggagcccg gcagatacag gttcatgggg actgaagcct
      Q  T  M  D  Q  Y  S   T  E  P    G  R  Y    R  F  M  G    T  E  A
1201 atgcagagag tattgacagg accgtgatgt actatggatt gccatttatc caagaagctg
      Y  A  E    S  I  D  R    T  V  M    Y  Y  G    L  P  F  I    Q  E  A
1261 attttccatt caacaattac ctcagcatgc tagacactgt ttctgggaac agcgtgtatg
      D  F  P  F    N  N  Y    L  S  M    L  D  T    V  S  G  N    S  V  Y
1321 aggttatcac atcctggatg aaaacatgc cagaaggaaa atggcctaac tggatgattg
      E  V  I  T    S  W  M    E  N  M    P  E  G    K  W  P  N    W  M  I
1381 gtggaccaga cagttcacgg ctgacttcgc gtttggggaa tcagtatgtc aacgtgatga
      G  G  P    D  S  S  R    L  T  S    R  L  G    N  Q  Y  V    N  V  M
1441 acatgcttct tttcacactc cctggaactc ctataactta ctatggagaa gaaattggaa
      N  M  L    L  F  T  L    P  G  T    P  I  T    Y  Y  G  E    E  I  G
1501 tgggaaatat tgtagccgca aatctcaatg aaagctatga tattastacc cttcgctcaa
      M  G  N    I  V  A  A    N  L  N    E  S  Y    D  I  N  T    L  R  S
1561 agtcaccaat gcagtgggac aatagttcaa atgctggttt ttctgaagct agtaacacct
      K  S  P    M  Q  W  D    N  S  S    N  A  G    F  S  E  A    S  N  T
1621 ggttacctac caattcagat taccacactg tgaatgttga tgtccaaaag actcagccca
      W  L  P    T  N  S  D    Y  H  T    V  N  V    D  V  Q  K    T  Q  P
1681 gatcggcttt gaagttatat caagatttaa gtctacttca tgccaatgag ctactcctca
      R  S  A    L  K  L  Y    Q  D  L    S  L  L    H  A  N  E    L  L  L
1741 acaggggctg gttttgccat tgaggaatg acagccacta tgttgtgtac acaagagagc
      N  R  G    W  F  C  H    L  R  N    D  S  H    Y  V  V  Y    T  R  E
1801 tggatggcat cgacagaatc tttatcgtgg ttctgaattt tggagaatca acactgttaa
      L  D  G    I  D  R  I    F  I  V    V  L  N    F  G  E  S    T  L  L
1861 atctacataa tatgatttcg ggccttcccg ctaaaataag aataaggtta agtaccaatt
      N  L  H    N  M  I  S    G  L  P    A  K  I    R  I  R  L    S  T  N
1921 ctgccgacaa aggcagtaaa gttgatacaa gtggcatttt tctggacaag ggagagggac
      S  A  D    K  G  S  K    V  D  T    S  G  I    F  L  D  K    G  E  G
1981 tcatctttga acacaacacg aagaatctcc ttcatcgcca aacagctttc agagatagat
      L  I  F    E  H  N  T    K  N  L    L  H  R    Q  T  A  F    R  D  R
2041 gctttgtttc caatcgagca tgctattcca gtgtactgaa catactgtat acctcgtgtt
      C  F  V    S  N  R  A    C  Y  S    S  V  L    N  I  L  Y    T  S  C
2101 aggcaccttt atgaagagat gaagacactg gcatttcagt gggattgtaa gcatttgtaa
2161 tagcttcatg tacagcatgc tgcttggtga caatcatta attcttcgat atttctgtag
2221 cttgaatgta accgctttaa gaaaggttct caaatgtttt gaaaaaaata aaatgtttaa
2281 aagt
```

FIG.4B

```
P31   1         10        20        30                    Clone #
      |         |         |         |
      SARDSGPAEDGSRAVRLNGVENANTRKSSRSNPRGRRHP
      SARDSGPAEDGSRAVRLNG                                  101
              DGSRAVRLNGVENANTRKSSR                        102
                        ENANTRKSSRSNPRGRRHP                103
                             TRKSSRSNPRG                   119

Pax2  1         10        20        30                    Clone #
      |         |         |         |
      STPPSREAYSRPYSVDSDSDTNAKHSSHNRRLRTRSRPN
      STPPSREAYSRPYSVDSDSD                                 104
              SRPYSVDSDSDTNAKHSSHNR                        105
                        TNAKHSSHNRRLRTRSRPN                106

DCX8  1         10        20        30                    Clone #
      |         |         |         |
      RYKHDIGCDAGVDKKSSSVRGGCGAHSSPPRAGRGPRGTMVSRL
      RYKHDIGCDAGVDKKSSSVRGGCG                             107
              GCDAGVDKKSSSVRGGCGAHSSPPRA                   108
                            GAHSSPPRAGRGPRGTMVSRL          109
```

FIG.5B

```
P31    1         10        20        30                          Clone #
       |         |         |         |
       SARDSGPAEDGSRAVRLNGVENANTRKSSRSNPRGRRHP
                             ENANTRKSSRSNPRGRRHP                    103
                             ENANTRKSSR                             110
                                  TRKSSRSNPRG                       119
                                   RKSSRSNPRG                       111
                                       SNPRGRRHP                    112

Pax2   1         10        20        30                          Clone #
       |         |         |         |
       STPPSREAYSRPYSVDSDSDTNAKHSSHNRRLRTRSRPN
                           TNAKHSSHNRRLRTRSRPN                      106
                           TNAKHSSHN                                113
                                 SSHNRRLRTR                         114
                                     RRLRTRSRPN                     115

SNi10  1         10        20        30                          Clone#
       |         |         |         |
       RVGQCTDSDVRRPWARSCAHQGCGAGTRNSHGCITRPLRQASAH
       RVGQCTDSDVRRPWARSCA                                          116
                 VRRPWARSCAHQGCGAGTRNS                              117
                            GTRNSHGCITRPLRQASAH                     118
```

FIG.5C

| Peptide Name | Sequence | pI | IC$_{50}$ | GST/C2BBe1 |
|---|---|---|---|---|
| ELAN024(P31) | SARDSGPAEDGSRAVRLNGVENANTRKSSRSNPRGRRHPG | 11.88 | 0.5-2.2 | |
| 101 | SARDSGPAEDGSRAVRLNG | | | |
| 102 | DGSRAVRLNGVENANTRKSSR | | | |
| 103 | ENANTRKSSRSNPRGRRHP | | | +++ |
| 110 | ENANTRKSSR | | | |
| 111 | RKSSRSNPRG | | | |
| 112 | SNPRGRRKP | | | ‡ |
| 119 | TRKSSRSNPRG | | | |
| 228 | ZENANTRKSSRSNPRGRRHPG | 12.28 | 0.5-1.7 | |
| 229 | ZTRKSSRSNPRG | 12.40 | 5.5-15 | |
| 230 | ZENANTRKSSRSNPRG | 11.81 | >50 | |
| 231 | ZTRKSSRSNPRGRRHPG | 12.70 | 0.6-3.2 | |
| 239 | ZENANTRKSSR | 10.89 | >50 | |
| 240 | ZSNPRGRRHPG | 12.40 | 5.9-29 | |
| 241 | ZENANT | 3.75 | >50 | |
| 242 | ZANTRKS | | 11.05 >50 | |
| 243 | ZTRKSS | | 11.05 >50 | |
| 244 | ZRKSSR | 12.11 | 13->50 | |
| 245 | ZKSSRSN | | 11.05 40-48 | |
| 246 | ZSSRSNPG | | 10.04 >50 | |
| 247 | ZRSNPRG | 12.40 | >50 | |
| 248 | ZSNPRG | 10.04 | >50 | |
| 249 | ZPRGRRH | 12.40 | 11-20 | |
| 250 | ZRRHPG | 12.10 | 30 | |
| Z51 (HepC core) | ZKSSRGN | 12.40 | >50 | |
| Z52 (HepC p26664) | ZKTSERSQPRGRRQPG | 12.10 | 9.8 | |
| Z53 | ZTrKSSrSNPrGrrHPG | | 1.6 | |
| Z54 | ZTRKSSrSNPrGrRHPG | | 1.6 | |
| Z21(HAX42)SDHALGTNLRSDNAKEPGDYNCCGNGNSTGRKVFNRRRPSAIPT | | 11.27 | 1.7 | |

FIG.10A

| Peptide Name | Sequence | pI | IC$_{50}$ | GST/C2BBe1 | |
|---|---|---|---|---|---|
| | 1          10          20          30          40 | | | | |
| ELANO18(PAX2) | STPPSREAYSRPYSVDSDSDTNAKHSSHNRRLRTRSRPNG | 10.88 | 0.6-0.9.1 | +++ | |
| 104 | STPPSREAYSRPYSVDSDSD | | | | |
| 105 | SRPYSVDSDSDTNAKHSSHNR | | | | |
| 106 | TNAKHSSHNRRLRTRSRPN | | | | ++ |
| 113 | TNAKHSSHN | | | | - |
| 114 | SSHNRRLRTR | | | | |
| 115 | RRLRTRSRPN | | | +/- | +/- |
| Z32 | ZTNAKHSSHNRRLRTRSRPN | | 12.7 | 1.2 | |
| Z33 | ZTNAKHSSHNRRLRTR | 12.58 | 1.6 | | |
| Z34 | ZSSHNRRLRTRSRPN | | 12.7 | 1.6. | 1.3. |
| Z35 | ZSSHNRRLRTR | 12.58 | 0.38 - 1.8 | 2.7 | 1.5 |
| Z26 | ZSEANLDGRKSRYSSPRRNSSTRPRTSPNSVHARYPSTDHD | 10.88 | 7-8.3 | | 0.68. |
| Z38 | ZSRANTDGRKSRYSSPRRNSSTEPRLSPNSVHARYPSTDHD | 10.88 | 1.7. | 0.9 | |
| Z55 | ZTNAKHSSHN | | | 42 | |
| Z56 | ZRRLRTRSRPN | | | 1.7 | |
| Z57 | ZRRLRTRSRP | | | 1.9 | |
| Z58 | ZRRLRTR | | 3.4 | | |
| Z59 | ZrrLrTrSrPN | | | NOT DONE | |
| Z73 | ZASHNRRLRTR | | 1.5. | 5.5 | |
| Z74 | ZSAHNRRLRTR | | 6.2 | | |
| Z75 | ZSSANRRLRTR | | 1.6 | | |
| Z76 | ZSSHARRLRTR | | 1.8 | | |
| Z77 | ZSSHNARLRTR | | 3.9. | 5.2 | |
| Z78 | ZSSHNRALRTR | | 4.5. | 4.6 | |
| Z79 | ZSSHNRRARTR | | 1.4 | | |
| Z80 | ZSSHNRRLATR | | 3.4. | 5.2 | |
| Z81 | ZSSHNRRLRAR | | 2.2 | | |
| Z82 | ZSSHNRRLRTA | | 3.4 | | |
| Z21 (HAX42) | ZSDHALGTNLRSDNAKEPGDYNCCGNGNSTGRKVFNRRRPSAIPT | 11.27 | 0.7 | | |

FIG.10B

SN:10

| Peptide Name | Sequence | pI | IC$_{50}$ | GST/C2BBe1 |
|---|---|---|---|---|
| ELAN016 (SN110) | RVGQCTDSDVRRPWARSCAHQGGAGTRNSHGCITRPLRQASAH | 10.19 | 0.22 | ++ |
| 116 | RVGQCTDSDVRRPWARSCA | | | – |
| 117 | VRRPWARSCAHQGGAGTRNS | | | + |
| 118 | GTRNSHGCITRPLRQASAH | | | +/– |
| Z17 | ZRVGQCTDSDVRRPWARSCAH | 8.66 | 3.6 | |
| Z16C23 | ZCGAGTRNSHGCITRPLRQASAH | 9.03 | 0.7 | |
| Z36 | ZVRRPWARSCAHQGGAGTRNS | 11.62 | 0.27 | |
| Z37 | ZCTDSDVRRPWARSC | 8.01 | 3 | |

| Peptide Name | Sequence | pI | IC$_{50}$ | GST/C2BBe1 |
|---|---|---|---|---|
| ELAN021(HAX42) | SDHALGTNLRSDNAKEPGDYNCCGNGNSTGRKVFNRRRPSAIPT | 11.27 | 5.5 | ++ |
| ELAN018(PAX2) | STPPSREAYSRPYSVDSDSDTNAKHSSHNRRLRTRSRPNG | 10.88 | 0.23 | +++ |
| Z26 | ZSEANLDGRKSRYSSPRRNSSTRPRTSPNSVHARYPSTDHD | 10.88 | <0.2 | |
| Z38 | ZSRANTDGRKSRYSSPRRNSSTEPRLSPNSVHARYPSTDHD | 10.88 | <0.2 | |
| Z34 (PAX2 14mer) | ZSSHNRRLRTRSRPN | 12.7 | 0.33 | |

FIG.10C

| P31 AA SEQ. POSITION | KNOWN PROTEIN | HOMOLOGOUS SEQ. POSITION |
|---|---|---|
| 12–34 | FASCICULIN 2 | 10–32 |
| 4–12 | MESENTERICOPEPTIDASE | 54–62 |
| 15–31 | | 175–191 |
| 26–39 | CORE PROTEIN (HEPATITIS C VIRUS) | 5–18 |
| 26–39 | | 11–24 |
| 26–39 | | 21–34 |
| 26–39 | | 38–51 |
| 23–30 | | 39–55 |
| 25–39 | | 41–55 |
| 26–39 | | 51–64 |
| 16–39 | PT–NANBH POLYPROTEIN N–TERMINUS | 51–64 |
| 28–40 | AL2 PROTEIN (CAENORHABDITISELEGANS) | 70–82 |
| 26–38 | CAPSID PROTEIN (HEPATITIS C VIRUS TYPE 3g) | 48–60 |
| 26–39 | GENOME POLYPROTEIN (HEPATITIS C VIRUS) | 57–70 |

FIG.20

| DCX8AA SEQ. POSITION | KNOWN PROTEIN | HOMOLOGOUS SEQ. POSITION |
|---|---|---|
| 20-27 | ENDO-1,4-BETA-D-GLUCANASE | 78-85 |
| 30-37 | | 221-228 |
| 21-34 | P-HYDROXYBENZOATE HYDROXYLASE | 285-298 |
| 5-15 | | 54-64 |
| 7-21 | CYTOCHROME | 50-64 |
| 7-21 | CYTOCHROME C3 | 50-64 |
| | TRIMETHYLARNINE DEHYDROGENASE | 208-219 |
| 32-43 | | 396-407 |
| 30-37 | Gag-JunD FUSION PROTEIN | 24-31 |
| 26-30 | | 16-20 |
| 23-44 | SECRETIN PRECURSOR, N-PROSECRITIN, SECRITIN AINIDE | 18-39 |
| 33-44 | T-CELL RECEPTOR V BETA CHAIN | 15-26 |
| 27-33 | | 3-9 |
| 23-44 | SECRETIN PRECURSOR PIR | 18-39 |
| 31-44 | HYPOTHETICAL PROTEIN V (SYNECHOCYSTIS) | 275-288 |
| 24-30 | | 251-257 |
| 23-43 | PUTATIVE RNA BINDING PROTEIN | 230-250 |
| 28-40 | Mu SON OF SEVENLESS 1 | 1-13 |
| 24-35 | NEUROPEPTIDE PRECURSOR | 80-91 |
| 29-43 | | 5-19 |
| 23-43 | RNA-BINDING PROTEIN (MACACAFASCICULARIS) | 230-250 |
| 23-43 | RNA-BINDING PROTEIN (HOMOSAPIENS) | 230-250 |
| 23-43 | AUTOSOMAL GENE-AZOOSPERMIA FACTOR | 230-250 |
| 25-38 | COLLAGEN | 25-28 |
| 24-35 | | 4-15 |
| 29-41 | PROBABLE CELL GROWTH REGULATOR | 306-318 |
| 24-35 | RIBOSOMAL PROTEIN S2 | 24-35 |
| 16-39 | | 182-185 |
| 24-44 | CAENORHABDITIS ELEGANS | 296-316 |
| 23-34 | pid:e208155 (HOMO SAPIENS) | 61-72 |
| 36-43 | | 116-123 |

FIG.21A

| DCX8A SEQ. POSITION | KNOWN PROTEIN | HOMOLOGOUS SEQ. POSITION |
|---|---|---|
| 24-38 | XYLULOSE KINASE | 16-30 |
| 24-39 | CAENORHABDITIS ELEGANS | 57-72 |
| 26-42 | | 65-81 |
| 27-33 | HYPOTHETICAL PROTEIN-PHAGE BZ13 | 22-28 |
| 35-39 | | 31-35 |
| 30-42 | CEREBELLIN-LIKE GLYCOPROTEIN | 2-14 |
| 8-22 | DNA PRIMASE | 170-184 |
| 2-7 | | 76-81 |
| 5-21 | COAT PROTEIN (BEAN COMMON MOSAIC VIRUS) | 12-28 |
| 5-21 | COAT PROTEIN (BEAN COMMON MOSAIC VIRUS) | 33-49 |
| 5-21 | | 19-35 |
| 5-21 | POLYPROTEIN (BEAN COMMON MOSAIC VIRUS) | 215-231 |
| 5-21 | | 39-55 |
| 5-21 | Nib PROTEINLCOAT PROTEIN (COWPEA APHID-BOME MOSAIC VIRUS) | 92-108 |
| 2-13 | MHC CLASS 1 PIPI (PITHECIA) | 111-122 |
| 14-22 | | 236-334 |
| 3-19 | TALIN (CAENORHABDITIS ELEGANS) | 1538-1554 |
| 2-9 | ACETAMIDASE PIR | 359-366 |
| 9-20 | | 483-494 |
| 10-16 | RHIZOBIONS ETLI STRAIN | 134-140 |
| 17-30 | | 173-186 |
| 31-39 | | 200-208 |
| 2-11 | NEUROTOXIN 1 (TOXIN B) A. STOKESI | 7-16 |
| 12-33 | | 26-47 |
| 21-27 | SUID HERPES VIRUS 1 EARLY PROTEIN | 425-432 |
| 30-43 | | 51-64 |
| 13-42 | RICE cDNA PARTIAL SEQUENCE | 50-151 |
| 8-15 | FUSION PROTEIN | 24-31 |
| 4-8 | | 16-20 |
| 1-22 | SECRETIN PRECURSOR, N-PROSECRETIN, SECRETIN-AMIDE | 18-39 |
| 11-22 | T-CELL RECEPTOR V BETA CHAIN | 15-26 |
| 5-11 | | 3-9 |
| 9-22 | HYPOTHETICAL PROTEIN | 275-288 |
| 2-8 | | 251-257 |

FIG.21B

| DCX8A SEQ. POSITION | KNOWN PROTEIN | HOMOLOGOUS SEQ. POSITION |
|---|---|---|
| 1-21 | PUTATIVE RNA BINDING PROTEIN | 230-250 |
| 6-18 | HYPOTHETICAL PROTEIN-MOUSE PIR | 1-13 |
| 2-13 | NEUROPEPTIDE PRECURSOR | 80-91 |
| 7-21 | orf3-HUMAN | 5-19 |
| 1-21 | RNA-BINDING PROTEIN | 230-250 |
| 13-16 | COLLAGEN | 25-28 |
| 7-19 | PROBABLE CELL GROWTH OR DIFFERENTIATION REGULATOR | 306-318 |
| 2-13 | RIBOSOMAL PROTEIN S2 | 14-25 |
| 14-17 | | 182-185 |
| 2-22 | CAENORHABDITIS ELEGANS | 296-316 |
| 1-12 | HOMOSAPIENS | 61-72 |
| 14-21 | | 116-123 |
| 2-16 | XYLULOSE KINASE | 16-30 |
| 8-15 | T CELL RECEPTOR DELTA CHAIN | 55-62 |
| 5-8 | | 12-15 |
| 8-17 | SEQ. 43 FROM PATENT US | 12-21 |

FIG.21C

| DAB10 AA SEQ. POSITION | KNOWN PROTEIN | HOMOLOGOUS SEQ. POSITION |
|---|---|---|
| 13-34 | 1,3-BETA-GLLUCANASE | 231-252 |
| 3-11 | PHOTOSYNTHETIC REACTION CENTER | 20-28 |
| 16-27 | | 128-139 |
| 28-35 | MYB PROTO-ONCOGENE PROTEIN | 131-138 |
| 5-18 | | 32-45 |
| 23-36 | LYSOZYME MUTANT | 130-143 |
| 28-35 | LIPASE | 400-407 |
| 3-15 | | 159-171 |
| 3-37 | TRYPSIN | 169-203 |
| 13-34 | 1,3-1,4-BETA-GLUCANASE | 232-253 |
| 4-10 | LACTATE DEHYDROGENASE | 190-196 |
| 11-7 | | 244-250 |
| 4-10 | APO-LACTATE DEHYDROGENASE | 190-196 |
| 11-17 | | 244-250 |
| 4-10 | LACTATE DEHYDROGENASE | 191-197 |
| 11-17 | | 245-251 |
| 16-26 | OVOTRANSFERRIN | 240-250 |
| 23-36 | GENOME POLYPROTEIN MATRIX PROTEIN | 1022-1035 |
| 14-20 | ROUS SARCOMA VIRUS | 43-49 |
| 2-12 | | 13-23 |
| 14-20 | HYPOTHETICAL PROTEIN-AVIAN LEUKOSIS VIRUS | 43-49 |
| 4-20 | T CELL RECEPTOR DELTA CHAIN VARIABLE REGION | 1-4 |
| 14-18 | | 12-16 |
| 2-12 | GAG POLYPROTEIN-AVIAN ENDOGENOUS VIRUS RAV-0 | 139-149 |
| 14-20 | | 169-175 |
| | p19 PROTEIN-AVIAN ERYTHROBLASTOSIS VIRUS | 189-199 |
| 14-20 | | 219-225 |
| 7-19 | ALI PROTEIN-POTATO YELLOW MOSAIC VIRUS | 222-234 |
| 3-22 | ENDO-1,4-BETA GLUCANASE | 186-205 |
| 6-18 | I a PROTEIN-BROME MOSAIC VIRUS | 430-442 |
| 2-12 | GAG POLYPROTEIN-FUJINAMI SARCOMA VIRUS | 186-196 |
| 14-22 | | 216-222 |
| 2-12 | GAG PROTEIN-ROUS SARCOMA VIRUS | 190-200 |
| 14-20 | | 220-226 |
| 1-12 | CORTICOTROPIN-LIKE INTERMEDIATE LOBE PEPTIDE | 7-18 |
| 1-22 | GENE PRODUCT (CAENORHABDITIS ELEGANS) | 4-25 |
| 31-37 | T CELL RECEPTOR DELTA CHAIN | 56-62 |
| 26-39 | | 12-15 |
| 26-37 | LYSOZYME MUTANT | 133-144 |

FIG.22

```
ATG TCC CCT ATA CTA GGT TAT TGG AAA ATT AAG GGC CTT GTG CAA CCC      48
Met Ser Pro Ile Leu Gly Tyr Trp Lys Ile Lys Gly Leu Val Gln Pro
 1           5                  10                  15

ACT CGA CTT CTT TTG GAA TAT CTT GAA GAA AAA TAT GAA GAG CAT TTG      96
Thr Arg Leu Leu Leu Glu Tyr Leu Glu Glu Lys Tyr Glu Glu His Leu
             20                  25                  30

TAT GAG CGC GAT GAA GGT GAT AAA TGG CGA AAC AAA AAG TTT GAA TTG     144
Tyr Glu Arg Asp Glu Gly Asp Lys Trp Arg Asn Lys Lys Phe Glu Leu
         35                  40                  45

GGT TTG GAG TTT CCC AAT CTT CCT TAT TAT ATT GAT GGT GAT GTT AAA     192
Gly Leu Glu Phe Pro Asn Leu Pro Tyr Tyr Ile Asp Gly Asp Val Lys
     50                  55                  60

TTA ACA CAG TCT ATG GCC ATC ATA CGT TAT ATA GCT GAC AAG CAC AAC     240
Leu Thr Gln Ser Met Ala Ile Ile Arg Tyr Ile Ala Asp Lys His Asn
65                   70                  75                  80

ATG TTG GGT GGT TGT CCA AAA GAG CGT GCA GAG ATT TCA ATG CTT GAA     288
Met Leu Gly Gly Cys Pro Lys Glu Arg Ala Glu Ile Ser Met Leu Glu
                 85                  90                  95

GGA GCG GTT TTG GAT ATT AGA TAC GGT GTT TCG AGA ATT GCA TAT AGT     336
Gly Ala Val Leu Asp Ile Arg Tyr Gly Val Ser Arg Ile Ala Tyr Ser
             100                 105                 110

AAA GAC TTT GAA ACT CTC AAA GTT GAT TTT CTT AGC AAG CTA CCT GAA     384
Lys Asp Phe Glu Thr Leu Lys Val Asp Phe Leu Ser Lys Leu Pro Glu
         115                 120                 125

ATG CTG AAA ATG TTC GAA GAT CGT TTA TGT CAT AAA ACA TAT TTA AAT     432
Met Leu Lys Met Phe Glu Asp Arg Leu Cys His Lys Thr Tyr Leu Asn
     130                 135                 140

GGT GAT CAT GTA ACC CAT CCT GAC TTC ATG TTG TAT GAC GCT CTT GAT     480
Gly Asp His Val Thr His Pro Asp Phe Met Leu Tyr Asp Ala Leu Asp
145                 150                 155                 160

GTT GTT TTA TAC ATG GAC CCA ATG TGC CTG GAT GCG TTC CCA AAA TTA     528
Val Val Leu Tyr Met Asp Pro Met Cys Leu Asp Ala Phe Pro Lys Leu
                 165                 170                 175

GTT TGT TTT AAA AAA CGT ATT GAA GCT ATC CCA CAA ATT GAT AAG TAC     576
Val Cys Phe Lys Lys Arg Ile Glu Ala Ile Pro Gln Ile Asp Lys Tyr
             180                 185                 190

TTG AAA TCC AGC AAG TAT ATA GCA TGG CCT TTG CAG GGC TGG CAA GCC     624
Leu Lys Ser Ser Lys Tyr Ile Ala Trp Pro Leu Gln Gly Trp Gln Ala
         195                 200                 205

ACG TTT GGT GGT GGC GAC CAT CCT CCA AAA TCG GAT CTG GTT CCG CGT     672
Thr Phe Gly Gly Gly Asp His Pro Pro Lys Ser Asp Leu Val Pro Arg
     210                 215                 220

GGA TCC CCA GGA ATT CCC GGG TCG ACT CGA GCG GCC GCA TCG TGA         717
Gly Ser Pro Gly Ile Pro Gly Ser Thr Arg Ala Ala Ala Ser
225                 230                 235
```

FIG.23

SEQUENCE LISTING (1) GENERAL INFORMATION:

(iii) NUMBER OF SEQUENCES: 407

(2) INFORMATION FOR SEQ ID NO: 1:

(i) SEQUENCE CHARACTERISTICS:
      (A) LENGTH: 44 amino acids
      (B) TYPE: amino acid
      (C) STRANDEDNESS: <Unknown>
      (D) TOPOLOGY: unknown (ii) MOLECULE TYPE: peptide (xi) SEQUENCE DESCRIPTION: SEQ ID NO: 1:

```
Arg Ser Gly Ala Tyr Glu Ser Pro Asp Gly Arg Gly Arg Ser Tyr
 1               5                  10                  15

Val Gly Gly Gly Gly Cys Gly Asn Ile Gly Arg Lys His Asn Leu
            20                  25                  30

Trp Gly Leu Arg Thr Ala Ser Pro Ala Cys Trp Asp
            35                  40
```

(2) INFORMATION FOR SEQ ID NO: 2:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 2:

```
Ser Pro Arg Ser Phe Trp Pro Val Val Ser Arg His Glu Ser Phe Gly
 1               5                  10                  15

Ile Ser Asn Tyr Leu Gly Cys Gly Tyr Arg Thr Cys Ile Ser Gly Thr
            20                  25                  30

Met Thr Lys Ser Ser Pro Ile Tyr Pro Arg His Ser
            35                  40
```

(2) INFORMATION FOR SEQ ID NO: 3:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 3:

```
Ser Ser Ser Ser Asp Trp Gly Gly Val Pro Gly Lys Val Val Arg Glu
 1               5                  10                  15

Arg Phe Lys Gly Arg Gly Cys Gly Ile Ser Ile Thr Ser Val Leu Thr
            20                  25                  30

Gly Lys Pro Asn Pro Cys Pro Glu Pro Lys Ala Ala
            35                  40
```

(2) INFORMATION FOR SEQ ID NO: 4:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 4:

```
Arg Val Gly Gln Cys Thr Asp Ser Asp Val Arg Arg Pro Trp Ala Arg
 1               5                  10                  15

Ser Cys Ala His Gln Gly Cys Gly Ala Gly Thr Arg Asn Ser His Gly
            20                  25                  30

Cys Ile Thr Arg Pro Leu Arg Gln Ala Ser Ala His
            35                  40
```

(2) INFORMATION FOR SEQ ID NO: 5:

-continued

```
        (i) SEQUENCE CHARACTERISTICS:
            (A) LENGTH: 39 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 5:

Ser His Ser Gly Gly Met Asn Arg Ala Tyr Gly Asp Val Phe Arg Glu
1               5                   10                  15

Leu Arg Asp Arg Trp Asn Ala Thr Ser His His Thr Arg Pro Thr Pro
            20                  25                  30

Gln Leu Pro Arg Gly Pro Asn
        35

(2) INFORMATION FOR SEQ ID NO: 6:

(i) SEQUENCE CHARACTERISTICS:
            (A) LENGTH: 41 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 6:

Ser Pro Cys Gly Gly Ser Trp Gly Arg Phe Met Gln Gly Gly Leu Phe
1               5                   10                  15

Gly Gly Arg Thr Asp Gly Cys Gly Ala His Arg Asn Arg Thr Ser Ala
            20                  25                  30

Ser Leu Glu Pro Pro Ser Ser Asp Tyr
        35                  40

(2) INFORMATION FOR SEQ ID NO: 7:

(i) SEQUENCE CHARACTERISTICS:
            (A) LENGTH: 39 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 7:

Arg Gly Ala Ala Asp Gln Arg Arg Gly Trp Ser Glu Asn Leu Gly Leu
1               5                   10                  15

Pro Arg Val Gly Trp Asp Ala Ile Ala His Asn Ser Tyr Thr Phe Thr
            20                  25                  30

Ser Arg Arg Pro Arg Pro Pro
        35

(2) INFORMATION FOR SEQ ID NO: 8:

(i) SEQUENCE CHARACTERISTICS:
            (A) LENGTH: 44 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 8:

Ser Gly Gly Glu Val Ser Ser Trp Gly Arg Val Asn Asp Leu Cys Ala
1               5                   10                  15
```

```
Arg Val Ser Trp Thr Gly Cys Gly Thr Ala Arg Ser Ala Arg Thr Asp
            20                  25                  30

Asn Lys Gly Phe Leu Pro Lys His Ser Ser Leu Arg
            35                  40
```

(2) INFORMATION FOR SEQ ID NO: 9:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 9:

```
Ser Asp Ser Asp Gly Asp His Tyr Gly Leu Arg Gly Gly Val Arg Cys
1               5                   10                  15

Ser Leu Arg Asp Arg Gly Cys Gly Leu Ala Leu Ser Thr Val His Ala
            20                  25                  30

Gly Pro Pro Ser Phe Tyr Pro Lys Leu Ser Ser Pro
            35                  40
```

(2) INFORMATION FOR SEQ ID NO: 10:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 10:

```
Arg Ser Leu Gly Asn Tyr Gly Val Thr Gly Thr Val Asp Val Thr Val
1               5                   10                  15

Leu Pro Met Pro Gly His Ala Asn His Leu Gly Val Ser Ser Ala Ser
            20                  25                  30

Ser Ser Asp Pro Pro Arg Arg
            35
```

(2) INFORMATION FOR SEQ ID NO: 11:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 11:

```
Arg Thr Thr Thr Ala Lys Gly Cys Leu Leu Gly Ser Phe Gly Val Leu
1               5                   10                  15

Ser Gly Cys Ser Phe Thr Pro Thr Ser Pro Pro His Leu Gly Tyr
            20                  25                  30

Pro Pro His Ser Val Asn
            35
```

(2) INFORMATION FOR SEQ ID NO: 12:

(i) SEQUENCE CHARACTERISTICS:
        (A) LENGTH: 39 amino acids
        (B) TYPE: amino acid
        (C) STRANDEDNESS: <Unknown>

(D) TOPOLOGY: unknown (ii) MOLECULE TYPE: peptide (xi) SEQUENCE DESCRIPTION: SEQ ID NO: 12:

Ser Pro Lys Leu Ser Ser Val Gly Val Met Thr Lys Val Thr Glu Leu
1               5                  10                  15

Pro Thr Glu Gly Pro Asn Ala Ile Ser Ile Pro Ile Ser Ala Thr Leu
                20                  25                  30

Gly Pro Arg Asn Pro Leu Arg
            35

(2) INFORMATION FOR SEQ ID NO: 13:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 13:

Arg Trp Cys Gly Ala Glu Leu Cys Asn Ser Val Thr Lys Lys Phe Arg
1               5                  10                  15

Pro Gly Trp Arg Asp His Ala Asn Pro Ser Thr His Arg Thr Pro
                20                  25                  30

Pro Pro Ser Gln Ser Ser Pro
            35

(2) INFORMATION FOR SEQ ID NO: 14:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 14:

Arg Trp Cys Gly Ala Asp Asp Pro Cys Gly Ala Ser Arg Trp Arg Gly
1               5                  10                  15

Gly Asn Ser Leu Phe Gly Cys Gly Leu Arg Cys Ser Ala Ala Gln Ser
                20                  25                  30

Thr Pro Ser Gly Arg Ile His Ser Thr Ser Thr Ser
            35                  40

(2) INFORMATION FOR SEQ ID NO: 15:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 15:

Ser Lys Ser Gly Glu Gly Gly Asp Ser Ser Arg Gly Glu Thr Gly Trp
1               5                  10                  15

Ala Arg Val Arg Ser His Ala Met Thr Ala Gly Arg Phe Arg Trp Tyr
                20                  25                  30

Asn Gln Leu Pro Ser Asp Arg (2) INFORMATION FOR SEQ ID NO: 16:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 16:

```
Arg Ser Ser Ala Asn Asn Cys Glu Trp Lys Ser Asp Trp Met Arg Arg
 1               5                  10                  15

Ala Cys Ile Ala Arg Tyr Ala Asn Ser Ser Gly Pro Ala Arg Ala Val
            20                  25                  30

Asp Thr Lys Ala Ala Pro
            35
```

(2) INFORMATION FOR SEQ ID NO: 17:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 17:

```
Ser Lys Trp Ser Trp Ser Ser Arg Trp Gly Ser Pro Gln Asp Lys Val
 1               5                  10                  15

Glu Lys Thr Arg Ala Gly Cys Gly Gly Ser Pro Ser Ser Thr Asn Cys
            20                  25                  30

His Pro Tyr Thr Phe Ala Pro Pro Gln Ala Gly
            35                  40
```

(2) INFORMATION FOR SEQ ID NO: 18:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 18:

```
Ser Gly Phe Trp Glu Phe Ser Arg Gly Leu Trp Asp Gly Glu Asn Arg
 1               5                  10                  15

Lys Ser Val Arg Ser Gly Cys Gly Phe Arg Gly Ser Ser Ala Gln Gly
            20                  25                  30

Pro Cys Pro Val Thr Pro Ala Thr Ile Asp Lys His
            35                  40
```

(2) INFORMATION FOR SEQ ID NO: 19:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 19:

Ser Glu Ser Gly Arg Cys Arg Ser Val Ser Arg Trp Met Thr Thr Trp
 1               5                  10                  15

Gln Thr Gln Lys Gly Gly Cys Gly Ser Asn Val Ser Arg Gly Ser Pro
            20                  25                  30

Leu Asp Pro Ser His Gln Thr Gly His Ala Thr Thr
         35                  40

(2) INFORMATION FOR SEQ ID NO: 20:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 20:

Arg Glu Trp Arg Phe Ala Gly Pro Pro Leu Asp Leu Trp Ala Gly Pro
 1               5                  10                  15

Ser Leu Pro Ser Phe Asn Ala Ser Ser His Pro Arg Ala Leu Arg Thr
            20                  25                  30

Tyr Trp Ser Gln Arg Pro Arg
         35

(2) INFORMATION FOR SEQ ID NO: 21:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 21:

Arg Met Glu Asp Ile Lys Asn Ser Gly Trp Arg Asp Ser Cys Arg Trp
 1               5                  10                  15

Gly Asp Leu Arg Pro Gly Cys Gly Ser Arg Gln Trp Tyr Pro Ser Asn
            20                  25                  30

Met Arg Ser Ser Arg Asp Tyr Pro Ala Gly Gly His
         35                  40

(2) INFORMATION FOR SEQ ID NO: 22:

(i) SEQUENCE CHARACTERISTICS:
        (A) LENGTH: 36 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 22:

Ser His Pro Trp Tyr Arg His Trp Asn His Gly Asp Phe Ser Gly Ser
 1               5                  10                  15

Gly Gln Ser Arg His Thr Pro Pro Glu Ser Pro His Pro Gly Arg Pro
            20                  25                  30

Asn Ala Thr Ile
         35

(2) INFORMATION FOR SEQ ID NO: 23:

(i) SEQUENCE CHARACTERISTICS:
    (A) LENGTH: 44 amino acids
    (B) TYPE: amino acid
    (C) STRANDEDNESS: <Unknown>
    (D) TOPOLOGY: unknown (ii) MOLECULE TYPE: peptide (xi) SEQUENCE DESCRIPTION: SEQ ID NO: 23:

Arg Tyr Lys His Asp Ile Gly Cys Asp Ala Gly Val Asp Lys Lys Ser
1               5                  10                  15

Ser Ser Val Arg Gly Gly Cys Gly Ala His Ser Ser Pro Pro Arg Ala
            20                  25                  30

Gly Arg Gly Pro Arg Gly Thr Met Val Ser Arg Leu
        35                  40

(2) INFORMATION FOR SEQ ID NO: 24:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 24:

Ser Gln Gly Ser Lys Gln Cys Met Gln Tyr Arg Thr Gly Arg Leu Thr
1               5                  10                  15

Val Gly Ser Glu Tyr Gly Cys Gly Met Asn Pro Ala Arg His Ala Thr
            20                  25                  30

Pro Ala Tyr Pro Ala Arg Leu Leu Pro Arg Tyr Arg
        35                  40

(2) INFORMATION FOR SEQ ID NO: 25:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 25:

Ser Gly Arg Thr Thr Ser Glu Ile Ser Gly Leu Trp Gly Trp Gly Asp
1               5                  10                  15

Asp Arg Ser Gly Tyr Gly Trp Gly Asn Thr Leu Arg Pro Asn Tyr Ile
            20                  25                  30

Pro Tyr Arg Gln Ala Thr Asn Arg His Arg Tyr Thr
        35                  40

(2) INFORMATION FOR SEQ ID NO: 26:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 26:

Arg Trp Asn Trp Thr Val Leu Pro Ala Thr Gly Gly His Tyr Trp Thr
1               5                  10                  15

```
Arg Ser Thr Asp Tyr His Ala Ile Asn Asn His Arg Pro Ser Ile Pro
            20                  25                  30

His Gln His Pro Thr Pro Ile
        35

(2) INFORMATION FOR SEQ ID NO: 27:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 27:

Ser Trp Ser Ser Trp Asn Trp Ser Ser Lys Thr Thr Arg Leu Gly Asp
1               5                   10                  15

Arg Ala Thr Arg Glu Gly Cys Gly Pro Ser Gln Ser Asp Gly Cys Pro
            20                  25                  30

Tyr Asn Gly Arg Leu Thr Thr Val Lys Pro Arg Thr
        35                  40

(2) INFORMATION FOR SEQ ID NO: 28:

(i) SEQUENCE CHARACTERISTICS:
        (A) LENGTH: 37 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 28:

Ser Gly Ser Leu Asn Ala Trp Gln Pro Arg Ser Trp Val Gly Gly Ala
1               5                   10                  15

Phe Arg Ser His Ala Asn Asn Asn Leu Asn Pro Lys Pro Thr Met Val
            20                  25                  30

Thr Arg His Pro Thr
        35

(2) INFORMATION FOR SEQ ID NO: 29:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 29:

Arg Tyr Ser Gly Leu Ser Pro Arg Asp Asn Gly Pro Ala Cys Ser Gln
1               5                   10                  15

Glu Ala Thr Leu Glu Gly Cys Gly Ala Gln Arg Leu Met Ser Thr Arg
            20                  25                  30

Arg Lys Gly Arg Asn Ser Arg Pro Gly Trp Thr Leu
        35                  40

(2) INFORMATION FOR SEQ ID NO: 30:

(i) SEQUENCE CHARACTERISTICS:
        (A) LENGTH: 39 amino acids
        (B) TYPE: amino acid
```

(C) STRANDEDNESS: <Unknown>
        (D) TOPOLOGY: unknown (ii) MOLECULE TYPE: peptide (xi) SEQUENCE DESCRIPTION: SEQ ID NO: 30:

Ser Val Gly Asn Asp Lys Thr Ser Arg Pro Val Ser Phe Tyr Gly Arg
1               5                   10                  15

Val Ser Asp Leu Trp Asn Ala Ser Leu Met Pro Lys Arg Thr Pro Ser
            20                  25                  30

Ser Lys Arg His Asp Asp Gly
        35

(2) INFORMATION FOR SEQ ID NO: 31:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 31:

Arg Trp Pro Ser Val Gly Tyr Lys Gly Asn Gly Ser Asp Thr Ile Asp
1               5                   10                  15

Val His Ser Asn Asp Ala Ser Thr Lys Arg Ser Leu Ile Tyr Asn His
            20                  25                  30

Arg Arg Pro Leu Phe Pro
        35

(2) INFORMATION FOR SEQ ID NO: 32:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 32:

Arg Thr Phe Glu Asn Asp Gly Leu Gly Val Gly Arg Ser Ile Gln Lys
1               5                   10                  15

Lys Ser Asp Arg Trp Tyr Ala Ser His Asn Ile Arg Ser His Phe Ala
            20                  25                  30

Ser Met Ser Pro Ala Gly Lys
        35

(2) INFORMATION FOR SEQ ID NO: 33:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 33:

Ser Tyr Cys Arg Val Lys Gly Gly Gly Glu Gly His Thr Asp Ser
1               5                   10                  15

Asn Leu Ala Arg Ser Gly Cys Gly Lys Val Ala Arg Thr Ser Arg Leu
            20                  25                  30

```
Gln His Ile Asn Pro Arg Ala Thr Pro Pro Ser Arg
        35                  40
```

(2) INFORMATION FOR SEQ ID NO: 34:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 34:

```
Ser Trp Thr Arg Trp Gly Lys His Thr His Gly Gly Phe Val Asn Lys
1               5                   10                  15
Ser Pro Pro Gly Lys Asn Ala Thr Ser Pro Tyr Thr Asp Ala Gln Leu
            20                  25                  30
Pro Ser Asp Gln Gly Pro Pro
            35
```

(2) INFORMATION FOR SEQ ID NO: 35:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 35:

```
Ser Gln Val Asp Ser Phe Arg Asn Ser Phe Arg Trp Tyr Glu Pro Ser
1               5                   10                  15
Arg Ala Leu Cys His Gly Cys Gly Lys Arg Asp Thr Ser Thr Thr Arg
            20                  25                  30
Ile His Asn Ser Pro Ser Asp Ser Tyr Pro Thr Arg
            35                  40
```

(2) INFORMATION FOR SEQ ID NO: 36:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 36:

```
Ser Phe Leu Arg Phe Gln Ser Pro Arg Phe Glu Asp Tyr Ser Arg Thr
1               5                   10                  15
Ile Ser Arg Leu Arg Asn Ala Thr Asn Pro Ser Asn Val Ser Asp Ala
            20                  25                  30
His Asn Asn Arg Ala Leu Ala
            35
```

(2) INFORMATION FOR SEQ ID NO: 37:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide -continued (xi) SEQUENCE DESCRIPTION: SEQ ID NO: 37:

Arg Ser Ile Thr Asp Gly Gly Ile Asn Glu Val Asp Leu Ser Ser Val
1               5                   10                  15

Ser Asn Val Leu Glu Asn Ala Asn Ser His Arg Ala Tyr Arg Lys His
                20                  25                  30

Arg Pro Thr Leu Lys Arg Pro
        35

(2) INFORMATION FOR SEQ ID NO: 38:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 38:

Ser Ser Lys Val Ser Ser Pro Arg Asp Pro Thr Val Pro Arg Lys Gly
1               5                   10                  15

Gly Asn Val Asp Tyr Gly Cys Gly His Arg Ser Ser Ala Arg Met Pro
                20                  25                  30

Thr Ser Ala Leu Ser Ser Ile Thr Lys Cys Tyr Thr
        35                  40

(2) INFORMATION FOR SEQ ID NO: 39:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 39:

Arg Ala Ser Thr Gln Gly Gly Arg Gly Val Ala Pro Glu Phe Gly Ala
1               5                   10                  15

Ser Val Leu Gly Arg Gly Cys Gly Ser Ala Thr Tyr Tyr Thr Asn Ser
                20                  25                  30

Thr Ser Cys Lys Asp Ala Met Gly His Asn Tyr Ser
        35                  40

(2) INFORMATION FOR SEQ ID NO: 40:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 40:

Arg Trp Cys Glu Lys His Lys Phe Thr Ala Ala Arg Cys Ser Ala Gly
1               5                   10                  15

Ala Gly Phe Glu Arg Asp Ala Ser Arg Pro Pro Gln Pro Ala His Arg
                20                  25                  30

Asp Asn Thr Asn Arg Asn Ala
        35

(2) INFORMATION FOR SEQ ID NO: 41:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 41:

```
Ser Phe Gln Val Tyr Pro Asp His Gly Leu Glu Arg His Ala Leu Asp
 1               5                  10                  15
Gly Thr Gly Pro Leu Tyr Ala Met Pro Gly Arg Trp Ile Arg Ala Arg
            20                  25                  30
Pro Gln Asn Arg Asp Arg Gln
            35
```

(2) INFORMATION FOR SEQ ID NO: 42:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 42:

```
Ser Arg Cys Thr Asp Asn Glu Gln Cys Pro Asp Thr Gly Thr Arg Ser
 1               5                  10                  15
Arg Ser Val Ser Asn Ala Arg Tyr Phe Ser Ser Arg Leu Leu Lys Thr
            20                  25                  30
His Ala Pro His Arg Pro
            35
```

(2) INFORMATION FOR SEQ ID NO: 43:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 43:

```
Ser Ala Arg Asp Ser Gly Pro Ala Glu Asp Gly Ser Arg Ala Val Arg
 1               5                  10                  15
Leu Asn Gly Val Glu Asn Ala Asn Thr Arg Lys Ser Ser Arg Ser Asn
            20                  25                  30
Pro Arg Gly Arg Arg His Pro
            35
```

(2) INFORMATION FOR SEQ ID NO: 44:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 44:

```
Ser Ser Ala Asp Ala Glu Lys Cys Ala Gly Ser Leu Leu Trp Trp Gly
```

```
               1               5              10              15
Arg Gln Asn Asn Ser Gly Cys Gly Ser Pro Thr Lys Lys His Leu Lys
                        20              25              30

His Arg Asn Arg Ser Gln Thr Ser Ser Ser His
            35              40

(2) INFORMATION FOR SEQ ID NO: 45:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 45:

Arg Pro Lys Asn Val Ala Asp Ala Tyr Ser Ser Gln Asp Gly Ala Ala
 1               5                  10                  15

Ala Glu Glu Thr Ser His Ala Ser Asn Ala Ala Arg Lys Ser Pro Lys
            20                  25                  30

His Lys Pro Leu Arg Arg Pro
            35

(2) INFORMATION FOR SEQ ID NO: 46:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 46:

Arg Gly Ser Thr Gly Thr Ala Gly Gly Glu Arg Ser Gly Val Leu Asn
 1               5                  10                  15

Leu His Thr Arg Asp Asn Ala Ser Gly Ser Gly Phe Lys Pro Trp Tyr
            20                  25                  30

Pro Ser Asn Arg Gly His Lys
            35

(2) INFORMATION FOR SEQ ID NO: 47:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 47:

Arg Trp Gly Trp Glu Arg Ser Pro Ser Asp Tyr Asp Ser Asp Met Asp
 1               5                  10                  15

Leu Gly Ala Arg Arg Tyr Ala Thr Arg Thr His Arg Ala Pro Pro Arg
            20                  25                  30

Val Leu Lys Ala Pro Leu Pro
            35

(2) INFORMATION FOR SEQ ID NO: 48:

(i) SEQUENCE CHARACTERISTICS:
        (A) LENGTH: 44 amino acids
```

(B) TYPE: amino acid
          (C) STRANDEDNESS: <Unknown>
          (D) TOPOLOGY: unknown (ii) MOLECULE TYPE: peptide (xi) SEQUENCE DESCRIPTION: SEQ ID NO: 48:

Arg Gly Trp Lys Cys Glu Gly Ser Gln Ala Ala Tyr Gly Asp Lys Asp
 1               5                  10                  15

Ile Gly Arg Ser Arg Gly Cys Gly Ser Ile Thr Lys Asn Asn Thr Asn
             20                  25                  30

His Ala His Pro Ser His Gly Ala Val Ala Lys Ile
         35                  40

(2) INFORMATION FOR SEQ ID NO: 49:

(i) SEQUENCE CHARACTERISTICS:
          (A) LENGTH: 39 amino acids
          (B) TYPE: amino acid
          (C) STRANDEDNESS: <Unknown>
          (D) TOPOLOGY: unknown (ii) MOLECULE TYPE: peptide (xi) SEQUENCE DESCRIPTION: SEQ ID NO: 49:

Ser Arg Glu Glu Ala Asn Trp Asp Gly Tyr Lys Arg Glu Met Ser His
 1               5                  10                  15

Arg Ser Arg Phe Trp Asp Ala Thr His Leu Ser Arg Pro Arg Arg Pro
             20                  25                  30

Ala Asn Ser Gly Asp Pro Asn
         35

(2) INFORMATION FOR SEQ ID NO: 50:

(i) SEQUENCE CHARACTERISTICS:
          (A) LENGTH: 44 amino acids
          (B) TYPE: amino acid
          (C) STRANDEDNESS: <Unknown>
          (D) TOPOLOGY: unknown (ii) MOLECULE TYPE: peptide (xi) SEQUENCE DESCRIPTION: SEQ ID NO: 50:

Glu Trp Tyr Ser Trp Lys Arg Ser Ser Lys Ser Thr Gly Leu Gly Asp
 1               5                  10                  15

Thr Ala Thr Arg Glu Gly Cys Gly Pro Ser Gln Ser Asp Gly Cys Pro
             20                  25                  30

Tyr Asn Gly Arg Leu Thr Thr Val Lys Pro Arg Lys
         35                  40

(2) INFORMATION FOR SEQ ID NO: 51:

(i) SEQUENCE CHARACTERISTICS:
          (A) LENGTH: 44 amino acids
          (B) TYPE: amino acid
          (C) STRANDEDNESS: <Unknown>
          (D) TOPOLOGY: unknown (ii) MOLECULE TYPE: peptide (xi) SEQUENCE DESCRIPTION: SEQ ID NO: 51:

Arg Glu Phe Ala Glu Arg Arg Leu Trp Gly Cys Asp Asp Leu Ser Trp
 1               5                  10                  15

Arg Leu Asp Ala Glu Gly Cys Gly Pro Thr Pro Ser Asn Arg Ala Val
             20                  25                  30

```
Lys His Arg Lys Pro Arg Pro Arg Ser Pro Ala Leu
            35                  40
```

(2) INFORMATION FOR SEQ ID NO: 52:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 52:

```
Ser Asp His Ala Leu Gly Thr Asn Leu Arg Ser Asp Asn Ala Lys Glu
 1               5                  10                  15

Pro Gly Asp Tyr Asn Cys Cys Gly Asn Gly Asn Ser Thr Gly Arg Lys
            20                  25                  30

Val Phe Asn Arg Arg Arg Pro Ser Ala Ile Pro Thr
            35                  40
```

(2) INFORMATION FOR SEQ ID NO: 53:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 53:

```
Arg His Ile Ser Glu Tyr Ser Phe Ala Asn Ser His Leu Met Gly Gly
 1               5                  10                  15

Glu Ser Lys Arg Lys Gly Cys Gly Ile Asn Gly Ser Phe Ser Pro Thr
            20                  25                  30

Cys Pro Arg Ser Pro Thr Pro Ala Phe Arg Arg Thr
            35                  40
```

(2) INFORMATION FOR SEQ ID NO: 54:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 54:

```
Ser Arg Glu Ser Gly Met Trp Gly Ser Trp Arg Gly His Arg Leu
 1               5                  10                  15

Asn Ser Thr Gly Gly Asn Ala Asn Met Asn Ala Ser Leu Pro Pro Asp
            20                  25                  30

Pro Pro Val Ser Thr Pro
            35
```

(2) INFORMATION FOR SEQ ID NO: 55:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 55:

Ser Thr Pro Pro Ser Arg Glu Ala Tyr Ser Arg Pro Tyr Ser Val Asp
1               5                   10                  15

Ser Asp Ser Asp Thr Asn Ala Lys His Ser Ser His Asn Arg Arg Leu
            20                  25                  30

Arg Thr Arg Ser Arg Pro Asn
        35

(2) INFORMATION FOR SEQ ID NO: 56:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 56:

TCTCACTCCT CGAGATCCGG CGCTTATGAG AGTCCGGATG GTCGGGGGGG TCGGAGCTAT    60

GTGGGGGGCG GGGGTGGNTG TGGTAACATT GGTCGGAAGC ATAACCTGTG GGGGCTGCGT   120

ACCGCGTCGC CGGCCTGCTG GGACTCTAGA ATCGAAGGTC GCGCTAGACC TTCGAGA     177

(2) INFORMATION FOR SEQ ID NO: 57:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 57:

TCTCACTCCT CGAGTCCTCG CTCTTTCTGG CCCGTTGTGT CCCGGCATGA GTCGTTTGGG    60

ATCTCTAACT ATTTGGGNTG TGGTTATCGT ACATGTATCT CCGGCACGAT GACTAAGTCT   120

AGCCCGATTT ACCCTCGGCA TTCGTCTAGA ATCGAAGGTC GCGCTAGACC TTCGAGA     177

(2) INFORMATION FOR SEQ ID NO: 58:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 58:

TCTCACTCCT CGAGTAGTAG CTCCGATTGG GGTGGTGTGC CTGGGAAGGT GGTTAGGGAG    60

CGCTTTAAGG GGCGCGGTTG TGGTATTTCC ATCACCTCCG TGCTCACTGG GAAGCCCAAT   120

CCGTGTCCGG AGCCTAAGGC GGCCTCTAGA ATCGAAGGTC GCGCTAGACC TTCGAGA     177

(2) INFORMATION FOR SEQ ID NO: 59:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 59:

| | |
|---|---|
| TCTCACTCCT CGAGAGTTGG CCAGTGCACG GATTCTGATG TGCGGCGTCC TTGGGCCAGG | 60 |
| TCTTGCGCTC ATCAGGGTTG TGGTGCGGGC ACTCGCAACT CGCACGGCTG CATCACCCGT | 120 |
| CCTCTCCGCC AGGCTAGCGC TCATTCTAGA ATCGAAGGTC GCGCTAGACC TTCGAGA | 177 |

(2) INFORMATION FOR SEQ ID NO: 60:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 60:

| | |
|---|---|
| TCTCACTCCT CGAGCCACTC CGGTGGTATG AATAGGGCCT ACGGGGATGT GTTTAGGGAG | 60 |
| CTTCGTGATC GGTGGAACGC CACTTCCCAC CACACTCGCC CCACCCCTCA GCTCCCCCGT | 120 |
| GGGCCTAATT CTAGAATCGA AGGTCGCGCT AGACCTTCGA GA | 162 |

(2) INFORMATION FOR SEQ ID NO: 61:

(i) SEQUENCE CHARACTERISTICS:
        (A) LENGTH: 168 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 61:

| | |
|---|---|
| TCTCACTCCT CGAGTCCGTG CGGGGGGTCG TGGGGGCGTT TTATGCAGGG TGGCCTTTTC | 60 |
| GGCGGTAGGA CTGATGGTTG TGGTGCCCAT AGAAACCGCA CTTCTGCGTC GTTAGAGCCC | 120 |
| CCGAGCAGCG ACTACTCTAG AATCGAAGGT CGCGCTAGAC CTTCGAGA | 168 |

(2) INFORMATION FOR SEQ ID NO: 62:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 62:

| | |
|---|---|
| TCTCACTCCT CGAGGGGCGC CGCCGATCAG CGGCGGGGGT GGTCCGAGAA CTTGGGGTTG | 60 |
| CCTAGGGTGG GGTGGGACGC CATCGCTCAC AATAGCTATA CGTTCACCTC GCGCCGCCCG | 120 |
| CGCCCCCCCT CTAGA | 135 |

(2) INFORMATION FOR SEQ ID NO: 63:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 63:

```
TCTCACTCCT CGAGCGGTGG GGAGGTCAGC TCCTGGGGCC GCGTGAATGA CCTCTGCGCT      60

AGGGTGAGTT GGACTGGTTG TGGTACTGCT CGTTCCGCGC GTACCGACAA CAAAGGCTTT     120

CTTCCTAAGC ACTCGTCACT CCGCTCTAGA ATCGAAGGTC GCGCTAGACC TTCGAGA       177
```

(2) INFORMATION FOR SEQ ID NO: 64:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 64:

```
TCTCACTCCT CGAGTGATAG TGACGGGGAT CATTATGGGC TTCGGGGGGG GGTGCGTTGT      60

TCGCTTCGTG ATAGGGGTTG TGGTCTGGCC CTGTCCACCG TCCATGCTGG TCCCCCCTCT     120

TTTTACCCCA AGCTCTCCAG CCCCTCTAGA ATCGAAGGTC GCGCTAGACC TTCGAGA       177
```

(2) INFORMATION FOR SEQ ID NO: 65:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 65:

```
TCTCACTCCT CGAGGAGCTT GGGTAATTAT GGCGTCACCG GGACTGTGGA CGTGACGGTT      60

TTGCCCATGC CTGGCCACGC CAACCACCTT GGTGTCTCCT CCGCCTCTAG CTCTGATCCT     120

CCGCGGCGCT CTAGAATCGA AGGTCGCGCT AGACCTTCGA GA                       162
```

(2) INFORMATION FOR SEQ ID NO: 66:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 66:

```
TCTCACTCCT CGAGAACTAC GACGGCTAAG GGGTGTCTTC TCGGAAGCTT CGGCGTTCTT      60

AGTGGGTGCT CATTTACGCC AACCTCTCCA CCGCCCCACC TAGGATACCC CCCCCACTCC     120

GTCAATTCTA GAATCGAAGG TCGCGCTAGA CCTTCGAGA                            159
```

(2) INFORMATION FOR SEQ ID NO: 67:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 67:

```
TCTCACTCCT CGAGCCCGAA GTTGTCCAGC GTGGGTGTTA TGACTAAGGT CACGGAGCTG      60
```

```
CCCACGGAGG GGCCTAACGC CATTAGTATT CCGATCTCCG CGACCCTCGG CCCGCGCAAC      120

CCGCTCCGCT CTAGAATCGA AGGTCGCGCT AGACCTTCGA GA                        162
```

(2) INFORMATION FOR SEQ ID NO: 68:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 68:

```
TCTCACTCCT CGAGGTGGTG CGGCGCTGAG CTGTGCAACT CGGTGACTAA GAAGTTTCGC      60

CCGGGCTGGC GGGATCACGC CAATCCCTCC ACCCATCATC GTACTCCCCC GCCCAGCCAG     120

TCCAGCCCTT CTAGAATCGA AGGTCGCGCT AGACCTTCGA GA                        162
```

(2) INFORMATION FOR SEQ ID NO: 69:

(i) SEQUENCE CHARACTERISTICS:
        (A) LENGTH: 176 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 69:

```
TCTCACTCCT CGAGGTGGTG CGGCGCTGAT GACCCGTGTG GTGCCAGTCG TTGGCGGGGG      60

GGCAACAGCT TGTTTGGTTG TGGTCTTCGT TGTAGTGCGG CGCAGAGCAC CCCGAGTGGC     120

AGGATCCATT CCACTTCGAC CAGCTCTAGA ATCGAAGGTG CGCTAGACCT TCGAGA        176
```

(2) INFORMATION FOR SEQ ID NO: 70:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 70:

```
TCTCACTCCT CGAGTAAGTC CGGGGAGGGG GGTGACAGTA GCAGGGGCGA GACGGGCTGG      60

GCGAGGGTTC GGTCTCACGC CATGACTGCT GGCCGCTTTC GGTGGTACAA CCAGTTGCCC     120

TCTGATCGGT CTAGAATCGA AGGTCGCGCT AGACCTTCGA GA                        162
```

(2) INFORMATION FOR SEQ ID NO: 71:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 71:

```
TCTCACTCCT CGAGGTCGAG CGCCAATAAT TGCGAGTGGA AGTCTGATTG GATGCGCAGG      60

GCCTGTATTG CTCGTTACGC CAACAGTTCG GGCCCCGCCC GCGCCGTCGA CACTAAGGCC     120

GCGCCCTCTA GAATCGAAGG TCGCGCTAGA CCTTCGAGA                            159
```

(2) INFORMATION FOR SEQ ID NO: 72:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 72:

```
TCTCACTCCT CGAGTAAGTG GTCGTGGAGT TCGAGGTGGG GCTCCCCGCA GGATAAGGTT      60

GAGAAGACCA GGGCGGGTTG TGGTGGTAGT CCCAGCAGCA CCAATTGTCA CCCCTACACC     120

TTTGCCCCCC CCCCGCAAGC CGGCTCTAGA ATCGAAGGTC GCGCTAGACC TTCGAGA       177
```

(2) INFORMATION FOR SEQ ID NO: 73:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 73:

```
TCTCACTCCT CGAGTGGGTT CTGGGAGTTT AGCAGGGGGC TTTGGGATGG GGAGAACCGT      60

AAGAGTGTCC GGTCGGGTTG TGGTTTTCGT GGCTCCTCTG CTCAGGGCCC GTGTCCGGTC     120

ACGCCTGCCA CCATTGACAA ACACTCTAGA ATCGAAGGTC GCGCTAGACC TTCGAGA       177
```

(2) INFORMATION FOR SEQ ID NO: 74:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 74:

```
TCTCACTCCT CGAGTGAGAG CGGGCGGTGC CGTAGCGTGA GCCGGTGGAT GACGACGTGG      60

CAGACGCAGA AGGGCGGTTG TGGTTCCAAT GTTTCCCGCG GTTCGCCCCT CGACCCCTCT     120

CACCAGACCG GGCATGCCAC TACTTCTAGA ATCGAAGGTC GCGCTAGACC TTCGAGA       177
```

(2) INFORMATION FOR SEQ ID NO: 75:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 75:

```
TCTCACTCCT CGAGGGAGTG GAGGTTTGCC GGGCCGCCGT TGGACCTGTG GGCGGGTCCG      60

AGCTTGCCCT CTTTTAACGC CAGTTCCCAC CCTCGCGCCC TGCGCACCTA TTGGTCCCAG     120

CGGCCCCGCT CTAGAATCGA AGGTCGCGCT AGACCTTCGA GA                       162
```

(2) INFORMATION FOR SEQ ID NO: 76:

```
    (i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 76:

TCTCACTCCT CGAGGATGGA GGACATCAAG AACTCGGGGT GGAGGGACTC TTGTAGGTGG      60

GGTGACCTGA GGCCTGGTTG TGGTAGCCGC CAGTGGTACC CCTCGAATAT GCGTTCTAGC     120

AGAGATTACC CCGCGGGGGG CCACTCTAGA ATCGAAGGTC GCGCTAGACC TTCGAGA       177

(2) INFORMATION FOR SEQ ID NO: 77:

(i) SEQUENCE CHARACTERISTICS:
        (A) LENGTH: 152 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 77:

TCTCACTCCT CGAGTCATCC GTGGTACAGG CATTGGAACC ATGGTGACTT CTCTGGTTCG      60

GGCCAGTCAC GCCACACCCC GCCGGAGAGC CCCCACCCCG GCCGCCCTAA TGCCACCATT    120

TCTAGAATCG AAGGTCGCGC TAGACCTTCG AG                                  152

(2) INFORMATION FOR SEQ ID NO: 78:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 78:

TCTCACTCCT CGAGATATAA GCACGATATC GGTTGCGATG CTGGGGTTGA CAAGAAGTCG      60

TCGTCTGTGC GTGGTGGTTG TGGTGCTCAT TNGTCGCCAC CCCGCGCCGG CCGTGGTCCT    120

CGCGGCACGA TGGTTAGCAG GCTTTCTAGA ATCGAAGGTC GCGCTAGACC TTCGAGA       177

(2) INFORMATION FOR SEQ ID NO: 79:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 79:

TCTCACTCCT CGAGTCAGGG CTCCAAGCAG TGTATGCAGT ACCGCACCGG TCGTTTGACG      60

GTGGGGTCTG AGTATGGTTG TGGTATGAAC CCCGCCCGCC ATGCCACGCC CGCTTATCCG    120

GCGCGCCTGC TGCCACGCTA TCGCTCTAGA ATCGAAGGTC GCGCTAGACC TTCGAGA       177

(2) INFORMATION FOR SEQ ID NO: 80:

(i) SEQUENCE CHARACTERISTICS:
        (A) LENGTH: 177 base pairs
```

(B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 80:

TCTCACTCCT CGAGTGGGCG GACTACTAGT GAGATTTCTG GGCTCTGGGG TTGGGGTGAC        60

GACCGGAGCG GTTATGGTTG GGGTAACACG CTCCGCCCCA ACTACATCCC TTATAGGCAG       120

GCGACGAACA GGCATCGTTA TACGTCTAGA ATCGAAGGTC GCGCTAGACC TTCGAGA         177

(2) INFORMATION FOR SEQ ID NO: 81:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 81:

TCTCACTCCT CGAGGTGGAA TTGGACTGTC TTGCCCGCCA CTGGCGGCCA TTACTGGACG        60

CGTTCGACGG ACTATCACGC CATTAACAAT CACAGGCCGA GCATCCCCCA CCAGCATCCG       120

ACCCCTATCT CTAGAATCGA AGGTCGCGCT AGACCTTCGA GA                          162

(2) INFORMATION FOR SEQ ID NO: 82:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 82:

TCTCACTCCT CGAGTTGGTC GTCGTGGAAT TGGAGCTCTA AGACTACTCG TCTGGGCGAC        60

AGGGCGACTC GGGAGGGTTG TGGTCCCAGC CAGTCTGATG GCTGTCCTTA TAACGGCCGC       120

CTTACGACCG TCAAGCCTCG CACGTCTAGA ATCGAAGGTC GCGCTAGACC TTCGAGA         177

(2) INFORMATION FOR SEQ ID NO: 83:

(i) SEQUENCE CHARACTERISTICS:
        (A) LENGTH: 156 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 83:

TCTCACTCCT CGAGTGGTAG TTTGAACGCA TGGCAACCGC GGTCATGGGT GGGGGGCGCG        60

TTCCGGTCAC ACGCCAACAA TAACTTGAAC CCCAAGCCCA CCATGGTTAC TNGTCACCCT      120

ACCTCTAGAA TCGAAGGTCG CGCTAGACCT TCGAGA                                156

(2) INFORMATION FOR SEQ ID NO: 84:

(i) SEQUENCE CHARACTERISTICS:
        (A) LENGTH: 178 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 84:

| | | | | | |
|---|---|---|---|---|---|
| TCTCACTCCT | CGAGGTATTC | GGGTTTGTCC | CCGCGGGACA | ACGGTCCCGC | TTGTAGTCAG | 60 |
| GAGGCTACCT | TGGAGGGTTG | TGGTGCGCAG | AGGCTGATGT | CCACCCGTCG | CAAGGGCCGC | 120 |
| AACTCCCGCC | CCGGGTGGAC | GCTCTCTAGA | ATCGAAGGTC | GCGCTAGACC | CTTCGAGA | 178 |

(2) INFORMATION FOR SEQ ID NO: 85:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 85:

| | | | | | |
|---|---|---|---|---|---|
| TCTCACTCCT | CGAGCGTGGG | GAATGATAAG | ACTAGCAGGC | CGGTTTCCTT | CTACGGGCGC | 60 |
| GTTAGTGATC | TGTGGAACGC | CAGCTTGATG | CCGAAGCGTA | CTCCCAGCTC | GAAGCGCCAC | 120 |
| GATGATGGCT | CTAGAATCGA | AGGTCGCGCT | AGACCTTCGA | GA | | 162 |

(2) INFORMATION FOR SEQ ID NO: 86:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 86:

| | | | | | |
|---|---|---|---|---|---|
| TCTCACTCCT | CGAGTACTCC | CCCCAGTAGG | GAGGCGTATA | GTAGGCCCTA | TAGTGTCGAT | 60 |
| AGCGATTCGG | ATACGAACGC | CAAGCACAGC | TCCCACAACC | GCCGTNTGCG | GACGCGCAGC | 120 |
| CGCCCGAACT | CTAGAATCGA | AGGTCGCGCT | AGACCTTCGA | GA | | 162 |

(2) INFORMATION FOR SEQ ID NO: 87:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 87:

| | | | | | |
|---|---|---|---|---|---|
| TCTCACTCCT | CGAGATGGCC | TAGTGTGGGT | TACAAGGGTA | ATGGCAGTGA | CACTATTGAT | 60 |
| GTTCACAGCA | ATGACGCCAG | TACTAAGAGG | TCCCTCATCT | ATAACCACCG | CCGCCCCNTC | 120 |
| TTTCCCTCTA | GAATCGAAGG | TCGCGCTAGA | CCTTCGAGA | | | 159 |

(2) INFORMATION FOR SEQ ID NO: 88:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 88:

TCTCACTCCT CGAGAACGTT TGAGAACGAC GGGCTGGGCG TCGGCCGGTC TATTCAGAAG      60

AAGTCGGATA GGTGGTACGC CAGCCACAAC ATTCGTAGCC ATTTCGCGTC CATGTCTCCC     120

GCTGGTAAGT CTAGAATCGA AGGTCGCGCT AGACCTTCGA GA                       162

(2) INFORMATION FOR SEQ ID NO: 89:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 89:

TCTCACTCCT CGAGCTATTG TCGGGTTAAG GGTGGTGGGG AGGGGGGGCA TACGGATTCC      60

AATCTGGCTA GGTCGGGTTG TGGTAAGGTG GCCAGGACCA GCAGGCTTCA GCATATCAAC    120

CCGCGCGCTA CCCCCCCCTC CCGGTCTAGA ATCGAAGGTC                          160

(2) INFORMATION FOR SEQ ID NO: 90:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 90:

TCTCACTCCT CGAGTTGGAC TCGGTGGGGC AAGCACANTC ATGGGGGGTT TGTGAACAAG      60

TCTCCCCCTG GGAAGAACGC CACGAGCCCC TACACCGACG CCCAGCTGCC CAGTGATCAG    120

GGTCCTCCCT CTAGAATCGA AGGTCGCGCT AGACCTTCGA GA                       162

(2) INFORMATION FOR SEQ ID NO: 91:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 91:

TCTCACTCCT CGAGTCAGGT TGATTCGTTT CGTAATAGCT TTCGGTGGTA TGAGCCGAGC      60

AGGGCTCTGT GCCATGGTTG TGGTAAGCGC GACACCTCCA CCACTCGTAT CCACAATAGC    120

CCCAGCGACT CCTATCCTAC ACGCTCTAGA ATCGAAGGTC GCGCTAGACC TTCGAGA       177

(2) INFORMATION FOR SEQ ID NO: 92:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 92:

TCTCACTCCT CGAGCTTTTT GCGGTTCCAG AGTCCGAGGT TCGAGGATTA CAGTAGGACG      60

```
ATCTNTCGGT TGCGCAACGC CACGAACCCG AGTAATGTCT CCGATGCGCA CAATAACCGG        120

GCCTTGGCCT CTAGAATCGA AGGTCGCGCT AGACCTTCGA GA                           162

(2) INFORMATION FOR SEQ ID NO: 93:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 93:

TCTCACTCCT CGAGGAGCAT CACCGACGGG GGCATCAATG AGGTGGACCT GAGTAGTGTG        60

TCGAACGTTC TTGAGAACGC CAACTCGCAT AGGGCCTACA GGAAGCATCG CCCGACCTTG        120

AAGCGTCCTT CTAGAATCGA AGGTCGCGCT AGACCTTCGA GA                           162

(2) INFORMATION FOR SEQ ID NO: 94:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 94:

TCTCACTCCT CGAGTTCGAA GGTGAGCAGC CCGAGGGATC CGACGGTCCC GCGGAAGGGC        60

GGCAATGTTG ATTATGGTTG TGGTCACAGG TCTTCCGCCC GGATGCCTAC CTCCGCTCTG       120

TCGTCGATCA CGAAGTGCTA CACTTCTAGA ATCGAAGGTC GCGCTAGACC TTCGAGA         177

(2) INFORMATION FOR SEQ ID NO: 95:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 95:

TCTCACTCCT CGAGAGCCAG TANGCAGGGC GGCCGGGGTG TTGCCCCTGA GTTTGGGGCG        60

AGCGTTTTGG GTNGTGGTTG TGGTAGCGCC ACTTATTACA CGAACTCCAC CAGCTGCAAG       120

GATGCTATGG GCCACAACTA CTCGTCTAGA ATCGAAGGTC GCGNTAGACC TTCGAGA         177

(2) INFORMATION FOR SEQ ID NO: 96:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 96:

TCTCACTCCT CGAGATGGTG CGAGAAGCAC AAGTTTACGG CTGCGCGTTG CAGCGCGGGG        60

GCGGGTTTTG AGAGGGANGC CAGCCGTCCG CCCCAGCCTG CCCACCGGGA TAATACCAAC      120
```

```
CGTAATGCNT NTAGAATCGA AGGTCGCGCT AGACCTTCGA GA                  162
```

(2) INFORMATION FOR SEQ ID NO: 97:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 97:

```
TCTCACTCCT CGAGTTTTCA GGTGTACCCG GACCATGGTC TGGAGAGGCA TGCTTTGGAC    60

GGGACGGGTC CGCTTTACGC CATGCCCGGC CGCTGGATTA GGGCGCGTCC GCAGAACAGG   120

GACCGCCAGT CTAGAATCGA AGGTCGCGCT AGACCTTCGA GA                     162
```

(2) INFORMATION FOR SEQ ID NO: 98:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 98:

```
TCTCACTCCT CGAGCAGGTG TACGGACAAC GAGCAGTGCC CCGATACCGG GANTAGGTCT    60

CGTTCCGTTA GTAACGCCAG GTACTTTTCG AGCAGGTTGC TCAAGACTCA CGCCCCCCAT   120

CGCCCTTCTA GAATCGAAGG TCGCGCTAGA CCTTCGAGA                         159
```

(2) INFORMATION FOR SEQ ID NO: 99:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 99:

```
TCTCACTCCT CGAGTGCCAG GGATAGCGGG CCTGCGGAGG ATGGGTCCCG CGCCGTCCGG    60

TTGAACGGGG TTGAGAACGC CAACACTAGG AAGTCCTCCC GCAGTAACCC GCGGGGTAGG   120

CGCCATCCCT CTAGAATCGA AGGTCGCGCT AGACCTTCGA GA                     162
```

(2) INFORMATION FOR SEQ ID NO: 100:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 100:

```
TCTCACTCCT CGAGTTCCGC CGATGCGGAG AAGTGTGCGG GCAGTCTGTT GTGGTGGGGT    60

AGGCAGAACA ACTCCGGTTG TGGTTCGCCC ACGAAGAAGC ATCTGAAGCA CCGCAATCGC   120

AGTCAGACCT CCTCTTCGTC CCACTCTAGA ATCGAAGGTC GCGCTAGACC TTCGAGA     177
```

(2) INFORMATION FOR SEQ ID NO: 101:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 101:

```
TCTCACTCCT CGAGACCGAA GAACGTGGCC GATGCTTATT CGTCTCAGGA CGGGGCGGCG    60
GCCGAGGAGA CGTCTCACGC CAGTAATGCC GCGCGGAAGT CCCCTAAGCA CAAGCCCTTG   120
AGGCGGCCTT CTAGAATCGA AGGTCGCGCT AGACCTTCGA GA                     162
```

(2) INFORMATION FOR SEQ ID NO: 102:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 102:

```
TCTCACTCCT CGAGAGGCAG TACGGGGACG GCCGGCGGCG AGCGTTCCGG GGTGCTCAAC    60
CTGCACACCA GGGATAACGC CAGCGGCAGC GGTTTCAAAC CGTGGTACCC TTCGAATCGG   120
GGTCACAAGT CTAGAATCGA AGGTCGCGCT AGACCTTCGA GA                     162
```

(2) INFORMATION FOR SEQ ID NO: 103:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 103:

```
TCTCACTCCT CGAGGTGGGG GTGGGAGAGG AGTCCGTCCG ACTACGATTC TGATATGGAC    60
TTGGGGGCGA GGAGGTACGC CACCCGCACC CACCGCGCGC CCCCTCGCGT CTTGAAGGCT   120
CCCCTGCCCT CTAGAATCGA AGGTCGCGCT AGACCTTCGA GA                     162
```

(2) INFORMATION FOR SEQ ID NO: 104:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 104:

```
TCTCACTCCT CGAGGCACTG GAAGTGCGAG GGCTCTCAGG CTGCCTACGG GGACAAGGAT    60
ATCGGGAGGT CCAGGGGTTG TGGTTCCATT ACAAAGAATA ACACTAATCA CGCCCATCCT   120
AGCCACGGCG CCGTTGCTAA GATCTCTAGA ATCGAAGGTC GCGCTAGACC TTCGAGA     177
```

(2) INFORMATION FOR SEQ ID NO: 105:

(i) SEQUENCE CHARACTERISTICS:

(A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 105:

TCTCACTCCT CGAGCCGCGA GGAGGCGAAC TGGGACGGCT ATAAGAGGGA GATGAGCCAC      60

CGGAGTCGCT TTTGGGACGC CACCCACCTG TCCCGCCCTC GCCGCCCCGC TAACTCTGGT     120

GACCCTAACT CTAGAATCGA AGGTCGCGCT AGACCTTCGA GA                       162

(2) INFORMATION FOR SEQ ID NO: 106:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 106:

TCTCACTCNT CGAGAGAGTT CGCGGAGAGG AGGTTGTGGG GGTGTGATGA CCTGAGTTGG      60

CGTCTCGACG CGGAGGGTTG TGGTCCCACT CCGAGCAATC GGGCCGTCAA GCATCGCAAG    120

CCCCGCCCAC GCTCCCCCGC ACTCTCTAGA ATCGAAGGTC GCGCTAGACC TTCGAGA       177

(2) INFORMATION FOR SEQ ID NO: 107:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 107:

TCTCACTCNT NGAGTGATCA CGCGTTGGGG ACGAATCTGA GGTCTGACAA TGCCAAGGAG      60

CCGGGTGATT ACAACTGTTG TGGTAACGGG AACTCTACCG GGCGAAAGGT TTTTAACCGT    120

AGGCGCCCCT CCGCCATCCC CANTTCTAGA ATCGAAGGTC GCGCTAGACC TTCGAGA       177

(2) INFORMATION FOR SEQ ID NO: 108:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 108:

TCTCACTCCT CGAGGCATAT TTCTGAGTAT AGCTTTGCGA ATTCCCACTT GATGGGTGGC      60

GAGTCCAAGC GGAAGGGTTG TGGTATTAAC GGCTCCTTTT CTCCCACTTG TCCCCGCTCC    120

CCCACCCCAG CCTTCCGCCG CACCTCTAGA ATCGAAGGTC GCGCTAGACC TTCGAGA       177

(2) INFORMATION FOR SEQ ID NO: 109:

(i) SEQUENCE CHARACTERISTICS:
        (A) LENGTH: 158 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO: 109:

```
TCTCACTCCT CGAGCCGGGA GAGCGGGATG TGGGGTAGTT GGTGGCGTGG TCACAGGTTG      60

AATTCCACGG GGGGTAACGC CAACATGAAT GCTAGTCTGC CCCCCGACCC CCCTGTTTCC     120

ACTCCGTCTA GAATCGAAGG TCGCGCTAGA CCTTCGAG                             158
```

(2) INFORMATION FOR SEQ ID NO: 110:

(i) SEQUENCE CHARACTERISTICS:
        (A) LENGTH: 708 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 110:

```
Met Gly Met Ser Lys Ser His Ser Phe Phe Gly Tyr Pro Leu Ser Ile
 1               5                  10                  15

Phe Phe Ile Val Val Asn Glu Phe Cys Glu Arg Phe Ser Tyr Tyr Gly
                20                  25                  30

Met Arg Ala Ile Leu Ile Leu Tyr Phe Thr Asn Phe Ile Ser Trp Asp
            35                  40                  45

Asp Asn Leu Ser Thr Ala Ile Tyr His Thr Phe Val Ala Leu Cys Tyr
 50                  55                  60

Leu Thr Pro Ile Leu Gly Ala Leu Ile Ala Asp Ser Trp Leu Gly Lys
 65                  70                  75                  80

Phe Lys Thr Ile Val Ser Leu Ser Ile Val Tyr Thr Ile Gly Gln Ala
                85                  90                  95

Val Thr Ser Val Ser Ser Ile Asn Asp Leu Thr Asp His Asn His Asp
            100                 105                 110

Gly Thr Pro Asp Ser Leu Pro Val His Val Val Leu Ser Leu Ile Gly
            115                 120                 125

Leu Ala Leu Ile Ala Leu Gly Thr Gly Gly Ile Lys Pro Cys Val Ser
130                 135                 140

Ala Phe Gly Gly Asp Gln Phe Glu Glu Gly Gln Glu Lys Gln Arg Asn
145                 150                 155                 160

Arg Phe Phe Ser Ile Phe Tyr Leu Ala Ile Asn Ala Gly Ser Leu Leu
                165                 170                 175

Ser Thr Ile Ile Thr Pro Met Leu Arg Val Gln Gln Cys Gly Ile His
            180                 185                 190

Ser Lys Gln Ala Cys Tyr Pro Leu Ala Phe Gly Val Pro Ala Ala Leu
            195                 200                 205

Met Ala Val Ala Leu Ile Val Phe Val Leu Gly Ser Gly Met Tyr Lys
210                 215                 220

Lys Phe Lys Pro Gln Gly Asn Ile Met Gly Lys Val Ala Lys Cys Ile
225                 230                 235                 240

Gly Phe Ala Ile Lys Asn Arg Phe Arg His Arg Ser Lys Ala Phe Pro
                245                 250                 255

Lys Arg Glu His Trp Leu Asp Trp Ala Lys Glu Lys Tyr Asp Glu Arg
            260                 265                 270

Leu Ile Ser Gln Ile Lys Met Val Thr Arg Val Met Phe Leu Tyr Ile
            275                 280                 285
```

-continued

```
Pro Leu Pro Met Phe Trp Ala Leu Phe Asp Gln Gln Gly Ser Arg Trp
    290                 295                 300

Thr Leu Gln Ala Thr Thr Met Ser Gly Lys Ile Gly Ala Leu Glu Ile
305                 310                 315                 320

Gln Pro Asp Gln Met Gln Thr Val Asn Ala Ile Leu Ile Val Ile Met
                325                 330                 335

Val Pro Ile Phe Asp Ala Val Leu Tyr Pro Leu Ile Ala Lys Cys Gly
            340                 345                 350

Phe Asn Phe Thr Ser Leu Lys Lys Met Ala Val Gly Met Val Leu Ala
        355                 360                 365

Ser Met Ala Phe Val Val Ala Ile Val Gln Val Glu Ile Asp Lys
    370                 375                 380

Thr Leu Pro Val Phe Pro Lys Gly Asn Glu Val Gln Ile Lys Val Leu
385                 390                 395                 400

Asn Ile Gly Asn Asn Thr Met Asn Ile Ser Leu Pro Gly Glu Met Val
                405                 410                 415

Thr Leu Gly Pro Met Ser Gln Thr Asn Ala Phe Met Thr Phe Asp Val
            420                 425                 430

Asn Lys Leu Thr Arg Ile Asn Ile Ser Ser Pro Gly Ser Pro Val Thr
        435                 440                 445

Ala Val Thr Asp Asp Phe Lys Gln Gly Gln Arg His Thr Leu Leu Val
    450                 455                 460

Trp Ala Pro Asn His Tyr Gln Val Val Lys Asp Gly Leu Asn Gln Lys
465                 470                 475                 480

Pro Glu Lys Gly Glu Asn Gly Ile Arg Phe Val Asn Thr Phe Asn Glu
                485                 490                 495

Leu Ile Thr Ile Thr Met Ser Gly Lys Val Tyr Ala Asn Ile Ser Ser
            500                 505                 510

Tyr Asn Ala Ser Thr Tyr Gln Phe Phe Pro Ser Gly Ile Lys Gly Phe
        515                 520                 525

Thr Ile Ser Ser Thr Glu Ile Pro Pro Gln Cys Gln Pro Asn Phe Asn
    530                 535                 540

Thr Phe Tyr Leu Glu Phe Gly Ser Ala Tyr Thr Tyr Ile Val Gln Arg
545                 550                 555                 560

Lys Asn Asp Ser Cys Pro Glu Val Lys Val Phe Glu Asp Ile Ser Ala
                565                 570                 575

Asn Thr Val Asn Met Ala Leu Gln Ile Pro Gln Tyr Phe Leu Leu Thr
            580                 585                 590

Cys Gly Glu Val Val Phe Ser Val Thr Gly Leu Glu Phe Ser Tyr Ser
        595                 600                 605

Gln Ala Pro Ser Asn Met Lys Ser Val Leu Gln Ala Gly Trp Leu Leu
    610                 615                 620

Thr Val Ala Val Gly Asn Ile Ile Val Leu Ile Val Ala Gly Ala Gly
625                 630                 635                 640

Gln Phe Ser Lys Gln Trp Ala Glu Tyr Ile Leu Phe Ala Ala Leu Leu
                645                 650                 655

Leu Val Val Cys Val Val Phe Ala Ile Met Ala Arg Phe Tyr Thr Tyr
            660                 665                 670

Ile Asn Pro Ala Glu Ile Glu Ala Gln Phe Asp Glu Asp Lys Lys
        675                 680                 685

Asn Arg Leu Glu Lys Ser Asn Pro Tyr Phe Met Ser Gly Ala Asn Ser
    690                 695                 700

Gln Lys Gln Met
```

(2) INFORMATION FOR SEQ ID NO: 111:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 111:

TCCGGACTCT CATAAGCGCC GG                                              22

(2) INFORMATION FOR SEQ ID NO: 112:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 112:

ACAACGGGCC AGAAAGAGCG AG                                              22

(2) INFORMATION FOR SEQ ID NO: 113:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 113:

ACACCACCCC AATCGGAGCT AC                                              22

(2) INFORMATION FOR SEQ ID NO: 114:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 114:

TCAGAATCCG TGCACTGGCC AA                                              22

(2) INFORMATION FOR SEQ ID NO: 115:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 115:

GCCCTATTCA TACCACCGGA GT                                              22

(2) INFORMATION FOR SEQ ID NO: 116:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 116:

CATCAGTCCT ACCGCCGAAA AG                          22

(2) INFORMATION FOR SEQ ID NO: 117:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 117:

CGTATAGCTA TTGTGAGCGA TG                          22

(2) INFORMATION FOR SEQ ID NO: 118:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 118:

ACGCGCGGAA CGAGCAGTAC CA                          22

(2) INFORMATION FOR SEQ ID NO: 119:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 119:

CCATAATGAT CCCCGTCACT AT                          22

(2) INFORMATION FOR SEQ ID NO: 120:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 120:

AGACACCCCT TAGCCGTCGT AG                          22

(2) INFORMATION FOR SEQ ID NO: 121:

(i) SEQUENCE CHARACTERISTICS:
        (A) LENGTH: 22 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO: 121:

AGCTCCGTGA CCTTAGTCAT AA                                            22

(2) INFORMATION FOR SEQ ID NO: 122:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 122:

TGCACAGCTC AGCGCCGCAC CA                                            22

(2) INFORMATION FOR SEQ ID NO: 123:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 123:

ACGGGTCATC AGCGCCGCAC CA                                            22

(2) INFORMATION FOR SEQ ID NO: 124:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 124:

TGTCACCCCC CTCCCCGGAC TT                                            22

(2) INFORMATION FOR SEQ ID NO: 125:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 125:

ACTCGCAATT ATTGGCGCTC GA                                            22

(2) INFORMATION FOR SEQ ID NO: 126:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO: 126:

GTCTTCTCAA CCTTATCCTG CG                                              22

(2) INFORMATION FOR SEQ ID NO: 127:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 127:

AAAGCCCCCT GCTAAACTCC CA                                              22

(2) INFORMATION FOR SEQ ID NO: 128:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 128:

CTGCGTCTGC CACGTCGTCA TC                                              22

(2) INFORMATION FOR SEQ ID NO: 129:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 129:

GTTAAAAGAG GGCAAGCTCG GA                                              22

(2) INFORMATION FOR SEQ ID NO: 130:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 130:

CCGAGTTCTT GATGTCCTCC AT                                              22

(2) INFORMATION FOR SEQ ID NO: 131:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 131:

TCCAATGCCT GTACCACGGA TG                                              22

(2) INFORMATION FOR SEQ ID NO: 132:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 132:

TCGCAACCGA TATCGTGCTT AT                                22

(2) INFORMATION FOR SEQ ID NO: 133:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 133:

TGCATACACT GCTTGGAGCC CT                                22

(2) INFORMATION FOR SEQ ID NO: 134:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 134:

GAAATCTCAC TAGTAGTCCG CC                                22

(2) INFORMATION FOR SEQ ID NO: 135:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 135:

GCGGGCAAGA CAGTCCAATT CC                                22

(2) INFORMATION FOR SEQ ID NO: 136:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 136:

GAGCTCCAAT TCCACGACGA CC                                22

(2) INFORMATION FOR SEQ ID NO: 137:

-continued

```
    (i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 137:

GGTTGCCATG CGTTCAAACT AC                                          22

(2) INFORMATION FOR SEQ ID NO: 138:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 138:

TCCCGCGGGG ACAAACCCGA AT                                          22

(2) INFORMATION FOR SEQ ID NO: 139:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 139:

CTGCTAGTCT TATCATTCCC CA                                          22

(2) INFORMATION FOR SEQ ID NO: 140:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 140:

CTATCGACAC TATAGGGCCT AC                                          22

(2) INFORMATION FOR SEQ ID NO: 141:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 141:

TACCCTTGTA ACCCACACTA GG                                          22

(2) INFORMATION FOR SEQ ID NO: 142:

(i) SEQUENCE CHARACTERISTICS:
        (A) LENGTH: 22 base pairs
        (B) TYPE: nucleic acid
        (C) STRANDEDNESS: single
```

(D) TOPOLOGY: linear (ii) MOLECULE TYPE: DNA (xi) SEQUENCE DESCRIPTION: SEQ ID NO: 142:

TTCTTCTGAA TAGACCGGCC GA                                            22

(2) INFORMATION FOR SEQ ID NO: 143:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 143:

CCACCACCCT TAACCCGACA AT                                            22

(2) INFORMATION FOR SEQ ID NO: 144:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 144:

AGGGGGAGAC TTGTTCACAA AC                                            22

(2) INFORMATION FOR SEQ ID NO: 145:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 145:

CGGCTCATAC CACCGAAAGC TA                                            22

(2) INFORMATION FOR SEQ ID NO: 146:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 146:

ATCGTCCTAC TGTAATCCTC GA                                            22

(2) INFORMATION FOR SEQ ID NO: 147:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 147:

GACACACTAC TCAGGTCCAC CT                    22

(2) INFORMATION FOR SEQ ID NO: 148:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 148:

CCATAATCAA CATTGCCGCC CT                    22

(2) INFORMATION FOR SEQ ID NO: 149:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 149:

CAAAACGCTC GCCCCAAACT CA                    22

(2) INFORMATION FOR SEQ ID NO: 150:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 150:

GTAAACTTGT GCTTCTCGCA CC                    22

(2) INFORMATION FOR SEQ ID NO: 151:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 151:

CCATGGTCCG GGTACACCTG AA                    22

(2) INFORMATION FOR SEQ ID NO: 152:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 152:

GTTACTAACG GAACGAGACC TA                    22

(2) INFORMATION FOR SEQ ID NO: 153:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 153:

TGTTGGCGTT CTCAACCCCG TT                              22

(2) INFORMATION FOR SEQ ID NO: 154:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 154:

ACAACCGGAG TTGTTCTGCC TA                              22

(2) INFORMATION FOR SEQ ID NO: 155:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 155:

TAAGCATCGG CCACGTTCTT CG                              22

(2) INFORMATION FOR SEQ ID NO: 156:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 156:

TTATCCCTGG TGTGCAGGTT GA                              22

(2) INFORMATION FOR SEQ ID NO: 157:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 157:

TATCAGAATC GTAGTCGGAC GG                              22

(2) INFORMATION FOR SEQ ID NO: 158:

(i) SEQUENCE CHARACTERISTICS:

```
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 158:

CTTTGTAATG GAACCACAAC CC                                              22

(2) INFORMATION FOR SEQ ID NO: 159:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 159:

CGGTGGCTCA TCTCCCTCTT AT                                              22

(2) INFORMATION FOR SEQ ID NO: 160:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 160:

ATCAGACTGG CTGGGACCAC AA                                              22

(2) INFORMATION FOR SEQ ID NO: 161:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 161:

CACAACCTCC TCTCCGCGAA CT                                              22

(2) INFORMATION FOR SEQ ID NO: 162:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 162:

AGATTCGTCC CCAACGCGTG AT                                              22

(2) INFORMATION FOR SEQ ID NO: 163:

(i) SEQUENCE CHARACTERISTICS:
        (A) LENGTH: 22 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO: 163:

GGGAATTCGC AAAGCTATAC TC  22

(2) INFORMATION FOR SEQ ID NO: 164:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 164:

CCCCGTGGAA TTCAACCTGT GA  22

(2) INFORMATION FOR SEQ ID NO: 165:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 165:

GTCGTCTTTC CAGACGT  17

(2) INFORMATION FOR SEQ ID NO: 166:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 166:

CTTGCATGCC TGCAGGTCGA C  21

(2) INFORMATION FOR SEQ ID NO: 167:

(i) SEQUENCE CHARACTERISTICS:
        (A) LENGTH: 37 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 167:

Arg Ile Ala Gly Leu Pro Trp Tyr Arg Cys Arg Thr Val Ala Phe Glu
 1               5                  10                  15

Thr Gly Met Gln Asn Thr Gln Leu Cys Ser Thr Ile Val Gln Leu Ser
             20                  25                  30

Phe Thr Pro Glu Glu
         35

(2) INFORMATION FOR SEQ ID NO: 168:

(i) SEQUENCE CHARACTERISTICS:
        (A) LENGTH: 44 amino acids (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 168:

Arg Glu Phe Ala Glu Arg Arg Leu Trp Gly Cys Asp Asp Leu Ser Trp
 1               5                  10                  15

Arg Leu Asp Ala Glu Gly Cys Gly Pro Thr Pro Ser Asn Arg Ala Val
            20                  25                  30

Lys His Arg Lys Pro Arg Pro Arg Ser Pro Ala Leu
        35                  40

(2) INFORMATION FOR SEQ ID NO: 169:

(i) SEQUENCE CHARACTERISTICS:
        (A) LENGTH: 41 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 169:

Ser Gly Ser His Ser Gly Gly Met Asn Arg Ala Tyr Gly Asp Val Phe
 1               5                  10                  15

Arg Glu Leu Arg Asp Arg Trp Tyr Ala Thr Ser His His Thr Arg Pro
            20                  25                  30

Thr Pro Gln Leu Pro Arg Gly Pro Asn
        35                  40

(2) INFORMATION FOR SEQ ID NO: 170:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 170:

Ser Thr Pro Pro Ser Arg Glu Ala Tyr Ser Arg Pro Tyr Ser Val Asp
 1               5                  10                  15

Ser Asp Ser Asp
        20

(2) INFORMATION FOR SEQ ID NO: 171:

(i) SEQUENCE CHARACTERISTICS:
        (A) LENGTH: 29 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 171:

Ser Thr Pro Pro Ser Arg Glu Ala Tyr Ser Arg Pro Tyr Ser Val Asp
 1               5                  10                  15

Ser Asp Ser Asp Thr Asn Ala Lys His Ser Ser His Asn
        20                  25

(2) INFORMATION FOR SEQ ID NO: 172:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 172:

Thr Asn Ala Lys His Ser Ser His Asn Arg Arg Leu Arg Thr Arg Ser
1               5                   10                  15

Arg Pro Asn (2) INFORMATION FOR SEQ ID NO: 173:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 173:

Thr Asn Ala Lys His Ser Ser His Asn
1               5

(2) INFORMATION FOR SEQ ID NO: 174:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 174:

Ser Ser His Asn Arg Arg Leu Arg Thr Arg Ser Arg Pro Asn
1               5                   10

(2) INFORMATION FOR SEQ ID NO: 175:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 175:

Arg Arg Leu Arg Thr Arg Ser Arg Pro Asn
1               5                   10

(2) INFORMATION FOR SEQ ID NO: 176:

(i) SEQUENCE CHARACTERISTICS:
        (A) LENGTH: 708 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 176:

Met Gly Met Ser Lys Ser His Ser Phe Phe Gly Tyr Pro Leu Ser Ile
1               5                   10                  15

```
Phe Phe Ile Val Val Asn Glu Phe Cys Glu Arg Phe Ser Tyr Tyr Gly
            20                  25                  30

Met Arg Ala Ile Leu Ile Leu Tyr Phe Thr Asn Phe Ile Ser Trp Asp
        35                  40                  45

Asp Asn Leu Ser Thr Ala Ile Tyr His Thr Phe Val Ala Leu Cys Tyr
        50                  55                  60

Leu Thr Pro Ile Leu Gly Ala Leu Ile Ala Asp Ser Trp Leu Gly Lys
65                  70                  75                  80

Phe Lys Thr Ile Val Ser Leu Ser Ile Val Tyr Thr Ile Gly Gln Ala
                85                  90                  95

Val Thr Ser Val Ser Ser Ile Asn Asp Leu Thr Asp His Asn His Asp
            100                 105                 110

Gly Thr Pro Asp Ser Leu Pro Val His Val Leu Ser Leu Ile Gly
            115                 120                 125

Leu Ala Leu Ile Ala Leu Gly Thr Gly Gly Ile Lys Pro Cys Val Ser
130                 135                 140

Ala Phe Gly Gly Asp Gln Phe Glu Glu Gly Gln Glu Lys Gln Arg Asn
145                 150                 155                 160

Arg Phe Phe Ser Ile Phe Tyr Leu Ala Ile Asn Ala Gly Ser Leu Leu
                165                 170                 175

Ser Thr Ile Ile Thr Pro Met Leu Arg Val Gln Gln Cys Gly Ile His
            180                 185                 190

Ser Lys Gln Ala Cys Tyr Pro Leu Ala Phe Gly Val Pro Ala Ala Leu
        195                 200                 205

Met Ala Val Ala Leu Ile Val Phe Val Leu Gly Ser Gly Met Tyr Lys
    210                 215                 220

Lys Phe Lys Pro Gln Gly Asn Ile Met Gly Lys Val Ala Lys Cys Ile
225                 230                 235                 240

Gly Phe Ala Ile Lys Asn Arg Phe Arg His Arg Ser Lys Ala Phe Pro
                245                 250                 255

Lys Arg Glu His Trp Leu Asp Trp Ala Lys Glu Lys Tyr Asp Glu Arg
            260                 265                 270

Leu Ile Ser Gln Ile Lys Met Val Thr Arg Val Met Phe Leu Tyr Ile
        275                 280                 285

Pro Leu Pro Met Phe Trp Ala Leu Phe Asp Gln Gln Gly Ser Arg Trp
    290                 295                 300

Thr Leu Gln Ala Thr Thr Met Ser Gly Lys Ile Gly Ala Leu Glu Ile
305                 310                 315                 320

Gln Pro Asp Gln Met Gln Thr Val Asn Ala Ile Leu Ile Val Ile Met
                325                 330                 335

Val Pro Ile Phe Asp Ala Val Leu Tyr Pro Leu Ile Ala Lys Cys Gly
            340                 345                 350

Phe Asn Phe Thr Ser Leu Lys Lys Met Ala Val Gly Met Val Leu Ala
        355                 360                 365

Ser Met Ala Phe Val Val Ala Ala Ile Val Gln Val Glu Ile Asp Lys
    370                 375                 380

Thr Leu Pro Val Phe Pro Lys Gly Asn Glu Val Gln Ile Lys Val Leu
385                 390                 395                 400

Asn Ile Gly Asn Asn Thr Met Asn Ile Ser Leu Pro Gly Glu Met Val
                405                 410                 415

Thr Leu Gly Pro Met Ser Gln Thr Asn Ala Phe Met Thr Phe Asp Val
            420                 425                 430
```

```
Asn Lys Leu Thr Arg Ile Asn Ile Ser Ser Pro Gly Ser Pro Val Thr
        435                 440                 445

Ala Val Thr Asp Asp Phe Lys Gln Gly Gln Arg His Thr Leu Leu Val
    450                 455                 460

Trp Ala Pro Asn His Tyr Gln Val Val Lys Asp Gly Leu Asn Gln Lys
465                 470                 475                 480

Pro Glu Lys Gly Glu Asn Gly Ile Arg Phe Val Asn Thr Phe Asn Glu
                485                 490                 495

Leu Ile Thr Ile Thr Met Ser Gly Lys Val Tyr Ala Asn Ile Ser Ser
            500                 505                 510

Tyr Asn Ala Ser Thr Tyr Gln Phe Phe Pro Ser Gly Ile Lys Gly Phe
        515                 520                 525

Thr Ile Ser Ser Thr Glu Ile Pro Pro Gln Cys Gln Pro Asn Phe Asn
    530                 535                 540

Thr Phe Tyr Leu Glu Phe Gly Ser Ala Tyr Thr Tyr Ile Val Gln Arg
545                 550                 555                 560

Lys Asn Asp Ser Cys Pro Glu Val Lys Val Phe Glu Asp Ile Ser Ala
                565                 570                 575

Asn Thr Val Asn Met Ala Leu Gln Ile Pro Gln Tyr Phe Leu Leu Thr
            580                 585                 590

Cys Gly Glu Val Val Phe Ser Val Thr Gly Leu Glu Phe Ser Tyr Ser
        595                 600                 605

Gln Ala Pro Ser Asn Met Lys Ser Val Leu Gln Ala Gly Trp Leu Leu
    610                 615                 620

Thr Val Ala Val Gly Asn Ile Ile Val Leu Ile Val Ala Gly Ala Gly
625                 630                 635                 640

Gln Phe Ser Lys Gln Trp Ala Glu Tyr Ile Leu Phe Ala Ala Leu Leu
                645                 650                 655

Leu Val Val Cys Val Val Phe Ala Ile Met Ala Arg Phe Tyr Thr Tyr
            660                 665                 670

Ile Asn Pro Ala Glu Ile Glu Ala Gln Phe Asp Glu Asp Glu Lys Lys
        675                 680                 685

Asn Arg Leu Glu Lys Ser Asn Pro Tyr Phe Met Ser Gly Ala Asn Ser
    690                 695                 700

Gln Lys Gln Met
705

(2) INFORMATION FOR SEQ ID NO: 177:

(i) SEQUENCE CHARACTERISTICS:
        (A) LENGTH: 3345 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 88...2583
        (D) OTHER INFORMATION:

(xi) SEQUENCE DESCRIPTION: SEQ ID NO: 177:

GAATTCCGTC TCGACCACTG AATGGAAGAA AAGGACTTTT AACCACCATT TTGTGACTTA       60

CAGAAAGGAA TTTGAATAAA GAAAACT ATG ATA CTT CAG GCC CAT CTT CAC TCC     114
                             Met Ile Leu Gln Ala His Leu His Ser
                              1               5

CTG TGT CTT CTT ATG CTT TAT TTG GCA ACT GGA TAT GGC CAA GAG GGG       162
```

```
Leu Cys Leu Leu Met Leu Tyr Leu Ala Thr Gly Tyr Gly Gln Glu Gly
 10              15                  20              25

AAG TTT AGT GGA CCC CTG AAA CCC ATG ACA TTT TCT ATT TAT GAA GGC        210
Lys Phe Ser Gly Pro Leu Lys Pro Met Thr Phe Ser Ile Tyr Glu Gly
             30                  35                  40

CAA GAA CCG AGT CAA ATT ATA TTC CAG TTT AAG GCC AAT CCT CCT GCT        258
Gln Glu Pro Ser Gln Ile Ile Phe Gln Phe Lys Ala Asn Pro Pro Ala
             45                  50                  55

GTG ACT TTT GAA CTA ACT GGG GAG ACA GAC AAC ATA TTT GTG ATA GAA        306
Val Thr Phe Glu Leu Thr Gly Glu Thr Asp Asn Ile Phe Val Ile Glu
             60                  65                  70

CGG GAG GGA CTT CTG TAT TAC AAC AGA GCC TTG GAC AGG GAA ACA AGA        354
Arg Glu Gly Leu Leu Tyr Tyr Asn Arg Ala Leu Asp Arg Glu Thr Arg
     75                  80                  85

TCT ACT CAC AAT CTC CAG GTT GCA GCC CTG GAC GCT AAT GGA ATT ATA        402
Ser Thr His Asn Leu Gln Val Ala Ala Leu Asp Ala Asn Gly Ile Ile
 90                  95                 100                 105

GTG GAG GGT CCA GTC CCT ATC ACC ATA GAA GTG AAG GAC ATC AAC GAC        450
Val Glu Gly Pro Val Pro Ile Thr Ile Glu Val Lys Asp Ile Asn Asp
                110                 115                 120

AAT CGA CCC ACG TTT CTC CAG TCA AAG TAC GAA GGC TCA GTA AGG CAG        498
Asn Arg Pro Thr Phe Leu Gln Ser Lys Tyr Glu Gly Ser Val Arg Gln
             125                 130                 135

AAC TCT CGC CCA GGA AAG CCC TTC TTG TAT GTC AAT GCC ACA GAC CTG        546
Asn Ser Arg Pro Gly Lys Pro Phe Leu Tyr Val Asn Ala Thr Asp Leu
         140                 145                 150

GAT GAT CCG GCC ACT CCC AAT GGC CAG CTT TAT TAC CAG ATT GTC ATC        594
Asp Asp Pro Ala Thr Pro Asn Gly Gln Leu Tyr Tyr Gln Ile Val Ile
 155                 160                 165

CAG CTT CCC ATG ATC AAC AAT GTC ATG TAC TTT CAG ATC AAC AAC AAA        642
Gln Leu Pro Met Ile Asn Asn Val Met Tyr Phe Gln Ile Asn Asn Lys
 170                 175                 180                 185

ACG GGA GCC ATC TCT CTT ACC CGA GAG GGA TCT CAG GAA TTG AAT CCT        690
Thr Gly Ala Ile Ser Leu Thr Arg Glu Gly Ser Gln Glu Leu Asn Pro
             190                 195                 200

GCT AAG AAT CCT TCC TAT AAT CTG GTG ATC TCA GTG AAG GAC ATG GGA        738
Ala Lys Asn Pro Ser Tyr Asn Leu Val Ile Ser Val Lys Asp Met Gly
         205                 210                 215

GGC CAG AGT GAG AAT TCC TTC AGT GAT ACC ACA TCT GTG GAT ATC ATA        786
Gly Gln Ser Glu Asn Ser Phe Ser Asp Thr Thr Ser Val Asp Ile Ile
             220                 225                 230

GTG ACA GAG AAT ATT TGG AAA GCA CCA AAA CCT GTG GAG ATG GTG GAA        834
Val Thr Glu Asn Ile Trp Lys Ala Pro Lys Pro Val Glu Met Val Glu
 235                 240                 245

AAC TCA ACT GAT CCT CAC CCC ATC AAA ATC ACT CAG GTG CGG TGG AAT        882
Asn Ser Thr Asp Pro His Pro Ile Lys Ile Thr Gln Val Arg Trp Asn
 250                 255                 260                 265

GAT CCC GGT GCA CAA TAT TCC TTA GTT GAC AAA GAG AAG CTG CCA AGA        930
Asp Pro Gly Ala Gln Tyr Ser Leu Val Asp Lys Glu Lys Leu Pro Arg
             270                 275                 280

TTC CCA TTT TCA ATT GAC CAG GAA GGA GAT ATT TAC GTG ACT CAG CCC        978
Phe Pro Phe Ser Ile Asp Gln Glu Gly Asp Ile Tyr Val Thr Gln Pro
             285                 290                 295

TTG GAC CGA GAA GAA AAG GAT GCA TAT GTT TTT TAT GCA GTT GCA AAG       1026
Leu Asp Arg Glu Glu Lys Asp Ala Tyr Val Phe Tyr Ala Val Ala Lys
             300                 305                 310

GAT GAG TAC GGA AAA CCA CTT TCA TAT CCG CTG GAA ATT CAT GTA AAA       1074
Asp Glu Tyr Gly Lys Pro Leu Ser Tyr Pro Leu Glu Ile His Val Lys
 315                 320                 325
```

-continued

```
GTT AAA GAT ATT AAT GAT AAT CCA CCT ACA TGT CCG TCA CCA GTA ACC            1122
Val Lys Asp Ile Asn Asp Asn Pro Pro Thr Cys Pro Ser Pro Val Thr
330             335             340             345

GTA TTT GAG GTC CAG GAG AAT GAA CGA CTG GGT AAC AGT ATC GGG ACC            1170
Val Phe Glu Val Gln Glu Asn Glu Arg Leu Gly Asn Ser Ile Gly Thr
            350             355             360

CTT ACT GCA CAT GAC AGG GAT GAA GAA AAT ACT GCC AAC AGT TTT CTA            1218
Leu Thr Ala His Asp Arg Asp Glu Glu Asn Thr Ala Asn Ser Phe Leu
        365             370             375

AAC TAC AGG ATT GTG GAG CAA ACT CCC AAA CTT CCC ATG GAT GGA CTC            1266
Asn Tyr Arg Ile Val Glu Gln Thr Pro Lys Leu Pro Met Asp Gly Leu
    380             385             390

TTC CTA ATC CAA ACC TAT GCT GGA ATG TTA CAG TTA GCT AAA CAG TCC            1314
Phe Leu Ile Gln Thr Tyr Ala Gly Met Leu Gln Leu Ala Lys Gln Ser
395             400             405

TTG AAG AAG CAA GAT ACT CCT CAG TAC AAC TTA ACG ATA GAG GTG TCT            1362
Leu Lys Lys Gln Asp Thr Pro Gln Tyr Asn Leu Thr Ile Glu Val Ser
410             415             420             425

GAC AAA GAT TTC AAG ACC CTT TGT TTT GTG CAA ATC AAC GTT ATT GAT            1410
Asp Lys Asp Phe Lys Thr Leu Cys Phe Val Gln Ile Asn Val Ile Asp
            430             435             440

ATC AAT GAT CAG ATC CCC ATC TTT GAA AAA TCA GAT TAT GGA AAC CTG            1458
Ile Asn Asp Gln Ile Pro Ile Phe Glu Lys Ser Asp Tyr Gly Asn Leu
        445             450             455

ACT CTT GCT GAA GAC ACA AAC ATT GGG TCC ACC ATC TTA ACC ATC CAG            1506
Thr Leu Ala Glu Asp Thr Asn Ile Gly Ser Thr Ile Leu Thr Ile Gln
    460             465             470

GCC ACT GAT GCT GAT GAG CCA TTT ACT GGG AGT TCT AAA ATT CTG TAT            1554
Ala Thr Asp Ala Asp Glu Pro Phe Thr Gly Ser Ser Lys Ile Leu Tyr
475             480             485

CAT ATC ATA AAG GGA GAC AGT GAG GGA CGC CTG GGG GTT GAC ACA GAT            1602
His Ile Ile Lys Gly Asp Ser Glu Gly Arg Leu Gly Val Asp Thr Asp
490             495             500             505

CCC CAT ACC AAC ACC GGA TAT GTC ATA ATT AAA AAG CCT CTT GAT TTT            1650
Pro His Thr Asn Thr Gly Tyr Val Ile Ile Lys Lys Pro Leu Asp Phe
            510             515             520

GAA ACA GCA GCT GTT TCC AAC ATT GTG TTC AAA GCA GAA AAT CCT GAG            1698
Glu Thr Ala Ala Val Ser Asn Ile Val Phe Lys Ala Glu Asn Pro Glu
        525             530             535

CCT CTA GTG TTT GGT GTG AAG TAC AAT GCA AGT TCT TTT GCC AAG TTC            1746
Pro Leu Val Phe Gly Val Lys Tyr Asn Ala Ser Ser Phe Ala Lys Phe
    540             545             550

ACG CTT ATT GTG ACA GAT GTG AAT GAA GCA CCT CAA TTT TCC CAA CAC            1794
Thr Leu Ile Val Thr Asp Val Asn Glu Ala Pro Gln Phe Ser Gln His
555             560             565

GTA TTC CAA GCG AAA GTC AGT GAG GAT GTA GCT ATA GGC ACT AAA GTG            1842
Val Phe Gln Ala Lys Val Ser Glu Asp Val Ala Ile Gly Thr Lys Val
570             575             580             585

GGC AAT GTG ACT GCC AAG GAT CCA GAA GGT CTG GAC ATA AGC TAT TCA            1890
Gly Asn Val Thr Ala Lys Asp Pro Glu Gly Leu Asp Ile Ser Tyr Ser
            590             595             600

CTG AGG GGA GAC ACA AGA GGT TGG CTT AAA ATT GAC CAC GTG ACT GGT            1938
Leu Arg Gly Asp Thr Arg Gly Trp Leu Lys Ile Asp His Val Thr Gly
        605             610             615

GAG ATC TTT AGT GTG GCT CCA TTG GAC AGA GAA GCC GGA AGT CCA TAT            1986
Glu Ile Phe Ser Val Ala Pro Leu Asp Arg Glu Ala Gly Ser Pro Tyr
    620             625             630

CGG GTA CAA GTG GTG GCC ACA GAA GTA GGG GGG TCT TCC TTA AGC TCT            2034
Arg Val Gln Val Val Ala Thr Glu Val Gly Gly Ser Ser Leu Ser Ser
635             640             645
```

-continued

| | | |
|---|---|---|
| GTG TCA GAG TTC CAC CTG ATC CTT ATG GAT GTG AAT GAC AAC CCT CCC<br>Val Ser Glu Phe His Leu Ile Leu Met Asp Val Asn Asp Asn Pro Pro<br>650                         655                  660                       665 | 2082 |
| AGG CTA GCC AAG GAC TAC ACG GGC TTG TTC TTC TGC CAT CCC CTC AGT<br>Arg Leu Ala Lys Asp Tyr Thr Gly Leu Phe Phe Cys His Pro Leu Ser<br>                  670                         675                       680 | 2130 |
| GCA CCT GGA AGT CTC ATT TTC GAG GCT ACT GAT GAT GAT CAG CAC TTA<br>Ala Pro Gly Ser Leu Ile Phe Glu Ala Thr Asp Asp Asp Gln His Leu<br>                       685                       690                   695 | 2178 |
| TTT CGG GGT CCC CAT TTT ACA TTT TCC CTC GGC AGT GGA AGC TTA CAA<br>Phe Arg Gly Pro His Phe Thr Phe Ser Leu Gly Ser Gly Ser Leu Gln<br>700                         705                  710 | 2226 |
| AAC GAC TGG GAA GTT TCC AAA ATC AAT GGT ACT CAT GCC CGA CTG TCT<br>Asn Asp Trp Glu Val Ser Lys Ile Asn Gly Thr His Ala Arg Leu Ser<br>                 715                      720                     725 | 2274 |
| ACC AGG CAC ACA GAC TTT GAG GAG AGG GCG TAT GTC GTC TTG ATC CGC<br>Thr Arg His Thr Asp Phe Glu Glu Arg Ala Tyr Val Val Leu Ile Arg<br>730                         735                  740                     745 | 2322 |
| ATC AAT GAT GGG GGT CGG CCA CCC TTG GAA GGC ATT GTT TCT TTA CCA<br>Ile Asn Asp Gly Gly Arg Pro Pro Leu Glu Gly Ile Val Ser Leu Pro<br>                   750                      755                    760 | 2370 |
| GTT ACA TTC TGC AGT TGT GTG GAA GGA AGT TGT TTC CGG CCA GCA GGT<br>Val Thr Phe Cys Ser Cys Val Glu Gly Ser Cys Phe Arg Pro Ala Gly<br>               765                      770                     775 | 2418 |
| CAC CAG ACT GGG ATA CCC ACT GTG GGC ATG GCA GTT GGT ATA CTG CTG<br>His Gln Thr Gly Ile Pro Thr Val Gly Met Ala Val Gly Ile Leu Leu<br>             780                      785                     790 | 2466 |
| ACC ACC CTT CTG GTG ATT GGT ATA ATT TTA GCA GTT GTG TTT ATC CGC<br>Thr Thr Leu Leu Val Ile Gly Ile Ile Leu Ala Val Val Phe Ile Arg<br>795                         800                  805 | 2514 |
| ATA AAG AAG GAT AAA GGC AAA GAT AAT GTT GAA AGT GCT CAA GCA TCT<br>Ile Lys Lys Asp Lys Gly Lys Asp Asn Val Glu Ser Ala Gln Ala Ser<br>810                         815                  820                   825 | 2562 |
| GAA GTC AAA CCT CTG AGA AGC TGAATTTGAA AAGGAATGTT TGAATTTATA TAGC<br>Glu Val Lys Pro Leu Arg Ser<br>                       830 | 2617 |
| AAGTGCTATT TCAGCAACAA CCATCTCATC CTATTACTTT TCATCTAACG TGCATTATAA | 2677 |
| TTTTTTAAAC AGATATTCCC TCTTGTCCTT AATATTTGC TAAATATTTC TTTTTTGAGG | 2737 |
| TGGAGTCTTG CTCTGTCGCC CAGGCTGGAG TACAGTGGTG TGATCCCAGC TCACTGCAAC | 2797 |
| CTCCGCCTCC TGGGTTCACA TGATTCTCCT GCCTCAGCTT CCTAAGTAGC TGGGTTTACA | 2857 |
| GGCACCCACC ACCATGCCCA GCTAATTTTT GTATTTTTAA TAGAGACGGG GTTTCGCCAT | 2917 |
| TTGGCCAGGC TGGTCTTGAA CTCCTGACGT CAAGTGATCT GCCTGCCTTG GTCTCCCAAT | 2977 |
| ACAGGCATGA ACCACTGCAC CCACCTACTT AGATATTTCA TGTGCTATAG ACATTAGAGA | 3037 |
| GATTTTTCAT TTTTCCATGA CATTTTTCCT CTCTGCAAAT GGCTTAGCTA CTTGTGTTTT | 3097 |
| TCCCTTTTGG GGCAAGACAG ACTCATTAAA TATTCTGTAC ATTTTTTCTT TATCAAGGAG | 3157 |
| ATATATCAGT GTTGTCTCAT AGAACTGCCT GGATTCCATT TATGTTTTTT CTGATTCCAT | 3217 |
| CCTGTGTCCC CTTCATCCTT GACTCCTTTG GTATTTCACT GAATTTCAAA CATTTGTCAG | 3277 |
| AGAAGAAAAA AGTGAGGACT CAGGAAAAAT AAATAAATAA AGAACAGCC TTTTGCGGCC | 3337 |
| GCGAATTC | 3345 |

(2) INFORMATION FOR SEQ ID NO: 178:

(i) SEQUENCE CHARACTERISTICS:

(A) LENGTH: 832 amino acids
      (B) TYPE: amino acid
      (C) STRANDEDNESS: <Unknown>
      (D) TOPOLOGY: unknown (ii) MOLECULE TYPE: protein (xi) SEQUENCE DESCRIPTION: SEQ ID NO: 178:

Met Ile Leu Gln Ala His Leu His Ser Leu Cys Leu Leu Met Leu Tyr
 1               5                  10                  15

Leu Ala Thr Gly Tyr Gly Gln Glu Gly Lys Phe Ser Gly Pro Leu Lys
            20                  25                  30

Pro Met Thr Phe Ser Ile Tyr Glu Gly Gln Glu Pro Ser Gln Ile Ile
            35                  40                  45

Phe Gln Phe Lys Ala Asn Pro Pro Ala Val Thr Phe Glu Leu Thr Gly
 50                  55                  60

Glu Thr Asp Asn Ile Phe Val Ile Glu Arg Glu Gly Leu Leu Tyr Tyr
 65                  70                  75                  80

Asn Arg Ala Leu Asp Arg Glu Thr Arg Ser Thr His Asn Leu Gln Val
            85                  90                  95

Ala Ala Leu Asp Ala Asn Gly Ile Ile Val Glu Gly Pro Val Pro Ile
            100                 105                 110

Thr Ile Glu Val Lys Asp Ile Asn Asp Asn Arg Pro Thr Phe Leu Gln
            115                 120                 125

Ser Lys Tyr Glu Gly Ser Val Arg Gln Asn Ser Arg Pro Gly Lys Pro
 130                 135                 140

Phe Leu Tyr Val Asn Ala Thr Asp Leu Asp Asp Pro Ala Thr Pro Asn
145                 150                 155                 160

Gly Gln Leu Tyr Tyr Gln Ile Val Ile Gln Leu Pro Met Ile Asn Asn
            165                 170                 175

Val Met Tyr Phe Gln Ile Asn Asn Lys Thr Gly Ala Ile Ser Leu Thr
            180                 185                 190

Arg Glu Gly Ser Gln Glu Leu Asn Pro Ala Lys Asn Pro Ser Tyr Asn
            195                 200                 205

Leu Val Ile Ser Val Lys Asp Met Gly Gly Gln Ser Glu Asn Ser Phe
 210                 215                 220

Ser Asp Thr Thr Ser Val Asp Ile Ile Val Thr Glu Asn Ile Trp Lys
225                 230                 235                 240

Ala Pro Lys Pro Val Glu Met Val Glu Asn Ser Thr Asp Pro His Pro
            245                 250                 255

Ile Lys Ile Thr Gln Val Arg Trp Asn Asp Pro Gly Ala Gln Tyr Ser
            260                 265                 270

Leu Val Asp Lys Glu Lys Leu Pro Arg Phe Pro Phe Ser Ile Asp Gln
            275                 280                 285

Glu Gly Asp Ile Tyr Val Thr Gln Pro Leu Asp Arg Glu Glu Lys Asp
 290                 295                 300

Ala Tyr Val Phe Tyr Ala Val Ala Lys Asp Glu Tyr Gly Lys Pro Leu
305                 310                 315                 320

Ser Tyr Pro Leu Glu Ile His Val Lys Val Lys Asp Ile Asn Asp Asn
            325                 330                 335

Pro Pro Thr Cys Pro Ser Pro Val Thr Val Phe Glu Val Gln Glu Asn
            340                 345                 350

Glu Arg Leu Gly Asn Ser Ile Gly Thr Leu Thr Ala His Asp Arg Asp
            355                 360                 365

Glu Glu Asn Thr Ala Asn Ser Phe Leu Asn Tyr Arg Ile Val Glu Gln

-continued

```
            370                 375                 380
Thr Pro Lys Leu Pro Met Asp Gly Leu Phe Leu Ile Gln Thr Tyr Ala
385                 390                 395                 400
Gly Met Leu Gln Leu Ala Lys Gln Ser Leu Lys Lys Gln Asp Thr Pro
                405                 410                 415
Gln Tyr Asn Leu Thr Ile Glu Val Ser Asp Lys Asp Phe Lys Thr Leu
            420                 425                 430
Cys Phe Val Gln Ile Asn Val Ile Asp Ile Asn Asp Gln Ile Pro Ile
        435                 440                 445
Phe Glu Lys Ser Asp Tyr Gly Asn Leu Thr Leu Ala Glu Asp Thr Asn
450                 455                 460
Ile Gly Ser Thr Ile Leu Thr Ile Gln Ala Thr Asp Ala Asp Glu Pro
465                 470                 475                 480
Phe Thr Gly Ser Ser Lys Ile Leu Tyr His Ile Ile Lys Gly Asp Ser
                485                 490                 495
Glu Gly Arg Leu Gly Val Asp Thr Asp Pro His Thr Asn Thr Gly Tyr
            500                 505                 510
Val Ile Ile Lys Lys Pro Leu Asp Phe Glu Thr Ala Ala Val Ser Asn
        515                 520                 525
Ile Val Phe Lys Ala Glu Asn Pro Glu Pro Leu Val Phe Gly Val Lys
530                 535                 540
Tyr Asn Ala Ser Ser Phe Ala Lys Phe Thr Leu Ile Val Thr Asp Val
545                 550                 555                 560
Asn Glu Ala Pro Gln Phe Ser Gln His Val Phe Gln Ala Lys Val Ser
                565                 570                 575
Glu Asp Val Ala Ile Gly Thr Lys Val Gly Asn Val Thr Ala Lys Asp
            580                 585                 590
Pro Glu Gly Leu Asp Ile Ser Tyr Ser Leu Arg Gly Asp Thr Arg Gly
        595                 600                 605
Trp Leu Lys Ile Asp His Val Thr Gly Glu Ile Phe Ser Val Ala Pro
610                 615                 620
Leu Asp Arg Glu Ala Gly Ser Pro Tyr Arg Val Gln Val Val Ala Thr
625                 630                 635                 640
Glu Val Gly Gly Ser Ser Leu Ser Ser Val Ser Glu Phe His Leu Ile
                645                 650                 655
Leu Met Asp Val Asn Asp Asn Pro Pro Arg Leu Ala Lys Asp Tyr Thr
            660                 665                 670
Gly Leu Phe Phe Cys His Pro Leu Ser Ala Pro Gly Ser Leu Ile Phe
        675                 680                 685
Glu Ala Thr Asp Asp Asp Gln His Leu Phe Arg Gly Pro His Phe Thr
690                 695                 700
Phe Ser Leu Gly Ser Gly Ser Leu Gln Asn Asp Trp Glu Val Ser Lys
705                 710                 715                 720
Ile Asn Gly Thr His Ala Arg Leu Ser Thr Arg His Thr Asp Phe Glu
                725                 730                 735
Glu Arg Ala Tyr Val Val Leu Ile Arg Ile Asn Asp Gly Gly Arg Pro
            740                 745                 750
Pro Leu Glu Gly Ile Val Ser Leu Pro Val Thr Phe Cys Ser Cys Val
        755                 760                 765
Glu Gly Ser Cys Phe Arg Pro Ala Gly His Gln Thr Gly Ile Pro Thr
770                 775                 780
Val Gly Met Ala Val Gly Ile Leu Leu Thr Thr Leu Leu Val Ile Gly
785                 790                 795                 800
```

```
Ile Ile Leu Ala Val Val Phe Ile Arg Ile Lys Lys Asp Lys Gly Lys
                805                 810                 815

Asp Asn Val Glu Ser Ala Gln Ala Ser Glu Val Lys Pro Leu Arg Ser
                820                 825                 830

(2) INFORMATION FOR SEQ ID NO: 179:

(i) SEQUENCE CHARACTERISTICS:
        (A) LENGTH: 1827 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 179:

Met Ala Arg Lys Lys Phe Ser Gly Leu Glu Ile Ser Leu Ile Val Leu
  1                 5                  10                  15

Phe Val Ile Val Thr Ile Ile Ala Ile Ala Leu Ile Val Val Leu Ala
                 20                  25                  30

Thr Lys Thr Pro Ala Val Asp Glu Ile Ser Asp Ser Thr Ser Thr Pro
                 35                  40                  45

Ala Thr Thr Arg Val Thr Thr Asn Pro Ser Asp Ser Gly Lys Cys Pro
 50                  55                  60

Asn Val Leu Asn Asp Pro Val Asn Val Arg Ile Asn Cys Ile Pro Glu
 65                  70                  75                  80

Gln Phe Pro Thr Glu Gly Ile Cys Ala Gln Arg Gly Cys Cys Trp Arg
                 85                  90                  95

Pro Trp Asn Asp Ser Leu Ile Pro Trp Cys Phe Phe Val Asp Asn His
                100                 105                 110

Gly Tyr Asn Val Gln Asp Met Thr Thr Thr Ser Ile Gly Val Glu Ala
                115                 120                 125

Lys Leu Asn Arg Ile Pro Ser Pro Thr Leu Phe Gly Asn Asp Ile Asn
130                 135                 140

Ser Val Leu Phe Thr Thr Gln Asn Gln Thr Pro Asn Arg Phe Arg Phe
145                 150                 155                 160

Lys Ile Thr Asp Pro Asn Asn Arg Arg Tyr Glu Val Pro His Gln Tyr
                165                 170                 175

Val Lys Glu Phe Thr Gly Pro Thr Val Ser Asp Thr Leu Tyr Asp Val
                180                 185                 190

Lys Val Ala Gln Asn Pro Phe Ser Ile Gln Val Ile Arg Lys Ser Asn
                195                 200                 205

Gly Lys Thr Leu Phe Asp Thr Ser Ile Gly Pro Leu Val Tyr Ser Asp
            210                 215                 220

Gln Tyr Leu Gln Ile Ser Ala Arg Leu Pro Ser Asp Tyr Ile Tyr Gly
225                 230                 235                 240

Ile Gly Glu Gln Val His Lys Arg Phe Arg His Asp Leu Ser Trp Lys
                245                 250                 255

Thr Trp Pro Ile Phe Thr Arg Asp Gln Leu Pro Gly Asp Asn Asn Asn
                260                 265                 270

Asn Leu Tyr Gly His Gln Thr Phe Phe Met Cys Ile Glu Asp Thr Ser
                275                 280                 285

Gly Lys Ser Phe Gly Val Phe Leu Met Asn Ser Asn Ala Met Glu Ile
            290                 295                 300

Phe Ile Gln Pro Thr Pro Ile Val Thr Tyr Arg Val Thr Gly Gly Ile
305                 310                 315                 320
```

```
Leu Asp Phe Tyr Ile Leu Leu Gly Asp Thr Pro Glu Gln Val Val Gln
                325                 330                 335

Gln Tyr Gln Gln Leu Val Gly Leu Pro Ala Met Pro Ala Tyr Trp Asn
            340                 345                 350

Leu Gly Phe Gln Leu Ser Arg Trp Asn Tyr Lys Ser Leu Asp Val Val
        355                 360                 365

Lys Glu Val Val Arg Arg Asn Arg Glu Ala Gly Ile Pro Phe Asp Thr
370                 375                 380

Gln Val Thr Asp Ile Asp Tyr Met Glu Asp Lys Lys Asp Phe Thr Tyr
385                 390                 395                 400

Asp Gln Val Ala Phe Asn Gly Leu Pro Gln Phe Val Gln Asp Leu His
                405                 410                 415

Asp His Gly Gln Lys Tyr Val Ile Ile Leu Asp Pro Ala Ile Ser Ile
            420                 425                 430

Gly Arg Arg Ala Asn Gly Thr Thr Tyr Ala Thr Tyr Glu Arg Gly Asn
        435                 440                 445

Thr Gln His Val Trp Ile Asn Glu Ser Asp Gly Ser Thr Pro Ile Ile
    450                 455                 460

Gly Glu Val Trp Pro Gly Leu Thr Val Tyr Pro Asp Phe Thr Asn Pro
465                 470                 475                 480

Asn Cys Ile Asp Trp Trp Ala Asn Glu Cys Ser Ile Phe His Gln Glu
                485                 490                 495

Val Gln Tyr Asp Gly Leu Trp Ile Asp Met Asn Glu Val Ser Ser Phe
            500                 505                 510

Ile Gln Gly Ser Thr Lys Gly Cys Asn Val Asn Lys Leu Asn Tyr Pro
        515                 520                 525

Pro Phe Thr Pro Asp Ile Leu Asp Lys Leu Met Tyr Ser Lys Thr Ile
    530                 535                 540

Cys Met Asp Ala Val Gln Asn Trp Gly Lys Gln Tyr Asp Val His Ser
545                 550                 555                 560

Leu Tyr Gly Tyr Ser Met Ala Ile Ala Thr Glu Gln Ala Val Gln Lys
                565                 570                 575

Val Phe Pro Asn Lys Arg Ser Phe Ile Leu Thr Arg Ser Thr Phe Ala
            580                 585                 590

Gly Ser Gly Arg His Ala Ala His Trp Leu Gly Asp Asn Thr Ala Ser
        595                 600                 605

Trp Glu Gln Met Glu Trp Ser Ile Thr Gly Met Leu Glu Phe Ser Leu
    610                 615                 620

Phe Gly Ile Pro Leu Val Gly Ala Asp Ile Cys Gly Phe Val Ala Glu
625                 630                 635                 640

Thr Thr Glu Glu Leu Cys Arg Arg Trp Met Gln Leu Gly Ala Phe Tyr
                645                 650                 655

Pro Phe Ser Arg Asn His Asn Ser Asp Gly Tyr Glu His Gln Asp Pro
            660                 665                 670

Ala Phe Phe Gly Gln Asn Ser Leu Leu Val Lys Ser Ser Arg Gln Tyr
        675                 680                 685

Leu Thr Ile Arg Tyr Thr Leu Leu Pro Phe Leu Tyr Thr Leu Phe Tyr
    690                 695                 700

Lys Ala His Val Phe Gly Glu Thr Val Ala Arg Pro Val Leu His Glu
705                 710                 715                 720

Phe Tyr Glu Asp Thr Asn Ser Trp Ile Glu Asp Thr Glu Phe Leu Trp
                725                 730                 735
```

-continued

```
Gly Pro Ala Leu Leu Ile Thr Pro Val Leu Lys Gln Gly Ala Asp Thr
            740                 745                 750

Val Ser Ala Tyr Ile Pro Asp Ala Ile Trp Tyr Asp Tyr Glu Ser Gly
            755                 760                 765

Ala Lys Arg Pro Trp Arg Lys Gln Arg Val Asp Met Tyr Leu Pro Ala
            770                 775                 780

Asp Lys Ile Gly Leu His Leu Arg Gly Tyr Ile Ile Pro Ile Gln
785                 790                 795                 800

Glu Pro Asp Val Thr Thr Ala Ser Arg Lys Asn Pro Leu Gly Leu
                805                 810                 815

Ile Val Ala Leu Gly Glu Asn Asn Thr Ala Lys Gly Asp Phe Phe Trp
            820                 825                 830

Asp Asp Gly Glu Thr Lys Asp Thr Ile Gln Asn Gly Asn Tyr Ile Leu
            835                 840                 845

Tyr Thr Phe Ser Val Ser Asn Asn Thr Leu Asp Ile Val Cys Thr His
            850                 855                 860

Ser Ser Tyr Gln Glu Gly Thr Thr Leu Ala Phe Gln Thr Val Lys Ile
865                 870                 875                 880

Leu Gly Leu Thr Asp Ser Val Thr Glu Val Arg Val Ala Glu Asn Asn
                885                 890                 895

Gln Pro Met Asn Ala His Ser Asn Phe Thr Tyr Asp Ala Ser Asn Gln
            900                 905                 910

Val Leu Leu Ile Ala Asp Leu Lys Leu Asn Leu Gly Arg Asn Phe Ser
            915                 920                 925

Val Gln Trp Asn Gln Ile Phe Ser Glu Asn Glu Arg Phe Asn Cys Tyr
            930                 935                 940

Pro Asp Ala Asp Leu Ala Thr Glu Gln Lys Cys Thr Gln Arg Gly Cys
945                 950                 955                 960

Val Trp Arg Thr Gly Ser Ser Leu Ser Lys Ala Pro Glu Cys Tyr Phe
                965                 970                 975

Pro Arg Gln Asp Asn Ser Tyr Ser Val Asn Ser Ala Arg Tyr Ser Ser
            980                 985                 990

Met Gly Ile Thr Ala Asp Leu Gln Leu Asn Thr Ala Asn Ala Arg Ile
            995                 1000                1005

Lys Leu Pro Ser Asp Pro Ile Ser Thr Leu Arg Val Glu Val Lys Tyr
1010                1015                1020

His Lys Asn Asp Met Leu Gln Phe Lys Ile Tyr Asp Pro Gln Lys Lys
1025                1030                1035                1040

Arg Tyr Glu Val Pro Val Pro Leu Asn Ile Pro Thr Thr Pro Ile Ser
                1045                1050                1055

Thr Tyr Glu Asp Arg Leu Tyr Asp Val Glu Ile Lys Glu Asn Pro Phe
            1060                1065                1070

Gly Ile Gln Ile Arg Arg Arg Ser Ser Gly Arg Val Ile Trp Asp Ser
            1075                1080                1085

Trp Leu Pro Gly Phe Ala Phe Asn Asp Gln Phe Ile Gln Ile Ser Thr
1090                1095                1100

Arg Leu Pro Ser Glu Tyr Ile Tyr Gly Phe Gly Glu Val Glu His Thr
1105                1110                1115                1120

Ala Phe Lys Arg Asp Leu Asn Trp Asn Thr Trp Gly Met Phe Thr Arg
                1125                1130                1135

Asp Gln Pro Pro Gly Tyr Lys Leu Asn Ser Tyr Gly Phe His Pro Tyr
            1140                1145                1150

Tyr Met Ala Leu Glu Glu Glu Gly Asn Ala His Gly Val Phe Leu Leu
```

-continued

```
            1155                1160                1165
Asn Ser Asn Ala Met Asp Val Thr Phe Gln Pro Thr Pro Ala Leu Thr
    1170                1175                1180
Tyr Arg Thr Val Gly Gly Ile Leu Asp Phe Tyr Met Phe Leu Gly Pro
1185                1190                1195                1200
Thr Pro Gln Val Ala Thr Lys Gln Tyr His Glu Val Ile Gly His Pro
            1205                1210                1215
Val Met Pro Ala Tyr Trp Ala Leu Gly Phe Gln Leu Cys Arg Tyr Gly
        1220                1225                1230
Tyr Ala Asn Thr Ser Glu Val Arg Glu Leu Tyr Asp Ala Met Val Ala
    1235                1240                1245
Ala Asn Ile Pro Tyr Asp Val Gln Tyr Thr Asp Ile Asp Tyr Met Glu
    1250                1255                1260
Arg Gln Leu Asp Phe Thr Ile Gly Glu Ala Phe Gln Asp Leu Pro Gln
1265                1270                1275                1280
Phe Val Asp Lys Ile Arg Gly Glu Gly Met Arg Tyr Ile Ile Ile Leu
            1285                1290                1295
Asp Pro Ala Ile Ser Gly Asn Glu Thr Lys Thr Tyr Pro Ala Phe Glu
        1300                1305                1310
Arg Gly Gln Gln Asn Asp Val Phe Val Lys Trp Pro Asn Thr Asn Asp
    1315                1320                1325
Ile Cys Trp Ala Lys Val Trp Pro Asp Leu Pro Asn Ile Thr Ile Asp
    1330                1335                1340
Lys Thr Leu Thr Glu Asp Glu Ala Val Asn Ala Ser Arg Ala His Val
1345                1350                1355                1360
Ala Phe Pro Asp Phe Phe Arg Thr Ser Thr Ala Glu Trp Trp Ala Arg
            1365                1370                1375
Glu Ile Val Asp Phe Tyr Asn Glu Lys Met Lys Phe Asp Gly Leu Trp
        1380                1385                1390
Ile Asp Met Asn Glu Pro Ser Ser Phe Val Asn Gly Thr Thr Thr Asn
    1395                1400                1405
Gln Cys Arg Asn Asp Glu Leu Asn Tyr Pro Pro Tyr Phe Pro Glu Leu
    1410                1415                1420
Thr Lys Arg Thr Asp Gly Leu His Phe Arg Thr Ile Cys Met Glu Ala
1425                1430                1435                1440
Glu Gln Ile Leu Ser Asp Gly Thr Ser Val Leu His Tyr Asp Val His
            1445                1450                1455
Asn Leu Tyr Gly Trp Ser Gln Met Lys Pro Thr His Asp Ala Leu Gln
        1460                1465                1470
Lys Thr Thr Gly Lys Arg Gly Ile Val Ile Ser Arg Ser Thr Tyr Pro
    1475                1480                1485
Thr Ser Gly Arg Trp Gly Gly His Trp Leu Gly Asp Asn Tyr Ala Arg
    1490                1495                1500
Trp Asp Asn Met Asp Lys Ser Ile Ile Gly Met Met Glu Phe Ser Leu
1505                1510                1515                1520
Phe Gly Ile Ser Tyr Thr Gly Ala Asp Ile Cys Gly Phe Phe Asn Asn
            1525                1530                1535
Ser Glu Tyr His Leu Cys Thr Arg Trp Met Gln Leu Gly Ala Phe Tyr
        1540                1545                1550
Pro Tyr Ser Arg Asn His Asn Ile Ala Asn Thr Arg Arg Gln Asp Pro
    1555                1560                1565
Ala Ser Trp Asn Glu Thr Phe Ala Glu Met Ser Arg Asn Ile Leu Asn
    1570                1575                1580
```

-continued

```
Ile Arg Tyr Thr Leu Leu Pro Tyr Phe Tyr Thr Gln Met His Glu Ile
1585                1590                1595                1600

His Ala Asn Gly Gly Thr Val Ile Arg Pro Leu Leu His Glu Phe Phe
            1605                1610                1615

Asp Glu Lys Pro Thr Trp Asp Ile Phe Lys Gln Phe Leu Trp Gly Pro
            1620                1625                1630

Ala Phe Met Val Thr Pro Val Leu Glu Pro Tyr Val Gln Thr Val Asn
            1635                1640                1645

Ala Tyr Val Pro Asn Ala Arg Trp Phe Asp Tyr His Thr Gly Lys Asp
            1650                1655                1660

Ile Gly Val Arg Gly Gln Phe Gln Thr Phe Asn Ala Ser Tyr Asp Thr
1665                1670                1675                1680

Ile Asn Leu His Val Arg Gly Gly His Ile Leu Pro Cys Gln Glu Pro
            1685                1690                1695

Ala Gln Asn Thr Phe Tyr Ser Arg Gln Lys His Met Lys Leu Ile Val
            1700                1705                1710

Ala Ala Asp Asp Asn Gln Met Ala Gln Gly Ser Leu Phe Trp Asp Asp
            1715                1720                1725

Gly Glu Ser Ile Asp Thr Tyr Glu Arg Asp Leu Tyr Leu Ser Val Gln
1730                1735                1740

Phe Asn Leu Asn Gln Thr Thr Leu Thr Ser Thr Ile Leu Lys Arg Gly
1745                1750                1755                1760

Tyr Ile Asn Lys Ser Glu Thr Arg Leu Gly Ser Leu His Val Trp Gly
            1765                1770                1775

Lys Gly Thr Thr Pro Val Asn Ala Val Thr Leu Thr Tyr Asn Gly Asn
            1780                1785                1790

Lys Asn Ser Leu Pro Phe Asn Glu Asp Thr Thr Asn Met Ile Leu Arg
            1795                1800                1805

Ile Asp Leu Thr Thr His Asn Val Thr Leu Glu Glu Pro Ile Glu Ile
    1810                1815                1820

Asn Trp Ser
1825

(2) INFORMATION FOR SEQ ID NO: 180:

(i) SEQUENCE CHARACTERISTICS:
        (A) LENGTH: 2284 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 45...2099
        (D) OTHER INFORMATION:

(xi) SEQUENCE DESCRIPTION: SEQ ID NO: 180:

GCCTTACTGC AGGAAGGCAC TCCGAAGACA TAAGTCGGTG AGAC ATG GCT GAA GAT      56
                                                 Met Ala Glu Asp
                                                   1

AAA AGC AAG AGA GAC TCC ATC GAG ATG AGT ATG AAG GGA TGC CAG ACA      104
Lys Ser Lys Arg Asp Ser Ile Glu Met Ser Met Lys Gly Cys Gln Thr
  5                  10                  15                  20

AAC AAC GGG TTT GTC CAT AAT GAA GAC ATT CTG GAG CAG ACC CCG GAT      152
Asn Asn Gly Phe Val His Asn Glu Asp Ile Leu Glu Gln Thr Pro Asp
            25                  30                  35
```

```
                                                        -continued

CCA GGC AGC TCA ACA GAC AAC CTG AAG CAC AGC ACC AGG GGC ATC CTT        200
Pro Gly Ser Ser Thr Asp Asn Leu Lys His Ser Thr Arg Gly Ile Leu
            40                  45                  50

GGC TCC CAG GAG CCC GAC TTC AAG GGC GTC CAG CCC TAT GCG GGG ATG        248
Gly Ser Gln Glu Pro Asp Phe Lys Gly Val Gln Pro Tyr Ala Gly Met
        55                  60                  65

CCC AAG GAG GTG CTG TTC CAG TTC TCT GGC CAG GCC CGC TAC CGC ATA        296
Pro Lys Glu Val Leu Phe Gln Phe Ser Gly Gln Ala Arg Tyr Arg Ile
    70                  75                  80

CCT CGG GAG ATC CTC TTC TGG CTC ACA GTG GCT TCT GTG CTG GTG CTC        344
Pro Arg Glu Ile Leu Phe Trp Leu Thr Val Ala Ser Val Leu Val Leu
85                  90                  95                 100

ATC GCG GCC ACC ATA GCC ATC ATT GCC CTC TCT CCA AAG TGC CTA GAC        392
Ile Ala Ala Thr Ile Ala Ile Ile Ala Leu Ser Pro Lys Cys Leu Asp
                105                 110                 115

TGG TGG CAG GAG GGG CCC ATG TAC CAG ATC TAC CCA AGG TCT TTC AAG        440
Trp Trp Gln Glu Gly Pro Met Tyr Gln Ile Tyr Pro Arg Ser Phe Lys
            120                 125                 130

GAC AGT AAC AAG GAT GGG AAC GGA GAT CTG AAA GGT ATT CAA GAT AAA        488
Asp Ser Asn Lys Asp Gly Asn Gly Asp Leu Lys Gly Ile Gln Asp Lys
        135                 140                 145

CTG GAC TAC ATC ACA GCT TTA AAT ATA AAA ACT GTT TGG ATT ACT TCA        536
Leu Asp Tyr Ile Thr Ala Leu Asn Ile Lys Thr Val Trp Ile Thr Ser
    150                 155                 160

TTT TAT AAA TCG TCC CTT AAA GAT TTC AGA TAT GGT GTT GAA GAT TTC        584
Phe Tyr Lys Ser Ser Leu Lys Asp Phe Arg Tyr Gly Val Glu Asp Phe
165                 170                 175                 180

CGG GAA GTT GAT CCC ATT TTT GGA ACG ATG GAA GAT TTT GAG AAT CTG        632
Arg Glu Val Asp Pro Ile Phe Gly Thr Met Glu Asp Phe Glu Asn Leu
                185                 190                 195

GTT GCA GCC ATA CAT GAT AAA GGT TTA AAA TTA ATC ATC GAT TTC ATA        680
Val Ala Ala Ile His Asp Lys Gly Leu Lys Leu Ile Ile Asp Phe Ile
            200                 205                 210

CCA AAC CAC ACG AGT GAT AAA CAT ATT TGG TTT CAA TTG AGT CGG ACA        728
Pro Asn His Thr Ser Asp Lys His Ile Trp Phe Gln Leu Ser Arg Thr
        215                 220                 225

CGG ACA GGA AAA TAT ACT GAT TAT TAT ATC TGG CAT GAC TGT ACC CAT        776
Arg Thr Gly Lys Tyr Thr Asp Tyr Tyr Ile Trp His Asp Cys Thr His
    230                 235                 240

GAA AAT GGC AAA ACC ATT CCA CCC AAC AAC TGG TTA AGT GTG TAT GGA        824
Glu Asn Gly Lys Thr Ile Pro Pro Asn Asn Trp Leu Ser Val Tyr Gly
245                 250                 255                 260

AAC TCC AGT TGG CAC TTT GAC GAA GTG CGA AAC CAA TGT TAT TTT CAT        872
Asn Ser Ser Trp His Phe Asp Glu Val Arg Asn Gln Cys Tyr Phe His
                265                 270                 275

CAG TTT ATG AAA GAG CAA CCT GAT TTA AAT TTC CGC AAT CCT GAT GTT        920
Gln Phe Met Lys Glu Gln Pro Asp Leu Asn Phe Arg Asn Pro Asp Val
            280                 285                 290

CAA GAA GAA ATA AAA GAA ATT TTA CGG TTC TGG CTC ACA AAG GGT GTT        968
Gln Glu Glu Ile Lys Glu Ile Leu Arg Phe Trp Leu Thr Lys Gly Val
        295                 300                 305

GAT GGT TTT AGT TTG GAT GCT GTT AAA TTC CTC CTA GAA GCA AAG CAC        1016
Asp Gly Phe Ser Leu Asp Ala Val Lys Phe Leu Leu Glu Ala Lys His
    310                 315                 320

CTG AGA GAT GAG ATC CAA GTA AAT AAG ACC CAA ATC CCG GAC ACG GTC        1064
Leu Arg Asp Glu Ile Gln Val Asn Lys Thr Gln Ile Pro Asp Thr Val
325                 330                 335                 340

ACA CAA TAC TCG GAG CTG TAC CAT GAC TTC ACC ACC ACG CAG GTG GGA        1112
Thr Gln Tyr Ser Glu Leu Tyr His Asp Phe Thr Thr Thr Gln Val Gly
                345                 350                 355
```

```
ATG CAC GAC ATT GTC CGC AGC TTC CGG CAG ACC ATG GAC CAA TAC AGC      1160
Met His Asp Ile Val Arg Ser Phe Arg Gln Thr Met Asp Gln Tyr Ser
        360                 365                 370

ACG GAG CCC GGC AGA TAC AGG TTC ATG GGG ACT GAA GCC TAT GCA GAG      1208
Thr Glu Pro Gly Arg Tyr Arg Phe Met Gly Thr Glu Ala Tyr Ala Glu
            375                 380                 385

AGT ATT GAC AGG ACC GTG ATG TAC TAT GGA TTG CCA TTT ATC CAA GAA      1256
Ser Ile Asp Arg Thr Val Met Tyr Tyr Gly Leu Pro Phe Ile Gln Glu
390                 395                 400

GCT GAT TTT CCC TTC AAC AAT TAC CTC AGC ATG CTA GAC ACT GTT TCT      1304
Ala Asp Phe Pro Phe Asn Asn Tyr Leu Ser Met Leu Asp Thr Val Ser
405                 410                 415                 420

GGG AAC AGC GTG TAT GAG GTT ATC ACA TCC TGG ATG GAA AAC ATG CCA      1352
Gly Asn Ser Val Tyr Glu Val Ile Thr Ser Trp Met Glu Asn Met Pro
                425                 430                 435

GAA GGA AAA TGG CCT AAC TGG ATG ATT GGT GGA CCA GAC AGT TCA CGG      1400
Glu Gly Lys Trp Pro Asn Trp Met Ile Gly Gly Pro Asp Ser Ser Arg
            440                 445                 450

CTG ACT TCG CGT TTG GGG AAT CAG TAT GTC AAC GTG ATG AAC ATG CTT      1448
Leu Thr Ser Arg Leu Gly Asn Gln Tyr Val Asn Val Met Asn Met Leu
        455                 460                 465

CTT TTC ACA CTC CCT GGA ACT CCT ATA ACT TAC TAT GGA GAA GAA ATT      1496
Leu Phe Thr Leu Pro Gly Thr Pro Ile Thr Tyr Tyr Gly Glu Glu Ile
470                 475                 480

GGA ATG GGA AAT ATT GTA GCC GCA AAT CTC AAT GAA AGC TAT GAT ATT      1544
Gly Met Gly Asn Ile Val Ala Ala Asn Leu Asn Glu Ser Tyr Asp Ile
485                 490                 495                 500

AAT ACC CTT CGC TCA AAG TCA CCA ATG CAG TGG GAC AAT AGT TCA AAT      1592
Asn Thr Leu Arg Ser Lys Ser Pro Met Gln Trp Asp Asn Ser Ser Asn
                505                 510                 515

GCT GGT TTT TCT GAA GCT AGT AAC ACC TGG TTA CCT ACC AAT TCA GAT      1640
Ala Gly Phe Ser Glu Ala Ser Asn Thr Trp Leu Pro Thr Asn Ser Asp
            520                 525                 530

TAC CAC ACT GTG AAT GTT GAT GTC CAA AAG ACT CAG CCC AGA TCG GCT      1688
Tyr His Thr Val Asn Val Asp Val Gln Lys Thr Gln Pro Arg Ser Ala
        535                 540                 545

TTG AAG TTA TAT CAA GAT TTA AGT CTA CTT CAT GCC AAT GAG CTA CTC      1736
Leu Lys Leu Tyr Gln Asp Leu Ser Leu Leu His Ala Asn Glu Leu Leu
550                 555                 560

CTC AAC AGG GGC TGG TTT TGC CAT TTG AGG AAT GAC AGC CAC TAT GTT      1784
Leu Asn Arg Gly Trp Phe Cys His Leu Arg Asn Asp Ser His Tyr Val
565                 570                 575                 580

GTG TAC ACA AGA GAG CTG GAT GGC ATC GAC AGA ATC TTT ATC GTG GTT      1832
Val Tyr Thr Arg Glu Leu Asp Gly Ile Asp Arg Ile Phe Ile Val Val
                585                 590                 595

CTG AAT TTT GGA GAA TCA ACA CTG TTA AAT CTA CAT AAT ATG ATT TCG      1880
Leu Asn Phe Gly Glu Ser Thr Leu Leu Asn Leu His Asn Met Ile Ser
            600                 605                 610

GGC CTT CCC GCT AAA ATA AGA ATA AGG TTA AGT ACC AAT TCT GCC GAC      1928
Gly Leu Pro Ala Lys Ile Arg Ile Arg Leu Ser Thr Asn Ser Ala Asp
        615                 620                 625

AAA GGC AGT AAA GTT GAT ACA AGT GGC ATT TTT CTG GAC AAG GGA GAG      1976
Lys Gly Ser Lys Val Asp Thr Ser Gly Ile Phe Leu Asp Lys Gly Glu
630                 635                 640

GGA CTC ATC TTT GAA CAC AAC ACG AAG AAT CTC CTT CAT CGC CAA ACA      2024
Gly Leu Ile Phe Glu His Asn Thr Lys Asn Leu Leu His Arg Gln Thr
645                 650                 655                 660

GCT TTC AGA GAT AGA TGC TTT GTT TCC AAT CGA GCA TGC TAT TCC AGT      2072
Ala Phe Arg Asp Arg Cys Phe Val Ser Asn Arg Ala Cys Tyr Ser Ser
```

```
                         665                 670                 675
GTA CTG AAC ATA CTG TAT ACC TCG TGT TAGGCACCTT TATGAAGAGA TGAAGAC    2126
Val Leu Asn Ile Leu Tyr Thr Ser Cys
             680                 685

ACTGGCATTT CAGTGGGATT GTAAGCATTT GTAATAGCTT CATGTACAGC ATGCTGCTTG    2186

GTGAACAATC ATTAATTCTT CGATATTTCT GTAGCTTGAA TGTAACCGCT TTAAGAAAGG    2246

TTCTCAAATG TTTTGAAAAA AATAAAATGT TTAAAAGT                            2284
```

(2) INFORMATION FOR SEQ ID NO: 181:

(i) SEQUENCE CHARACTERISTICS:
        (A) LENGTH: 685 amino acids
        (B) TYPE: amino acid
        (C) STRANDEDNESS: <Unknown>
        (D) TOPOLOGY: unknown (ii) MOLECULE TYPE: protein (xi) SEQUENCE DESCRIPTION: SEQ ID NO: 181:

```
Met Ala Glu Asp Lys Ser Lys Arg Asp Ser Ile Glu Met Ser Met Lys
1               5                   10                  15

Gly Cys Gln Thr Asn Asn Gly Phe Val His Asn Glu Asp Ile Leu Glu
            20                  25                  30

Gln Thr Pro Asp Pro Gly Ser Ser Thr Asp Asn Leu Lys His Ser Thr
        35                  40                  45

Arg Gly Ile Leu Gly Ser Gln Glu Pro Asp Phe Lys Gly Val Gln Pro
    50                  55                  60

Tyr Ala Gly Met Pro Lys Glu Val Leu Phe Gln Phe Ser Gly Gln Ala
65                  70                  75                  80

Arg Tyr Arg Ile Pro Arg Glu Ile Leu Phe Trp Leu Thr Val Ala Ser
                85                  90                  95

Val Leu Val Leu Ile Ala Ala Thr Ile Ala Ile Ile Ala Leu Ser Pro
            100                 105                 110

Lys Cys Leu Asp Trp Trp Gln Glu Gly Pro Met Tyr Gln Ile Tyr Pro
        115                 120                 125

Arg Ser Phe Lys Asp Ser Asn Lys Asp Gly Asn Gly Asp Leu Lys Gly
    130                 135                 140

Ile Gln Asp Lys Leu Asp Tyr Ile Thr Ala Leu Asn Ile Lys Thr Val
145                 150                 155                 160

Trp Ile Thr Ser Phe Tyr Lys Ser Ser Leu Lys Asp Phe Arg Tyr Gly
                165                 170                 175

Val Glu Asp Phe Arg Glu Val Asp Pro Ile Phe Gly Thr Met Glu Asp
            180                 185                 190

Phe Glu Asn Leu Val Ala Ala Ile His Asp Lys Gly Leu Lys Leu Ile
        195                 200                 205

Ile Asp Phe Ile Pro Asn His Thr Ser Asp Lys His Ile Trp Phe Gln
    210                 215                 220

Leu Ser Arg Thr Arg Thr Gly Lys Tyr Thr Asp Tyr Tyr Ile Trp His
225                 230                 235                 240

Asp Cys Thr His Glu Asn Gly Lys Thr Ile Pro Pro Asn Asn Trp Leu
                245                 250                 255

Ser Val Tyr Gly Asn Ser Ser Trp His Phe Asp Glu Val Arg Asn Gln
            260                 265                 270

Cys Tyr Phe His Gln Phe Met Lys Glu Gln Pro Asp Leu Asn Phe Arg
        275                 280                 285
```

```
Asn Pro Asp Val Gln Glu Ile Lys Glu Ile Leu Arg Phe Trp Leu
    290                 295                 300

Thr Lys Gly Val Asp Gly Phe Ser Leu Asp Ala Val Lys Phe Leu Leu
305             310                 315                 320

Glu Ala Lys His Leu Arg Asp Glu Ile Gln Val Asn Lys Thr Gln Ile
                325                 330                 335

Pro Asp Thr Val Thr Gln Tyr Ser Glu Leu Tyr His Asp Phe Thr Thr
            340                 345                 350

Thr Gln Val Gly Met His Asp Ile Val Arg Ser Phe Arg Gln Thr Met
                355                 360                 365

Asp Gln Tyr Ser Thr Glu Pro Gly Arg Tyr Arg Phe Met Gly Thr Glu
    370                 375                 380

Ala Tyr Ala Glu Ser Ile Asp Arg Thr Val Met Tyr Tyr Gly Leu Pro
385             390                 395                 400

Phe Ile Gln Glu Ala Asp Phe Pro Phe Asn Asn Tyr Leu Ser Met Leu
                405                 410                 415

Asp Thr Val Ser Gly Asn Ser Val Tyr Glu Val Ile Thr Ser Trp Met
            420                 425                 430

Glu Asn Met Pro Glu Gly Lys Trp Pro Asn Trp Met Ile Gly Gly Pro
            435                 440                 445

Asp Ser Ser Arg Leu Thr Ser Arg Leu Gly Asn Gln Tyr Val Asn Val
    450                 455                 460

Met Asn Met Leu Leu Phe Thr Leu Pro Gly Thr Pro Ile Thr Tyr Tyr
465             470                 475                 480

Gly Glu Glu Ile Gly Met Gly Asn Ile Val Ala Ala Asn Leu Asn Glu
                485                 490                 495

Ser Tyr Asp Ile Asn Thr Leu Arg Ser Lys Ser Pro Met Gln Trp Asp
            500                 505                 510

Asn Ser Ser Asn Ala Gly Phe Ser Glu Ala Ser Asn Thr Trp Leu Pro
    515                 520                 525

Thr Asn Ser Asp Tyr His Thr Val Asn Val Asp Val Gln Lys Thr Gln
    530                 535                 540

Pro Arg Ser Ala Leu Lys Leu Tyr Gln Asp Leu Ser Leu Leu His Ala
545             550                 555                 560

Asn Glu Leu Leu Leu Asn Arg Gly Trp Phe Cys His Leu Arg Asn Asp
                565                 570                 575

Ser His Tyr Val Val Tyr Thr Arg Glu Leu Asp Gly Ile Asp Arg Ile
            580                 585                 590

Phe Ile Val Val Leu Asn Phe Gly Glu Ser Thr Leu Leu Asn Leu His
            595                 600                 605

Asn Met Ile Ser Gly Leu Pro Ala Lys Ile Arg Ile Arg Leu Ser Thr
    610                 615                 620

Asn Ser Ala Asp Lys Gly Ser Lys Val Asp Thr Ser Gly Ile Phe Leu
625             630                 635                 640

Asp Lys Gly Glu Gly Leu Ile Phe Glu His Asn Thr Lys Asn Leu Leu
                645                 650                 655

His Arg Gln Thr Ala Phe Arg Asp Arg Cys Phe Val Ser Asn Arg Ala
            660                 665                 670

Cys Tyr Ser Ser Val Leu Asn Ile Leu Tyr Thr Ser Cys
            675                 680                 685

(2) INFORMATION FOR SEQ ID NO: 182:

(i) SEQUENCE CHARACTERISTICS:
```

(A) LENGTH: 54 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 182:

Leu Val Pro Arg Gly Ser Pro Gly Ile Pro Gly Ser Arg Val Gly Gln
1               5                   10                  15

Cys Thr Asp Ser Asp Val Arg Arg Pro Trp Ala Arg Ser Cys Ala His
                20                  25                  30

Gln Gly Cys Gly Ala Gly Thr Arg Asn Ser His Gly Cys Ile Thr Arg
            35                  40                  45

Pro Leu Arg Gln Ala Ser
            50

(2) INFORMATION FOR SEQ ID NO: 183:

(i) SEQUENCE CHARACTERISTICS:
            (A) LENGTH: 19 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 183:

Ser Ala Arg Asp Ser Gly Pro Ala Glu Asp Gly Ser Arg Ala Val Arg
1               5                   10                  15

Leu Asn Gly (2) INFORMATION FOR SEQ ID NO: 184:

(i) SEQUENCE CHARACTERISTICS:
            (A) LENGTH: 21 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 184:

Asp Gly Ser Arg Ala Val Arg Leu Asn Gly Val Glu Asn Ala Asn Thr
1               5                   10                  15

Arg Lys Ser Ser Arg
                20

(2) INFORMATION FOR SEQ ID NO: 185:

(i) SEQUENCE CHARACTERISTICS:
            (A) LENGTH: 19 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 185:

Glu Asn Ala Asn Thr Arg Lys Ser Ser Arg Ser Asn Pro Arg Gly Arg
1               5                   10                  15

Arg His Pro (2) INFORMATION FOR SEQ ID NO: 186:

```
    (i) SEQUENCE CHARACTERISTICS:
        (A) LENGTH: 11 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 186:

Thr Arg Lys Ser Ser Arg Ser Asn Pro Arg Gly
1               5                   10

(2) INFORMATION FOR SEQ ID NO: 187:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 187:

Ser Arg Pro Tyr Ser Val Asp Ser Asp Ser Asp Thr Asn Ala Lys His
1               5                   10                  15

Ser Ser His Asn Arg
            20

(2) INFORMATION FOR SEQ ID NO: 188:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 188:

Thr Asn Ala Lys His Ser Ser His Asn Arg Arg Leu Arg Thr Arg Ser
1               5                   10                  15

Arg Pro Asn (2) INFORMATION FOR SEQ ID NO: 189:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 189:

Arg Tyr Lys His Asp Ile Gly Cys Asp Ala Gly Val Asp Lys Lys Ser
1               5                   10                  15

Ser Ser Val Arg Gly Gly Cys Gly
            20

(2) INFORMATION FOR SEQ ID NO: 190:

(i) SEQUENCE CHARACTERISTICS:
        (A) LENGTH: 26 amino acids
        (B) TYPE: amino acid
        (C) STRANDEDNESS: <Unknown>
        (D) TOPOLOGY: linear (ii) MOLECULE TYPE: peptide
```

(xi) SEQUENCE DESCRIPTION: SEQ ID NO: 190:

Gly Cys Asp Ala Gly Val Asp Lys Lys Ser Ser Val Arg Gly Gly
1               5                   10                  15

Cys Gly Ala His Ser Ser Pro Pro Arg Ala
            20                  25

(2) INFORMATION FOR SEQ ID NO: 191:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 191:

Gly Ala His Ser Ser Pro Pro Arg Ala Gly Arg Gly Pro Arg Gly Thr
1               5                   10                  15

Met Val Ser Arg Leu
            20

(2) INFORMATION FOR SEQ ID NO: 192:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 192:

Glu Asn Ala Asn Thr Arg Lys Ser Ser Arg
1               5                   10

(2) INFORMATION FOR SEQ ID NO: 193:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 193:

Lys Lys Arg Ile Ala Gly Leu Pro Trp Tyr Arg Cys Arg Thr Val Ala
1               5                   10                  15

Phe Glu Thr Gly Met Gln Asn Thr Gln Leu Cys Ser Thr Ile Val Gln
            20                  25                  30

Leu Ser Phe Thr Pro Glu Glu
            35

(2) INFORMATION FOR SEQ ID NO: 194:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 194:

```
Arg Lys Ser Ser Arg Ser Asn Pro Arg Gly
 1               5                  10
```

(2) INFORMATION FOR SEQ ID NO: 195:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 195:

```
Ser Asn Pro Arg Gly Arg Arg His Pro
 1               5
```

(2) INFORMATION FOR SEQ ID NO: 196:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 196:

```
Thr Asn Ala Lys His Ser Ser His Asn
 1               5
```

(2) INFORMATION FOR SEQ ID NO: 197:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 197:

```
Ser Ser His Asn Arg Arg Leu Arg Thr Arg
 1               5                  10
```

(2) INFORMATION FOR SEQ ID NO: 198:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 198:

```
Arg Arg Leu Arg Thr Arg Ser Arg Pro Asn
 1               5                  10
```

(2) INFORMATION FOR SEQ ID NO: 199:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 199:

```
Arg Val Gly Gln Cys Thr Asp Ser Asp Val Arg Arg Pro Trp Ala Arg
 1               5                  10                  15

Ser Cys Ala
```

(2) INFORMATION FOR SEQ ID NO: 200:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 200:

```
Val Arg Arg Pro Trp Ala Arg Ser Cys Ala His Gln Gly Cys Gly Ala
 1               5                  10                  15

Gly Thr Arg Asn Ser
                20
```

(2) INFORMATION FOR SEQ ID NO: 201:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 201:

```
Gly Thr Arg Asn Ser His Gly Cys Ile Thr Arg Pro Leu Arg Gln Ala
 1               5                  10                  15

Ser Gln His
```

(2) INFORMATION FOR SEQ ID NO: 202:

(i) SEQUENCE CHARACTERISTICS:
        (A) LENGTH: 40 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 202:

```
Ser Thr Pro Pro Ser Arg Glu Ala Tyr Ser Arg Pro Tyr Ser Val Asp
 1               5                  10                  15

Ser Asp Ser Asp Thr Met Ala Lys His Ser Ser His Asn Arg Arg Leu
                20                  25                  30

Arg Thr Arg Ser Arg Pro Asn Gly
            35                  40
```

(2) INFORMATION FOR SEQ ID NO: 203:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 203:

```
Tyr Ser Lys Val
```

(2) INFORMATION FOR SEQ ID NO: 204:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 204:

Phe Pro His Leu
1

(2) INFORMATION FOR SEQ ID NO: 205:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 205:

Tyr Arg Gly Val
1

(2) INFORMATION FOR SEQ ID NO: 206:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 206:

Tyr Gln Thr Ile
1

(2) INFORMATION FOR SEQ ID NO: 207:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 207:

Thr Glu Gln Phe
1

(2) INFORMATION FOR SEQ ID NO: 208:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 208:

Thr Glu Val Met
1

(2) INFORMATION FOR SEQ ID NO: 209:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 209:

Thr Ser Ala Phe
1

(2) INFORMATION FOR SEQ ID NO: 210:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 210:

Tyr Thr Arg Phe
1

(2) INFORMATION FOR SEQ ID NO: 211:

(i) SEQUENCE CHARACTERISTICS:
        (A) LENGTH: 717 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 1...714
        (D) OTHER INFORMATION:

(xi) SEQUENCE DESCRIPTION: SEQ ID NO: 211:

```
ATG TCC CCT ATA CTA GGT TAT TGG AAA ATT AAG GGC CTT GTG CAA CCC      48
Met Ser Pro Ile Leu Gly Tyr Trp Lys Ile Lys Gly Leu Val Gln Pro
 1               5                  10                  15

ACT CGA CTT CTT TTG GAA TAT CTT GAA GAA AAA TAT GAA GAG CAT TTG      96
Thr Arg Leu Leu Leu Glu Tyr Leu Glu Glu Lys Tyr Glu Glu His Leu
                20                  25                  30

TAT GAG CGC GAT GAA GGT GAT AAA TGG CGA AAC AAA AAG TTT GAA TTG     144
Tyr Glu Arg Asp Glu Gly Asp Lys Trp Arg Asn Lys Lys Phe Glu Leu
            35                  40                  45

GGT TTG GAG TTT CCC AAT CTT CCT TAT TAT ATT GAT GGT GAT GTT AAA     192
Gly Leu Glu Phe Pro Asn Leu Pro Tyr Tyr Ile Asp Gly Asp Val Lys
        50                  55                  60

TTA ACA CAG TCT ATG GCC ATC ATA CGT TAT ATA GCT GAC AAG CAC AAC     240
Leu Thr Gln Ser Met Ala Ile Ile Arg Tyr Ile Ala Asp Lys His Asn
 65                 70                  75                  80

ATG TTG GGT GGT TGT CCA AAA GAG CGT GCA GAG ATT TCA ATG CTT GAA     288
Met Leu Gly Gly Cys Pro Lys Glu Arg Ala Glu Ile Ser Met Leu Glu
                85                  90                  95

GGA GCG GTT TTG GAT ATT AGA TAC GGT GTT TCG AGA ATT GCA TAT AGT     336
Gly Ala Val Leu Asp Ile Arg Tyr Gly Val Ser Arg Ile Ala Tyr Ser
```

```
            100                 105                 110
AAA GAC TTT GAA ACT CTC AAA GTT GAT TTT CTT AGC AAG CTA CCT GAA    384
Lys Asp Phe Glu Thr Leu Lys Val Asp Phe Leu Ser Lys Leu Pro Glu
        115                 120                 125

ATG CTG AAA ATG TTC GAA GAT CGT TTA TGT CAT AAA ACA TAT TTA AAT    432
Met Leu Lys Met Phe Glu Asp Arg Leu Cys His Lys Thr Tyr Leu Asn
        130                 135                 140

GGT GAT CAT GTA ACC CAT CCT GAC TTC ATG TTG TAT GAC GCT CTT GAT    480
Gly Asp His Val Thr His Pro Asp Phe Met Leu Tyr Asp Ala Leu Asp
145                 150                 155                 160

GTT GTT TTA TAC ATG GAC CCA ATG TGC CTG GAT GCG TTC CCA AAA TTA    528
Val Val Leu Tyr Met Asp Pro Met Cys Leu Asp Ala Phe Pro Lys Leu
                165                 170                 175

GTT TGT TTT AAA AAA CGT ATT GAA GCT ATC CCA CAA ATT GAT AAG TAC    576
Val Cys Phe Lys Lys Arg Ile Glu Ala Ile Pro Gln Ile Asp Lys Tyr
                180                 185                 190

TTG AAA TCC AGC AAG TAT ATA GCA TGG CCT TTG CAG GGC TGG CAA GCC    624
Leu Lys Ser Ser Lys Tyr Ile Ala Trp Pro Leu Gln Gly Trp Gln Ala
                195                 200                 205

ACG TTT GGT GGT GGC GAC CAT CCT CCA AAA TCG GAT CTG GTT CCG CGT    672
Thr Phe Gly Gly Gly Asp His Pro Pro Lys Ser Asp Leu Val Pro Arg
        210                 215                 220

GGA TCC CCA GGA ATT CCC GGG TCG ACT CGA GCG GCC GCA TCG TGA        717
Gly Ser Pro Gly Ile Pro Gly Ser Thr Arg Ala Ala Ala Ser
225                 230                 235

(2) INFORMATION FOR SEQ ID NO: 212:

(i) SEQUENCE CHARACTERISTICS:
        (A) LENGTH: 238 amino acids
        (B) TYPE: amino acid
        (C) STRANDEDNESS: <Unknown>
        (D) TOPOLOGY: unknown (ii) MOLECULE TYPE: protein (xi) SEQUENCE DESCRIPTION: SEQ ID NO: 212:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175
```

```
Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
            210                 215                 220

Gly Ser Pro Gly Ile Pro Gly Ser Thr Arg Ala Ala Ala Ser
225                 230                 235
```

(2) INFORMATION FOR SEQ ID NO: 213:

(i) SEQUENCE CHARACTERISTICS:
        (A) LENGTH: 282 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 213:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
            210                 215                 220

Gly Ser Pro Gly Ile Pro Gly Ser Thr Arg Ala Ala Ala Ser Ser Gln
225                 230                 235                 240

Gly Ser Lys Gln Cys Met Gln Tyr Arg Thr Gly Arg Leu Thr Val Gly
                245                 250                 255

Ser Glu Tyr Gly Cys Gly Met Asn Pro Ala Arg His Ala Thr Pro Ala
            260                 265                 270

Tyr Pro Ala Arg Leu Leu Pro Arg Tyr Arg
            275                 280
```

(2) INFORMATION FOR SEQ ID NO: 214:

(i) SEQUENCE CHARACTERISTICS:
        (A) LENGTH: 282 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 214:

```
Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
             20                  25                  30

Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
     50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Ser Asp
225                 230                 235                 240

His Ala Leu Gly Thr Asn Leu Arg Ser Asp Asn Ala Lys Glu Pro Gly
                245                 250                 255

Asp Tyr Asn Cys Cys Gly Asn Gly Asn Ser Thr Gly Arg Lys Val Phe
            260                 265                 270

Asn Arg Arg Arg Pro Ser Ala Ile Pro Thr
        275                 280
```

(2) INFORMATION FOR SEQ ID NO: 215:

(i) SEQUENCE CHARACTERISTICS:
        (A) LENGTH: 279 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 215:

```
Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Ser Pro
225                 230                 235                 240

Cys Gly Gly Ser Trp Gly Arg Phe Met Gln Gly Gly Leu Phe Gly Gly
                245                 250                 255

Arg Thr Asp Gly Cys Gly Ala His Arg Asn Arg Thr Ser Ala Ser Leu
            260                 265                 270

Glu Pro Pro Ser Ser Asp Tyr
        275
```

(2) INFORMATION FOR SEQ ID NO: 216:

(i) SEQUENCE CHARACTERISTICS:
        (A) LENGTH: 277 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 216:

```
Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
```

-continued

```
            50                   55                   60
Leu Thr Gln Ser Met Ala Ile Ile Arg Tyr Ile Ala Asp Lys His Asn
 65                   70                   75                   80

Met Leu Gly Gly Cys Pro Lys Glu Arg Ala Glu Ile Ser Met Leu Glu
                     85                   90                   95

Gly Ala Val Leu Asp Ile Arg Tyr Gly Val Ser Arg Ile Ala Tyr Ser
                    100                  105                  110

Lys Asp Phe Glu Thr Leu Lys Val Asp Phe Leu Ser Lys Leu Pro Glu
                    115                  120                  125

Met Leu Lys Met Phe Glu Asp Arg Leu Cys His Lys Thr Tyr Leu Asn
                    130                  135                  140

Gly Asp His Val Thr His Pro Asp Phe Met Leu Tyr Asp Ala Leu Asp
145                  150                  155                  160

Val Val Leu Tyr Met Asp Pro Met Cys Leu Asp Ala Phe Pro Lys Leu
                    165                  170                  175

Val Cys Phe Lys Lys Arg Ile Glu Ala Ile Pro Gln Ile Asp Lys Tyr
                    180                  185                  190

Leu Lys Ser Ser Lys Tyr Ile Ala Trp Pro Leu Gln Gly Trp Gln Ala
                    195                  200                  205

Thr Phe Gly Gly Gly Asp His Pro Pro Lys Ser Asp Leu Val Pro Arg
                    210                  215                  220

Gly Ser Pro Gly Ile Pro Gly Ser Thr Arg Ala Ala Ser Arg Gly
225                  230                  235                  240

Ser Thr Gly Thr Ala Gly Gly Glu Arg Ser Gly Val Leu Asn Leu His
                    245                  250                  255

Thr Arg Asp Asn Ala Ser Gly Ser Gly Phe Lys Pro Trp Tyr Pro Ser
                    260                  265                  270

Asn Arg Gly His Lys
                    275
```

(2) INFORMATION FOR SEQ ID NO: 217:

(i) SEQUENCE CHARACTERISTICS:
        (A) LENGTH: 277 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 217:

```
Met Ser Pro Ile Leu Gly Tyr Trp Lys Ile Lys Gly Leu Val Gln Pro
 1                    5                   10                   15

Thr Arg Leu Leu Leu Glu Tyr Leu Glu Glu Lys Tyr Glu Glu His Leu
                     20                   25                   30

Tyr Glu Arg Asp Glu Gly Asp Lys Trp Arg Asn Lys Lys Phe Glu Leu
                     35                   40                   45

Gly Leu Glu Phe Pro Asn Leu Pro Tyr Tyr Ile Asp Gly Asp Val Lys
                     50                   55                   60

Leu Thr Gln Ser Met Ala Ile Ile Arg Tyr Ile Ala Asp Lys His Asn
 65                   70                   75                   80

Met Leu Gly Gly Cys Pro Lys Glu Arg Ala Glu Ile Ser Met Leu Glu
                     85                   90                   95

Gly Ala Val Leu Asp Ile Arg Tyr Gly Val Ser Arg Ile Ala Tyr Ser
                    100                  105                  110

Lys Asp Phe Glu Thr Leu Lys Val Asp Phe Leu Ser Lys Leu Pro Glu
```

```
                115                 120                 125
Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Leu Val Pro Arg
        210                 215                 220

Gly Ser Pro Gly Ile Pro Gly Ser Thr Arg Ala Ala Ala Ser Ser His
225                 230                 235                 240

Ser Gly Gly Met Asn Arg Ala Tyr Gly Asp Val Phe Arg Glu Leu Arg
                245                 250                 255

Asp Arg Trp Asn Ala Thr Ser His His Thr Arg Pro Thr Pro Gln Leu
                260                 265                 270

Pro Arg Gly Pro Asn
        275

(2) INFORMATION FOR SEQ ID NO: 218:

(i) SEQUENCE CHARACTERISTICS:
        (A) LENGTH: 248 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 218:

Met Ser Pro Ile Leu Gly Tyr Trp Lys Ile Lys Gly Leu Val Gln Pro
1               5                   10                  15

Thr Arg Leu Leu Leu Glu Tyr Leu Glu Lys Tyr Glu Glu His Leu
                20                  25                  30

Tyr Glu Arg Asp Glu Gly Asp Lys Trp Arg Asn Lys Lys Phe Glu Leu
                35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
```

```
                    180                 185                 190
Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
        210                 215                 220

Gly Ser Pro Gly Ile Pro Gly Ser Thr Arg Ala Ala Ala Ser Ser His
225                 230                 235                 240

Ser Gly Gly Met Asn Arg Ala Tyr
                245

(2) INFORMATION FOR SEQ ID NO: 219:

(i) SEQUENCE CHARACTERISTICS:
        (A) LENGTH: 248 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 219:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Gly Asp
225                 230                 235                 240

Val Phe Arg Glu Leu Arg Asp Arg
                245

(2) INFORMATION FOR SEQ ID NO: 220:

(i) SEQUENCE CHARACTERISTICS:
```

(A) LENGTH: 248 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 220:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
50                      55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
210                 215                 220

Gly Ser Pro Gly Ile Pro Gly Ser Thr Arg Ala Ala Ala Ser Trp Asn
225                 230                 235                 240

Ala Thr Ser His His Thr Arg Pro
                245

(2) INFORMATION FOR SEQ ID NO: 221:

(i) SEQUENCE CHARACTERISTICS:
        (A) LENGTH: 247 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 221:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

```
Gly Leu Glu Phe Pro Asn Leu Pro Tyr Tyr Ile Asp Gly Asp Val Lys
            50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Asp His Pro Pro Lys Ser Asp Leu Val Pro Arg
        210                 215                 220

Gly Ser Pro Gly Ile Pro Gly Ser Thr Arg Ala Ala Ala Ser Thr Pro
225                 230                 235                 240

Gln Leu Pro Arg Gly Pro Asn
                245

(2) INFORMATION FOR SEQ ID NO: 222:

(i) SEQUENCE CHARACTERISTICS:
        (A) LENGTH: 258 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 222:

Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
                35                  40                  45

Gly Leu Glu Phe Pro Asn Leu Pro Tyr Tyr Ile Asp Gly Asp Val Lys
            50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
        130                 135                 140
```

```
Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Gly Asp
225                 230                 235                 240

Val Phe Arg Glu Leu Arg Asp Arg Trp Asn Ala Thr Ser His His Thr
                245                 250                 255

Arg Pro (2) INFORMATION FOR SEQ ID NO: 223:

(i) SEQUENCE CHARACTERISTICS:
        (A) LENGTH: 257 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 223:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Trp Asn
```

```
                 225             230             235             240
Ala Thr Ser His His Thr Arg Pro Thr Pro Gln Leu Pro Arg Gly Pro
                    245             250             255
Asn (2) INFORMATION FOR SEQ ID NO: 224:

(i) SEQUENCE CHARACTERISTICS:
        (A) LENGTH: 267 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 224:

Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
                35                  40                  45

Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
                130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Leu Val Pro Arg
                210                 215                 220

Gly Ser Pro Gly Ile Pro Gly Ser Thr Arg Ala Ala Ala Ser Gly Asp
225                 230                 235                 240

Val Phe Arg Glu Leu Arg Asp Arg Trp Asn Ala Thr Ser His His Thr
                245                 250                 255

Arg Pro Thr Pro Gln Leu Pro Arg Gly Pro Asn
                260                 265

(2) INFORMATION FOR SEQ ID NO: 225:

(i) SEQUENCE CHARACTERISTICS:
        (A) LENGTH: 277 amino acids
        (B) TYPE: amino acid
        (C) STRANDEDNESS: <Unknown>
        (D) TOPOLOGY: unknown
```

-continued (ii) MOLECULE TYPE: peptide (xi) SEQUENCE DESCRIPTION: SEQ ID NO: 225:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65              70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
210                 215                 220

Gly Ser Pro Gly Ile Pro Gly Ser Thr Arg Ala Ala Ala Ser Ser His
225                 230                 235                 240

Ser Gly Gly Met Asn Arg Ala Tyr Gly Asp Val Phe Arg Glu Leu Arg
                245                 250                 255

Asp Arg Trp Asn Ala Thr Ser Ala Ala Thr Arg Pro Thr Pro Gln Leu
            260                 265                 270

Pro Arg Gly Pro Asn
            275

(2) INFORMATION FOR SEQ ID NO: 226:

(i) SEQUENCE CHARACTERISTICS:
        (A) LENGTH: 277 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 226:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu

-continued

```
                    35                  40                  45
Gly Leu Glu Phe Pro Asn Leu Pro Tyr Tyr Ile Asp Gly Asp Val Lys
    50                  55                  60
Leu Thr Gln Ser Met Ala Ile Ile Arg Tyr Ile Ala Asp Lys His Asn
 65                  70                  75                  80
Met Leu Gly Gly Cys Pro Lys Glu Arg Ala Glu Ile Ser Met Leu Glu
                 85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
            115                 120                 125
Met Leu Lys Met Phe Glu Asp Arg Leu Cys His Lys Thr Tyr Leu Asn
    130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
        195                 200                 205
Thr Phe Gly Gly Asp His Pro Pro Lys Ser Asp Leu Val Pro Arg
    210                 215                 220
Gly Ser Pro Gly Ile Pro Gly Ser Thr Arg Ala Ala Ser Ser Ala
225                 230                 235                 240
Arg Asp Ser Gly Pro Ala Glu Asp Gly Ser Arg Ala Val Arg Leu Asn
                245                 250                 255
Gly Val Glu Asn Ala Asn Thr Arg Lys Ser Ser Arg Ser Asn Pro Arg
                260                 265                 270
Gly Arg Arg His Pro
            275
```

(2) INFORMATION FOR SEQ ID NO: 227:

(i) SEQUENCE CHARACTERISTICS:
        (A) LENGTH: 257 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 227:

```
Met Ser Pro Ile Leu Gly Tyr Trp Lys Ile Lys Gly Leu Val Gln Pro
  1               5                  10                  15
Thr Arg Leu Leu Leu Glu Tyr Leu Glu Glu Lys Tyr Glu Glu His Leu
             20                  25                  30
Tyr Glu Arg Asp Glu Gly Asp Lys Trp Arg Asn Lys Lys Phe Glu Leu
         35                  40                  45
Gly Leu Glu Phe Pro Asn Leu Pro Tyr Tyr Ile Asp Gly Asp Val Lys
    50                  55                  60
Leu Thr Gln Ser Met Ala Ile Ile Arg Tyr Ile Ala Asp Lys His Asn
 65                  70                  75                  80
Met Leu Gly Gly Cys Pro Lys Glu Arg Ala Glu Ile Ser Met Leu Glu
                 85                  90                  95
Gly Ala Val Leu Asp Ile Arg Tyr Gly Val Ser Arg Ile Ala Tyr Ser
```

```
                100                 105                 110
Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Leu Val Pro Arg
            210                 215                 220

Gly Ser Pro Gly Ile Pro Gly Ser Thr Arg Ala Ala Ser Ser Ala
225                 230                 235                 240

Arg Asp Ser Gly Pro Ala Glu Asp Gly Ser Arg Ala Val Arg Leu Asn
                245                 250                 255

Gly (2) INFORMATION FOR SEQ ID NO: 228:

(i) SEQUENCE CHARACTERISTICS:
        (A) LENGTH: 259 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 228:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190
```

```
Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Asp Gly
225                 230                 235                 240

Ser Arg Ala Val Arg Leu Asn Gly Val Glu Asn Ala Asn Thr Arg Lys
            245                 250                 255

Ser Ser Arg (2) INFORMATION FOR SEQ ID NO: 229:

(i) SEQUENCE CHARACTERISTICS:
        (A) LENGTH: 257 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 229:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
            130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Glu Asn
225                 230                 235                 240

Ala Asn Thr Arg Lys Ser Ser Arg Ser Asn Pro Arg Gly Arg Arg His
            245                 250                 255

Pro
```

-continued (2) INFORMATION FOR SEQ ID NO: 230:

(i) SEQUENCE CHARACTERISTICS:
        (A) LENGTH: 248 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 230:

```
Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Asp His Pro Pro Lys Ser Asp Leu Val Pro Arg
        210                 215                 220

Gly Ser Pro Gly Ile Pro Gly Ser Thr Arg Ala Ala Ala Ser Glu Asn
225                 230                 235                 240

Ala Asn Thr Arg Lys Ser Ser Arg
                245
```

(2) INFORMATION FOR SEQ ID NO: 231:

(i) SEQUENCE CHARACTERISTICS:
        (A) LENGTH: 248 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 231:

```
Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
                20                  25                  30
```

-continued

```
Tyr Glu Arg Asp Glu Gly Asp Lys Trp Arg Asn Lys Lys Phe Glu Leu
            35                  40                  45
Gly Leu Glu Phe Pro Asn Leu Pro Tyr Tyr Ile Asp Gly Asp Val Lys
 50                  55                  60
Leu Thr Gln Ser Met Ala Ile Ile Arg Tyr Ile Ala Asp Lys His Asn
 65                  70                  75                  80
Met Leu Gly Gly Cys Pro Lys Glu Arg Ala Glu Ile Ser Met Leu Glu
                 85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
            115                 120                 125
Met Leu Lys Met Phe Glu Asp Arg Leu Cys His Lys Thr Tyr Leu Asn
130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
            195                 200                 205
Thr Phe Gly Gly Gly Asp His Pro Pro Lys Ser Asp Leu Val Pro Arg
            210                 215                 220
Gly Ser Pro Gly Ile Pro Gly Ser Thr Arg Ala Ala Ser Arg Lys
225                 230                 235                 240
Ser Ser Arg Ser Asn Pro Arg Gly
                245
```

(2) INFORMATION FOR SEQ ID NO: 232:

(i) SEQUENCE CHARACTERISTICS:
        (A) LENGTH: 247 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 232:

```
Met Ser Pro Ile Leu Gly Tyr Trp Lys Ile Lys Gly Leu Val Gln Pro
 1               5                  10                  15
Thr Arg Leu Leu Leu Glu Tyr Leu Glu Glu Lys Tyr Glu Glu His Leu
            20                  25                  30
Tyr Glu Arg Asp Glu Gly Asp Lys Trp Arg Asn Lys Lys Phe Glu Leu
            35                  40                  45
Gly Leu Glu Phe Pro Asn Leu Pro Tyr Tyr Ile Asp Gly Asp Val Lys
 50                  55                  60
Leu Thr Gln Ser Met Ala Ile Ile Arg Tyr Ile Ala Asp Lys His Asn
 65                  70                  75                  80
Met Leu Gly Gly Cys Pro Lys Glu Arg Ala Glu Ile Ser Met Leu Glu
                 85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
            115                 120                 125
```

```
Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Val Pro Arg
    210                 215                 220

Gly Ser Pro Gly Ile Pro Gly Ser Thr Arg Ala Ala Ser Ser Asn
225                 230                 235                 240

Pro Arg Gly Arg Arg His Pro
                245
```

(2) INFORMATION FOR SEQ ID NO: 233:

(i) SEQUENCE CHARACTERISTICS:
        (A) LENGTH: 249 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 233:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Val Pro Arg
    210                 215                 220
```

```
Gly Ser Pro Gly Ile Pro Gly Ser Thr Arg Ala Ala Ala Ser Thr Arg
225                 230                 235                 240

Lys Ser Ser Arg Ser Asn Pro Arg Gly
                245
```

(2) INFORMATION FOR SEQ ID NO: 234:

(i) SEQUENCE CHARACTERISTICS:
        (A) LENGTH: 277 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 234:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
                35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Leu Val Pro Arg
        210                 215                 220

Gly Ser Pro Gly Ile Pro Gly Ser Thr Arg Ala Ala Ala Ser Ser Thr
225                 230                 235                 240

Pro Pro Ser Arg Glu Ala Tyr Ser Arg Pro Tyr Ser Val Asp Ser Asp
                245                 250                 255

Ser Asp Thr Asn Ala Lys His Ser Ser His Asn Arg Arg Leu Arg Thr
                260                 265                 270

Arg Ser Arg Pro Asn
                275
```

(2) INFORMATION FOR SEQ ID NO: 235:

(i) SEQUENCE CHARACTERISTICS:
        (A) LENGTH: 258 amino acids
        (B) TYPE: amino acid -continued (C) STRANDEDNESS: <Unknown>
        (D) TOPOLOGY: unknown (ii) MOLECULE TYPE: peptide (xi) SEQUENCE DESCRIPTION: SEQ ID NO: 235:

Met Ser Pro Ile Leu Gly Tyr Trp Lys Ile Lys Gly Leu Val Gln Pro
1               5                  10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Ser Thr
225                 230                 235                 240

Pro Pro Ser Arg Glu Ala Tyr Ser Arg Pro Tyr Ser Val Asp Ser Asp
                245                 250                 255

Ser Asp (2) INFORMATION FOR SEQ ID NO: 236:

(i) SEQUENCE CHARACTERISTICS:
        (A) LENGTH: 259 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 236:

Met Ser Pro Ile Leu Gly Tyr Trp Lys Ile Lys Gly Leu Val Gln Pro
1               5                  10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

```
Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Asp His Pro Pro Lys Ser Asp Leu Val Pro Arg
210                 215                 220

Gly Ser Pro Gly Ile Pro Gly Ser Thr Arg Ala Ala Ala Ser Ser Arg
225                 230                 235                 240

Pro Tyr Ser Val Asp Ser Asp Ser Asp Thr Asn Ala Lys His Ser Ser
                245                 250                 255

His Asn Arg
```

(2) INFORMATION FOR SEQ ID NO: 237:

(i) SEQUENCE CHARACTERISTICS:
        (A) LENGTH: 257 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 237:

```
Met Ser Pro Ile Leu Gly Tyr Trp Lys Ile Lys Gly Leu Val Gln Pro
 1                5                  10                  15

Thr Arg Leu Leu Leu Glu Tyr Leu Glu Glu Lys Tyr Glu Glu His Leu
                 20                  25                  30

Tyr Glu Arg Asp Glu Gly Asp Lys Trp Arg Asn Lys Lys Phe Glu Leu
             35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
```

```
            130                 135                 140
Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ser Thr Asn
225                 230                 235                 240

Ala Lys His Ser Ser His Asn Arg Arg Leu Arg Thr Arg Ser Arg Pro
                245                 250                 255

Asn (2) INFORMATION FOR SEQ ID NO: 238:

(i) SEQUENCE CHARACTERISTICS:
        (A) LENGTH: 247 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 238:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Leu Val Pro Arg
    210                 215                 220
```

```
Gly Ser Pro Gly Ile Pro Gly Ser Thr Arg Ala Ala Ala Ser Thr Asn
225                 230                 235                 240

Ala Lys His Ser Ser His Asn
                245
```

(2) INFORMATION FOR SEQ ID NO: 239:

(i) SEQUENCE CHARACTERISTICS:
        (A) LENGTH: 248 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 239:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Asp His Pro Pro Lys Ser Asp Leu Val Pro Arg
210                 215                 220

Gly Ser Pro Gly Ile Pro Gly Ser Thr Arg Ala Ala Ala Ser Ser Ser
225                 230                 235                 240

His Asn Arg Arg Leu Arg Thr Arg
                245
```

(2) INFORMATION FOR SEQ ID NO: 240:

(i) SEQUENCE CHARACTERISTICS:
        (A) LENGTH: 248 amino acids
        (B) TYPE: amino acid
        (C) STRANDEDNESS: <Unknown>
        (D) TOPOLOGY: unknown (ii) MOLECULE TYPE: peptide

```
    (xi) SEQUENCE DESCRIPTION: SEQ ID NO: 240:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
        210                 215                 220

Gly Ser Pro Gly Ile Pro Gly Ser Thr Arg Ala Ala Ala Ser Arg Arg
225                 230                 235                 240

Leu Arg Thr Arg Ser Arg Pro Asn
                245

(2) INFORMATION FOR SEQ ID NO: 241:

(i) SEQUENCE CHARACTERISTICS:
        (A) LENGTH: 282 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 241:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
```

```
                        85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
                115                 120                 125
Met Leu Lys Met Phe Glu Asp Arg Leu Cys His Lys Thr Tyr Leu Asn
                130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
                180                 185                 190
Leu Lys Ser Ser Lys Tyr Ile Ala Trp Pro Leu Gln Gly Trp Gln Ala
                195                 200                 205
Thr Phe Gly Gly Gly Asp His Pro Pro Lys Ser Asp Leu Val Pro Arg
                210                 215                 220
Gly Ser Pro Gly Ile Pro Gly Ser Thr Arg Ala Ala Ser Arg Val
225                 230                 235                 240
Gly Gln Cys Thr Asp Ser Asp Val Arg Arg Pro Trp Ala Arg Ser Cys
                245                 250                 255
Ala His Gln Gly Cys Gly Ala Gly Thr Arg Asn Ser His Gly Cys Ile
                260                 265                 270
Thr Arg Pro Leu Arg Gln Ala Ser Ala His
                275                 280

(2) INFORMATION FOR SEQ ID NO: 242:

(i) SEQUENCE CHARACTERISTICS:
        (A) LENGTH: 257 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 242:

Met Ser Pro Ile Leu Gly Tyr Trp Lys Ile Lys Gly Leu Val Gln Pro
1                   5                   10                  15
Thr Arg Leu Leu Leu Glu Tyr Leu Glu Glu Lys Tyr Glu Glu His Leu
                20                  25                  30
Tyr Glu Arg Asp Glu Gly Asp Lys Trp Arg Asn Lys Lys Phe Glu Leu
                35                  40                  45
Gly Leu Glu Phe Pro Asn Leu Pro Tyr Tyr Ile Asp Gly Asp Val Lys
                50                  55                  60
Leu Thr Gln Ser Met Ala Ile Ile Arg Tyr Ile Ala Asp Lys His Asn
65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
                115                 120                 125
Met Leu Lys Met Phe Glu Asp Arg Leu Cys His Lys Thr Tyr Leu Asn
                130                 135                 140
Gly Asp His Val Thr His Pro Asp Phe Met Leu Tyr Asp Ala Leu Asp
```

```
               145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
                180                 185                 190
Leu Lys Ser Ser Lys Tyr Ile Ala Trp Pro Leu Gln Gly Trp Gln Ala
                195                 200                 205
Thr Phe Gly Gly Gly Asp His Pro Pro Lys Ser Asp Leu Val Pro Arg
                210                 215                 220
Gly Ser Pro Gly Ile Pro Gly Ser Thr Arg Ala Ala Ser Arg Val
225                 230                 235                 240
Gly Gln Cys Thr Asp Ser Asp Val Arg Arg Pro Trp Ala Arg Ser Cys
                245                 250                 255
Ala (2) INFORMATION FOR SEQ ID NO: 243:

(i) SEQUENCE CHARACTERISTICS:
        (A) LENGTH: 259 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 243:

Met Ser Pro Ile Leu Gly Tyr Trp Lys Ile Lys Gly Leu Val Gln Pro
1                   5                   10                  15
Thr Arg Leu Leu Leu Glu Tyr Leu Glu Glu Lys Tyr Glu Glu His Leu
                20                  25                  30
Tyr Glu Arg Asp Glu Gly Asp Lys Trp Arg Asn Lys Lys Phe Glu Leu
                35                  40                  45
Gly Leu Glu Phe Pro Asn Leu Pro Tyr Tyr Ile Asp Gly Asp Val Lys
            50                  55                  60
Leu Thr Gln Ser Met Ala Ile Ile Arg Tyr Ile Ala Asp Lys His Asn
65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
            115                 120                 125
Met Leu Lys Met Phe Glu Asp Arg Leu Cys His Lys Thr Tyr Leu Asn
            130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
                180                 185                 190
Leu Lys Ser Ser Lys Tyr Ile Ala Trp Pro Leu Gln Gly Trp Gln Ala
                195                 200                 205
Thr Phe Gly Gly Gly Asp His Pro Pro Lys Ser Asp Leu Val Pro Arg
            210                 215                 220
Gly Ser Pro Gly Ile Pro Gly Ser Thr Arg Ala Ala Ser Val Arg
225                 230                 235                 240
```

-continued

```
Arg Pro Trp Ala Arg Ser Cys Ala His Gln Gly Cys Gly Ala Gly Thr
            245                 250                 255

Arg Asn Ser
```

(2) INFORMATION FOR SEQ ID NO: 244:

(i) SEQUENCE CHARACTERISTICS:
        (A) LENGTH: 257 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 244:

```
Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Gly Thr
225                 230                 235                 240

Arg Asn Ser His Gly Cys Ile Thr Arg Pro Leu Arg Gln Ala Ser Gln
                245                 250                 255

His
```

(2) INFORMATION FOR SEQ ID NO: 245:

(i) SEQUENCE CHARACTERISTICS:
        (A) LENGTH: 282 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 245:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Arg Tyr
225                 230                 235                 240

Lys His Asp Ile Gly Cys Asp Ala Gly Val Asp Lys Lys Ser Ser Ser
            245                 250                 255

Val Arg Gly Gly Cys Gly Ala His Ser Ser Pro Pro Arg Ala Gly Arg
            260                 265                 270

Gly Pro Arg Gly Thr Met Val Ser Arg Leu
        275                 280

(2) INFORMATION FOR SEQ ID NO: 246:

(i) SEQUENCE CHARACTERISTICS:
        (A) LENGTH: 262 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 246:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

```
Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Asp His Pro Pro Lys Ser Asp Leu Val Pro Arg
 210                215                 220

Gly Ser Pro Gly Ile Pro Gly Ser Thr Arg Ala Ala Ser Arg Tyr
225                 230                 235                 240

Lys His Asp Ile Gly Cys Asp Ala Gly Val Asp Lys Lys Ser Ser Ser
                245                 250                 255

Val Arg Gly Gly Cys Gly
            260

(2) INFORMATION FOR SEQ ID NO: 247:

(i) SEQUENCE CHARACTERISTICS:
        (A) LENGTH: 264 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 247:

Met Ser Pro Ile Leu Gly Tyr Trp Lys Ile Lys Gly Leu Val Gln Pro
 1                5                  10                  15

Thr Arg Leu Leu Leu Glu Tyr Leu Glu Glu Lys Tyr Glu Glu His Leu
                 20                  25                  30

Tyr Glu Arg Asp Glu Gly Asp Lys Trp Arg Asn Lys Lys Phe Glu Leu
             35                  40                  45

Gly Leu Glu Phe Pro Asn Leu Pro Tyr Tyr Ile Asp Gly Asp Val Lys
         50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125
```

```
Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
210                 215                 220

Gly Ser Pro Gly Ile Pro Gly Ser Thr Arg Ala Ala Ser Gly Cys
225                 230                 235                 240

Asp Ala Gly Val Asp Lys Lys Ser Ser Val Arg Gly Gly Cys Gly
                245                 250                 255

Ala His Ser Ser Pro Pro Arg Ala
            260

(2) INFORMATION FOR SEQ ID NO: 248:

(i) SEQUENCE CHARACTERISTICS:
        (A) LENGTH: 259 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 248:

Met Ser Pro Ile Leu Gly Tyr Trp Lys Ile Lys Gly Leu Val Gln Pro
1                   5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205
```

```
Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Gly Ala
225                 230                 235                 240

His Ser Ser Pro Pro Arg Ala Gly Arg Gly Pro Arg Gly Thr Met Val
                245                 250                 255

Ser Arg Leu (2) INFORMATION FOR SEQ ID NO: 249:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 249:

Ser Gly Ser Pro Pro Cys Cys Cys Ser Trp Gly Arg Phe Met Gln Gly
1               5                   10                  15

Gly Leu Phe Gly Gly Arg Thr Asp Gly Cys Gly Ala His Arg Asn Arg
                20                  25                  30

Thr Ser Ala Ser Leu Glu Pro Pro Ser Ser Asp Tyr
                35                  40

(2) INFORMATION FOR SEQ ID NO: 250:

(i) SEQUENCE CHARACTERISTICS:
        (A) LENGTH: 40 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 250:

Ser His Ser Gly Gly Met Asn Arg Ala Tyr Gly Asp Val Phe Arg Glu
1               5                   10                  15

Leu Arg Asp Arg Trp Asn Ala Thr Ser His His Thr Arg Pro Thr Pro
                20                  25                  30

Gln Leu Pro Arg Gly Pro Asn Ser
                35                  40

(2) INFORMATION FOR SEQ ID NO: 251:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 251:

Asp Thr Asn Ala Lys His Ser Ser His Asn Arg Arg Leu Arg Thr Arg
1               5                   10                  15

Ser Arg Pro Asn Gly
                20

(2) INFORMATION FOR SEQ ID NO: 252:

(i) SEQUENCE CHARACTERISTICS:
        (A) LENGTH: 23 amino acids
```

```
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 252:

Cys Gly Ala Gly Thr Arg Asn Ser His Gly Cys Ile Thr Arg Pro Leu
1               5                   10                  15

Arg Gln Ala Ser Ala His Gly
            20

(2) INFORMATION FOR SEQ ID NO: 253:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: unknown (ii) MOLECULE TYPE: peptide (ix) FEATURE:
        (A) NAME/KEY: Modified Site
        (B) LOCATION: 1
        (D) OTHER INFORMATION: "Xaa=Ser or Thr"

(xi) SEQUENCE DESCRIPTION: SEQ ID NO: 253:

Xaa Thr Xaa Xaa Ser Xaa Xaa Xaa Asn Xaa Arg
1               5                   10

(2) INFORMATION FOR SEQ ID NO: 254:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: unknown (ii) MOLECULE TYPE: peptide (ix) FEATURE:
        (A) NAME/KEY: Modified Site
        (B) LOCATION: 2
        (D) OTHER INFORMATION: "Xaa=Ser, Ala or Gly"

(xi) SEQUENCE DESCRIPTION: SEQ ID NO: 254:

Asp Xaa Asp Xaa Arg Arg Xaa Xaa
1               5

(2) INFORMATION FOR SEQ ID NO: 255:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (ix) FEATURE:
        (A) NAME/KEY: Modified Site
        (B) LOCATION: 7
        (D) OTHER INFORMATION: "Xaa=Ala or Phe"

(xi) SEQUENCE DESCRIPTION: SEQ ID NO: 255:

Val Arg Ser Gly Cys Gly Xaa Xaa Ser Ser
1               5                   10

(2) INFORMATION FOR SEQ ID NO: 256:
```

```
        (i) SEQUENCE CHARACTERISTICS:
            (A) LENGTH: 11 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 256:

Asn Thr Arg Lys Ser Ser Arg Ser Asn Pro Arg
1               5                   10

(2) INFORMATION FOR SEQ ID NO: 257:

(i) SEQUENCE CHARACTERISTICS:
            (A) LENGTH: 11 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 257:

Ser Thr Lys Arg Ser Leu Ile Tyr Asn His Arg
1               5                   10

(2) INFORMATION FOR SEQ ID NO: 258:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 258:

Ser Thr Gly Arg Lys Val Phe Asn Arg Arg
1               5                   10

(2) INFORMATION FOR SEQ ID NO: 259:

(i) SEQUENCE CHARACTERISTICS:
            (A) LENGTH: 11 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 259:

Thr Asn Ala Lys His Ser Ser His Asn Arg Arg
1               5                   10

(2) INFORMATION FOR SEQ ID NO: 260:

(i) SEQUENCE CHARACTERISTICS:
            (A) LENGTH: 8 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 260:

Asp Ser Asp Val Arg Arg Pro Trp
1               5
```

(2) INFORMATION FOR SEQ ID NO: 261:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 261:

Ala Ala Asp Gln Arg Arg Gly Trp
 1               5

(2) INFORMATION FOR SEQ ID NO: 262:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 262:

Asp Gly Arg Gly Gly Arg Ser Tyr
 1               5

(2) INFORMATION FOR SEQ ID NO: 263:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 263:

Arg Val Arg Ser
 1

(2) INFORMATION FOR SEQ ID NO: 264:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 264:

Ser Val Arg Ser Gly Cys Gly Phe Arg Gly Ser Ser
 1               5                   10

(2) INFORMATION FOR SEQ ID NO: 265:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 265:

Ser Val Arg Gly Gly Cys Gly Ala His Ser Ser
 1               5                   10

(2) INFORMATION FOR SEQ ID NO: 266:

(i) SEQUENCE CHARACTERISTICS:
        (A) LENGTH: 37 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 2...2
        (D) OTHER INFORMATION: Xaa=Lys(dns)

(xi) SEQUENCE DESCRIPTION: SEQ ID NO: 266:

```
Cys Xaa Phe Ile Thr Lys Ala Leu Gly Ile Ser Tyr Gly Arg Lys Lys
 1               5                  10                  15

Arg Arg Gln Arg Arg Arg Pro Pro Gln Gly Ser Gln Thr His Gln Val
             20                  25                  30

Ser Leu Ser Lys Gln
         35
```

(2) INFORMATION FOR SEQ ID NO: 267:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Ac-Cys (xi) SEQUENCE DESCRIPTION: SEQ ID NO: 267:

```
Xaa Leu Asn Gly Gly Val Lys Met Tyr Val Glu Ser Val Asp Arg Tyr
 1               5                  10                  15

Val Cys
```

(2) INFORMATION FOR SEQ ID NO: 268:

(i) SEQUENCE CHARACTERISTICS:
        (A) LENGTH: 22 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Ac-Cys (xi) SEQUENCE DESCRIPTION: SEQ ID NO: 268:

```
Xaa Leu Asn Gly Gly Val Lys Phe Ile Thr Cys Met Tyr Val Glu Ser
 1               5                  10                  15

Val Asp Arg Tyr Val Cys
             20
```

(2) INFORMATION FOR SEQ ID NO: 269:

(i) SEQUENCE CHARACTERISTICS:
        (A) LENGTH: 21 amino acids (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 2...2
        (D) OTHER INFORMATION: Xaa=Lys(dns)

(xi) SEQUENCE DESCRIPTION: SEQ ID NO: 269:

Cys Xaa Arg Leu Asn Gly Gly Val Ser Met Tyr Val Glu Ser Val Asp
1               5                   10                  15

Arg Tyr Val Cys Arg
            20

(2) INFORMATION FOR SEQ ID NO: 270:

(i) SEQUENCE CHARACTERISTICS:
        (A) LENGTH: 40 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=biotin-Lys(dns)

(xi) SEQUENCE DESCRIPTION: SEQ ID NO: 270:

Xaa Ser Ala Arg Asp Ser Gly Pro Ala Glu Asp Gly Ser Arg Ala Val
1               5                   10                  15

Arg Leu Asn Gly Val Glu Asn Ala Asn Thr Arg Lys Ser Ser Arg Ser
            20                  25                  30

Asn Pro Arg Gly Arg Arg His Pro
            35                  40

(2) INFORMATION FOR SEQ ID NO: 271:

(i) SEQUENCE CHARACTERISTICS:
        (A) LENGTH: 45 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=biotin-Lys(dns)

(xi) SEQUENCE DESCRIPTION: SEQ ID NO: 271:

Xaa Ser Ser Ala Asp Ala Glu Lys Cys Ala Gly Ser Leu Leu Trp Trp
1               5                   10                  15

Gly Arg Gln Asn Asn Ser Gly Cys Gly Ser Pro Thr Lys Lys His Leu
            20                  25                  30

Lys His Arg Asn Arg Ser Gln Thr Ser Ser Ser Ser His
            35                  40                  45

(2) INFORMATION FOR SEQ ID NO: 272:

(i) SEQUENCE CHARACTERISTICS:
        (A) LENGTH: 45 amino acids
        (B) TYPE: amino acid (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=biotin-Lys(dns)

(xi) SEQUENCE DESCRIPTION: SEQ ID NO: 272:

Xaa Arg Glu Phe Ala Glu Arg Arg Leu Trp Gly Cys Asp Asp Leu Ser
 1               5                  10                  15

Trp Arg Leu Asp Ala Glu Gly Cys Gly Pro Thr Pro Ser Asn Arg Ala
            20                  25                  30

Val Lys His Arg Lys Pro Arg Pro Arg Ser Pro Ala Leu
        35                  40                  45

(2) INFORMATION FOR SEQ ID NO: 273:

(i) SEQUENCE CHARACTERISTICS:
        (A) LENGTH: 41 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=biotin-Ser (xi) SEQUENCE DESCRIPTION: SEQ ID NO: 273:

Xaa Gly Ser His Ser Gly Gly Met Asn Arg Ala Tyr Gly Asp Val Phe
 1               5                  10                  15

Arg Glu Leu Arg Asp Arg Trp Tyr Ala Thr Ser His His Thr Arg Pro
            20                  25                  30

Thr Pro Gln Leu Pro Arg Gly Pro Asn
        35                  40

(2) INFORMATION FOR SEQ ID NO: 274:

(i) SEQUENCE CHARACTERISTICS:
        (A) LENGTH: 42 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 274:

Xaa Ser Gly Ser His Ser Gly Gly Met Asn Arg Ala Tyr Gly Asp Val
 1               5                  10                  15

Phe Arg Glu Leu Arg Asp Arg Trp Tyr Ala Thr Ser His His Thr Arg
            20                  25                  30

Pro Thr Pro Gln Leu Pro Arg Gly Pro Asn
        35                  40

(2) INFORMATION FOR SEQ ID NO: 275:

(i) SEQUENCE CHARACTERISTICS:

```
        (A) LENGTH: 40 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=biotin-Lys(dns)

(xi) SEQUENCE DESCRIPTION: SEQ ID NO: 275:

Xaa Ser His Ser Gly Gly Met Asn Arg Ala Tyr Gly Asp Val Phe Arg
 1               5                  10                  15

Glu Leu Arg Asp Arg Trp Asn Ala Thr Ser His His Thr Arg Pro Thr
            20                  25                  30

Pro Gln Leu Pro Arg Gly Pro Asn
            35                  40

(2) INFORMATION FOR SEQ ID NO: 276:

(i) SEQUENCE CHARACTERISTICS:
        (A) LENGTH: 41 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 276:

Xaa Ser His Ser Gly Gly Met Asn Arg Ala Tyr Gly Asp Val Phe Arg
 1               5                  10                  15

Glu Leu Arg Asp Arg Trp Asn Ala Thr Ser His His Thr Arg Pro Thr
            20                  25                  30

Pro Gln Leu Pro Arg Gly Pro Asn Ser
            35                  40

(2) INFORMATION FOR SEQ ID NO: 277:

(i) SEQUENCE CHARACTERISTICS:
        (A) LENGTH: 45 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 277:

Xaa Ser Gln Gly Ser Lys Gln Cys Met Gln Tyr Arg Thr Gly Arg Leu
 1               5                  10                  15

Thr Val Gly Ser Glu Tyr Gly Cys Gly Met Asn Pro Ala Arg His Ala
            20                  25                  30

Thr Pro Ala Tyr Pro Ala Arg Leu Leu Pro Arg Tyr Arg
            35                  40                  45

(2) INFORMATION FOR SEQ ID NO: 278:
```

(i) SEQUENCE CHARACTERISTICS:
            (A) LENGTH: 45 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 278:

Xaa Arg Val Gly Gln Cys Thr Asp Ser Asp Val Arg Arg Pro Trp Ala
 1               5                  10                  15

Arg Ser Cys Ala His Gln Gly Cys Gly Ala Gly Thr Arg Asn Ser His
            20                  25                  30

Gly Cys Ile Thr Arg Pro Leu Arg Gln Ala Ser Ala His
        35                  40                  45

(2) INFORMATION FOR SEQ ID NO: 279:

(i) SEQUENCE CHARACTERISTICS:
            (A) LENGTH: 24 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=biotin-Lys(dns)

(xi) SEQUENCE DESCRIPTION: SEQ ID NO: 279:

Xaa Ser Gly Ser Gly Arg Val Gly Gln Cys Thr Asp Ser Asp Val Arg
 1               5                  10                  15

Arg Pro Trp Ala Arg Ser Cys Ala
            20

(2) INFORMATION FOR SEQ ID NO: 280:

(i) SEQUENCE CHARACTERISTICS:
            (A) LENGTH: 20 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 280:

Xaa Arg Val Gly Gln Cys Thr Asp Ser Asp Val Arg Arg Pro Trp Ala
 1               5                  10                  15

Arg Ser Cys Ala
            20

(2) INFORMATION FOR SEQ ID NO: 281:

(i) SEQUENCE CHARACTERISTICS:
            (A) LENGTH: 41 amino acids
            (B) TYPE: amino acid (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 281:

Xaa Ser Thr Pro Pro Ser Arg Glu Ala Tyr Ser Arg Pro Tyr Ser Val
 1               5                  10                  15

Asp Ser Asp Ser Asp Thr Asn Ala Lys His Ser Ser His Asn Arg Arg
            20                  25                  30

Leu Arg Thr Arg Ser Arg Pro Asn Gly
        35                  40

(2) INFORMATION FOR SEQ ID NO: 282:

(i) SEQUENCE CHARACTERISTICS:
            (A) LENGTH: 40 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 282:

Xaa Arg Gly Ser Thr Gly Thr Ala Gly Gly Glu Arg Ser Gly Val Leu
 1               5                  10                  15

Asn Leu His Thr Arg Asp Asn Ala Ser Gly Ser Gly Phe Lys Pro Trp
            20                  25                  30

Tyr Pro Ser Asn Arg Gly His Lys
        35                  40

(2) INFORMATION FOR SEQ ID NO: 283:

(i) SEQUENCE CHARACTERISTICS:
            (A) LENGTH: 20 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 283:

Xaa Ser Gly Ser Gly Leu Tyr Ala Asn Pro Gly Met Tyr Ser Arg Leu
 1               5                  10                  15

His Ser Pro Ala
        20

(2) INFORMATION FOR SEQ ID NO: 284:

(i) SEQUENCE CHARACTERISTICS:
            (A) LENGTH: 20 amino acids
            (B) TYPE: amino acid
            (C) STRANDEDNESS: single (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=biotin-Lys(dns)

(xi) SEQUENCE DESCRIPTION: SEQ ID NO: 284:

Xaa Ser Gly Ser Gly Leu Tyr Ala Asn Pro Gly Met Tyr Ser Arg Leu
 1               5                  10                  15

His Ser Pro Ala
            20

(2) INFORMATION FOR SEQ ID NO: 285:

(i) SEQUENCE CHARACTERISTICS:
            (A) LENGTH: 45 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 285:

Xaa Ser Asp His Ala Leu Gly Thr Asn Leu Arg Ser Asp Asn Ala Lys
 1               5                  10                  15

Glu Pro Gly Asp Tyr Asn Cys Cys Gly Asn Gly Asn Ser Thr Gly Arg
                20                  25                  30

Lys Val Phe Asn Arg Arg Arg Pro Ser Ala Ile Pro Thr
                35                  40                  45

(2) INFORMATION FOR SEQ ID NO: 286:

(i) SEQUENCE CHARACTERISTICS:
            (A) LENGTH: 42 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 286:

Xaa Ser Pro Cys Gly Gly Ser Trp Gly Arg Phe Met Gln Gly Gly Leu
 1               5                  10                  15

Phe Gly Gly Arg Thr Asp Gly Cys Gly Ala His Arg Asn Arg Thr Ser
                20                  25                  30

Ala Ser Leu Glu Pro Pro Ser Ser Asp Tyr
                35                  40

(2) INFORMATION FOR SEQ ID NO: 287:

(i) SEQUENCE CHARACTERISTICS:
            (A) LENGTH: 45 amino acids
            (B) TYPE: amino acid
            (C) STRANDEDNESS: single
            (D) TOPOLOGY: unknown (ii) MOLECULE TYPE: peptide (ix) FEATURE:
(A) NAME/KEY: Other
(B) LOCATION: 1...1
(D) OTHER INFORMATION: Xaa=Lys(dns)

(xi) SEQUENCE DESCRIPTION: SEQ ID NO: 287:

```
Xaa Arg Tyr Lys His Asp Ile Gly Cys Asp Ala Gly Val Asp Lys Lys
 1               5                  10                  15

Ser Ser Ser Val Arg Gly Gly Cys Gly Ala His Ser Ser Pro Pro Arg
                20                  25                  30

Ala Gly Arg Gly Pro Arg Gly Thr Met Val Ser Arg Leu
                35                  40                  45
```

(2) INFORMATION FOR SEQ ID NO: 288:

(i) SEQUENCE CHARACTERISTICS:
(A) LENGTH: 42 amino acids
(B) TYPE: amino acid
(C) STRANDEDNESS: single
(D) TOPOLOGY: unknown (ii) MOLECULE TYPE: peptide (ix) FEATURE:
(A) NAME/KEY: Other
(B) LOCATION: 1...1
(D) OTHER INFORMATION: Xaa=Lys(dns)

(xi) SEQUENCE DESCRIPTION: SEQ ID NO: 288:

```
Xaa Ser Ala Arg Asp Ser Gly Pro Ala Glu Asp Gly Ser Arg Ala Val
 1               5                  10                  15

Arg Leu Asn Gly Val Glu Asn Ala Asn Thr Arg Lys Ser Ser Arg Ser
                20                  25                  30

Asn Pro Arg Gly Arg Arg His Pro Gly Gly
                35                  40
```

(2) INFORMATION FOR SEQ ID NO: 289:

(i) SEQUENCE CHARACTERISTICS:
(A) LENGTH: 40 amino acids
(B) TYPE: amino acid
(C) STRANDEDNESS: single
(D) TOPOLOGY: unknown (ii) MOLECULE TYPE: peptide (ix) FEATURE:
(A) NAME/KEY: Other
(B) LOCATION: 1...1
(D) OTHER INFORMATION: Xaa=Lys(dns)

(xi) SEQUENCE DESCRIPTION: SEQ ID NO: 289:

```
Xaa Ser Lys Ser Gly Glu Gly Gly Asp Ser Ser Arg Gly Glu Thr Gly
 1               5                  10                  15

Trp Ala Arg Val Arg Ser His Ala Met Thr Ala Gly Arg Phe Arg Trp
                20                  25                  30

Tyr Asn Gln Leu Pro Ser Asp Arg
                35                  40
```

(2) INFORMATION FOR SEQ ID NO: 290:

(i) SEQUENCE CHARACTERISTICS:
(A) LENGTH: 41 amino acids
(B) TYPE: amino acid

```
         (C) STRANDEDNESS: single
         (D) TOPOLOGY: unknown (ii) MOLECULE TYPE: peptide (ix) FEATURE:
         (A) NAME/KEY: Other
         (B) LOCATION: 1...1
         (D) OTHER INFORMATION: Xaa=Lys(dns)

(xi) SEQUENCE DESCRIPTION: SEQ ID NO: 290:

Xaa Ser Glu Ala Asn Leu Asp Gly Arg Lys Ser Arg Tyr Ser Ser Pro
 1               5                  10                  15

Arg Arg Asn Ser Ser Thr Arg Pro Arg Thr Ser Pro Asn Ser Val His
            20                  25                  30

Ala Arg Tyr Pro Ser Thr Asp His Asp
            35                  40

(2) INFORMATION FOR SEQ ID NO: 291:

(i) SEQUENCE CHARACTERISTICS:
         (A) LENGTH: 44 amino acids
         (B) TYPE: amino acid
         (C) STRANDEDNESS: single
         (D) TOPOLOGY: unknown (ii) MOLECULE TYPE: peptide (ix) FEATURE:
         (A) NAME/KEY: Modified Base
         (B) LOCATION: 1...1
         (D) OTHER INFORMATION: Xaa=biotin-S (xi) SEQUENCE DESCRIPTION: SEQ ID NO: 291:

Xaa Gly Ser Gly Ser Thr Pro Pro Ser Arg Glu Ala Tyr Ser Arg Pro
 1               5                  10                  15

Tyr Ser Val Asp Ser Asp Ser Asp Thr Asn Ala Lys His Ser Ser His
            20                  25                  30

Asn Arg Arg Leu Arg Thr Arg Ser Arg Pro Asn Gly
            35                  40

(2) INFORMATION FOR SEQ ID NO: 292:

(i) SEQUENCE CHARACTERISTICS:
         (A) LENGTH: 23 amino acids
         (B) TYPE: amino acid
         (C) STRANDEDNESS: single
         (D) TOPOLOGY: unknown (ii) MOLECULE TYPE: peptide (ix) FEATURE:
         (A) NAME/KEY: Other
         (B) LOCATION: 1...1
         (D) OTHER INFORMATION: Xaa=Lys(dns)

(xi) SEQUENCE DESCRIPTION: SEQ ID NO: 292:

Xaa Arg Val Gly Gln Cys Thr Asp Ser Asp Val Arg Arg Pro Trp Ala
 1               5                  10                  15

Arg Ser Cys Ala His Gln Gly
            20

(2) INFORMATION FOR SEQ ID NO: 293:

(i) SEQUENCE CHARACTERISTICS:
         (A) LENGTH: 24 amino acids
         (B) TYPE: amino acid
         (C) STRANDEDNESS: single
```

(D) TOPOLOGY: unknown (ii) MOLECULE TYPE: peptide (ix) FEATURE:
          (A) NAME/KEY: Other
          (B) LOCATION: 1...1
          (D) OTHER INFORMATION: Xaa=Lys(dns)

(xi) SEQUENCE DESCRIPTION: SEQ ID NO: 293:

Xaa Cys Gly Ala Gly Thr Arg Asn Ser His Gly Cys Ile Thr Arg Pro
1               5                   10                  15

Leu Arg Gln Ala Ser Ala His Gly
            20

(2) INFORMATION FOR SEQ ID NO: 294:

(i) SEQUENCE CHARACTERISTICS:
          (A) LENGTH: 21 amino acids
          (B) TYPE: amino acid
          (C) STRANDEDNESS: single
          (D) TOPOLOGY: unknown (ii) MOLECULE TYPE: peptide (ix) FEATURE:
          (A) NAME/KEY: Other
          (B) LOCATION: 1...1
          (D) OTHER INFORMATION: Xaa=Lys(dns)

(xi) SEQUENCE DESCRIPTION: SEQ ID NO: 294:

Xaa Glu Asn Ala Asn Thr Arg Lys Ser Ser Arg Ser Asn Pro Arg Gly
1               5                   10                  15

Arg Arg His Pro Gly
            20

(2) INFORMATION FOR SEQ ID NO: 295:

(i) SEQUENCE CHARACTERISTICS:
          (A) LENGTH: 12 amino acids
          (B) TYPE: amino acid
          (C) STRANDEDNESS: single
          (D) TOPOLOGY: unknown (ii) MOLECULE TYPE: peptide (ix) FEATURE:
          (A) NAME/KEY: Other
          (B) LOCATION: 1...1
          (D) OTHER INFORMATION: Xaa=Lys(dns)

(xi) SEQUENCE DESCRIPTION: SEQ ID NO: 295:

Xaa Thr Arg Lys Ser Ser Arg Ser Asn Pro Arg Gly
1               5                   10

(2) INFORMATION FOR SEQ ID NO: 296:

(i) SEQUENCE CHARACTERISTICS:
          (A) LENGTH: 16 amino acids
          (B) TYPE: amino acid
          (C) STRANDEDNESS: single
          (D) TOPOLOGY: unknown (ii) MOLECULE TYPE: peptide (ix) FEATURE:
          (A) NAME/KEY: Other
          (B) LOCATION: 1...1
          (D) OTHER INFORMATION: Xaa=Lys(dns)

(xi) SEQUENCE DESCRIPTION: SEQ ID NO: 296:

```
Xaa Glu Asn Ala Asn Thr Arg Lys Ser Ser Arg Ser Asn Pro Arg Gly
 1               5                  10                  15
```

(2) INFORMATION FOR SEQ ID NO: 297:

(i) SEQUENCE CHARACTERISTICS:
        (A) LENGTH: 17 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 297:

```
Xaa Thr Arg Lys Ser Ser Arg Ser Asn Pro Arg Gly Arg Arg His Pro
 1               5                  10                  15
Gly
```

(2) INFORMATION FOR SEQ ID NO: 298:

(i) SEQUENCE CHARACTERISTICS:
        (A) LENGTH: 20 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 298:

```
Xaa Thr Asn Ala Lys His Ser Ser His Asn Arg Arg Leu Arg Thr Arg
 1               5                  10                  15
Ser Arg Pro Asn
            20
```

(2) INFORMATION FOR SEQ ID NO: 299:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 299:

```
Xaa Thr Asn Ala Lys His Ser Ser His Asn Arg Arg Leu Arg Thr Arg
 1               5                  10                  15
```

(2) INFORMATION FOR SEQ ID NO: 300:

(i) SEQUENCE CHARACTERISTICS:
        (A) LENGTH: 15 amino acids
        (B) TYPE: amino acid
        (C) STRANDEDNESS: single

```
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 300:

Xaa Ser Ser His Asn Arg Arg Leu Arg Thr Arg Ser Arg Pro Asn
 1               5                  10                  15

(2) INFORMATION FOR SEQ ID NO: 301:

(i) SEQUENCE CHARACTERISTICS:
            (A) LENGTH: 11 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 301:

Xaa Ser Ser His Asn Arg Arg Leu Arg Thr Arg
 1               5                  10

(2) INFORMATION FOR SEQ ID NO: 302:

(i) SEQUENCE CHARACTERISTICS:
            (A) LENGTH: 22 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 302:

Xaa Val Arg Arg Pro Trp Ala Arg Ser Cys Ala His Gln Gly Cys Gly
 1               5                  10                  15

Ala Gly Thr Arg Asn Ser
            20

(2) INFORMATION FOR SEQ ID NO: 303:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 303:

Xaa Cys Thr Asp Ser Asp Val Arg Arg Pro Trp Ala Arg Ser Cys
 1               5                  10                  15
```

(2) INFORMATION FOR SEQ ID NO: 304:

(i) SEQUENCE CHARACTERISTICS:
        (A) LENGTH: 41 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 304:

```
Xaa Ser Arg Ala Asn Thr Asp Gly Arg Lys Ser Arg Tyr Ser Ser Pro
 1               5                  10                  15

Arg Arg Asn Ser Ser Thr Glu Pro Arg Leu Ser Pro Asn Ser Val His
            20                  25                  30

Ala Arg Tyr Pro Ser Thr Asp His Asp
        35                  40
```

(2) INFORMATION FOR SEQ ID NO: 305:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 305:

```
Xaa Glu Asn Ala Asn Thr Arg Lys Ser Ser Arg
 1               5                  10
```

(2) INFORMATION FOR SEQ ID NO: 306:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 306:

```
Xaa Ser Asn Pro Arg Gly Arg Arg His Pro Gly
 1               5                  10
```

(2) INFORMATION FOR SEQ ID NO: 307:

(i) SEQUENCE CHARACTERISTICS:
        (A) LENGTH: 6 amino acids
        (B) TYPE: amino acid
        (C) STRANDEDNESS: single
        (D) TOPOLOGY: unknown

```
    (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 307:

Xaa Glu Asn Ala Asn Thr
1               5

(2) INFORMATION FOR SEQ ID NO: 308:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 308:

Xaa Ala Asn Thr Arg Lys Ser
1               5

(2) INFORMATION FOR SEQ ID NO: 309:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 309:

Xaa Thr Arg Lys Ser Ser
1               5

(2) INFORMATION FOR SEQ ID NO: 310:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 310:

Xaa Arg Lys Ser Ser Arg
1               5

(2) INFORMATION FOR SEQ ID NO: 311:

(i) SEQUENCE CHARACTERISTICS:
```

(A) LENGTH: 7 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 311:

Xaa Lys Ser Ser Arg Ser Asn
1               5

(2) INFORMATION FOR SEQ ID NO: 312:

(i) SEQUENCE CHARACTERISTICS:
            (A) LENGTH: 8 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 312:

Xaa Ser Ser Arg Ser Asn Pro Gly
1               5

(2) INFORMATION FOR SEQ ID NO: 313:

(i) SEQUENCE CHARACTERISTICS:
            (A) LENGTH: 7 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 313:

Xaa Arg Ser Asn Pro Arg Gly
1               5

(2) INFORMATION FOR SEQ ID NO: 314:

(i) SEQUENCE CHARACTERISTICS:
            (A) LENGTH: 6 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 314:

Xaa Ser Asn Pro Arg Gly
1               5

(2) INFORMATION FOR SEQ ID NO: 315:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 315:

Xaa Pro Arg Gly Arg Arg His
1               5

(2) INFORMATION FOR SEQ ID NO: 316:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 316:

Xaa Arg Arg His Pro Gly
1               5

(2) INFORMATION FOR SEQ ID NO: 317:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 317:

Xaa Lys Ser Ser Arg Gly Asn
1               5

(2) INFORMATION FOR SEQ ID NO: 318:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 318:

Xaa Lys Thr Ser Glu Arg Ser Gln Pro Arg Gly Arg Arg Gln Pro Gly
1               5                   10                  15

(2) INFORMATION FOR SEQ ID NO: 319:

(i) SEQUENCE CHARACTERISTICS:
        (A) LENGTH: 17 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 319:

Xaa Thr Arg Lys Ser Ser Arg Ser Asn Pro Arg Gly Arg Arg His Pro
1               5                   10                  15
Gly (2) INFORMATION FOR SEQ ID NO: 320:

(i) SEQUENCE CHARACTERISTICS:
        (A) LENGTH: 17 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 320:

Xaa Thr Arg Lys Ser Ser Arg Ser Asn Pro Arg Gly Arg Arg His Pro
1               5                   10                  15
Gly (2) INFORMATION FOR SEQ ID NO: 321:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 321:

Xaa Thr Asn Ala Lys His Ser Ser His Asn
1               5                   10

(2) INFORMATION FOR SEQ ID NO: 322:

(i) SEQUENCE CHARACTERISTICS:
        (A) LENGTH: 11 amino acids
        (B) TYPE: amino acid

```
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 322:

Xaa Arg Arg Leu Arg Thr Arg Ser Arg Pro Asn
 1               5                  10

(2) INFORMATION FOR SEQ ID NO: 323:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 323:

Xaa Arg Arg Leu Arg Thr Arg Ser Arg
 1               5

(2) INFORMATION FOR SEQ ID NO: 324:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 324:

Xaa Arg Arg Leu Arg Thr Arg
 1               5

(2) INFORMATION FOR SEQ ID NO: 325:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 325:

Xaa Arg Arg Leu Arg Thr Arg Ser Arg Pro Asn
 1               5                  10
```

(2) INFORMATION FOR SEQ ID NO: 326:

(i) SEQUENCE CHARACTERISTICS:
        (A) LENGTH: 27 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 326:

```
Xaa Ser Asp His Ala Leu Gly Thr Asn Leu Arg Ser Asp Asn Ala Lys
 1               5                  10                  15

Glu Pro Gly Asp Tyr Asn Cys Cys Gly Asn Gly
             20                  25
```

(2) INFORMATION FOR SEQ ID NO: 327:

(i) SEQUENCE CHARACTERISTICS:
        (A) LENGTH: 28 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 327:

```
Xaa Gly Asp Tyr Asn Cys Cys Gly Asn Gly Asn Ser Thr Gly Arg Lys
 1               5                  10                  15

Val Phe Asn Arg Arg Arg Pro Ser Ala Ile Pro Thr
             20                  25
```

(2) INFORMATION FOR SEQ ID NO: 328:

(i) SEQUENCE CHARACTERISTICS:
        (A) LENGTH: 20 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 328:

```
Xaa Ser Asp His Ala Leu Gly Thr Asn Leu Arg Ser Asp Asn Ala Lys
 1               5                  10                  15

Glu Pro Gly Cys
             20
```

(2) INFORMATION FOR SEQ ID NO: 329:

(i) SEQUENCE CHARACTERISTICS:
        (A) LENGTH: 14 amino acids
        (B) TYPE: amino acid
        (C) STRANDEDNESS: single
        (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 329:

Xaa Gly Asp Tyr Asn Cys Cys Gly Asn Gly Asn Ser Thr Gly
1               5                   10

(2) INFORMATION FOR SEQ ID NO: 330:

(i) SEQUENCE CHARACTERISTICS:
            (A) LENGTH: 15 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 330:

Xaa Arg Lys Val Phe Asn Arg Arg Arg Pro Ser Ala Ile Pro Thr
1               5                   10                  15

(2) INFORMATION FOR SEQ ID NO: 331:

(i) SEQUENCE CHARACTERISTICS:
            (A) LENGTH: 11 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 331:

Xaa Arg Lys Val Phe Asn Arg Arg Arg Pro Ser
1               5                   10

(2) INFORMATION FOR SEQ ID NO: 332:

(i) SEQUENCE CHARACTERISTICS:
            (A) LENGTH: 11 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 332:

Xaa Asn Arg Arg Arg Pro Ser Ala Ile Pro Thr
1               5                   10

(2) INFORMATION FOR SEQ ID NO: 333:

(i) SEQUENCE CHARACTERISTICS:
    (A) LENGTH: 7 amino acids
    (B) TYPE: amino acid
    (C) STRANDEDNESS: single
    (D) TOPOLOGY: unknown (ii) MOLECULE TYPE: peptide (ix) FEATURE:
    (A) NAME/KEY: Other
    (B) LOCATION: 1...1
    (D) OTHER INFORMATION: Xaa=Lys(dns)

(xi) SEQUENCE DESCRIPTION: SEQ ID NO: 333:

Xaa Asn Arg Arg Arg Pro Ser
 1               5

(2) INFORMATION FOR SEQ ID NO: 334:

(i) SEQUENCE CHARACTERISTICS:
        (A) LENGTH: 40 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 334:

Ser Thr Pro Pro Ser Arg Glu Ala Tyr Ser Arg Pro Tyr Ser Val Asp
 1               5                  10                  15

Ser Asp Ser Asp Thr Asn Ala Lys His Ser Ser His Asn Arg Arg Leu
            20                  25                  30

Arg Thr Arg Ser Arg Pro Asn Gly
        35                  40

(2) INFORMATION FOR SEQ ID NO: 335:

(i) SEQUENCE CHARACTERISTICS:
        (A) LENGTH: 44 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 335:

Ser Asp His Ala Leu Gly Thr Asn Leu Arg Ser Asp Asn Ala Lys Glu
 1               5                  10                  15

Pro Gly Asp Tyr Asn Cys Cys Gly Asn Gly Asn Ser Thr Gly Arg Lys
            20                  25                  30

Val Phe Asn Arg Arg Arg Pro Ser Ala Ile Pro Thr
        35                  40

(2) INFORMATION FOR SEQ ID NO: 336:

(i) SEQUENCE CHARACTERISTICS:
        (A) LENGTH: 30 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 336:

```
Xaa Ser Asp His Ala Leu Gly Thr Asn Leu Arg Ser Asp Asn Ala Lys
 1               5                  10                  15

Glu Pro Gly Asp Tyr Asn Cys Cys Gly Asn Gly Asn Ser Thr
                20                  25                  30

(2) INFORMATION FOR SEQ ID NO: 337:

(i) SEQUENCE CHARACTERISTICS:
        (A) LENGTH: 30 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 337:

Xaa Asn Leu Arg Ser Asp Asn Ala Lys Glu Pro Gly Asp Tyr Asn Cys
 1               5                  10                  15

Cys Gly Asn Gly Asn Ser Thr Gly Arg Lys Val Phe Asn Arg
                20                  25                  30

(2) INFORMATION FOR SEQ ID NO: 338:

(i) SEQUENCE CHARACTERISTICS:
        (A) LENGTH: 28 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 338:

Xaa Pro Gly Asp Tyr Asn Cys Cys Gly Asn Gly Asn Ser Thr Gly Arg
 1               5                  10                  15

Lys Val Phe Asn Arg Arg Pro Ser Ala Ile Pro Thr
                20                  25

(2) INFORMATION FOR SEQ ID NO: 339:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 339:

Xaa Ala Ser His Asn Arg Arg Leu Arg Thr Arg
 1               5                  10

(2) INFORMATION FOR SEQ ID NO: 340:
```

```
    (i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 340:

Xaa Ser Ala His Asn Arg Arg Leu Arg Thr Arg
 1               5                   10

(2) INFORMATION FOR SEQ ID NO: 341:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 341:

Xaa Ser Ser Ala Asn Arg Arg Leu Arg Thr Arg
 1               5                   10

(2) INFORMATION FOR SEQ ID NO: 342:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 342:

Xaa Ser Ser His Ala Arg Arg Leu Arg Thr Arg
 1               5                   10

(2) INFORMATION FOR SEQ ID NO: 343:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 343:

Xaa Ser Ser His Asn Ala Arg Leu Arg Thr Arg
```

```
                1               5                    10
```

(2) INFORMATION FOR SEQ ID NO: 344:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 344:

```
Xaa Ser Ser His Asn Arg Ala Leu Arg Thr Arg
1               5                    10
```

(2) INFORMATION FOR SEQ ID NO: 345:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 345:

```
Xaa Ser Ser His Asn Arg Arg Ala Arg Thr Arg
1               5                    10
```

(2) INFORMATION FOR SEQ ID NO: 346:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 346:

```
Xaa Ser Ser His Asn Arg Arg Leu Ala Thr Arg
1               5                    10
```

(2) INFORMATION FOR SEQ ID NO: 347:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1

(D) OTHER INFORMATION: Xaa=Lys(dns)

(xi) SEQUENCE DESCRIPTION: SEQ ID NO: 347:

Xaa Ser Ser His Asn Arg Arg Leu Arg Ala Arg
1               5                   10

(2) INFORMATION FOR SEQ ID NO: 348:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 348:

Xaa Ser Ser His Asn Arg Arg Leu Arg Thr Ala
1               5                   10

(2) INFORMATION FOR SEQ ID NO: 349:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 349:

Ser Ser His Asn Arg Arg Leu Arg Thr Arg
1               5                   10

(2) INFORMATION FOR SEQ ID NO: 350:

(i) SEQUENCE CHARACTERISTICS:
        (A) LENGTH: 41 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 350:

Xaa Gly Arg Asn His Asp Val Val Ser Ser Asn Thr His Lys Ser Tyr
1               5                   10                  15

Arg Ser Pro Arg Ser Ala Ser Tyr Pro Arg Leu Ser Asn Asp Arg Thr
                20                  25                  30

Asp Arg Thr Glu Pro Ala Pro Ser Ser
            35                  40

(2) INFORMATION FOR SEQ ID NO: 351:

(i) SEQUENCE CHARACTERISTICS:
        (A) LENGTH: 20 amino acids
        (B) TYPE: amino acid
        (C) STRANDEDNESS: single
        (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 351:

Xaa Arg Asn Thr Arg Asn Lys Thr Ser Arg Leu Ser Ala Asn Pro His
 1               5                  10                  15

Arg Ser His Arg
            20

(2) INFORMATION FOR SEQ ID NO: 352:

(i) SEQUENCE CHARACTERISTICS:
            (A) LENGTH: 20 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 20...20
            (D) OTHER INFORMATION: Xaa=Lys(dns)

(xi) SEQUENCE DESCRIPTION: SEQ ID NO: 352:

Thr Asn Ala Lys His Ser Ser His Asn Arg Arg Leu Arg Thr Arg Ser
 1               5                  10                  15

Arg Pro Asn Xaa
            20

(2) INFORMATION FOR SEQ ID NO: 353:

(i) SEQUENCE CHARACTERISTICS:
            (A) LENGTH: 10 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 10...10
            (D) OTHER INFORMATION: Xaa=Lys(dns)

(xi) SEQUENCE DESCRIPTION: SEQ ID NO: 353:

Arg Arg Leu Arg Thr Arg Ser Arg Lys Xaa
 1               5                  10

(2) INFORMATION FOR SEQ ID NO: 354:

(i) SEQUENCE CHARACTERISTICS:
            (A) LENGTH: 21 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 354:

-continued

```
Xaa Ser Asp His Ala Leu Gly Thr Asn Leu Arg Ser Asp Asn Ala Lys
 1               5                  10                  15
Glu Pro Gly Asp Tyr
            20

(2) INFORMATION FOR SEQ ID NO: 355:

(i) SEQUENCE CHARACTERISTICS:
         (A) LENGTH: 21 amino acids
         (B) TYPE: amino acid
         (C) STRANDEDNESS: single
         (D) TOPOLOGY: unknown (ii) MOLECULE TYPE: peptide (ix) FEATURE:
         (A) NAME/KEY: Other
         (B) LOCATION: 1...1
         (D) OTHER INFORMATION: Xaa=Lys(dns)

(xi) SEQUENCE DESCRIPTION: SEQ ID NO: 355:

Xaa Ser Asp Asn Ala Lys Glu Pro Gly Asp Tyr Asn Cys Cys Gly Asn
 1               5                  10                  15
Gly Asn Ser Thr Gly
            20

(2) INFORMATION FOR SEQ ID NO: 356:

(i) SEQUENCE CHARACTERISTICS:
         (A) LENGTH: 16 amino acids
         (B) TYPE: amino acid
         (C) STRANDEDNESS: single
         (D) TOPOLOGY: unknown (ii) MOLECULE TYPE: peptide (ix) FEATURE:
         (A) NAME/KEY: Other
         (B) LOCATION: 1...1
         (D) OTHER INFORMATION: Xaa=Lys(dns)

(xi) SEQUENCE DESCRIPTION: SEQ ID NO: 356:

Xaa Ser Asp His Ala Leu Gly Thr Asn Leu Arg Ser Asp Asn Ala Lys
 1               5                  10                  15

(2) INFORMATION FOR SEQ ID NO: 357:

(i) SEQUENCE CHARACTERISTICS:
         (A) LENGTH: 16 amino acids
         (B) TYPE: amino acid
         (C) STRANDEDNESS: single
         (D) TOPOLOGY: unknown (ii) MOLECULE TYPE: peptide (ix) FEATURE:
         (A) NAME/KEY: Other
         (B) LOCATION: 1...1
         (D) OTHER INFORMATION: Xaa=Lys(dns)

(xi) SEQUENCE DESCRIPTION: SEQ ID NO: 357:

Xaa Glu Pro Gly Asp Tyr Asn Cys Cys Gly Asn Gly Asn Ser Thr Gly
 1               5                  10                  15

(2) INFORMATION FOR SEQ ID NO: 358:

(i) SEQUENCE CHARACTERISTICS:
         (A) LENGTH: 15 amino acids
         (B) TYPE: amino acid
         (C) STRANDEDNESS: single
```

```
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 358:

Xaa Pro Gly Asp Tyr Asn Cys Cys Gly Asn Gly Asn Ser Thr Gly
 1               5                  10                  15

(2) INFORMATION FOR SEQ ID NO: 359:

(i) SEQUENCE CHARACTERISTICS:
            (A) LENGTH: 11 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 359:

Xaa Pro Gly Asp Tyr Asn Cys Cys Gly Asn Gly
 1               5                  10

(2) INFORMATION FOR SEQ ID NO: 360:

(i) SEQUENCE CHARACTERISTICS:
            (A) LENGTH: 11 amino acids
            (B) TYPE: amino acid
            (C) STRANDEDNESS: single
            (D) TOPOLOGY: unknown (ii) MOLECULE TYPE: peptide (vi) ORIGINAL SOURCE:
            (A) ORGANISM: MEMORY
            (B) STRAIN: DISPLAY MEMORY (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 360:

Xaa Asn Cys Cys Gly Asn Gly Asn Ser Thr Gly
 1               5                  10

(2) INFORMATION FOR SEQ ID NO: 361:

(i) SEQUENCE CHARACTERISTICS:
            (A) LENGTH: 18 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 361:

Xaa Lys Thr Arg Lys Ser Ser Arg Ser Asn Pro Arg Gly Arg Arg His
```

-continued

```
 1               5                  10                 15
Pro Gly (2) INFORMATION FOR SEQ ID NO: 362:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 362:

Xaa Lys Thr Arg Lys Ser Ser Arg Ser Asn Pro Arg Gly Arg Arg His
 1               5                  10                 15
Pro Gly (2) INFORMATION FOR SEQ ID NO: 363:

(i) SEQUENCE CHARACTERISTICS:
        (A) LENGTH: 17 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 363:

Xaa Lys Thr Asn Ala Lys His Ser Ser His Asn Arg Arg Leu Arg Thr
 1               5                  10                 15
Arg (2) INFORMATION FOR SEQ ID NO: 364:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 364:

Xaa Thr Asn Ala Lys His Ser Ser Cys Asn Arg Arg Cys Arg Thr Arg
 1               5                  10                 15

(2) INFORMATION FOR SEQ ID NO: 365:

(i) SEQUENCE CHARACTERISTICS:
        (A) LENGTH: 16 amino acids
        (B) TYPE: amino acid
        (C) STRANDEDNESS: single
        (D) TOPOLOGY: unknown
```

(ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 365:

Xaa Thr Asn Ala Lys His Ser Ser Cys Asn Arg Arg Leu Arg Cys Arg
 1               5                  10                  15

(2) INFORMATION FOR SEQ ID NO: 366:

(i) SEQUENCE CHARACTERISTICS:
            (A) LENGTH: 16 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 366:

Xaa Ala Asn Ala Lys His Ser Ser His Asn Arg Arg Leu Arg Thr Arg
 1               5                  10                  15

(2) INFORMATION FOR SEQ ID NO: 367:

(i) SEQUENCE CHARACTERISTICS:
            (A) LENGTH: 16 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 367:

Xaa Thr Ala Ala Lys Asn Ser Ser His Asn Arg Arg Leu Arg Thr Arg
 1               5                  10                  15

(2) INFORMATION FOR SEQ ID NO: 368:

(i) SEQUENCE CHARACTERISTICS:
            (A) LENGTH: 16 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 368:

Xaa Thr Asn Gly Lys Asn Ser Ser His Asn Arg Arg Leu Arg Thr Arg
 1               5                  10                  15

(2) INFORMATION FOR SEQ ID NO: 369:

```
    (i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 369:

Xaa Thr Asn Ala Lys Ala Ser Ser His Asn Arg Arg Leu Arg Thr Arg
 1               5                  10                  15

(2) INFORMATION FOR SEQ ID NO: 370:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 370:

Xaa Thr Asn Ala Lys His Ala Ser His Asn Arg Arg Leu Arg Thr Arg
 1               5                  10                  15

(2) INFORMATION FOR SEQ ID NO: 371:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 371:

Xaa Thr Asn Ala Lys His Ser Ala His Asn Arg Arg Leu Arg Thr Arg
 1               5                  10                  15

(2) INFORMATION FOR SEQ ID NO: 372:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 372:

Xaa Thr Asn Ala Lys His Ser Ser Ala Asn Arg Arg Leu Arg Thr Arg
```

(2) INFORMATION FOR SEQ ID NO: 373:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 373:

```
Xaa Thr Asn Ala Lys His Ser Ser His Ala Arg Arg Leu Arg Thr Arg
 1               5                  10                  15
```

(2) INFORMATION FOR SEQ ID NO: 374:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 374:

```
Xaa Thr Asn Ala Lys His Ser Ser His Asn Ala Arg Leu Arg Thr Arg
 1               5                  10                  15
```

(2) INFORMATION FOR SEQ ID NO: 375:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 375:

```
Xaa Thr Asn Ala Lys His Ser Ser His Asn Arg Ala Leu Arg Thr Arg
 1               5                  10                  15
```

(2) INFORMATION FOR SEQ ID NO: 376:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1

(D) OTHER INFORMATION: Xaa=Lys(dns)

(xi) SEQUENCE DESCRIPTION: SEQ ID NO: 376:

Xaa Thr Asn Ala Lys His Ser Ser His Asn Arg Arg Ala Arg Thr Arg
 1               5                   10                  15

(2) INFORMATION FOR SEQ ID NO: 377:

(i) SEQUENCE CHARACTERISTICS:
            (A) LENGTH: 16 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 377:

Xaa Thr Asn Ala Lys His Ser Ser His Asn Arg Arg Leu Ala Thr Arg
 1               5                   10                  15

(2) INFORMATION FOR SEQ ID NO: 378:

(i) SEQUENCE CHARACTERISTICS:
            (A) LENGTH: 16 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 378:

Xaa Thr Asn Ala Lys His Ser Ser His Asn Arg Arg Leu Arg Ala Arg
 1               5                   10                  15

(2) INFORMATION FOR SEQ ID NO: 379:

(i) SEQUENCE CHARACTERISTICS:
            (A) LENGTH: 16 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 379:

Xaa Thr Asn Ala Lys His Ser Ser His Asn Arg Arg Leu Arg Thr Ala
 1               5                   10                  15

(2) INFORMATION FOR SEQ ID NO: 380:

(i) SEQUENCE CHARACTERISTICS:
            (A) LENGTH: 16 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 380:

Xaa Thr Asn Ala Lys His Ser Ser His Asn Arg Arg Leu Arg Thr Arg
 1               5                  10                  15

(2) INFORMATION FOR SEQ ID NO: 381:

(i) SEQUENCE CHARACTERISTICS:
            (A) LENGTH: 17 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 381:

Xaa Lys Thr Asn Ala Lys His Ser Ser His Asn Arg Arg Leu Arg Thr
 1               5                  10                  15
Arg (2) INFORMATION FOR SEQ ID NO: 382:

(i) SEQUENCE CHARACTERISTICS:
            (A) LENGTH: 16 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 382:

Xaa Thr Asn Ala Lys His Ser Ser His Asn Arg Arg Leu Arg Thr Arg
 1               5                  10                  15

(2) INFORMATION FOR SEQ ID NO: 383:

(i) SEQUENCE CHARACTERISTICS:
            (A) LENGTH: 12 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 383:

Xaa Lys Ser Ser His Asn Arg Arg Leu Arg Thr Arg
 1               5                  10

(2) INFORMATION FOR SEQ ID NO: 384:

```
    (i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 384:

Xaa Lys Ser Ser His Asn Arg Arg Leu Arg Thr Arg
 1               5                  10

(2) INFORMATION FOR SEQ ID NO: 385:

(i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 385:

Xaa Lys Thr Asn Ala Lys His Ser Ser His Asn Arg
 1               5                  10

(2) INFORMATION FOR SEQ ID NO: 386:

(i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 386:

Xaa Lys Thr Asn Ala Lys His Ser Ser His Asn Arg
 1               5                  10

(2) INFORMATION FOR SEQ ID NO: 387:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 387:
```

```
Xaa Thr Asn Ala Lys His Ser Ser His Asn Arg Arg Leu Arg Thr Arg
1               5                   10                  15
```

(2) INFORMATION FOR SEQ ID NO: 388:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 388:

```
Xaa Ala Gly Asp Tyr Asn Cys Cys Gly Asn Gly Asn Ser Thr Gly
1               5                   10                  15
```

(2) INFORMATION FOR SEQ ID NO: 389:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 389:

```
Xaa Pro Ala Asp Tyr Asn Cys Cys Gly Asn Gly Asn Ser Thr Gly
1               5                   10                  15
```

(2) INFORMATION FOR SEQ ID NO: 390:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 390:

```
Xaa Pro Gly Ala Tyr Asn Cys Cys Gly Asn Gly Asn Ser Thr Gly
1               5                   10                  15
```

(2) INFORMATION FOR SEQ ID NO: 391:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other

```
        (B) LOCATION: 1...1
        (D) OTHER INFORMATION: Xaa=Lys(dns)

(xi) SEQUENCE DESCRIPTION: SEQ ID NO: 391:

Xaa Pro Gly Asp Ala Asn Cys Cys Gly Asn Gly Asn Ser Thr Gly
 1               5                  10                  15

(2) INFORMATION FOR SEQ ID NO: 392:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 392:

Xaa Pro Gly Asp Tyr Ala Cys Cys Gly Asn Gly Asn Ser Thr Gly
 1               5                  10                  15

(2) INFORMATION FOR SEQ ID NO: 393:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 393:

Xaa Pro Gly Asp Tyr Asn Ala Cys Gly Asn Gly Asn Ser Thr Gly
 1               5                  10                  15

(2) INFORMATION FOR SEQ ID NO: 394:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 394:

Xaa Pro Gly Asp Tyr Asn Cys Ala Gly Asn Gly Asn Ser Thr Gly
 1               5                  10                  15

(2) INFORMATION FOR SEQ ID NO: 395:

(i) SEQUENCE CHARACTERISTICS:
        (A) LENGTH: 15 amino acids
        (B) TYPE: amino acid
        (C) STRANDEDNESS: single
        (D) TOPOLOGY: unknown
```

```
        (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 395:

Xaa Pro Gly Asp Tyr Asn Cys Cys Ala Asn Gly Asn Ser Thr Gly
 1               5                  10                  15

(2) INFORMATION FOR SEQ ID NO: 396:

(i) SEQUENCE CHARACTERISTICS:
             (A) LENGTH: 15 amino acids
             (B) TYPE: amino acid
             (C) STRANDEDNESS: single
             (D) TOPOLOGY: unknown (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 396:

Xaa Pro Gly Asp Tyr Asn Cys Cys Gly Ala Gly Asn Ser Thr Gly
 1               5                  10                  15

(2) INFORMATION FOR SEQ ID NO: 397:

(i) SEQUENCE CHARACTERISTICS:
             (A) LENGTH: 15 amino acids
             (B) TYPE: amino acid
             (C) STRANDEDNESS: single
             (D) TOPOLOGY: unknown (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 397:

Xaa Pro Gly Asp Tyr Asn Cys Cys Gly Asn Ala Asn Ser Thr Gly
 1               5                  10                  15

(2) INFORMATION FOR SEQ ID NO: 398:

(i) SEQUENCE CHARACTERISTICS:
             (A) LENGTH: 15 amino acids
             (B) TYPE: amino acid
             (C) STRANDEDNESS: single
             (D) TOPOLOGY: unknown (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 398:

Xaa Pro Gly Asp Tyr Asn Cys Cys Gly Asn Gly Ala Ser Thr Gly
 1               5                  10                  15

(2) INFORMATION FOR SEQ ID NO: 399:
```

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 399:

Xaa Pro Gly Asp Tyr Asn Cys Cys Gly Asn Gly Asn Ala Thr Gly
 1               5                  10                  15

(2) INFORMATION FOR SEQ ID NO: 400:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 400:

Xaa Pro Gly Asp Tyr Asn Cys Cys Gly Asn Gly Asn Ser Ala Gly
 1               5                  10                  15

(2) INFORMATION FOR SEQ ID NO: 401:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 401:

Xaa Pro Gly Asp Tyr Asn Cys Cys Gly Asn Gly Asn Ser Thr Ala
 1               5                  10                  15

(2) INFORMATION FOR SEQ ID NO: 402:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 402:

Thr Asn Ala Lys His Ser Ser His Asn Arg Arg Leu Arg Thr Arg
 1               5                  10                  15

(2) INFORMATION FOR SEQ ID NO: 403:

```
    (i) SEQUENCE CHARACTERISTICS:
        (A) LENGTH: 14 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 403:

Pro Gly Asp Tyr Asn Cys Cys Gly Asn Cys Asn Ser Thr Gly
 1               5                  10

(2) INFORMATION FOR SEQ ID NO: 404:

(i) SEQUENCE CHARACTERISTICS:
        (A) LENGTH: 40 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 404:

Ser Ala Arg Asp Ser Gly Pro Ala Glu Asp Gly Ser Arg Ala Val Arg
 1               5                  10                  15

Leu Asn Gly Val Glu Asn Ala Asn Thr Arg Lys Ser Ser Arg Ser Asn
            20                  25                  30

Pro Arg Gly Arg Arg His Pro Gly
        35                  40

(2) INFORMATION FOR SEQ ID NO: 405:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 405:

Gly Thr Arg Asn Ser His Gly Cys Ile Thr Arg Pro Leu Arg Gln Ala
 1               5                  10                  15

Ser Ala His (2) INFORMATION FOR SEQ ID NO: 406:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 406:

Xaa Arg Val Gly Gln Cys Thr Asp Ser Asp Val Arg Arg Pro Trp Ala
 1               5                  10                  15

Arg Ser Cys Ala His
            20

(2) INFORMATION FOR SEQ ID NO: 407:
```

```
    (i) SEQUENCE CHARACTERISTICS:
        (A) LENGTH: 23 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 407:

Xaa Cys Gly Ala Gly Thr Arg Asn Ser His Gly Cys Ile Thr Arg Pro
 1               5                  10                  15

Leu Arg Gln Ala Ser Ala His
                20
```

RANDOM PEPTIDES THAT BIND TO GASTRO-INTESTINAL TRACT (GIT) TRANSPORT RECEPTORS AND RELATED METHODS

This application claims priority to U.S. provisional application Ser. No. 60/046,595 filed May 15, 1997, which is incorporated by reference herein in its entirety.

1. INTRODUCTION

The present invention relates generally to random peptides capable of specific binding to gastro-intestinal tract (GIT) transport receptors. In particular, this invention relates to peptide sequences and motifs, as well as derivatives thereof, which enhance drug delivery and transport through tissue, such as epithelial cells lining the lumenal side of the gastro-intestinal tract (GIT). Production of peptides, derivatives and antibodies is also provided. The invention further relates to pharmaceutical compositions, formulations and related methods.

2. BACKGROUND OF THE INVENTION

2.1. Peptide Libraries

There have been two different approaches to the construction of random peptide libraries. According to one approach, peptides have been chemically synthesized in vitro in several formats. Examples of chemically synthesized libraries can be found in Fodor, S., et al., 1991, Science 251: 767–773; Houghten, R., et al., 1991, Nature 354: 84–86; and Lam, K., et al., 1991, Nature 354: 82–84.

A second approach to the construction of random peptide libraries has been to use the M13 phage, and, in particular, protein pIII of M13. The viral capsid protein of M13, protein III (pIII), is responsible for infection of bacteria. Several investigators have determined from mutational analysis that the 406 amino acid long pIII capsid protein has two domains. The C-terminus anchors the protein to the viral coat, while portions of the N-terminus of pIII are essential for interaction with the *E. coli* pillin protein (Crissman, J. W. and Smith, G. P., 1984, Virology 132: 445–455). Although the N-terminus of the pIII protein has shown to be necessary for viral infection, the extreme N-terminus of the mature protein does tolerate alterations. In 1985, George Smith published experiments reporting the use of the pIII protein of bacteriophage M13 as an experimental system for expressing a heterologous protein on the viral coat surface (Smith, G. P., 1985, Science 228: 1315–1317). It was later recognized, independently by two groups, that the M13 phage pIII gene display system could be a useful one for mapping antibody epitopes (De la Cruz, V., et al., 1988, J. Biol. Chem. 263: 4318–4322; Parmley, S. F. and Smith, G. P., 1988, Gene 73: 305–318).

Parmley, S. F. and Smith, G. P., 1989, Adv. Exp. Med. Biol. 251: 215–218 suggested that short, synthetic DNA segments cloned into the pIII gene might represent a library of epitopes. These authors reasoned that since linear epitopes were often ~6 amino acids in length, it should be possible to use a random recombinant DNA library to express all possible hexapeptides to isolate epitopes that bind to antibodies. Scott, J. K. and Smith, G. P., 1990, Science 249: 386–390 describe construction and expression of an "epitope library" of hexapeptides on the surface of M13. Cwirla, S. E., et al., 1990, Proc. Natl. Acad. Sci. USA 87: 6378–6382 also described a somewhat similar library of hexapeptides expressed as gene pIII fusions of M13 fd phage. PCT Application WO 91/19818 published Dec. 26, 1991 by Dower and Cwirla describes a similar library of pentameric to octameric random amino acid sequences. Devlin et al., 1990, Science, 249: 404–406, describes a peptide library of about 15 residues generated using an (NNS) coding scheme for oligonucleotide synthesis in which S is G or C. Christian and colleagues have described a phage display library, expressing decapeptides (Christian, R. B., et al., 1992, J. Mol. Biol. 227: 711–718).

Other investigators have used other viral capsid proteins for expression of non-viral DNA on the surface of phage particles. For example, the major capsid protein pVIII was so used by Cesareni, G., 1992, FEBS Lett. 307: 66–70. Other bacteriophage than M13 have been used to construct peptide libraries. Four and six amino acid sequences corresponding to different segments of the *Plasmodium falciparum* major surface antigen have been cloned and expressed in the filamentous bacteriophage fd (Greenwood, J., et al., 1991, J. Mol. Biol. 220: 821–827).

Kay et al., 1993, Gene 128: 59–65 (Kay) discloses a method of constructing peptide libraries that encode peptides of totally random sequence that are longer than those of any prior conventional libraries. The libraries disclosed in Kay encode totally synthetic random peptides of greater than about 20 amino acids in length. Such libraries can be advantageously screened to identify peptides, polypeptides and/or other proteins having binding specificity for a variety of ligands. (See also U.S. Pat. No. 5,498,538 dated Mar. 12, 1996; and PCT Publication No. WO 94/18318 dated Aug. 18, 1994.)

A comprehensive review of various types of peptide libraries can be found in Gallop et al., 1994, J. Med. Chem. 37:1233–1251.

Screening of peptide libraries has often been done using an antibody as ligand (Parmley and Smith, 1989, Adv. Exp. Med. Biol. 251:215–218; Scott and Smith, 1990, Science 249:386–390). In many cases, the aim of the screening is to identify peptides from the library that mimic the epitopes to which the antibodies are directed. Thus, given an available antibody, peptide libraries are excellent sources for identifying epitopes or epitope-like molecules of that antibody (Yayon et al., 1993, Proc. Natl. Acad. Sci. USA 90:10643–10647).

McCafferty et al., 1990, Nature 348:552–554 used PCR to amplify immunoglobulin variable (V) region genes and cloned those genes into phage expression vectors. The authors suggested that phage libraries of V, diversity (D), and joining (J) regions could be screened with antigen. The phage that bound to antigen could then be mutated in the antigen-binding loops of the antibody genes and rescreened. The process could be repeated several times, ultimately giving rise to phage which bind the antigen strongly.

Marks et al., 1991, J. Mol. Biol. 222:581–597 also used PCR to amplify immunoglobulin variable (V) region genes and cloned those genes into phage expression vectors.

Kang et al., 1991, Proc. Natl. Acad. Sci. USA 88:4363–4366 created a phagemid vector that could be used to express the V and constant (C) regions of the heavy and light chains of an antibody specific for an antigen. The heavy and light chain V-C regions were engineered to combine in the periplasm to produce an antibody-like molecule with a functional antigen binding site. Infection of cells harboring this phagemid with helper phage resulted in the incorporation of the antibody-like molecule on the surface of phage that carried the phagemid DNA. This allowed for identification and enrichment of these phage by screening with the antigen. It was suggested that the enriched phage could be subject to mutation and further rounds of screening, leading to the isolation of antibody-like molecules that were capable of even stronger binding to the antigen.

Hoogenboom et al., 1991, Nucleic Acids Res. 19:4133–4137 suggested that naive antibody genes might be cloned into phage display libraries. This would be followed by random mutation of the cloned antibody genes to generate high affinity variants.

Bass et al., 1990, Proteins: Struct. Func. Genet. 8:309–314 fused human growth hormone (hGH) to the carboxy terminus of the gene III protein of phage fd. This fusion protein was built into a phagemid vector. When cells carrying the phagemid were infected with a helper phage, about 10% of the phage particles produced displayed the fusion protein on their surfaces. These phage particles were enriched by screening with hGH receptor-coated beads. It was suggested that this system could be used to develop mutants of hGH with altered receptor binding characteristics.

Lowman et al., 1991, Biochemistry 30:10832–10838 used an improved version of the system of Bass et al. described above to select for mutant hGH proteins with exceptionally high affinity for the hGH receptor. The authors randomly mutagenized the hGH-pIII fusion proteins at sites near the vicinity of 12 amino acids of hGH that had previously been identified as being important in receptor binding.

Balass et al., 1993, Proc. Natl. Acad. Sci. USA 90:10638–10642 used a phage display library to isolate linear peptides that mimicked a conformationally dependent epitope of the nicotinic acetylcholine receptor. This was done by screening the library with a monoclonal antibody specific for the conformationally dependent epitope. The monoclonal antibody used was thought to be specific to the acetylcholine receptor's binding site for its natural ligand, acetylcholine.

2.2. Drug Delivery Systems

The common routes of therapeutic drug administration are oral ingestion or parenteral (intravenous, subcutaneous and intramuscular) routes of administration. Intravenous drug administration suffers from numerous limitations, including (i) the risk of adverse effects resulting from rapid accumulation of high concentrations of drug, (ii) repeated injections which can cause patient discomfort; and (iii) the risk of infection at the site of repeated injections. Subcutaneous injection is not generally suitable for delivering large volumes or for irritating substances. Whereas oral administration is generally more convenient, it is limited where the therapeutic agent is not efficiently absorbed by the gastrointestinal tract. To date, the development of oral formulations for the effective delivery of peptides, proteins and macromolecules has been an elusive target. Poor membrane permeability; enzymatic instability, large molecular size, and hydrophilic properties are four factors that have remained major hurdles for peptide and protein formulations (reviewed by Fix, J. A., 1996, J. Pharmac. Sci. 85:1282–1285). In order to develop an efficacious oral formulation, the peptide must be protected from the enzymatic environment of the gastrointestinal tract (GIT), presented to the absorptive epithelial barrier in a sufficient concentration to effect transcellular flux (Fix, J. A., 1996, J. Pharmac. Sci. 85:1282–1285), and if possible "smuggled" across the epithelial barrier in an apical to basolateral direction.

Site specific drug delivery or drug targeting can be achieved at different levels, including (i) primary targeting to a specific organ, (ii) secondary targeting to a specific cell type within that organ and (iii) tertiary targeting where the drug is delivered to specific intracellular structures (e.g., the nucleus for genes) (reviewed in Davis and Jllum, 1994, In: Targeting of Drugs 4, (Eds), Gregoriadis, McCormack and Poste, 183–194). At present there is a considerable amount of ongoing research work in the Drug Delivery Systems (DDS) area, and much of it addresses (i) targeting delivery and (ii) the development of non-invasive ways of getting macromolecules, peptides, proteins, products of the biotechnology industry, etc. into the body (Evers, P., 1995, Developments in Drug Delivery: Technology and Markets, Financial Times Management Report). It is generally accepted that targeted drug delivery is crucial to the improved treatment of certain diseases, especially cancer, and not surprisingly many of the approaches to targeted drug delivery are focused in the cancer area. Many anticancer drugs are toxic to the body as well as to malignant cells. If a drug, or a delivery system, can be modified so that it "homes in" on the tumor, then by maximizing the drug concentration at the disease site, the anti-cancer effect can be exploited to the full, while toxicity is greatly reduced. Tumors contain antigens which provoke the body to respond by producing antibodies designed to attach to the antigens and destroy them. Monoclonal antibodies are being used as both delivery vehicles targeted to tumor cells (reviewed by Pietersz, G. A., 1990, Bioconjugate Chem. 1:89–95) and as imaging agents to carry molecules of drug or imaging agent to the tumor surface.

2.3. Transport Pathways

The epithelial cells lining the lumenal side of the GIT are a major barrier to drug delivery following oral administration. However, there are four recognized transport pathways which can be exploited to facilitate drug delivery and transport: the transcellular, paracellular, carrier-mediated, and transcytotic pathways. The ability of a conventional drug, peptide, protein, macromolecule or nano- or microparticulate system to "interact" with one of these transport pathways may result in increased delivery of that drug or particle from the GIT to the underlying circulation.

In the case of the receptor-mediated, carrier-mediated or transcytotic transport pathways, some of the uptake signals have been identified. These signals include, inter alia, folic acid, which interacts with the folate receptor, and cobalamin, which interacts with Intrinsic Factor. In addition, leucine- and tyrosine-based peptide sorting motifs or internalization sequences exist, such as YSKV, FPHL, YRGV, YQTI, TEQF, TEVM, TSAF, and YTRF (SEQ ID NOS:203, 204, 205, 206, 207, 208, 209, and 210, respectively), which facilitate uptake or targeting of proteins using specific membrane receptors or binding sites to identify peptides that bind specifically to the receptor or binding site.

Non-receptor based assays to discover particular ligands have also been used. For instance, a strategy for identifying peptides that alter cellular function by scanning whole cells with phage display libraries is disclosed in Fong et al., Drug Development Research 33:64–70 (1994). However, because whole cells, rather than intact tissue or polarized cell cultures, are used for screening phage display libraries, this procedure does not provide information regarding sequences whose primary function includes affecting transport across polarized cell layers.

Additionally, Stevenson et al., Pharmaceutical Res. 12(9), S94 (1995) discloses the use of Caco-2 monolayers to screen a synthetic tripeptide combinatorial library for information relating to the permeability of di- and tri-peptides.

A method of identifying a peptide which permits or facilitates the transport of an active agent through human or animal tissues has been developed (see U.S. patent application Ser. No. 08/746,411 filed Nov. 8, 1996, which is incorporated by reference herein in its entirety). Phage from a random phage library is plated onto or brought into contact with a first side, preferably the apical side, of a tissue sample, either in vitro, in vivo or in situ, or polarized tissue cell culture. The phage which is transported to a second side of the tissue opposite the first side, preferably the basolateral side, is harvested to select transported phages. The transported phages are amplified in a host and this cycle is repeated (using the transported phage from the most recent cycle) to obtain a selected phage library containing phage which can be transported from the first side to the second side.

Discussion or citation of a reference hereinabove shall not be construed as meaning that such reference is prior art to the present invention.

3. SUMMARY OF THE INVENTION

The present invention relates generally to random peptides and peptide motifs capable of specific binding to GIT transport receptors. Such proteins can be identified using any random peptide library, e.g., a chemically synthesized peptide library or a biologically expressed peptide library. If a biological peptide expression library is used, the nucleic acid which encodes the peptide which binds to the ligand of choice can be recovered, and then sequenced to determine its nucleotide sequence and hence deduce the amino acid sequence that mediates binding. Alternatively, the amino acid sequence of an appropriate binding domain can be determined by direct determination of the amino acid sequence of a peptide selected from a peptide library containing chemically synthesized peptides. In a less preferred aspect, direct amino acid sequencing of a binding peptide selected from a biological peptide expression library can also be performed.

In particular, this invention relates to proteins (e.g., peptides) that are capable of facilitating transport of an active agent through a human or animal gastro-intestinal tissue, and derivatives (e.g., fragments) and analogs thereof, and nucleotide sequences coding for said proteins and derivatives.

Preferably, the tissue through which transport is facilitated is of the duodenum, jejunum, ileum, ascending colon, transverse colon, descending colon, or pelvic colon. The tissue is most preferably epithelial cells lining the lumenal side of the GIT.

The proteins of the invention have use in facilitating transport of active agents from the lumenal side of the GIT into the systemic blood system, and/or in targeting active agents to the GIT. Thus, for example, by binding (covalently or noncovalently) a protein of the invention to an orally administered drug, the drug can be targeted to specific receptor sites or transport pathways which are known to operate in the human gastrointestinal tract, thus facilitating its absorption into the systemic system.

The invention also relates to derivatives and analogs of the invention which are functionally active, i.e., they are capable of displaying one or more known functional activities associated with a full-length peptide. Such functional activities include but are not limited to antigenicity (ability to bind or to compete with GIT transport receptor-binding peptides for binding to an anti-GIT transport receptor antibody) and ability to bind or compete with full-length peptide for binding to a GIT transport receptor.

The invention further relates to fragments of (and derivatives and analogs thereof) GIT transport receptor-binding peptides which comprise one or more motifs of a GIT transport receptor-binding peptide.

Antibodies to GIT transport receptor-binding peptides and GIT transport receptor-binding peptide derivatives and analogs are additionally provided.

Methods of production of the GIT transport receptor-binding peptides, derivatives, fragments and analogs, e.g., by recombinant means, are also provided.

The present invention also relates to therapeutic methods, pharmaceutical compositions and formulations based on GIT transport receptor-binding peptides. Formulations of the invention include but are not limited to GIT transport receptor-binding peptides or motifs and derivatives (including fragments) thereof; antibodies thereto; and nucleic acids encoding the GIT transport receptor-binding peptides or derivatives associated with an active agent. Preferably, the active agent is a drug or drug-containing nano- or microparticle.

The GIT transport-receptor binding proteins of the invention can also be used to determine levels of the GIT transport receptors in a sample by binding thereto.

The GIT transport-receptor binding proteins can also be used to identify molecules that bind thereto, by contacting candidate test molecules under conditions conducive to binding, and detecting any binding that occurs.

4. DESCRIPTION OF THE FIGURES

FIG. 1. FIG. 1 shows the human PEPT1 predicted amino acid sequence determined from the sequence of the cDNA clone coding for human PEPT1 (SEQ ID NO:176) (Liang R. et al. J.

Biol. Chem. 270(12):6456–6463 (1995)), including the extracellular domain from amino acid 391 to 573 (Fei et al., Nature 368:563 (1994)).

FIGS. 2A–2C. FIGS. 2A–2C show the DNA sequence of the cDNA coding for the human intestinal peptide-associated transporter HPT1 and the corresponding putative amino acid sequence (bases 1 to 3345; Medline:94204643) (SEQ ID NOS: 177 and 178, respectively).

FIGS. 3A–3B. FIGS. 3A–3B show the putative Human Sucrase-isomaltase complex(hSI) amino acid sequence determined from the sequence of the cDNA clone coding for human sucrase-isomaltase complex (SEQ ID NO:179) (Chantret I., et al., Biochem. J. 285(Pt 3):915–923 (1992).

FIGS. 4A–4B. FIGS. 4A–4B show the D2H nucleotide and deduced amino acid sequence for the human D2H transporter (SEQ ID NOS:180 and 181, respectively) (Wells, R. G. et al.,J. Clin. Invest. 90:1959–1963 (1993).

FIGS. 5A–5C. FIG. 5A is a schematic summary of the cloning of the DNA insert present in gene III of the phages selected from the phage display libraries into the expression vector pGex-4T-2. The gene insert in gene III of the phages was amplified by PCR using DNA primers which flank the gene insert and which contained recognition sequences for specific restriction endonucleases at their extreme 5' sides. Alternatively, specific primers which amplify specific regions of the DNA inserts in gene III of the phages, and which contained recognition sequences for specific restriction endonucleases at their extreme 5' sides, were used in PCR amplification experiments. Following amplification of the gene inserts, the amplified PCR fragments were digested with the restriction endonucleases Xho1 and Not1. Similarly the plasmid pGex-4T-2, which codes for the reporter protein glutathione S-transferase (GST), was digested with the restriction endonucleases Sal1 and Not1. The digested PCR fragments were ligated into the digested plasmid pGex-4T-2 using T4 DNA Ligase and the ligated products were transformed into competent *Escherichia coli*, with selection of transformants on agar plates containing selection antibiotic. The selected clones were cultured, the plasmids were recovered and the in-frame sequence of the DNA insert in the plasmids was confirmed by DNA sequencing. The correct clones were subsequently used for expression of the GST-fusion proteins (SEQ ID NO:182); FIG. 5B shows the series of full-length P31 (designated P31) (SEQ ID NO:43) and truncated peptides derived from P31 (clones #101, 102, 103 and 119), (SEQ ID NOS:183, 184, 185, and 186, respectively) full-length PAX2 (designated PAX2) (SEQ ID NO:55) and truncated peptides derived from PAX2 (clones #104, 105, 106) (SEQ ID NOS:170, 187, and 188, respectively) and full-length DCX8 (DCX8) (SEQ ID NO:23) and series of truncated peptides derived from DCX8 (clones #107, 108, 109) (SEQ ID NOS:189, 190, and 191, respectively) that were expressed as fusion proteins to GST. The construction of these GST-fusion proteins is shown in FIG. 5A. FIG. 5C shows the series of full-length P31 (designated P31) (SEQ ID NO:43) and truncated peptides derived from P51 (clones #103, 110, 119, 111, and 112) (SEQ ID NOS:185, 192, 193, 194, and 195, respectively), full-length PAX2 (designated PAX2) (SEQ ID NO:55) and truncated peptides derived from PAX2 (clones #106, 113, 114, 115) (SEQ ID NOS:188, 196, 197, and 198, respectively) and full-length SNi10 (designated SNi10) (SEQ ID NO:4) and series of truncated peptides derived from SNi10 (clones #116, 117, 118) (SEQ ID NOS:199, 200, and 201, respectively) that were expressed as fusion proteins to GST. The construction of these GST-fusion proteins is shown in FIG. 5A. (Underlining and bold in FIGS. 5A–5C are for orientation of the sequences.)

Figure 6A:
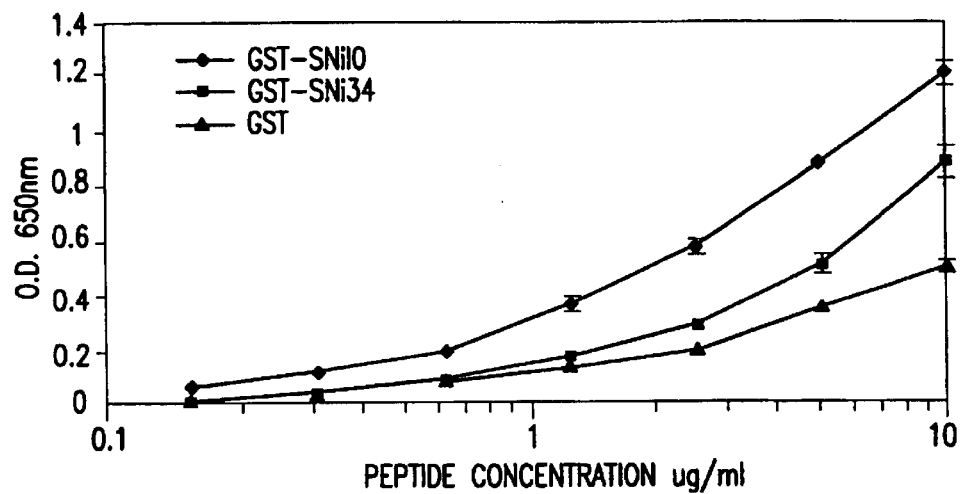
Figure 6B:
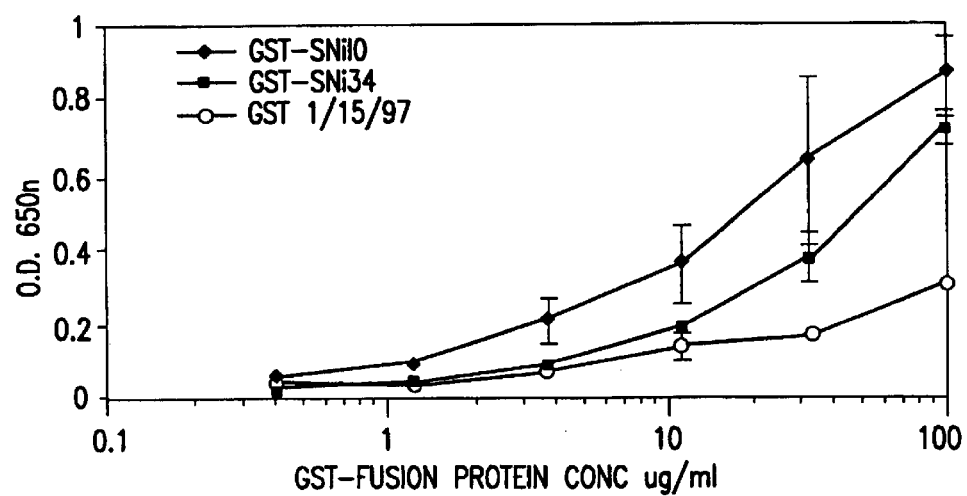

FIGS. 6A–6B. FIGS. 6A–6B show the binding of GST and GST-fusion proteins to recombinant hSI and to fixed C2BBe1 fixed cells as detected by ELISA assays. FIG. 6A shows the binding of the control protein GST, which does not contain a fusion peptide, and the GST-fusion proteins from SNi10 (designated GST-SNi10) and SNi34 (designated GST-SNi34) to recombinant hSI. FIG. 6B shows the binding of the control protein GST, which does not contain a fusion peptide, and the GST-fusion proteins from SNi10 (designated GST-SNi10) and SNi34 (designated GST-SNi34) to fixed C2BBe1 cells.

Figure 7A:
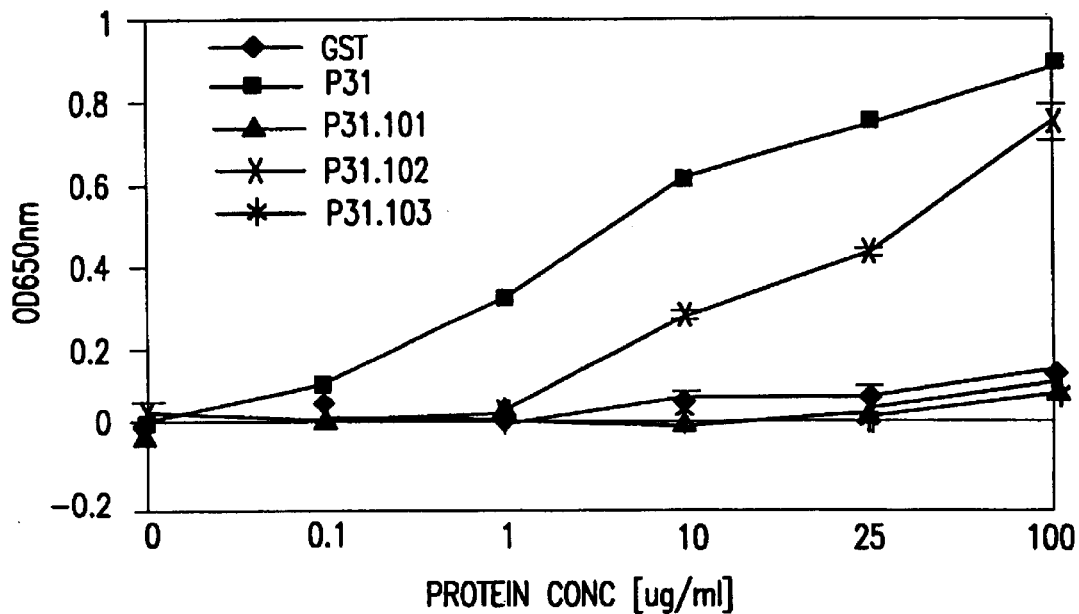
Figure 7B:
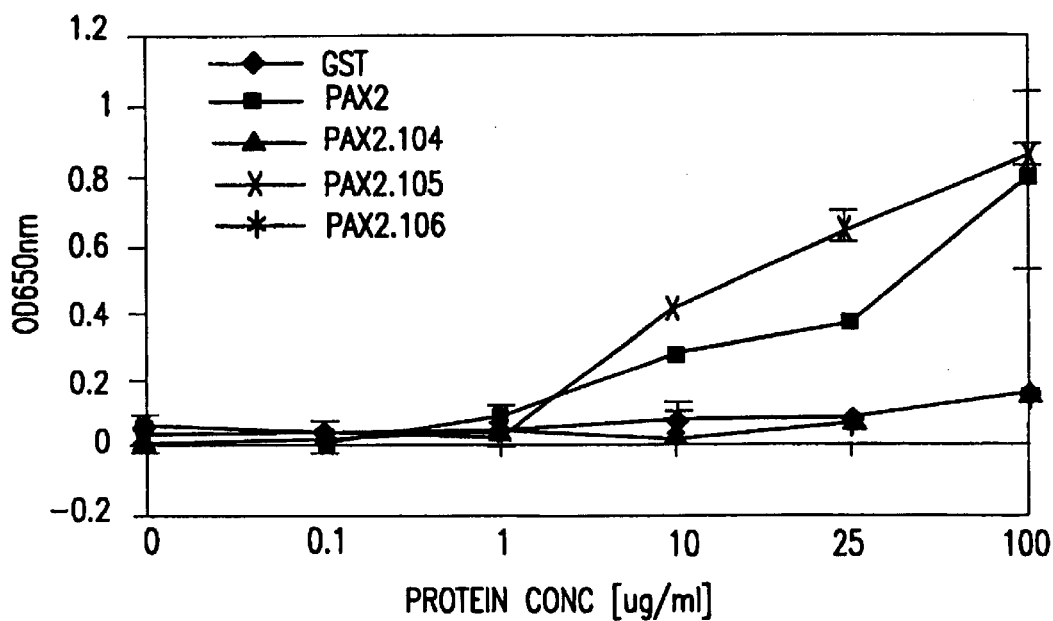
Figure 7C:
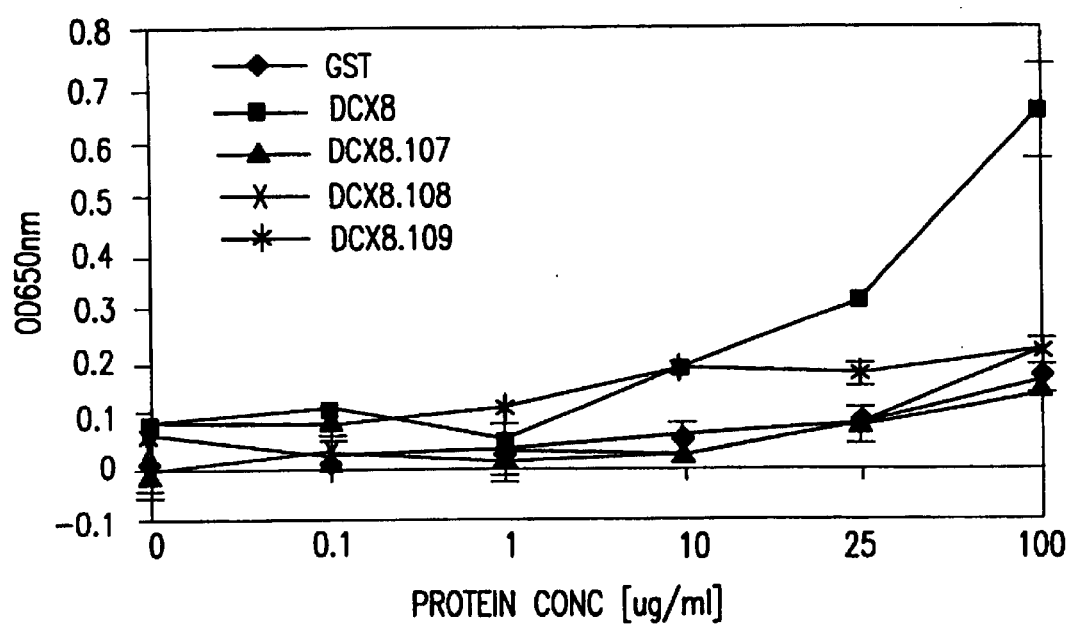
Figure 7D:
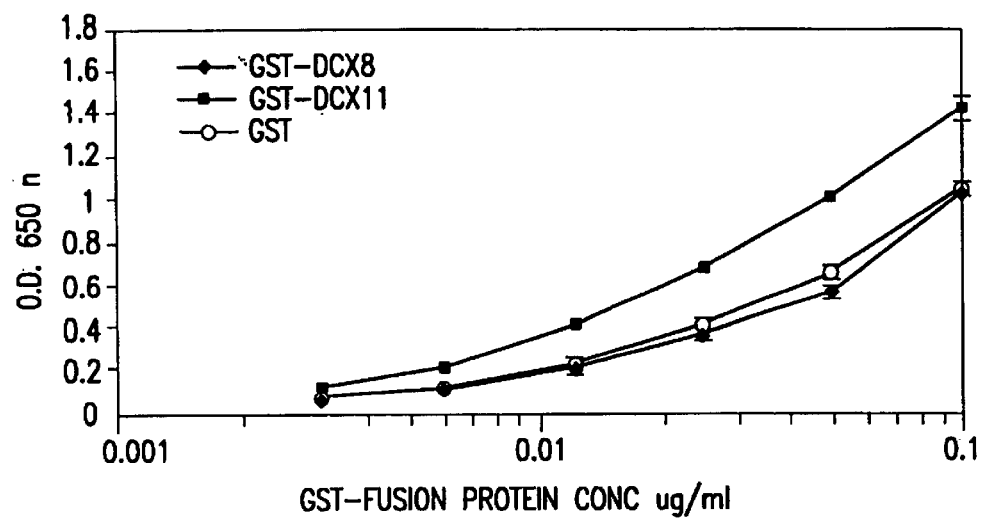
Figure 7E:
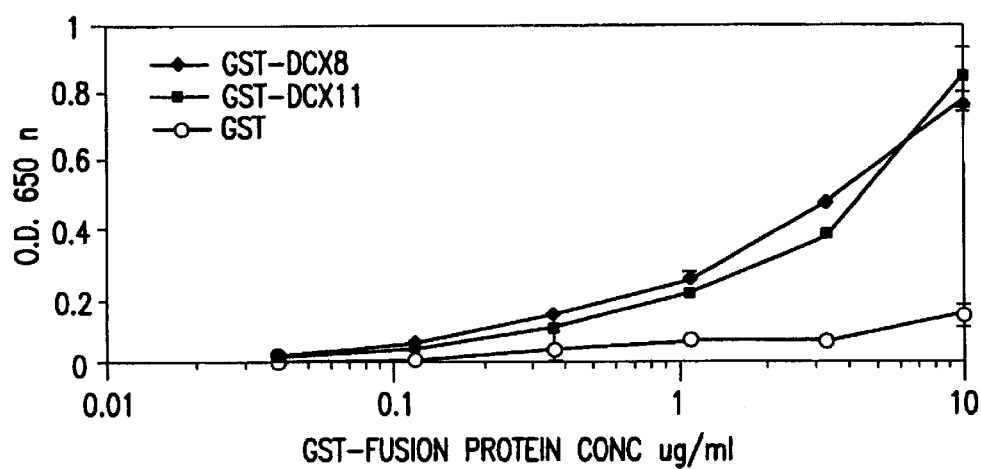
Figure 7F:
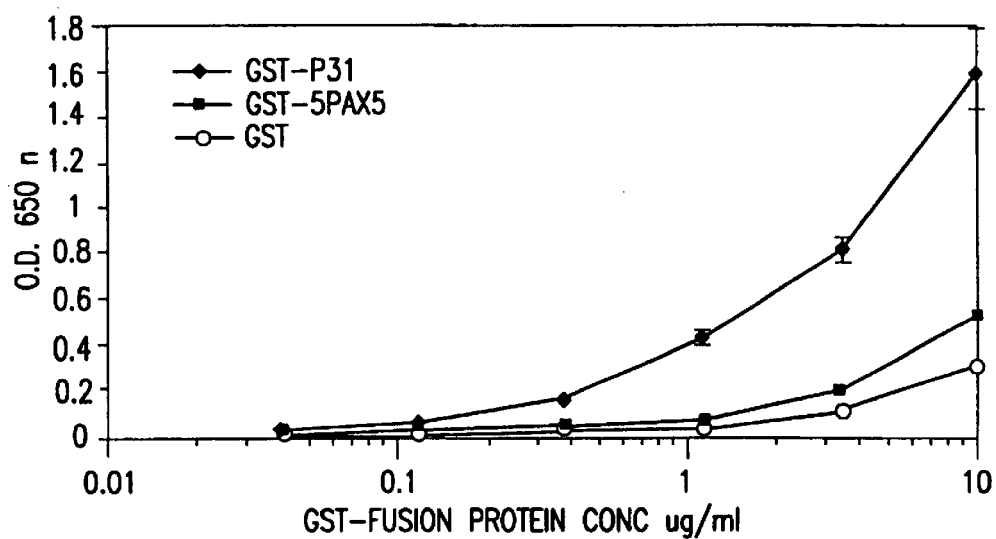
Figure 7G:
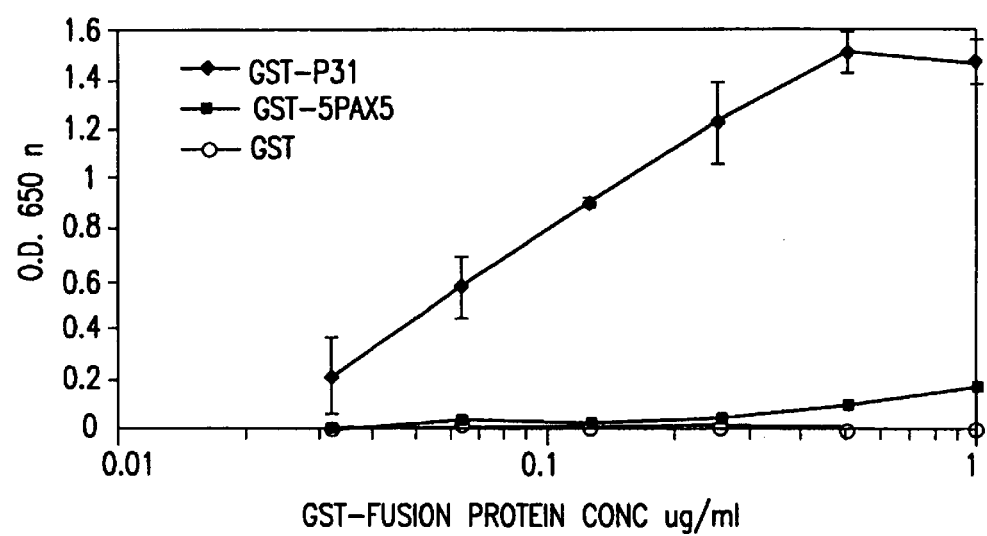
Figure 7H:
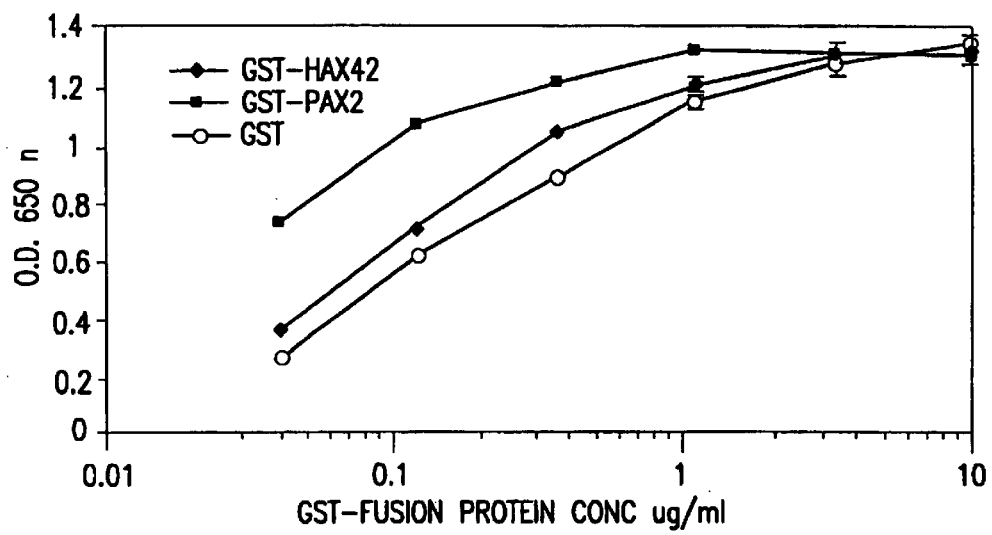
Figure 7I:
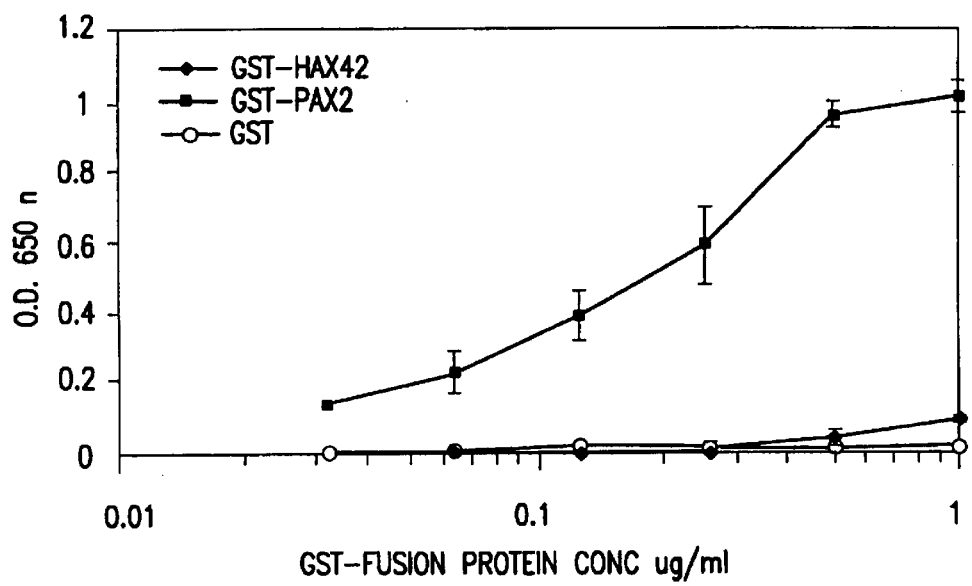
Figure 7J:
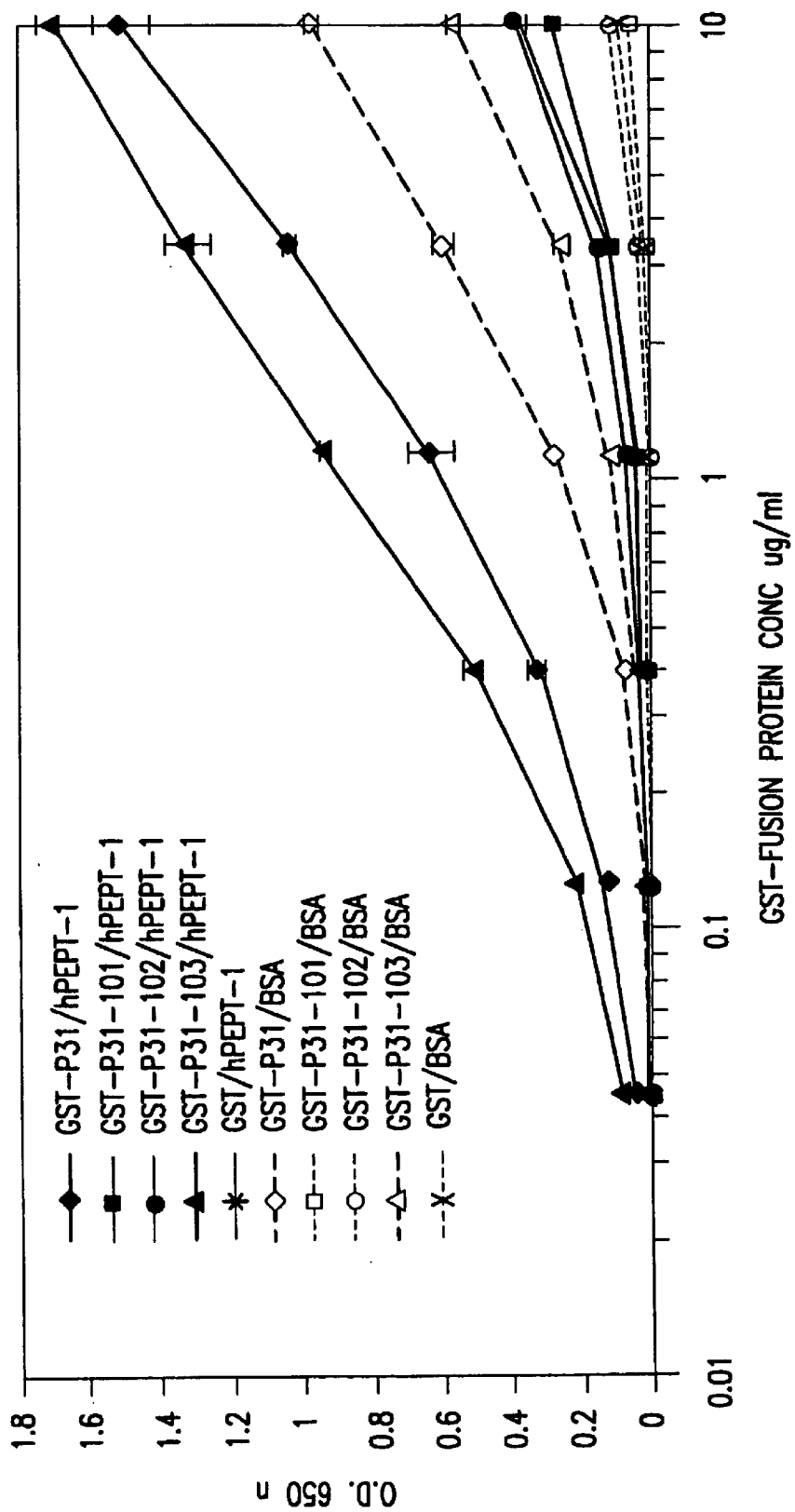
Figure 7K:
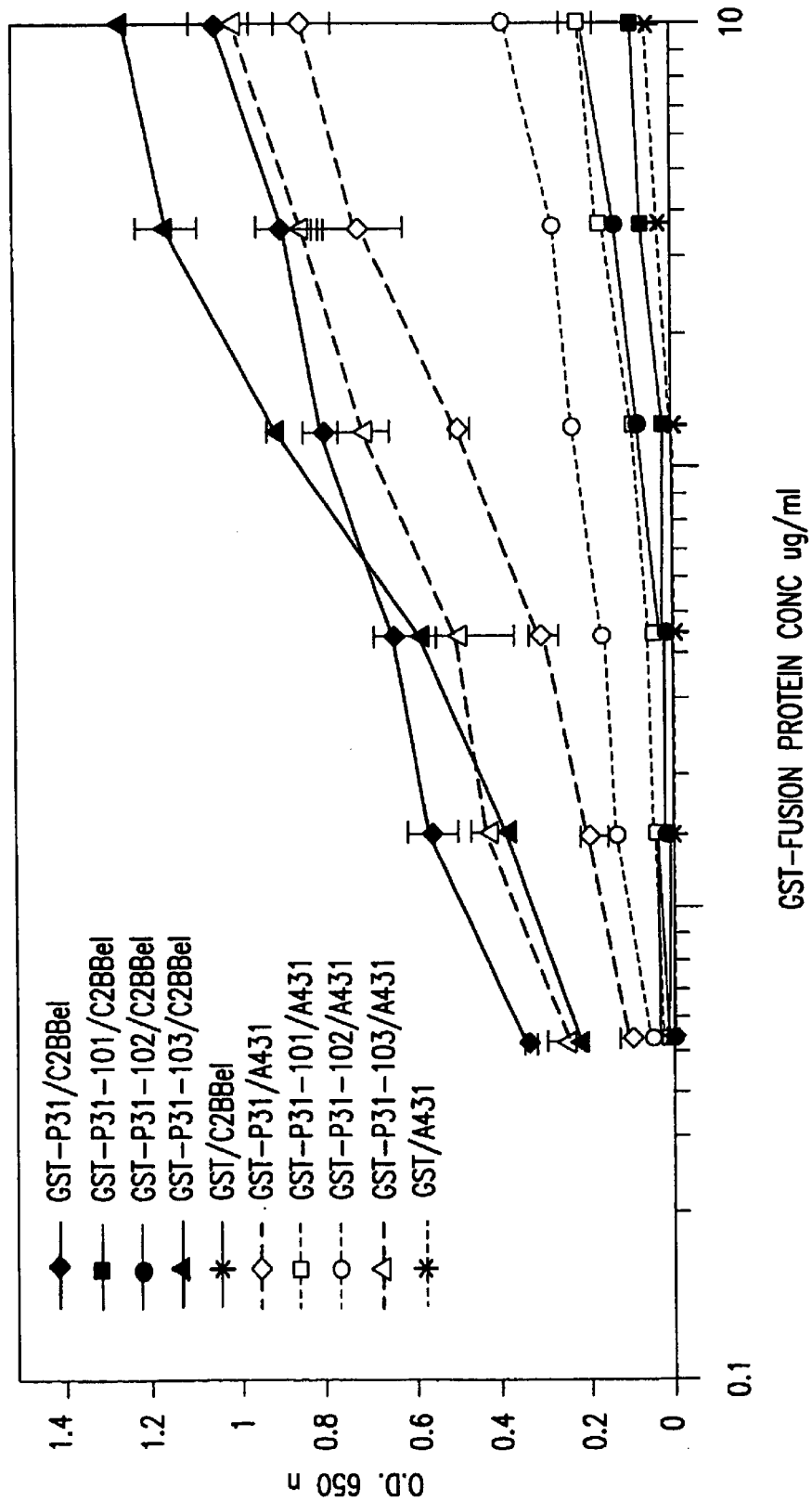
Figure 7L:
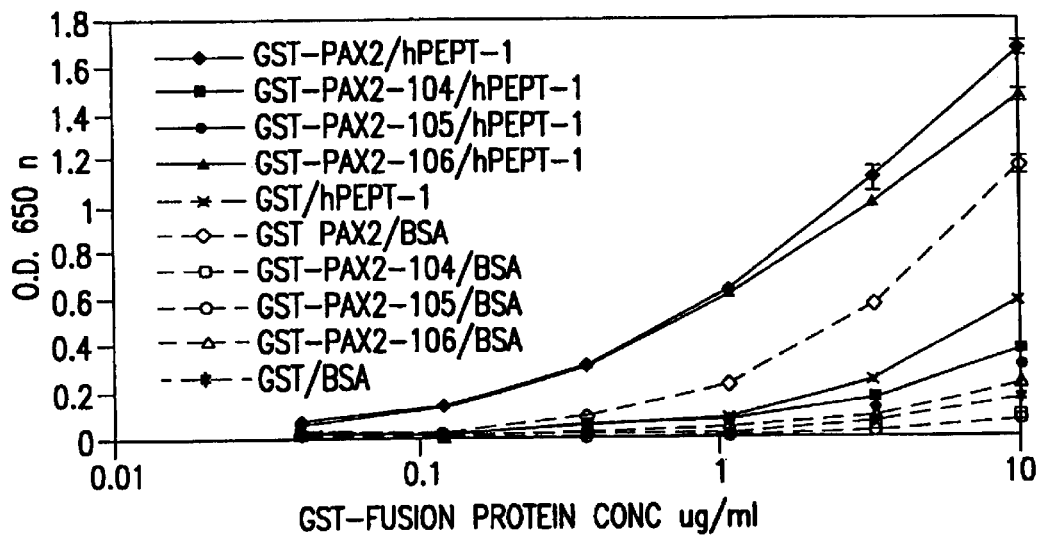
Figure 7M:
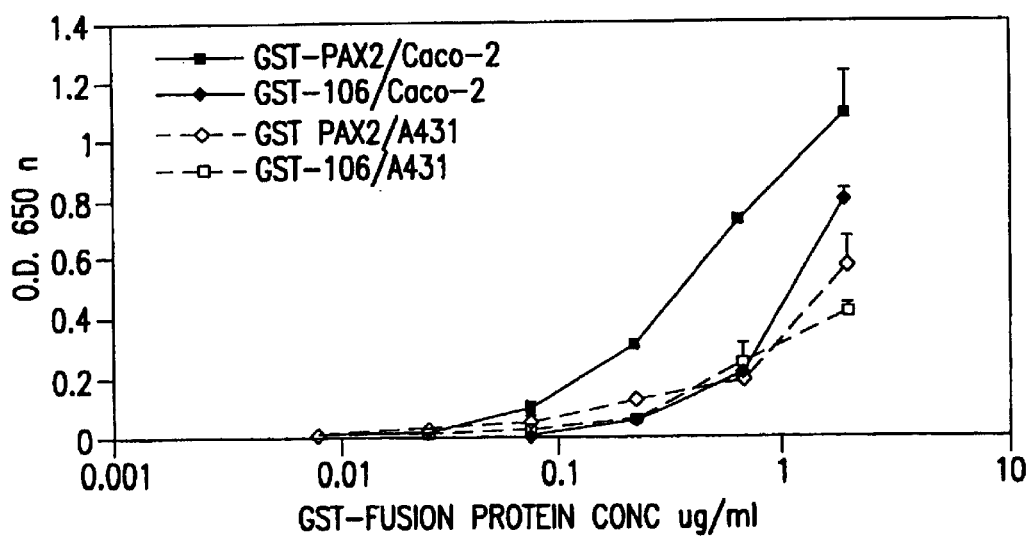

FIGS. 7A–7M. FIGS. 7A–7M show the binding of GST peptide and truncated fusion proteins to fixed Caco-2 cells, fixed C2BBe1 cells, and fixed A431 cells or to recombinant GIT transport receptors D2H, HPT1, hPEPT1 or to BSA using increasing concentrations (expressed as μg/ml on the X-axis) of the control GST protein and the GST-fusion proteins, as detected by ELISA assays. FIG. 7A shows the binding of the control protein GST, which does not contain a fusion peptide, and the series of GST-fusion proteins from P31 including the fusion to full-length P31 peptide (designated P31) (SEQ ID NO:43) and clone #101 (designated P31, 101), clone #102 (designated P31, 102) and clone #103 (designated P31, 103). FIG. 7B shows the binding of the control protein GST, which does not contain a fusion peptide, and the series of GST-fusion proteins from PAX2 including the fusion to full-length PAX2 peptide (designated PAX2) and clone #104 (designated PAX2, 104), clone #105 (designated PAX2, 105) and clone #106 (designated PAX2, 106) (SEQ ID NOS:55, 170, 187, and 188, respectively). FIG. 7C shows the binding of the control protein GST, which does not contain a fusion peptide, and the series of GST-fusion proteins from DCX8 including the fusion to full-length DCX8 peptide (designated DCX8) and clone #107 (designated DCX8, 107), clone #108 (designated DCX8, 108) and clone #109 (designated DCX8, 109) (SEQ ID NOS:23, 189, 190, and 191, respectively). FIG. 7D shows the binding of the control protein GST, which does not contain a fusion peptide, and the GST-fusion proteins from DCX8 (designated GST-DCX8) and DCX11 (designated GST-DCX11) to recombinant D2H. FIG. 7E shows the binding of the control protein GST, which does not contain a fusion peptide, and the GST-fusion proteins from DCX8 (designated GST-DCX8) and DCX11 (designated GST-DCX11) to fixed C2BBe1 cells. FIG. 7F shows the binding of the control protein GST, which does not contain a fusion peptide, and the GST-fusion proteins from P31 (designated GST-P31) and 5PAX5 (designated GST-5PAX5) to recombinant hPEPT1. FIG. 7G shows the binding of the control protein GST, which does not contain a fusion peptide, and the GST-fusion proteins from P31 (designated GST-P31) and 5PAX5 (designated GST-5PAX5) to fixed C2BBe1 cells. FIG. 7H shows the binding of the control protein GST, which does not contain a fusion peptide, and the GST-fusion proteins from HAX42 (designated GST-HAX42) and PAX2 (designated GST-PAX2) to recombinant HPT1. FIG. 7I shows the binding of the control protein GST, which does not contain a fusion peptide, and the GST-fusion proteins from HAX42 (designated GST-HAX42) and PAX2 (designated GST-PAX2) to fixed C2BBe1 cells. FIG. 7J shows the binding of the control protein GST, which does not contain a fusion peptide, and the GST-fusion proteins from P31 (designated GST-P31) and truncated derivatives clone #101 (designated GST-P31-101), clone #102 (designated GST-P31-102), clone #103 (designated GST-P31-103) to either recombinant hPEPT1 or to BSA. FIG. 7K shows the binding of the control protein GST, which does not contain a fusion peptide, and the GST-fusion proteins from P31 (designated GST-P31) and truncated derivatives clone #101 (designated GST-P31-101), clone #102 (designated GST-P31-102), clone #103 (designated GST-P31-103) to either fixed C2BBe1 cells or to fixed A431 cells. FIG. 7L shows the binding of the control protein GST, which does not contain a fusion peptide, and the GST-fusion proteins from PAX2 (designated GST-PAX2) and truncated derivatives clone #104 (designated GST-PAX2-104), clone #105 (designated GST-PAX2-105), clone #106 (designated GST-PAX2-106) to either recombinant hPEPT1 or to BSA. FIG. 7M shows the binding of the control protein GST, which does not contain a fusion peptide, and the GST-fusion proteins from PAX2 (designated GST-PAX2) and truncated derivatives clone #106 (designated GST-PAX2-106) to either fixed Caco-2 cells or to fixed A431 cells.

Figure 8A:
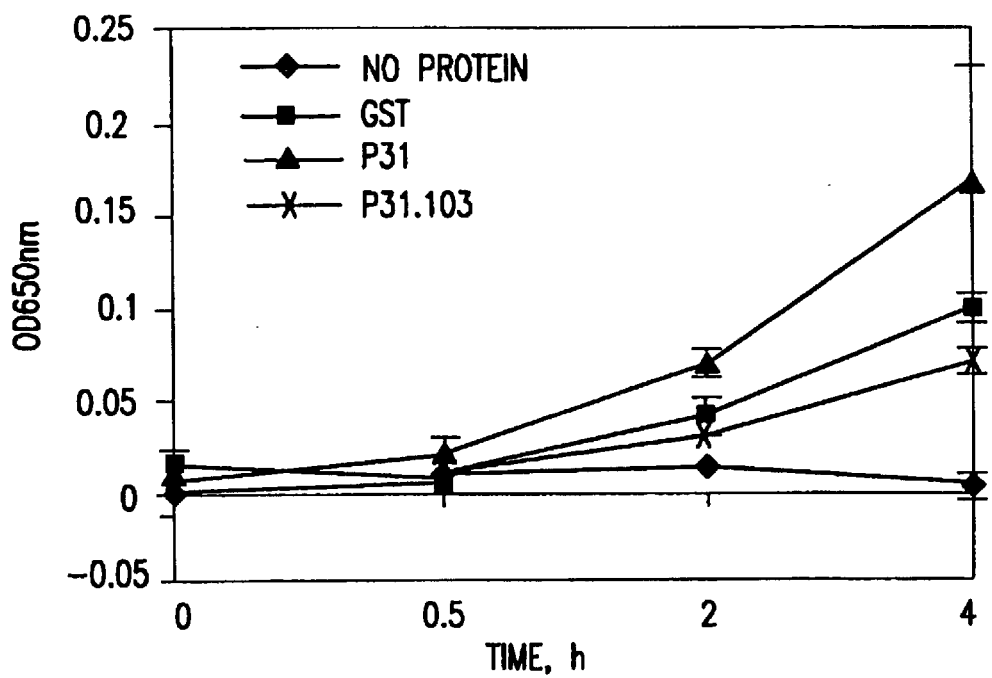
Figure 8B:
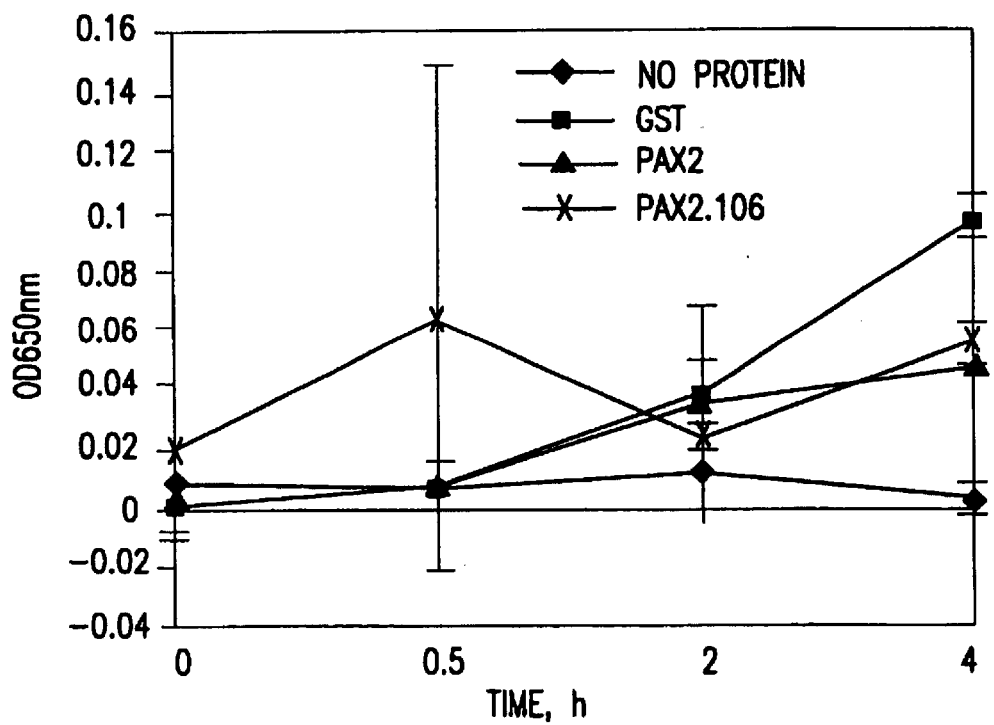
Figure 8C:
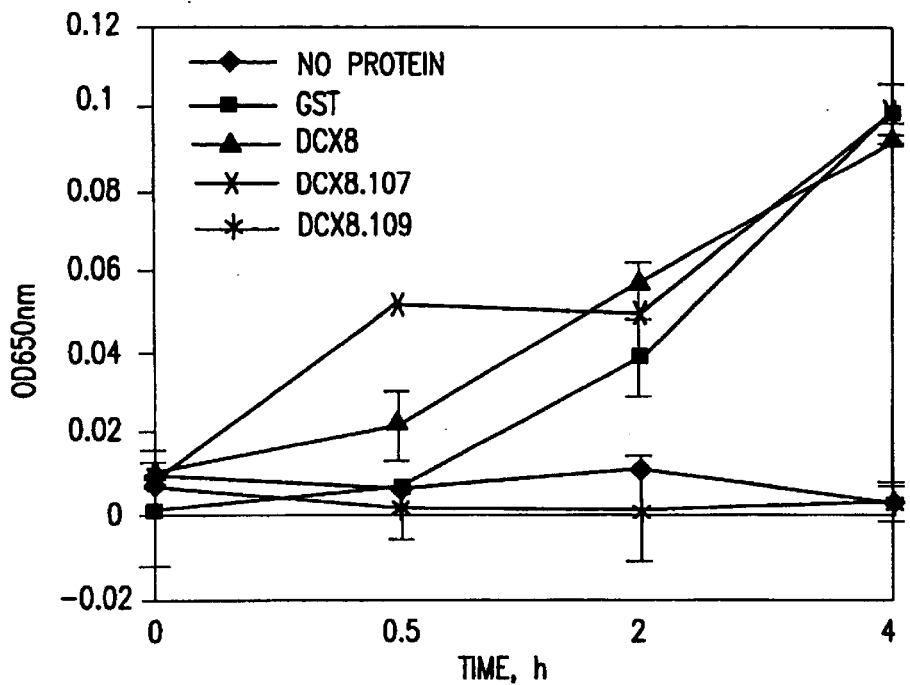
Figure 8D:
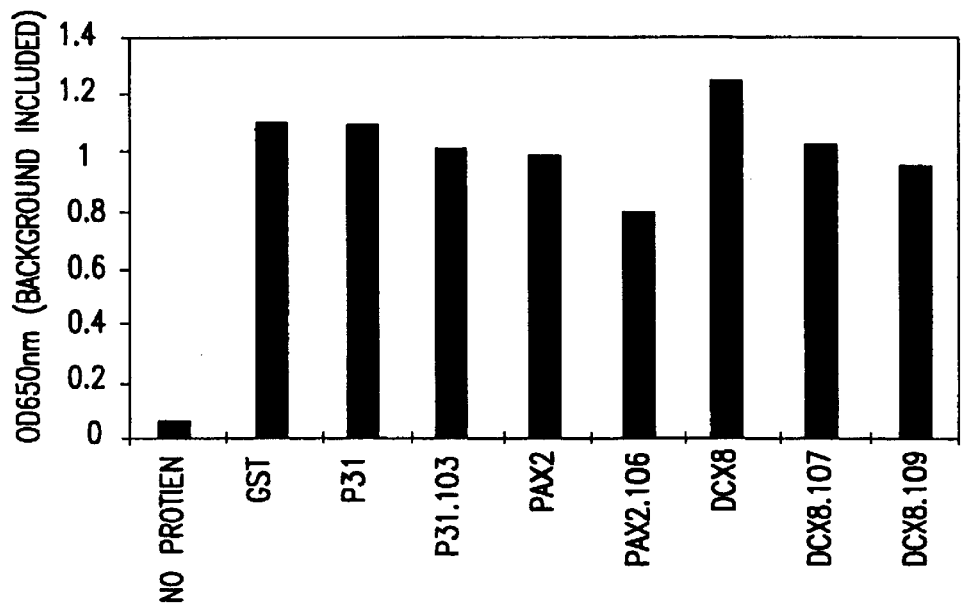

FIGS. 8A–8D. FIG. 8 shows the transport of GST or GST-peptide fusion derivatives across polarized Caco-2 cells in an apical to basolateral direction as a function of time (1–4 hours) as detected by ELISA assays. FIG. 8A shows the transport of either GST, the GST fusion to full-length P31 peptide (designated P31) (SEQ ID NO:43) and the GST clone derivative clone #103 (designated P31.103) across polarized Caco-2 cells in an apical to basolateral as a function of time (in hours) following initial administration of the proteins to the apical medium of polarized Caco-2 cells. The line designated No Protein corresponds to control assays in which buffer control was applied to the apical medium of polarized Caco-2 cells followed by sampling of the basolateral medium as a function of time (hours) and assay for GST by the ELISA assay. FIG. 8B shows the transport of either GST, the GST fusion to full-length PAX2 peptide (designated PAX2) and the GST clone derivative clone #106 (designated PAX2.106) across polarized Caco-2 cells in an apical to basolateral as a function of time (in hours) following initial administration of the proteins to the apical medium of polarized Caco-2 cells. The line designated No Protein corresponds to control assays in which buffer control was applied to the apical medium of polarized Caco-2 cells followed by sampling of the basolateral medium as a function of time (hours) and assay for GST by the ELISA assay. FIG. 8C shows the transport of either GST, the GST fusion to full-length DCX8 peptide (designated DCX8), and the GST clone derivatives clone #107 (designated DCX8.107) and clone #109 (designated DCX8.109) across polarized Caco-2 cells in an apical to basolateral as a function of time (in hours) following initial administration of the proteins to the apical medium of polarized Caco-2 cells. The line designated No Protein corresponds to control assays in which buffer control was applied to the apical medium of polarized Caco-2 cells followed by sampling of the basolateral medium as a function of time (hours) and assay for GST by the ELISA assay. FIG. 8D shows the amount of the GST and GST-fusion proteins (GST fusions to P31, P31-103, PAX2, PAX2.106, DCX8, DCX8-107, DCX8-109), used in the experiments shown in panels A–C above, in the apical medium of the polarized Caco-2 cells as detected by ELISA assay.

Figure 9A:
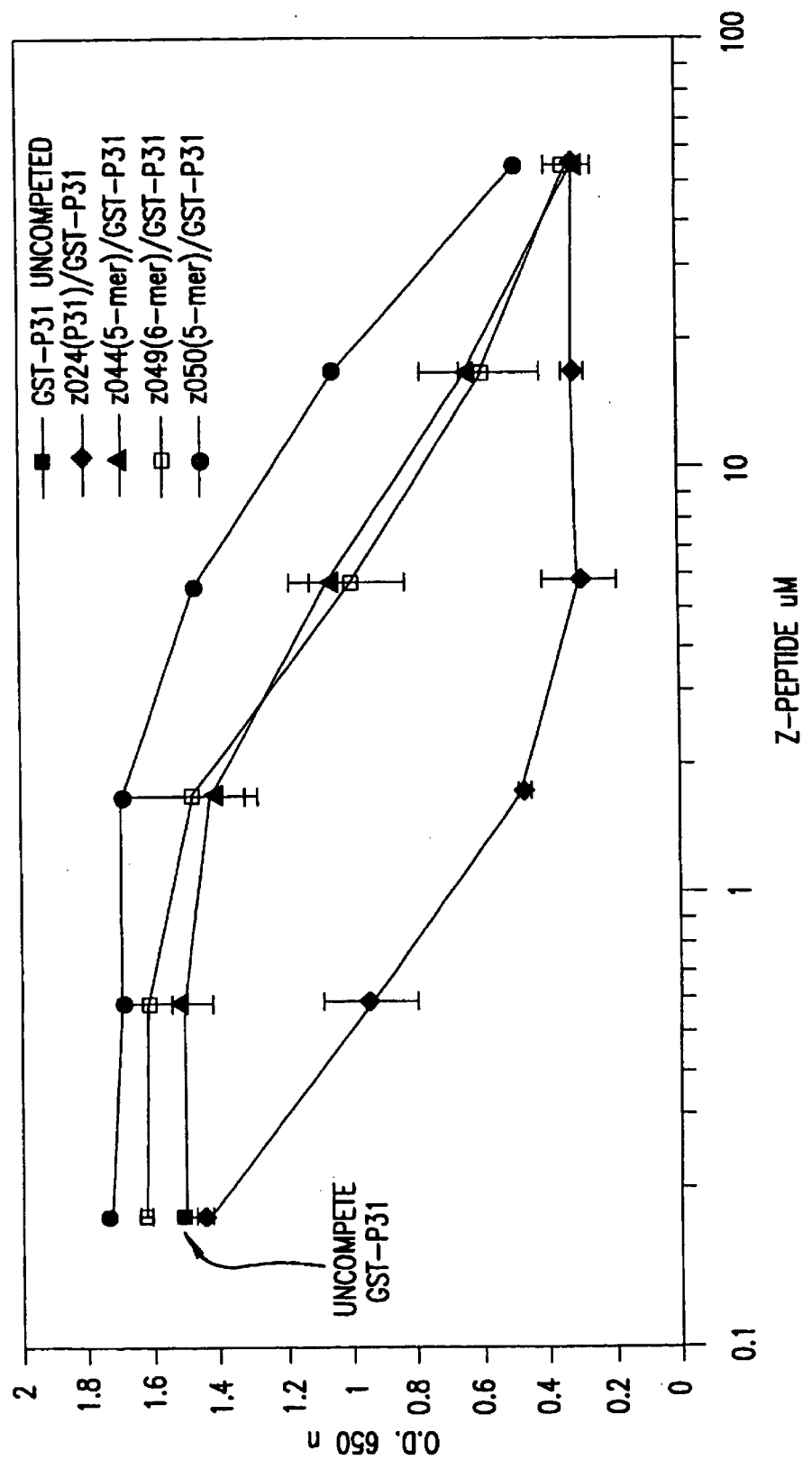
Figure 9B:
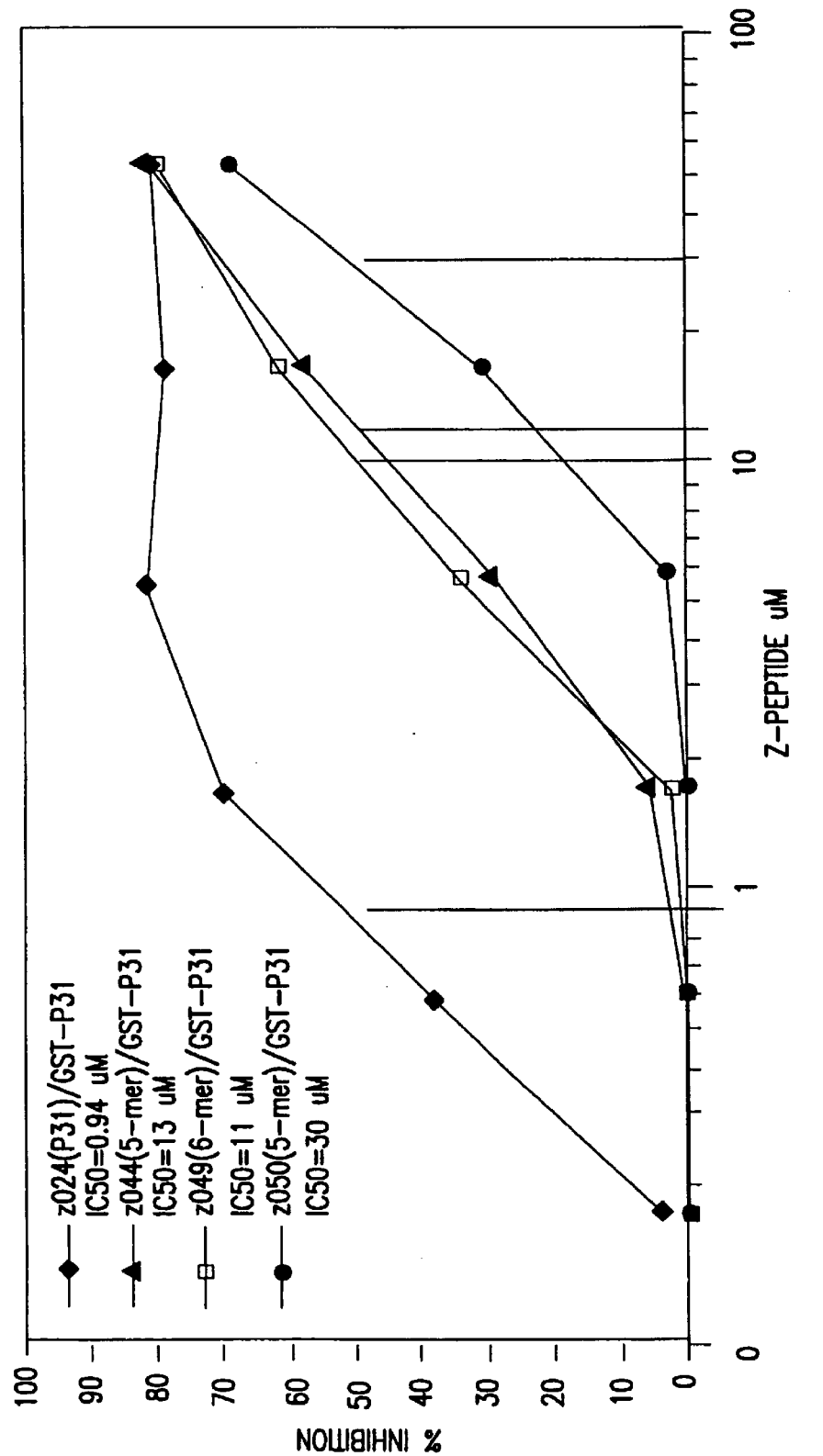

FIGS. 9A–9B. FIGS. 9A–9B show the inhibition of GST-P31 binding to C2BBe1 fixed cells with varying concentration of competitors while holding the concentration of GST-P31 constant at 0.015 µM; the peptide competitors are ZElan024 which is the dansylated peptide version of P31 (SEQ ID NO:43) and ZElan044, ZElan049 and ZElan050 which are truncated, dansylated pieces of P31 (SEQ ID NO:43). Data is presented as O.D. versus peptide concentration (FIG. 9A) and as percent inhibition of GST-P31 binding versus peptide concentration (FIG. 9B).

FIGS. 10A–10C. FIGS. 10A–10C present a compilation of the results of competition ELISA studies of GST-P31, GST-PAX2, GST-SNi10 and GST-HAX42 versus listed dansylated peptides on fixed C2BBe1 cells ("Z" denotes ε-amino dansyl lysine). The pI of the dansylated peptides is also included. Estimated $IC_{50}$ values are in µM and where present, $IC_{50}$ ranges refer to results from multiple assays. If the $IC_{50}$ value could not be determined, a ">" or "<" symbol is used. The GST/C2BBe1 column shows GST protein binding to fixed C2BBe1 cells.

Figure 11A:
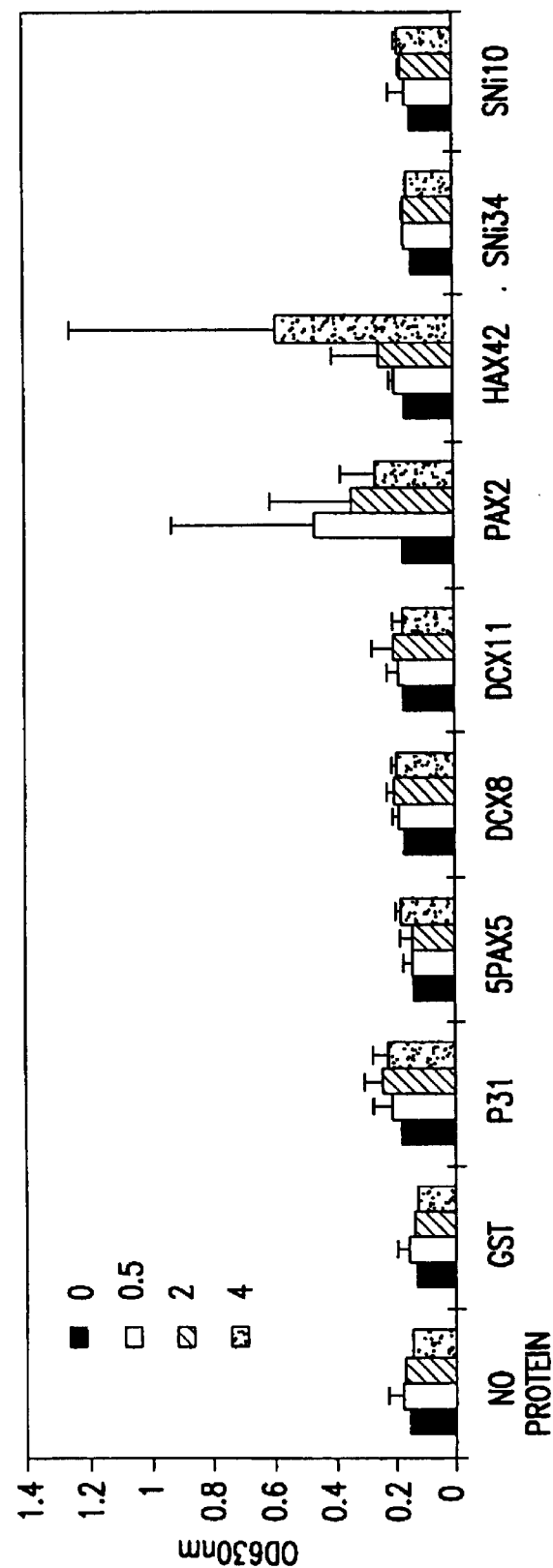
Figure 11B:
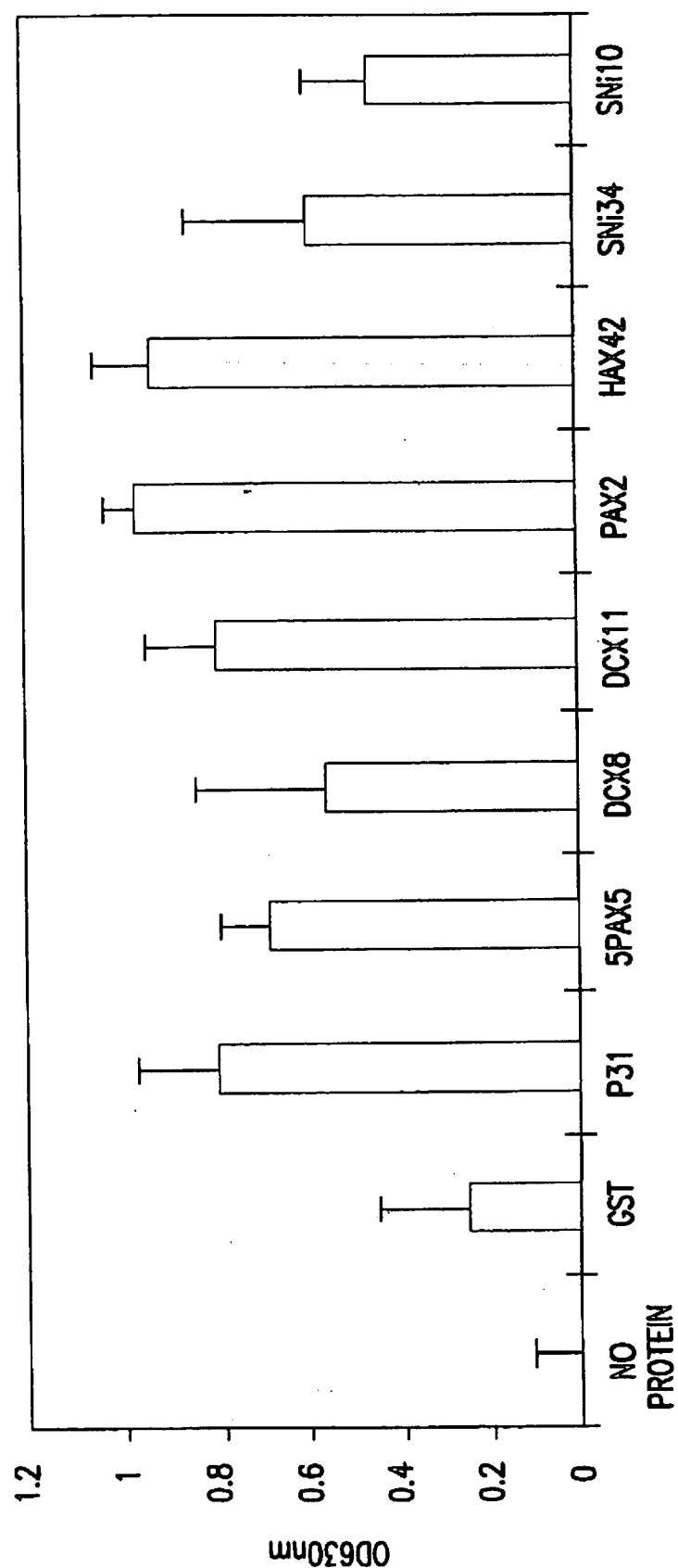

FIGS. 11A–11B. FIG. 11A shows the transport of GST or GST-peptide fusion derivatives across polarized Caco-2 cells in an apical to basolateral direction at 0, 0.5, 2 and 4 hours as detected by ELISA assays and described elsewhere in the text in full detail. The proteins used in the assay included GST, GST-P31 fusion, GST-5PAX5 fusion, GST-DCX8 fusion, GST-DCX11 fusion, GST-PAX2 fusion, GST-HAX42 fusion, GST-SNi34 fusion and GST-SNi10 fusion. The column designated No protein refers to control experiments in which buffer was applied to the apical medium of the cells and ELISA assay was performed on the corresponding basolateral medium of these cells at 0, 0.5, 2 and 4 hours post buffer addition. FIG. 11B shows the internalization of GST or GST-peptide fusion derivatives within polarized Caco-2 cells following administration of the GST or GST-fusion protein derivatives to the apical medium of polarized Caco-2 cells and subsequent recovery of the cells from the transwells and detection of the GST or GST fusions within the recovered cell lysates as detected by ELISA assays and as described elsewhere in the text in full detail. The proteins used in the assay included GST, GST-P31 fusion, GST-5PAX5 fusion, GST-DCX8 fusion, GST-DCX11 fusion, GST-PAX2 fusion, GST-HAX42 fusion, GST-SNi34 fusion and GST-SNi10 fusion. The column designated No protein refers to control experiments in which buffer was applied to the apical medium of the cells and ELISA assay was performed on the corresponding cell lysates of these cells at the end of the experiment.

Figure 12:
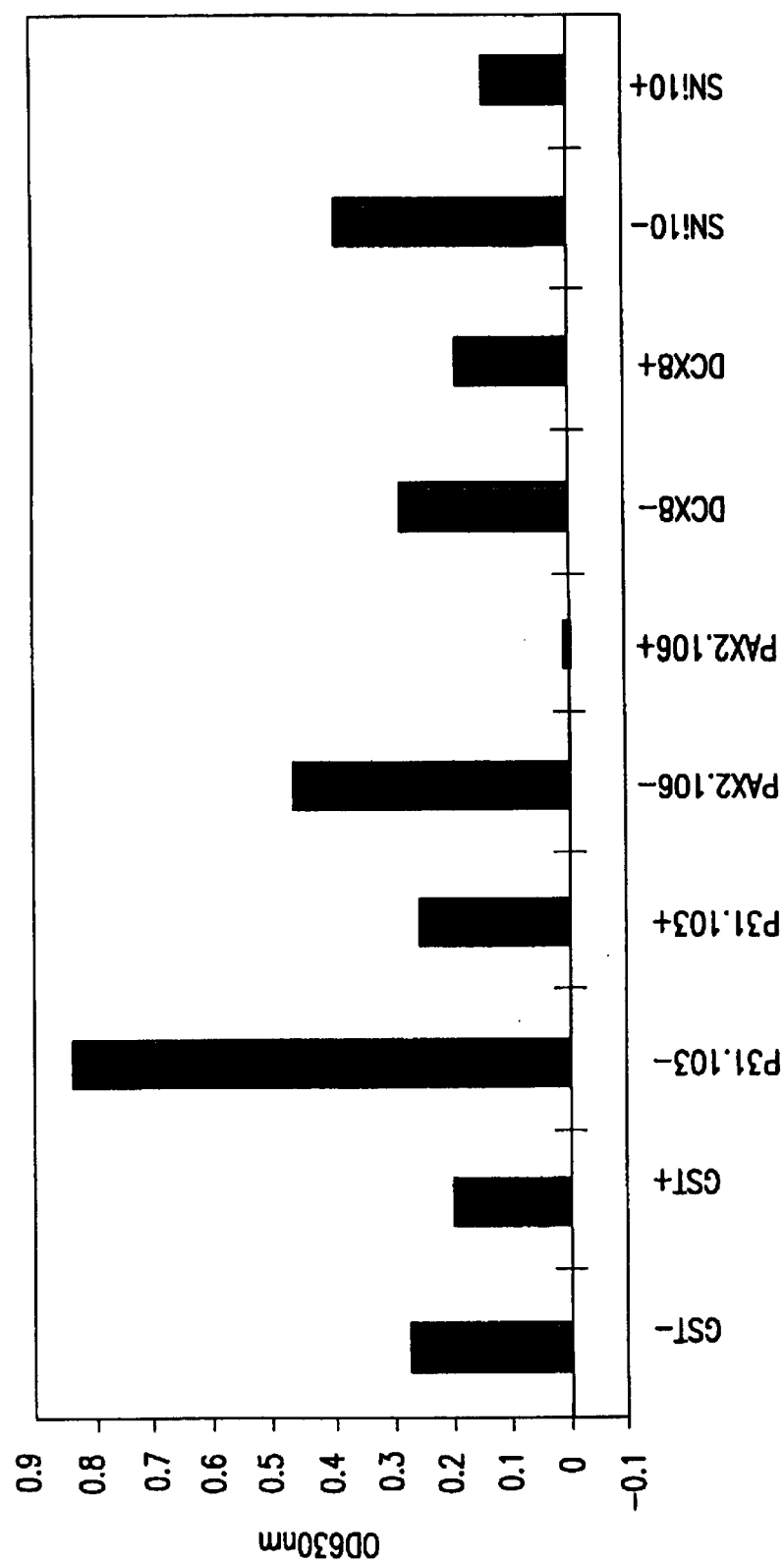

FIG. 12. FIG. 12 shows the binding of GST and GST-fusion proteins to fixed Caco-2 cells, and the corresponding proteins following digestion with the protease Thrombin which cleaves at a recognition site between the GST portion and the fused peptide portion of the GST-fusion protein. The symbol "–" refers to proteins which were not digested with thrombin and the symbol "+" refers to proteins which were digested with thrombin prior to use in the binding assay. The binding of the proteins to the fixed Caco-2 cells was detected by ELISA assays.

Figure 13A:
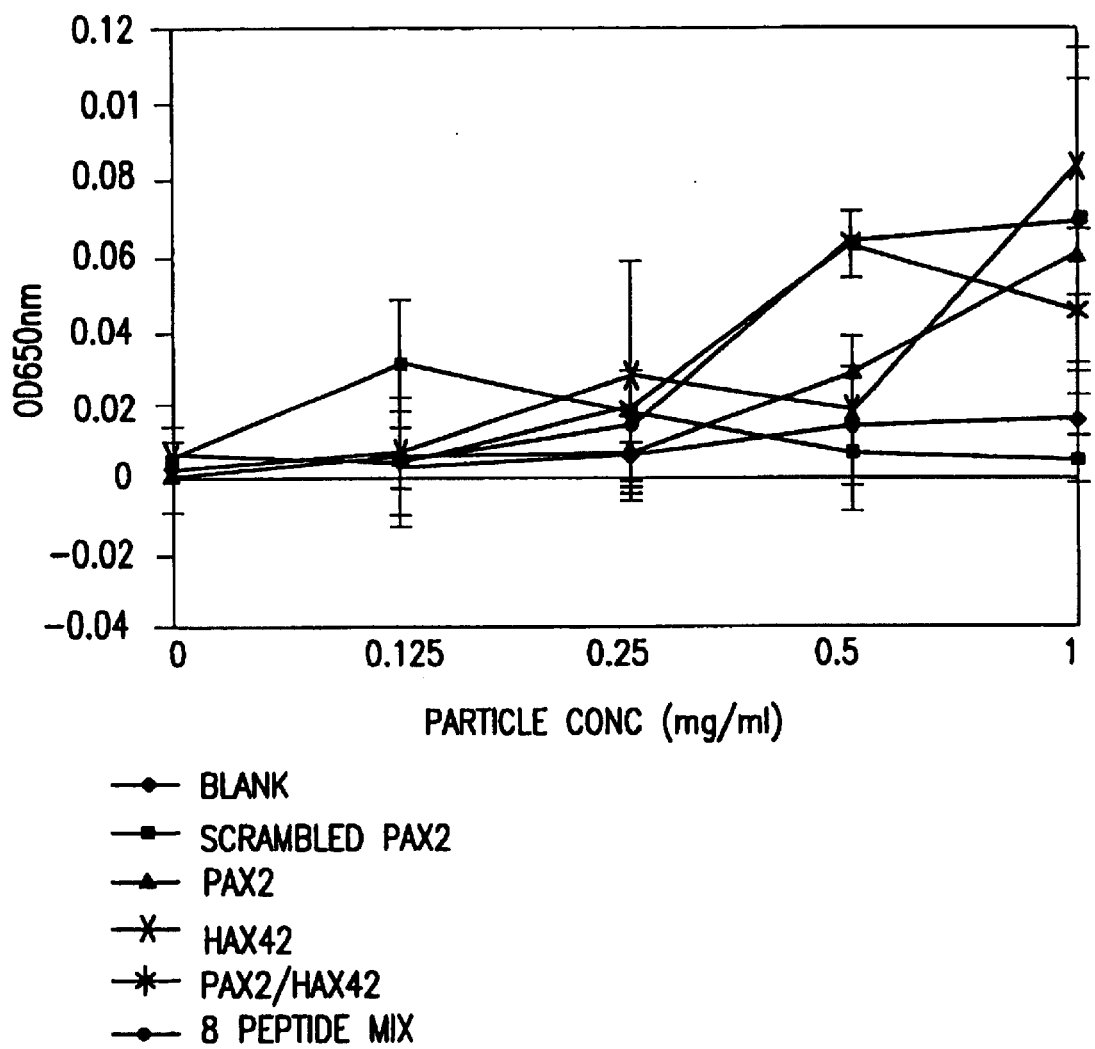
Figure 13B:
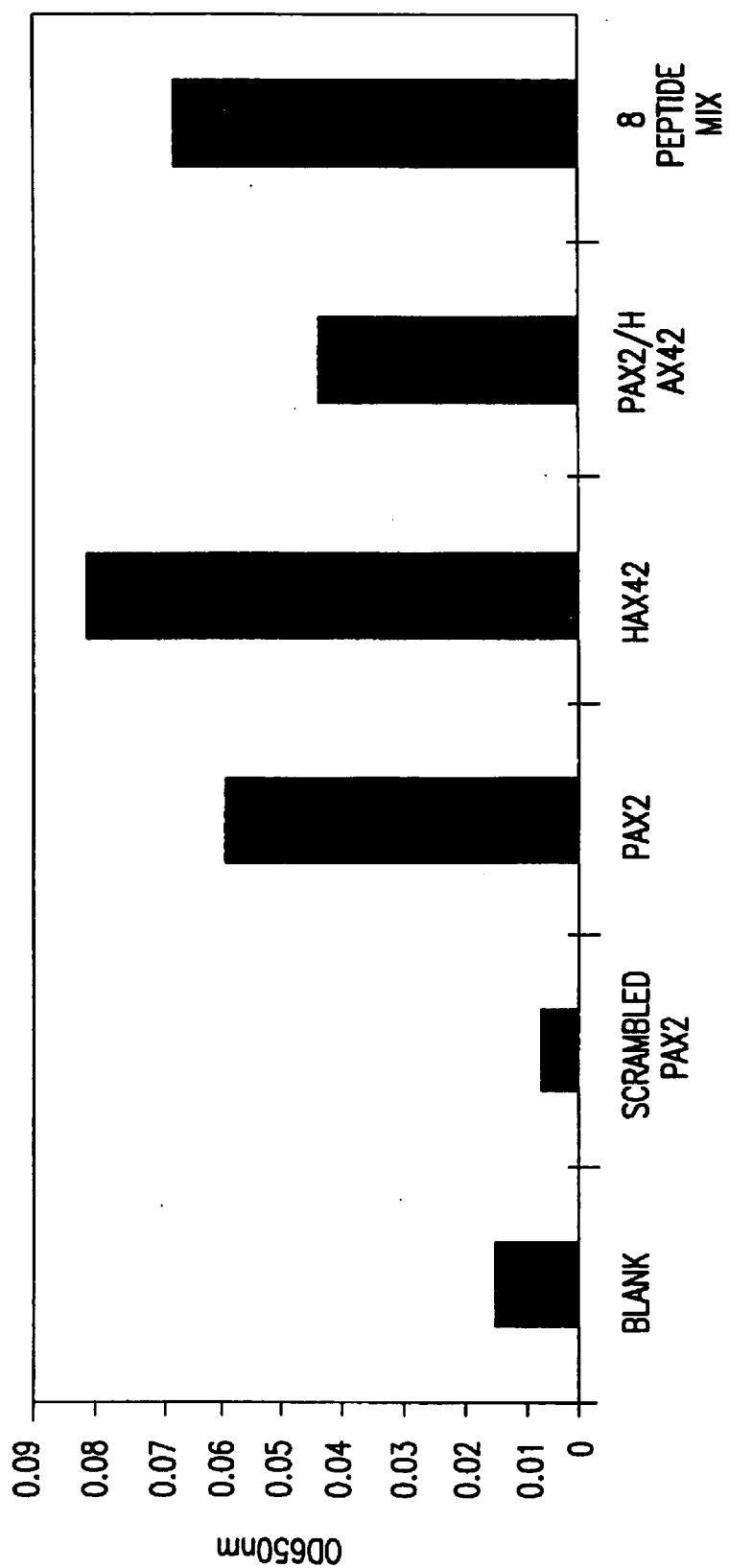

FIGS. 13A–13B. FIGS. 13A–13B show binding of peptide-coated nanoparticles to fixed Caco-2 cells.

Figure 14A:
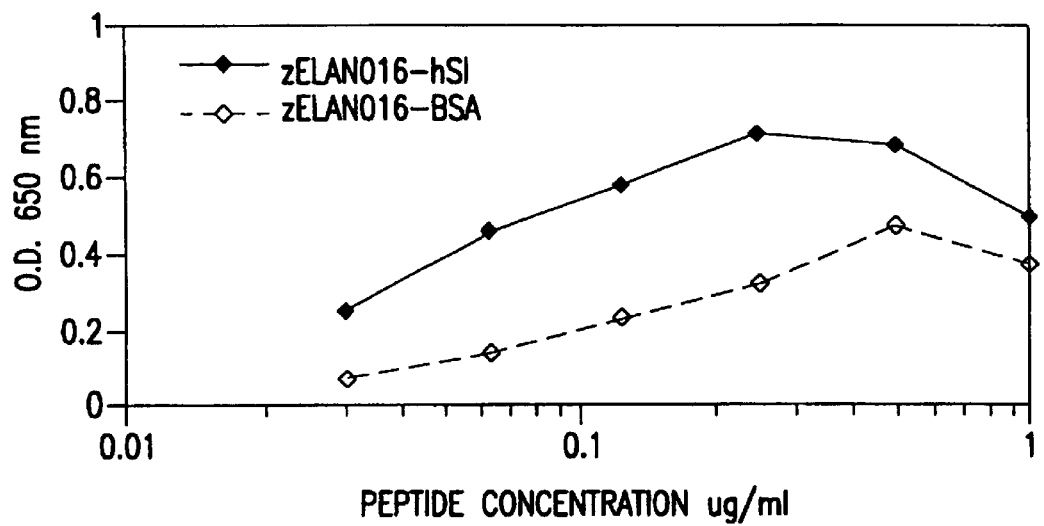
Figure 14B:
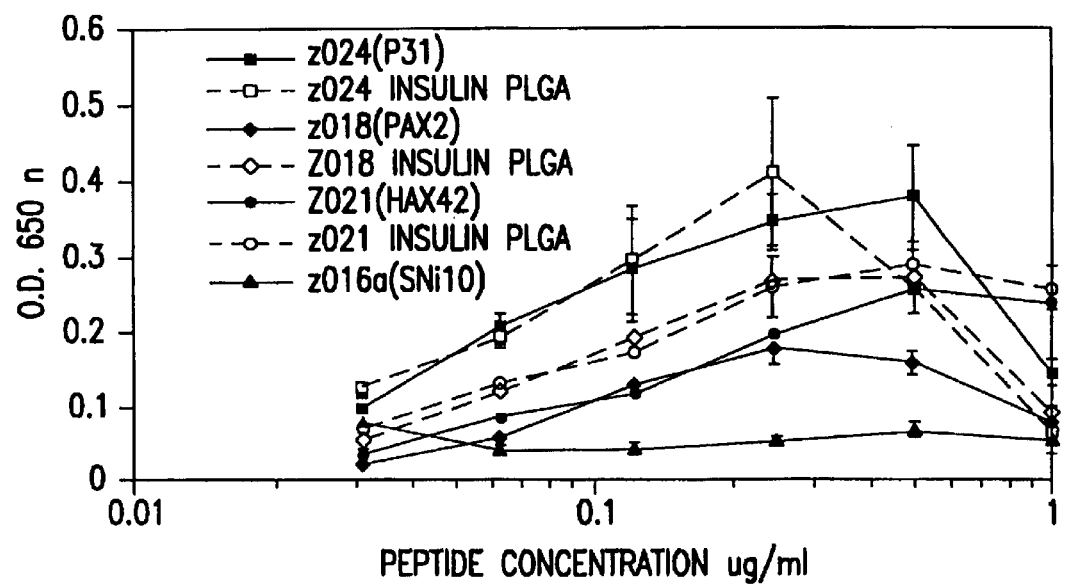

FIGS. 14A–14B. FIGS. 14A–14B show the binding of (A) dansylated peptide SNi10 to the purified hSI receptor and BSA and (B) dansylated peptides and peptide-loaded insulin-containing PLGA particles to fixed C2BBe1 cells. FIG. 14B depicts binding of dansylated peptides corresponding to P31 (SEQ ID NO:43), PAX2, HAX42, and SNi10 to fixed C2BBe1 cells, as well as the insulin-containing PLGA particles adsorbed with each of these peptides. Data is presented with background subtracted.

Figure 15A:
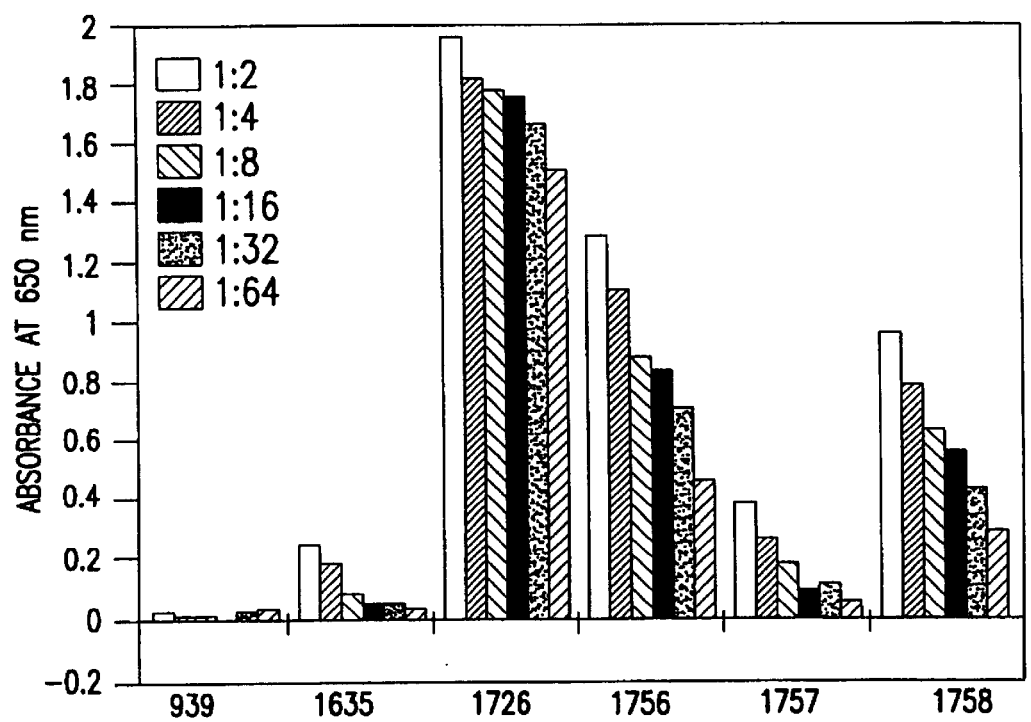
Figure 15B:
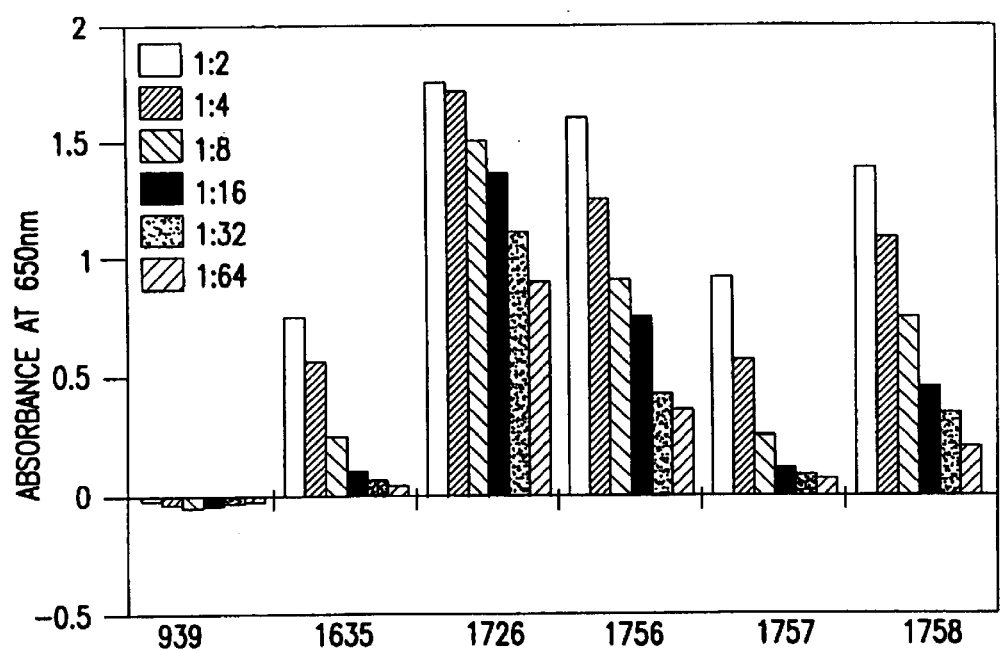

FIGS. 15A–15B. FIG. 15 shows the binding of peptide-coated particles to A) S100 and B) P100 fractions harvested from Caco-2 cells. The dilution series 1:2–1:64 represents particle concentrations in the range 0.0325–0.5 µg/well. Data is presented with background subtracted. The particles are identified as follows: 939, no peptide; 1635, scrambled PAX2; 1726, P31 D-Arg 16-mer (ZElan053); 1756, HAX42; 1757, PAX2; 1758, HAX42/PAX2.

Figure 16A:
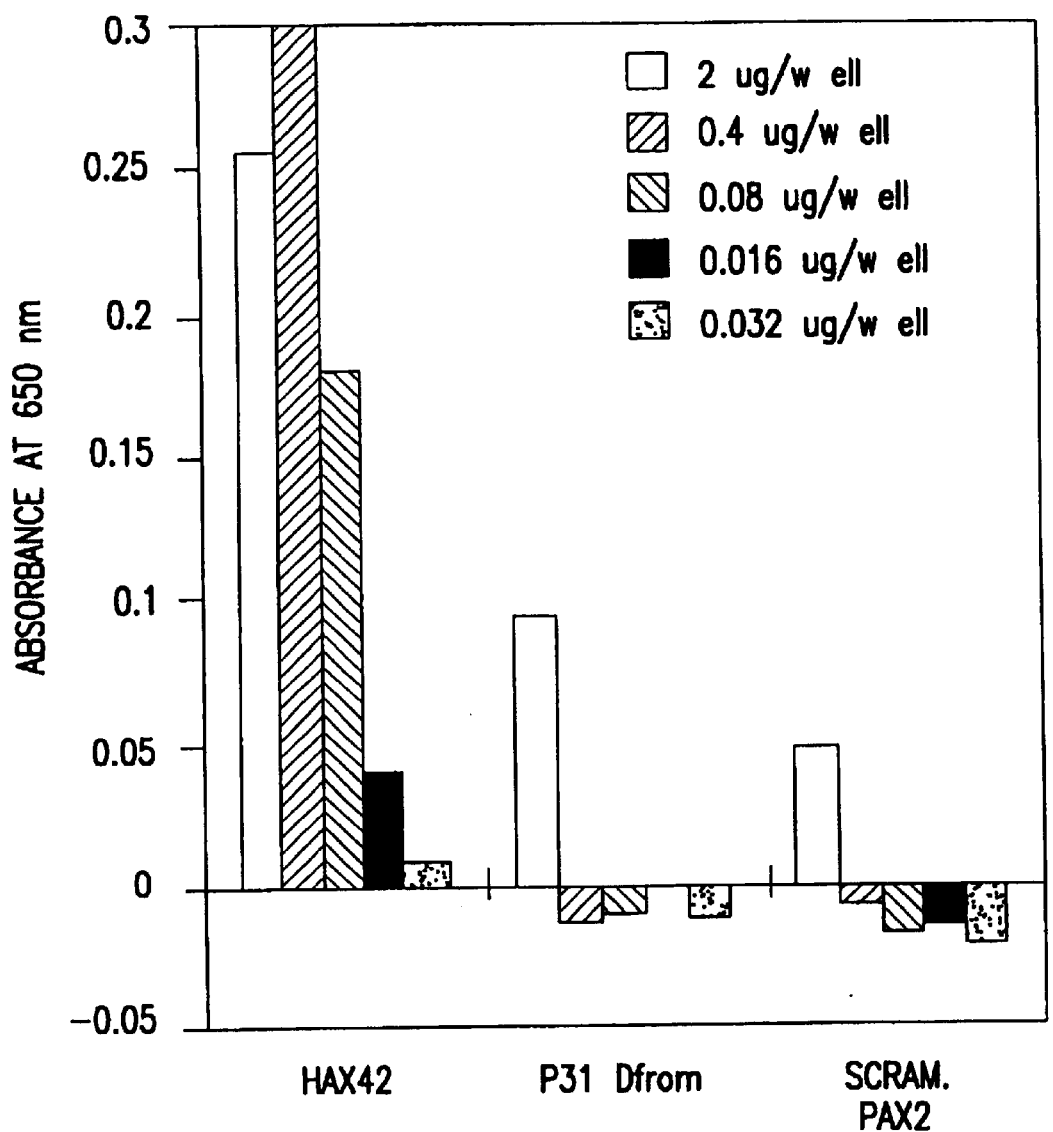
Figure 16B:
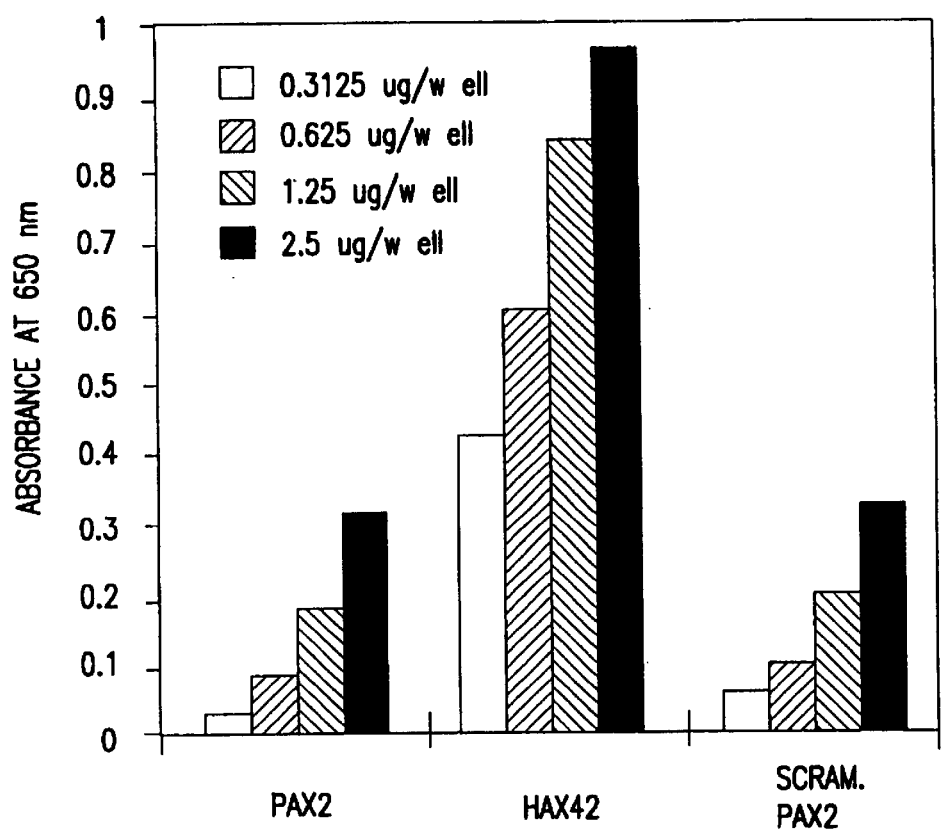

FIGS. 16A–16B. FIG. 16 shows the binding of dansylated peptides to P100 fractions harvested from Caco-2 cells. Peptides were assayed in the range 0.0032–2.5 µg/well. Data is presented with background subtracted. A) HAX42, P31 D-form (ZElan 053) and scrambled PAX2; B) PAX2, HAX42 and scrambled PAX2.

Figure 17A:
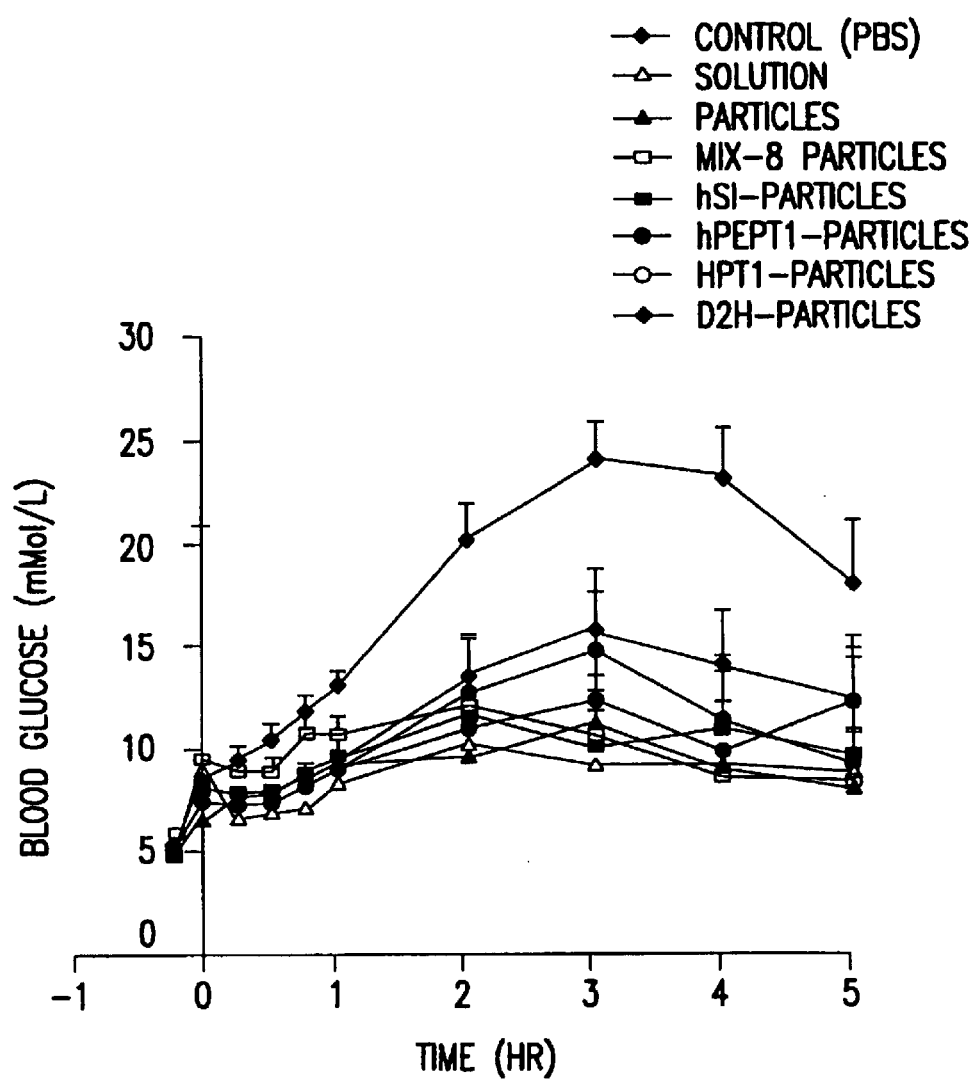
Figure 17B:
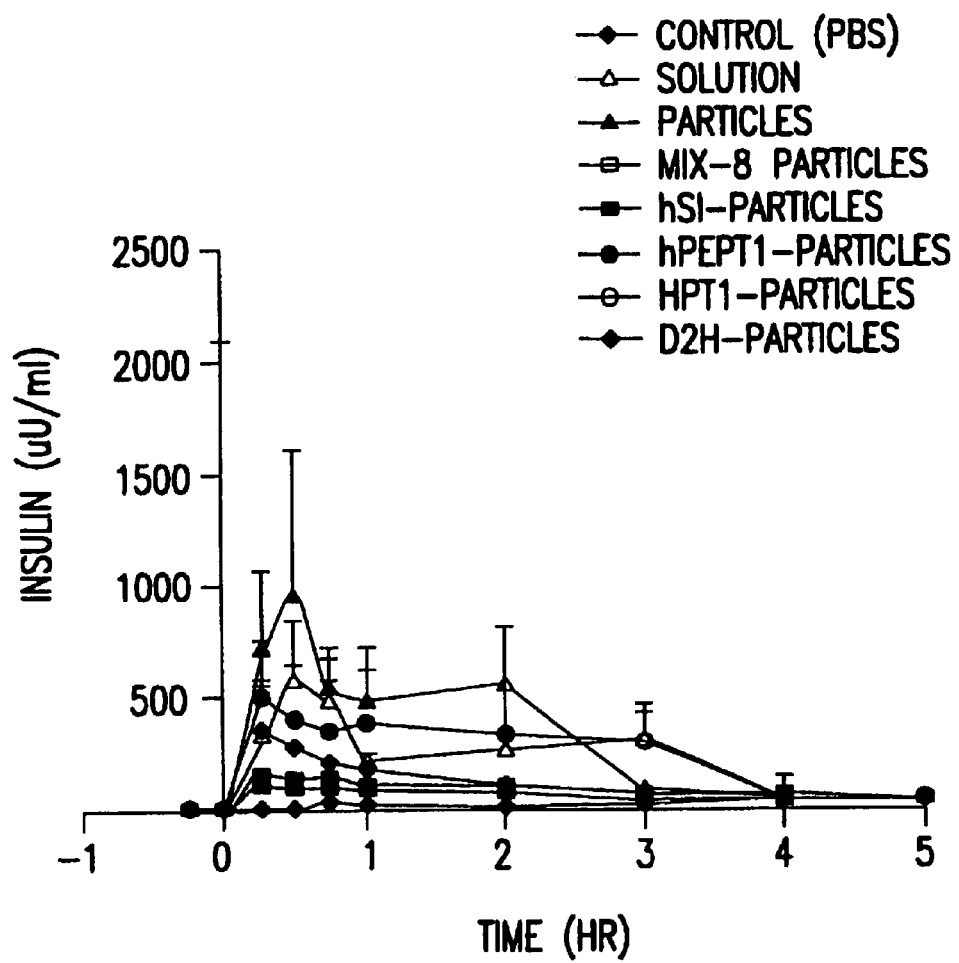

FIGS. 17A–17B. FIGS. 17A and 17B show (A) the systemic blood glucose and (B)insulin levels following intestinal administration of control (PBS); insulin solution; insulin particles; all 8 peptides mix particles and study group peptide-particles according to this invention (100 iu insulin loading).

Figure 18A:
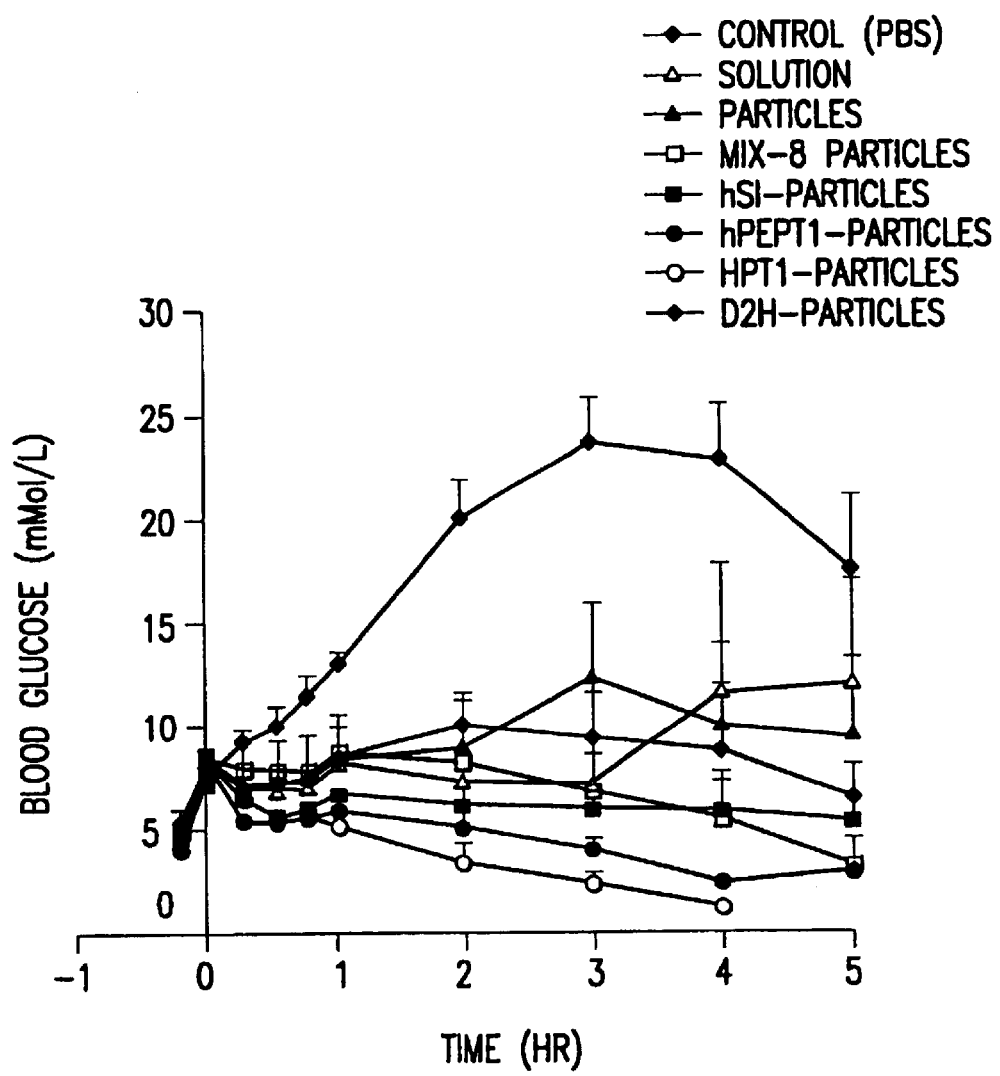
Figure 18B:
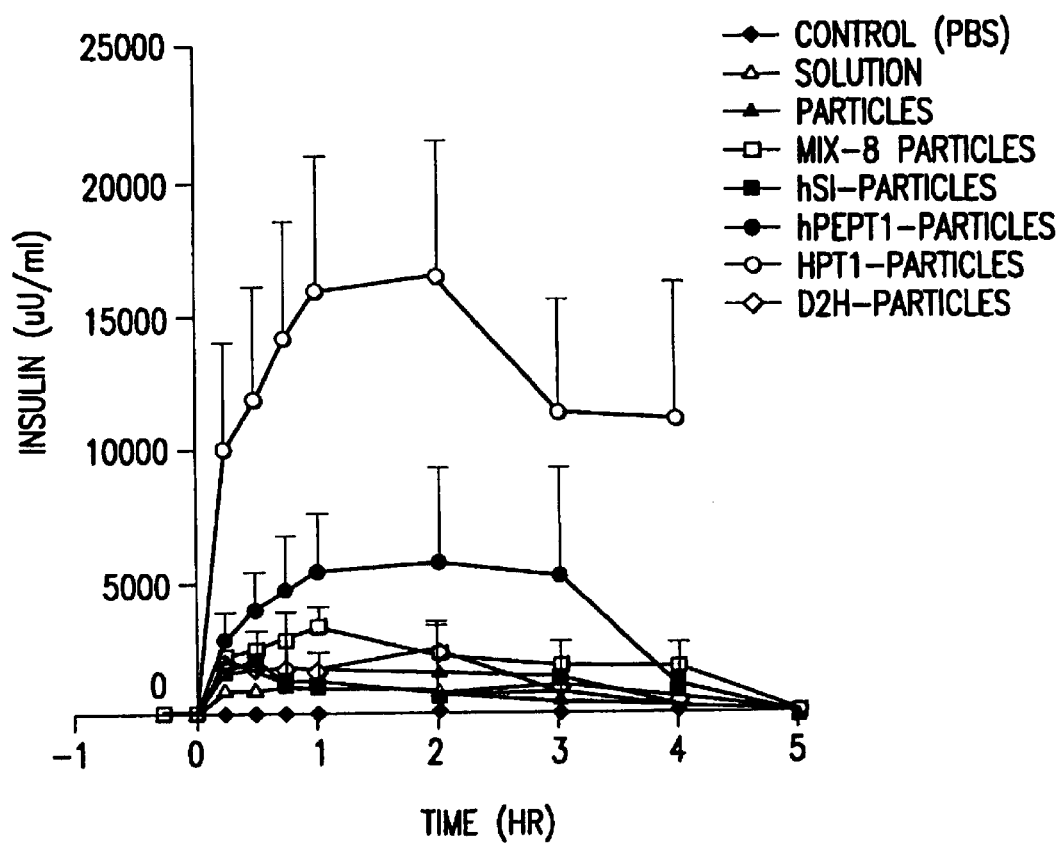

FIGS. 18A–18B. FIGS. 18A and 18B show the (A) systemic blood glucose and (B)insulin levels following intestinal administration of control (PBS); insulin solution; insulin particles and study group peptide-particles according to this invention (300 iu insulin loading).

Figure 19:
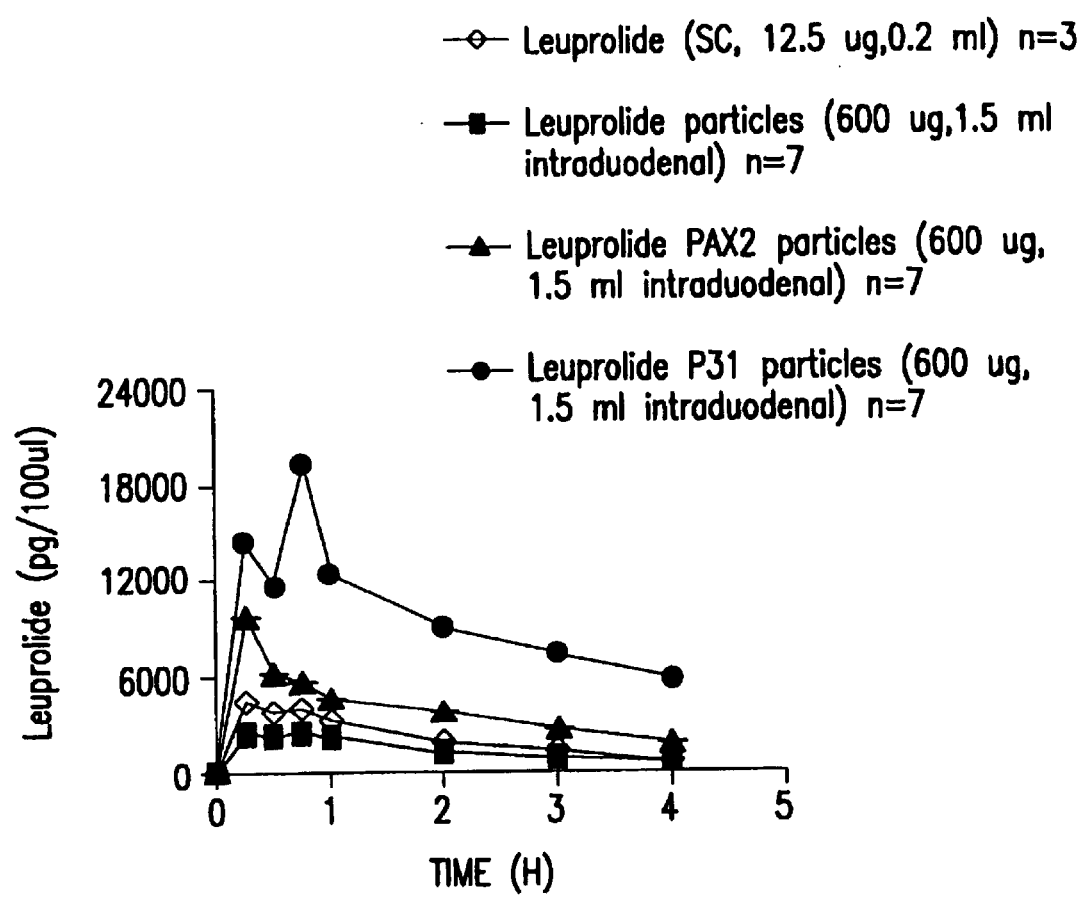

FIG. 19. FIG. 19 shows the enhanced plasma levels of leuprolide upon administration of P31 (SEQ ID NO:43) and PAX2 coated nanoparticles loaded with leuprolide relative to subcutaneous injection. Group 1 was administered leuprolide acetate (12.5 µg) subcutaneously. Group 2 was administered intraduodenally uncoated leuprolide acetate particles (600 µg, 1.5 ml). Group 3 was intraduodenally administered leuprolide acetate particles coated with PAX2 (600 µg; 1.5 ml). Group 4 was administered intraduodenally leuprolide acetate particles coated with P31 (SEQ ID NO:43) (600 µg, 1.5 ml).

FIG. 20. FIG. 20 lists P31 (SEQ ID NO:43) known protein homologies.

FIGS. 21A–21C. FIGS. 21A–21C list DCX8 known protein homologies.

FIG. 22. FIG. 22 lists DAB10 known protein homologies.

FIG. 23. FIG. 23 shows the DNA sequence (SEQ ID NO:211) and the corresponding amino acid sequence (SEQ ID NO:212) for glutathione S-transferase (Smith and Johnson, 1988, Gene 7:31–40).

5. DETAILED DESCRIPTION OF THE INVENTION

The present invention relates to proteins (e.g., peptides) that bind to GIT transport receptors and nucleic acids that encode such proteins. The invention further relates to fragments and other derivatives of such proteins. Nucleic acids encoding such fragments or derivatives are also within the scope of the invention. The invention further relates to fragments (and derivatives and analogs thereof) of GIT transport receptor-binding peptides which comprise one or more domains of the GIT transport receptor-binding peptides.

The invention also relates to derivatives of GIT transport receptor-binding proteins and analogs of the invention which are functionally active, i.e., they are capable of displaying one or more known functional activities associated with a full-length GIT transport receptor-binding peptide. Such functional activities include but are not limited to ability to bind to a GIT transport receptor, antigenicity [ability to bind (or compete with peptides for binding) to an anti-GIT transport receptor-binding peptide antibody], immunogenicity (ability to generate antibody which binds to GIT transport receptor-binding peptide), etc.

Production of the foregoing proteins and derivatives, by, e.g., recombinant methods, is also provided.

Antibodies to GIT transport receptor-binding proteins, derivatives and analogs, are additionally provided.

The present invention also relates to therapeutic and diagnostic methods and compositions based on GIT transport receptor-binding proteins and nucleic acids.

The invention is illustrated by way of examples infra.

For clarity of disclosure, and not by way of limitation, the detailed description of the invention is divided into the subsections which follow.

5.1. GIT Transport Receptor-binding Peptides, Derivatives and Analogs

The invention relates to peptides that bind GIT transport receptors and derivatives (including but not limited to fragments) and analogs thereof. In specific embodiments, of the present invention, such peptides that bind to GIT transport receptor include but are not limited to those containing as primary amino acid sequences, all or part of the amino acid sequences substantially as depicted in Table 7 (SEQ ID NOS:1–55). Nucleic acids encoding such peptides, derivatives and peptide analogs are also provided. In one embodiment, the GIT transport receptor-binding peptides are encoded by the nucleic acids having the nucleotide sequences set forth in Table 8 infra (SEQ ID NOS:56–109). Proteins whose amino acid sequence comprise, or alternatively, consist of SEQ ID NOS:1–55 or a portion thereof that mediates binding to a GIT transport receptor are provided.

The production and use of derivatives and analogs related to GIT transport receptor-binding peptides are within the scope of the present invention. In a specific embodiment, the derivative or analog is functionally active, i.e., capable of exhibiting one or more functional activities associated with a full-length GIT transport receptor-binding peptide. For example, such derivatives or analogs which have the desired immunogenicity or antigenicity can be used, in immunoassays, for immunization, etc. A specific embodiment relates to a GIT transport receptor-binding peptide fragment that can be bound by an anti-GIT transport receptor-binding peptide antibody. In a preferred aspect, the derivatives or analogs have the ability to bind to a GIT transport receptor. Derivatives or analogs of GIT transport receptor-binding peptides can be tested for the desired activity by procedures known in the art, including binding to a GIT transport receptor domain or to Caco-2 cells, in vitro, or to intestinal tissue, in vivo. (See the Examples infra.)

In particular, derivatives can be made by altering GIT transport receptor-binding peptide sequences by substitutions, additions or deletions that provide for functionally equivalent molecules. Due to the degeneracy of nucleotide coding sequences, other nucleotide sequences which encode substantially the same amino acid sequence may be used in the practice of the present invention. These include but are not limited to nucleotide sequences which are altered by the substitution of different codons that encode a functionally equivalent amino acid residue within the sequence, thus producing a silent change. Likewise, the GIT transport receptor-binding peptide derivatives of the invention include, but are not limited to, those containing, as a primary amino acid sequence, all or part of the amino acid sequence of a GIT transport receptor-binding peptide including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, proteins consisting of or, alternatively, comprising all or a fragment of a GIT transport receptor-binding peptide consisting of at least 5, 10, 15, 20, 25, 30 or 35 (contiguous) amino acids of the full-length GIT transport receptor-binding peptide are provided. In a specific embodiment, such proteins are not more than 20, 30, 40, 50, or 75 amino acids in length. Derivatives or analogs of GIT transport receptor-binding peptides include but are not limited to those molecules comprising regions that are substantially homologous to GIT transport receptor-binding peptides or fragments thereof (e.g., at least 50%, 60%, 70%, 80% or 90% identity) (e.g., over an identical size sequence or when compared to an aligned sequence in which the alignment is done by a computer homology program known in the art) or whose encoding nucleic acid is capable of hybridizing to a coding GIT transport receptor-binding peptide sequence, under stringent, moderately stringent, or nonstringent conditions.

In a specific embodiment, the GIT transport receptor-binding derivatives of the invention are not known proteins with homology to the GIT transport receptor-binding peptides of the invention or portions thereof.

The GIT transport receptor-binding peptide derivatives and analogs of the invention can be produced by various methods known in the art. The manipulations which result in their production can occur at the gene or protein level. For example, the cloned GIT transport receptor-binding peptide gene sequence can be modified by any of numerous strategies known in the art (Maniatis, T., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of GIT transport receptor-binding peptides, care should be taken to ensure that the modified gene remains within the same translational reading frame uninterrupted by translational stop signals, in the gene region where the desired GIT transport receptor-binding peptides activity is encoded.

Additionally, nucleic acid sequences encoding the GIT transport receptor-binding peptides can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem 253:6551), use of TAB® linkers (Pharmacia), use of PCR primers containing mutation(s) for use in amplification, etc.

Manipulations of GIT transport receptor-binding peptide sequences may also be made at the protein level. Included within the scope of the invention are GIT transport receptor-binding peptide fragments or other derivatives or analogs which are differentially modified during or after translation or chemical synthesis, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc. In a specific embodiment, the amino- and/or carboxy-termini are modified.

In addition, GIT transport receptor-binding peptides and analogs and derivatives thereof can be chemically synthesized. For example, a peptide corresponding to all or a portion of a GIT transport receptor-binding peptide which comprises the desired domain or which mediates the desired activity in vitro, can be synthesized by use of a peptide synthesizer. Furthermore, if desired, nonclassical amino acids or chemical amino acid analogs can be introduced as a substitution or addition into the GIT transport receptor-binding peptide sequence. Non-classical amino acids include but are not limited to the D-isomers of the common amino acids, α-amino isobutyric acid, 4-aminobutyric acid, Abu, 2-amino butyric acid, γ-Abu, ϵ-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In a specific embodiment, the GIT transport receptor-binding peptide derivative is a chimeric, or fusion, peptide comprising a GIT transport receptor-binding peptide or fragment thereof (preferably consisting of at least a domain or motif of the GIT transport receptor-binding peptide, or at least 6, 10, 15, 20, 25, 30 or all amino acids of the GIT transport receptor-binding peptides or a binding portion thereof) joined at its amino- or carboxy-terminus via a peptide bond to an amino acid sequence of a different peptide. In one embodiment, such a chimeric peptide is produced by recombinant expression of a nucleic acid encoding the protein (comprising a transport receptor-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising portions of GIT transport receptor fused to any heterologous protein-encoding sequences may be constructed. A specific embodiment relates to a chimeric protein comprising a fragment of GIT transport receptor-binding peptides of at least six amino acids.

In another specific embodiment, the GIT transport receptor-binding peptide derivative is a molecule comprising a region of homology with a GIT transport receptor-binding peptide. By way of example, in various embodiments, a first protein region can be considered "homologous" to a second protein region when the amino acid sequence of the first region is at least 30%, 40%, 50%, 60%, 70%, 75%, 80%, 90%, or 95% identical, when compared to any sequence in the second region of an equal number of amino acids as the number contained in the first region or when compared to an aligned sequence of the second region that has been aligned by a computer homology program known in the art. For example, a molecule can comprise one or more regions homologous to a GIT transport receptor-binding peptide domain (see infra) or a portion thereof.

The GIT transport receptor-binding proteins and derivatives thereof of the invention can be assayed for binding activity by suitable in vivo or in vitro assays, e.g., as described in the examples infra and/or as will be known to the skilled artisan.

Other specific embodiments of derivatives and analogs are described in the subsection below and examples sections infra.

5.2. Motifs/Derivatives of GIT Transport Receptor-binding Peptides Containing One or More Domains of the Protein In a specific embodiment, the invention relates to GIT transport receptor-binding peptide derivatives and analogs, in particular GIT transport receptor-binding peptide fragments and derivatives of such fragments, that comprise, or alternatively consist of, one or more domains of a GIT transport receptor-binding peptide. In particular, examples of such domains are identified in the examples infra.

5.3. Synthesis of Peptides

The peptides and derivatives of the present invention may be chemically synthesized or synthesized using recombinant DNA techniques.

5.3.1. Procedure for Solid Phase Synthesis

Peptides may be prepared chemically by methods that are known in the art. For example, in brief, solid phase peptide synthesis consists of coupling the carboxyl group of the C-terminal amino acid to a resin and successively adding N-alpha protected amino acids. The protecting groups may be any known in the art. Before each new amino acid is added to the growing chain, the protecting group of the previous amino acid added to the chain is removed. The coupling of amino acids to appropriate resins is described by Rivier et al., U.S. Pat. No. 4,244,946. Such solid phase syntheses have been described, for example, by Merrifield, 1964, J. Am. Chem. Soc. 85:2149; Vale et al., 1981, Science 213:1394–1397; Marki et al., 1981, J. Am. Chem. Soc. 103:3178 and in U.S. Pat. Nos. 4,305,872 and 4,316,891. In a preferred aspect, an automated peptide synthesizer is employed.

By way of example but not limitation, peptides can be synthesized on an Applied Biosystems Inc. ("ABI") model 431A automated peptide synthesizer using the "Fastmoc" synthesis protocol supplied by ABI, which uses 2-(1H-Benzotriazol-1-yl)-1,1,3,3,-tetramethyluronium hexafluorophosphate ("HBTU") (R. Knorr et al., 1989, Tet. Lett., 30:1927) as coupling agent. Syntheses can be carried out on 0.25 mmol of commercially available 4-(2',4'-dimethoxyphenyl-(9-fluorenyl-methoxycarbonyl)-aminomethyl)-phenoxy polystyrene resin ("Rink resin" from Advanced ChemTech) (H. Rink, 1987, Tet. Lett. 28:3787). Fmoc amino acids (1 mmol) are coupled according to the Fastmoc protocol. The following side chain protected Fmoc amino acid derivatives are used:

FmocArg(Pmc)OH; FmocAsn(Mbh)OH; FmocAsp($^t$Bu) OH; FmocCys(Acm)OH; FmocGlu($^t$Bu)OH; FmocGln (Mbh)OH; FmocHis(Tr)OH; FmocLys(Boc)OH; FmocSer($^t$Bu)OH; FmocThr($^t$Bu)OH; FmocTyr($^t$Bu) OH. [Abbreviations: Acm, acetamidomethyl; Boc, tert-butoxycarbonyl; $^t$Bu, tert-butyl; Fmoc, 9-fluorenylmethoxycarbonyl; Mbh, 4,4'-dimethoxybenzhydryl; Pmc, 2,2,5,7,8-pentamethylchroman-6-sulfonyl; Tr, trityl].

Synthesis is carried out using N-methylpyrrolidone (NMP) as solvent, with HBTU dissolved in N,N-dimethylformamide (DMF). Deprotection of the Fmoc group is effected using approximately 20% piperidine in NMP. At the end of each synthesis the amount of peptide present is assayed by ultraviolet spectroscopy. A sample of dry peptide resin (about 3–10 mg) is weighed, then 20% piperidine in DMA (10 ml) is added. After 30 min sonication, the UV (ultraviolet) absorbance of the dibenzofulvene-piperidine adduct (formed by cleavage of the N-terminal Fmoc group) is recorded at 301 nm. Peptide substitution (in mmol g$^{-1}$) can be calculated according to the equation:

$$\text{substitution} = \frac{A \times v}{7800 \times w} \times 1000$$

where A is the absorbance at 301 nm, v is the volume of 20% piperidine in DMA (in ml), 7800 is the extinction coefficient (in mol$^{-1}$dm$^3$cm$^{-1}$) of the dibenzofulvene-piperidine adduct, and w is the weight of the peptide-resin sample (in mg).

Finally, the N-terminal Fmoc group is cleaved using 20% piperidine in DMA, then acetylated using acetic anhydride and pyridine in DMA. The peptide resin is thoroughly washed with DMA, CH$_2$Cl$_2$ and finally diethyl ether.

5.3.2. Cleavage and Deprotection

By way of example but not limitation, cleavage and deprotection can be carried out as follows: The air-dried peptide resin is treated with ethylmethyl-sulfide (EtSMe), ethanedithiol (EDT), and thioanisole (PhSMe) for approximately 20 min. prior to addition of 95% aqueous trifluoracetic acid (TFA). A total volume of approximately 50 ml of these reagents per gram of peptide-resin is used.

The following ratio is used: TFA:EtSMe:EDT:PhSMe (10:0.5:0.5:0.5). The mixture is stirred for 3 h at room temperature under an atmosphere of N$_2$. The mixture is filtered and the resin washed with TFA (2×3 ml). The combined filtrate is evaporated in vacuo, and anhydrous diethyl ether added to the yellow/orange residue. The resulting white precipitate is isolated by filtration. See King et al., 1990, Int. J. Peptide Protein Res. 36:255–266 regarding various cleavage methods.

5.3.3. Purification of the Peptides

Purification of the synthesized peptides can be carried out by standard methods including chromatography (e.g., ion exchange, affinity, and sizing column chromatography, high performance liquid chromatography (HPLC)), centrifugation, differential solubility, or by any other standard technique.

5.3.4. Biological Peptide Libraries

Biological peptide libraries can be used to express and identify peptides that bind to GIT transport receptors. According to this second approach, involving recombinant DNA techniques, peptides can, by way of example, be expressed in biological systems as either soluble fusion proteins or viral capsid proteins.

5.3.4.1. Methods to Identify Binders: Construction Of Libraries

In a specific embodiment, the peptides of the invention that specifically bind to GIT transport receptors are identified by screening a random peptide library by contacting the library with a ligand selected from among HPT1, hPEPT1, D2H, or hSI (or a molecule consisting essentially of an extracellular domain thereof or fragment of the domain) to identify members of the library that specifically bind to the ligand.

In a particular embodiment, a process to identify the peptides of the present method utilizes a library of recombinant vectors constructed by methods well known in the art and comprises screening a library of recombinant vectors expressing inserted synthetic oligonucleotide sequences encoding extracellular GIT transport receptor domains, for example, attached to an accessible surface structural protein of a vector to isolate those members producing peptides that bind to HPT1, hPEPT1, D2H, or hSI. The nucleic acid sequence of the inserted synthetic oligonucleotides of the isolated vector is determined and the amino acid sequence encoded can be deduced to identify a binding domain that binds the ligand of choice (e.g., HPT1, hPEPT1, D2H, or hSI).

The present invention encompasses a method for identifying a peptide which binds to a ligand selected from among HPT1, hPEPT1, D2H, or hSI comprising: screening a library of random peptides with the ligand (or an extracellular domain or fragment thereof) under conditions conducive to ligand binding and isolating the peptide which binds to the ligand. Additionally, the methods of the invention further comprise determining the nucleotide sequence encoding the binding domain of the peptide identified to deduce the amino acid sequence of the binding domain.

5.3.4.2. Preparation of Extracellular Domain Ligand

In a specific embodiment, molecules consisting essentially of an extracellular domain of the desired GIT transport receptor or a fragment of an extracellular domain are used to screen a random peptide library for binding thereto. Preferably, a nucleic acid encoding the extracellular domain is cloned and recombinantly expressed, and the domain is then purified for use. The GIT transport receptor is preferably selected from among HPT1, hPEPT1, D2H, or hSI.

5.3.4.3. Methods to Identify Binders: Screening Libraries

Once a suitable random peptide library has been constructed (or otherwise obtained), the library is screened to identify peptides having binding affinity for the GIT transport receptor, e.g., HPT1, hPEPT1, D2H, or hSI. In a preferred aspect, the library is a TSAR library (see U.S. Pat. No. 5,498,538 dated Mar. 12, 1996 and PCT Publication WO 94/18318 dated Aug. 18, 1994, both of which are incorporated by reference herein in their entireties). Screening the libraries can be accomplished by any of a variety of methods known to those of skill in the art. See, e.g., the following references, which disclose screening of peptide libraries: Parmley and Smith, 1989, Adv. Exp. Med. Biol. 251: 215–218; Scott and Smith, 1990, Science 249: 386–390; Fowlkes et al., 1992; BioTechniques 13: 422–427; Oldenburg et al., 1992, Proc. Natl. Acad. Sci. USA 89: 5393–5397; Yu et al., 1994, Cell 76: 933–945; Staudt et al., 1988, Science 241: 577–580; Bock et al., 1992, Nature 355: 564–566; Tuerk et al., 1992, Proc. Natl. Acad. Sci. USA 89: 6988–6992; Ellington et al., 1992, Nature 355: 850–852; U.S. Pat. No. 5,096,815, U.S. Pat. No. 5,223,409, and U.S. Pat. No. 5,198,346, all to Ladner et al.; and Rebar and Pabo, 1993, Science 263: 671–673. See also PCT publication WO 94/18318, dated Aug. 18, 1994.

One of ordinary skill in the art will recognize that, with suitable modifications, the screening methods described below would be suitable for a wide variety of biological expression libraries.

Once a library has been constructed or otherwise obtained, the library is screened to identify binding molecules having specific binding affinity for a ligand for a GIT transport receptor preferably selected from among HPT1, hPEPT1, D2H, or hSI.

Screening the libraries can be accomplished by any of a variety of methods known to those of skill in the art. Exemplary screening methods are described in Fowlkes et al., 1992, BioTechniques, 13:422–427 and include contacting the vectors with an immobilized target ligand and harvesting those vectors that bind to said ligand. Such useful screening methods, are designated "panning" methods. In panning methods useful to screen the present libraries, the target ligand can be immobilized on plates, beads (such as magnetic beads), sepharose, beads used in columns, etc. If desired, the immobilized target ligand can be "tagged", e.g., using labels such as biotin, fluoroscein isothiocyanate, rhodamine, etc. e.g. for FACS sorting. Panning is also disclosed in Parmley, S. F. and Smith, G. P., 1988, Gene 73: 305–318.

In a particular embodiment of the invention, the library can be screened with a recombinant receptor domain. In another embodiment, the library can be screened successively with receptor domains and then on CaCO-2 cells.

For screening of the peptide libraries in vitro, the solvent requirements involved in screening are not limited to aqueous solvents; thus, nonphysiological binding interactions and conditions different from those found in vivo can be exploited.

Screening a library can be achieved using a method comprising a first "enrichment" step and a second filter lift as follows. The following description is given by way of example, not limitation.

Binders from an expressed library (e.g., in phage) capable of binding to a given ligand ("positives") are initially enriched by one or two cycles of panning or affinity chromatography. A microtiter well is passively coated with the ligand (e.g., about 10 µg in 100 µl). The well is then blocked with a solution of BSA to prevent non-specific adherence of the phage of the library to the plastic surface. For example, about $10^{11}$ phage particles expressing peptides are then added to the well and incubated for several hours. Unbound phage are removed by repeated washing of the plate, and specifically bound phage are eluted using an acidic glycine-HCl solution or other elution buffer. The eluted phage solution is neutralized with alkali, and amplified, e.g., by infection of E. coli and plating on large petri dishes containing Luria broth (LB) in agar. Amplified cultures expressing the binding peptides are then titered and the process repeated. Alternatively, the ligand can be covalently coupled to agarose or acrylamide beads using commercially available activated bead reagents. The phage solution is then simply passed over a small column containing the coupled bead matrix which is then washed extensively and eluted with acid or other eluant. In either case, the goal is to enrich the positives to a frequency of about $>1/10^5$.

Following enrichment, a filter lift assay is conducted. For example, when specific binders are expressed in phage, approximately $1-2\times10^5$ phage are added to 500 µl of log phase E. coli and plated on a large Luria Broth-agarose plate with 0.7% agarose in broth. The agarose is allowed to solidify, and a nitrocellulose filter (e.g., 0.45µ) is placed on the agarose surface. A series of registration marks is made with a sterile needle to allow re-alignment of the filter and plate following development as described below. Phage plaques are allowed to develop by overnight incubation at 37° C. (the presence of the filter does not inhibit this process). The filter is then removed from the plate with phage from each individual plaque adhered in situ. The filter is then exposed to a solution of BSA or other blocking agent for 1–2 hours to prevent non-specific binding of the ligand (or "probe").

The probe itself is labeled, for example, either by biotinylation (using commercial NHS-biotin) or direct enzyme labeling, e.g., with horse radish peroxidase or alkaline phosphatase. Probes labeled in this manner are indefinitely stable and can be re-used several times. The blocked filter is exposed to a solution of probe for several hours to allow the probe to bind in situ to any phage on the filter displaying a peptide with significant affinity to the probe. The filter is then washed to remove unbound probe, and then developed by exposure to enzyme substrate solution (in the case of directly labeled probe) or further exposed to a solution of enzyme-labeled avidin (in the case of biotinylated probe). Positive phage plaques are identified by localized deposition of colored enzymatic cleavage product on the filter which corresponds to plaques on the original plate. The developed filter is simply realigned with the plate using the registration marks, and the "positive" plaques are cored from the agarose to recover the phage. Because of the high density of plaques on the original plate, it may be difficult to isolate a single plaque from the plate on the first pass. Accordingly, phage recovered from the initial core can be re-plated at low density and the process can be repeated to allow isolation of individual plaques and hence single clones of phage.

Successful screening experiments are optimally conducted using 3 rounds of serial screening. The recovered cells are then plated at a low density to yield isolated colonies for individual analysis. The individual colonies are selected and used to inoculate LB culture medium containing ampicillin. After overnight culture at 37° C., the cultures are then spun down by centrifugation. Individual cell aliquots are then retested for binding to the target ligand attached to the beads. Binding to other beads having attached thereto a non-relevant ligand, can be used as a negative control.

One aspect of screening the libraries is that of elution. The following discussion is applicable to any system where the random peptide is expressed on a surface fusion molecule. It is conceivable that the conditions that disrupt the peptide-target interactions during recovery of the phage are specific for every given peptide sequence from a plurality of proteins expressed on phage. For example, certain interactions may be disrupted by acid pH but not by basic pH, and vice versa. Thus, it may be desirable to test a variety of elution conditions (including but not limited to pH 2–3, pH 12–13, excess target in competition, detergents, mild protein denaturants, urea, varying temperature, light, presence or absence of metal ions, chelators, etc.) and compare the primary structures of the binding proteins expressed on the phage recovered for each set of conditions to determine the appropriate elution conditions for each ligand/binding protein combination. Some of these elution conditions may be incompatible with phage infection because they are bactericidal and will need to be removed by dialysis (i.e., dialysis bag, Centricon/Amicon microconcentrators).

In a preferred embodiment, a phage display library of random peptides is screened to select phage expressing peptides that bind to a GIT transport receptor. Preferably, a first step is to isolate a preselected phage library. The "preselected phage library" is a library consisting of a subpopulation of a phage display library. This subpopulation can be formed by initially screening against either a target GIT transport receptor (or domain thereof) so as to permit the selection of a subpopulation of phages which specifically bind to the receptor. Alternatively, the subpopulation can be formed by screening against a target cell or cell type or tissue type or tissue barrier of the gastro-intestinal tract, so as to permit the selection of a subpopulation of phages which either bind specifically to the target cell or target cell type or target tissue or target tissue barrier, or which binds to and/or is transported across (or between) the target cell or target cell type or target tissue or target tissue barrier either in situ or in vivo. This preselected phage library or subpopulation of selected phages can also be rescreened against the target GIT transport receptor, permitting the further selection of a subpopulation of phages which bind to the GIT transport receptor or target cell or target cell type or target tissue or target tissue barrier or which bind to and/or is transported across the target cell, target tissue or target tissue barrier either in situ or in vivo. Such rescreening can be repeated from zero to 30 times with each successive "pre-selected phage library" generating additional pre-selected phage libraries.

In a preferred embodiment, a preselected phage library binding a ligand that is a GIT transport receptor preferably selected from among HPT1, hPEPT1, D2H, or hSI is obtained by an in vitro screening step as described above, and then the phage are optionally further characterized using in vitro assays consisting of binding phage directly to the receptor domain of interest or, alternatively, to Caco-2 cells or using in vivo assays. In another preferred embodiment, in vivo assays are used that measure uptake of phage by intestinal tissue or, alternatively, through the GIT. In alternative embodiments, such further in vitro or in vivo assays can be used as the initial screening step.

In vivo assays that may be used are described in the examples infra.

5.4. Generation of Antibodies to GIT Transport Receptor-binding Peptides and Derivatives Thereof According to the invention, a GIT transport receptor-binding peptide, fragments or other derivatives, or analogs thereof, may be used as an immunogen to generate antibodies which immunospecifically bind such an immunogen. Such antibodies include but are not limited to polyclonal, monoclonal, chimeric, single chain, Fab fragments, and an Fab expression library.

Various procedures known in the art may be used for the production of polyclonal antibodies to a GIT transport receptor-binding peptide or derivative or analog. For the production of antibody, various host animals can be immunized by injection with the native GIT transport receptor-binding peptides, or a synthetic version, or derivative (e.g., fragment) thereof, including but not limited to rabbits, mice, rats, fowl, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward a GIT transport receptor-binding peptide or analog thereof, any technique which provides for the production of antibody molecules by continuous cell lines in culture may be used. For example, the hybridoma-technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). According to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for GIT transport receptor-binding peptides together with genes from a human antibody molecule of appropriate biological activity can be used.

According to the invention, techniques described for the production of single chain antibodies (U.S. Pat. No. 4,946, 778) can be adapted to produce GIT transport receptor-binding peptide-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for GIT transport receptor-binding peptides, derivatives, or analogs.

Antibody fragments which contain the idiotype of the molecule can be generated by known techniques. For example, such fragments include but are not limited to: the F(ab')₂ fragment which can be produced by pepsin digestion of the antibody molecule; the Fab' fragments which can be generated by reducing the disulfide bridges of the F(ab')₂ fragment, the Fab fragments which can be generated by treating the antibody molecule with papain and a reducing agent, and Fv fragments.

In the production of antibodies, screening for the desired antibody can be accomplished by techniques known in the art, e.g. ELISA (enzyme-linked immunosorbent assay). For example, to select antibodies which recognize a specific domain of a GIT transport receptor-binding peptide, one may assay generated hybridomas for a product which binds to a GIT transport receptor-binding peptide fragment containing such a domain.

Antibodies specific to a domain of a GIT transport receptor-binding peptide are also provided.

The foregoing antibodies can be used in methods known in the art relating to the localization and activity of the GIT transport receptor-binding peptide sequences of the invention, e.g., for imaging these peptides after in vivo administration (e.g., to monitor treatment efficacy), measuring levels thereof in appropriate physiological samples, in diagnostic methods, etc. For instance, antibodies or antibody fragments specific to a domain of a GIT transport receptor-binding peptide or to a derivative of a peptide, such as a dansyl group or some other epitope introduced into the peptide, can be used to 1) identify the presence of the peptide on a nanoparticle or other substrate; 2) quantify the amount of peptide on the nanoparticle; 3)measure the level of the peptide in appropriate physiological samples; 4) perform immunohistology on tissue samples; 5) image the peptide after in vivo administration; 6) purify the peptide from a mixture using an immunoaffinity column or 7) bind or fix the peptide to the surface of nanoparticle. This last use envisions attaching the antibody (or fragment of the antibody) to the surface of drug-loaded nanoparticles or other substrate and then incubating this conjugate with the peptide. This procedure results in binding of the peptide in a certain fixed orientation, resulting in a particle that contains the peptide bound to the antibody in such a way that the peptide is fully active.

Abtides (or Antigen binding peptides) specific to a domain of a GIT transport receptor-binding peptide or to a derivative of a peptide, such as a dansyl group or some other epitope introduced into the peptide, can be used for the same seven purposes identified above for antibodies.

5.5. Assays of GIT Transport Receptor-binding Peptides, Derivatives and Analogs The functional activity of GIT transport receptor-binding peptides, derivatives and analogs can be assayed by various methods.

In a preferred embodiment, in which binding to a GIT transport receptor is being assayed, the binding can be assayed by in vivo or in vitro assays such as described in the examples infra, or by other means that are known in the art.

In another embodiment, where one is assaying for the ability to bind or compete with full-length GIT transport receptor-binding peptide for binding to anti-GIT transport receptor-binding peptide antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

Other methods will be known to the skilled artisan and are within the scope of the invention.

5.6. Uses

The invention provides compositions comprising the GIT transport receptor-binding proteins of the invention bound to a material comprising an active agent. Such compositions have use in targeting the active agent to the GIT and/or in facilitating transfer through the lumen of the GIT into the systemic circulation. Where the active agent is an imaging agent, such compositions can be administered in vivo to image the GIT (or particular transport receptors thereof). Other active agents include but are not limited to: any drug or antigen or any drug- or antigen-loaded or drug- or antigen-encapsulated nanoparticle, microparticle, liposome, or micellar formulation capable of eliciting a biological response in a human or animal. Examples of drug- or antigen-loaded or drug- or antigen-encapsulated formulations include those in which the active agent is encapsulated or loaded into nano- or microparticles, such as biodegradable nano- or microparticles, and which have the GIT transport receptor-binding protein or derivative or analog adsorbed, coated or covalently bound, such as directly linked or linked via a linking moiety, onto the surface of the nano- or microparticle. Additionally, the protein, derivative or analog can form the nano- or microparticle itself or the protein, derivative or analog can be covalently attached to the polymer or polymers used in the production of the biodegradable nano- or microparticles or drug-loaded or drug-encapsulated nano- or microparticles or the peptide can be directly conjugated to the active agent. Such conjugations to active agents include fusion proteins in which a DNA sequence coding for the peptide is fused in-frame to the gene or cDNA coding for a therapeutic peptide or protein such that the modified gene codes for a recombinant fusion protein.

In a preferred embodiment, the invention provides for treatment of various diseases and disorders by administration of a therapeutic compound (termed herein "Therapeutic"). Such "Therapeutics" include but are not limited to: GIT transport receptor-binding proteins, and analogs and derivatives (including fragments) thereof (e.g., as described hereinabove) that bind to GIT transport receptors, bound to an active agent of value in the treatment or prevention of a disease or disorder (preferably a mammalian, most preferably human, disease or disorder). Therapeutics also include but are not limited to nucleic acids encoding the GIT transport receptor-binding proteins, analogs, or derivatives bound to such a therapeutic or prophylactic active agent. The active agent is preferably a drug.

Any drug known in the art may be used, depending upon the disease or disorder to be treated or prevented, and the type of subject to which it is to be administered. As used herein, the term "drug" includes, without limitation, any pharmaceutically active agent. Representative drugs include, but are not limited to, peptides or proteins, hormones, analgesics, anti-migraine agents, anti-coagulant agents, anti-emetic agents, cardiovascular agents, anti-hypertensive agents, narcotic antagonists, chelating agents, anti-anginal agents, chemotherapy agents, sedatives, anti-neoplastics, prostaglandins, and antidiuretic agents. Typical drugs include peptides, proteins or hormones such as insulin, calcitonin, calcitonin gene regulating protein, atrial natriuretic protein, colony stimulating factor, betaseron, erythropoietin (EPO), interferons such as α, β or γ interferon, somatropin, somatotropin, somatostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor VIII, interleukins such as interleukin-2, and analogs thereof; analgesics such as fentanyl, sufentanil, butorphanol, buprenorphine, levorphanol, morphine, hydromorphone, hydocodone, oxymorphone, methadone, lidocaine, bupivacaine, diclofenac, naproxen, paverin, and analogs thereof; anti-migraine agents such as heparin, hirudin, and analogs thereof; anti-coagulant agents such as scopolamine, ondansetron, domperidone, etoclopramide, and analogs thereof; cardiovascular agents, anti-hypertensive agents and vasodilators such as diltiazem, clonidine, nifedipine, verapamil, isosorbide-5-mononitrate, organic nitrates, agents used in treatment of heart disorders and analogs thereof; sedatives such as benzodiazeines, phenothiozines and analogs thereof; narcotic antagonists such as naltrexone, naloxone and analogs thereof; chelating agents such as deferoxamine and analogs thereof; anti-diuretic agents such as desmopressin, vasopressin and analogs thereof; anti-anginal agents such as nitroglycerine and analogs thereof; anti-neoplastics such as 5-fluorouracil, bleomycin and analogs thereof; prostaglandins and analogs thereof; and chemotherapy agents such as vincristine and analogs thereof. Representative drugs also include but are not limited to antisense oligonucleotides, genes, gene correcting hybrid oligonucleotides, ribozymes, aptameric oligonucleotides, triple-helix forming oligonucleotides, inhibitors of signal transduction pathways, tyrosine kinase inhibitors and DNA modifying agents. Drugs that can be used also include, without limitation, systems containing gene therapeutics, including viral systems for therapeutic gene delivery such as adenovirus, adeno-associated virus, retroviruses, herpes simplex virus, sindbus virus, liposomes, cationic lipids, dendrimers, and enzymes. For instance, gene delivery viruses can be modified such that they express the targeting peptide on the surface so as to permit targeted gene delivery.

In a preferred embodiment, a Therapeutic is therapeutically or prophylactically administered to a human patient.

Additional descriptions and sources of Therapeutics that can be used according to the invention are found in various Sections herein.

5.7. Therapeutic/Prophylactic Administration, Compositions and Formulations

The invention provides methods of treatment (and prophylaxis) by administration to a subject of an effective amount of a Therapeutic of the invention. In a preferred aspect, the Therapeutic is substantially purified. The subject is preferably an animal, including but not limited to animals such as cows, pigs, horses, chickens, cats, dogs, etc., and is preferably a mammal, and most preferably a human.

As will be clear, any disease or disorder of interest amenable to therapy or prophylaxis by providing a drug in vivo systemically or by targeting a drug in vivo to the GIT (by linkage to a GIT transport-receptor binding protein, derivative or analog of the invention) can be treated or prevented by administration of a Therapeutic of the invention. Such diseases may include but are not limited to hypertension, diabetes, osteoporosis, hemophilia, anemia, cancer, migraine, and angina pectoris, to name but a few.

Any route of administration known in the art may be used, including but not limited to oral, nasal, topical, intravenous, intraperitoneal, intradermal, mucosal, intrathecal, intramuscular, etc. Preferably, administration is oral; in such an embodiment the GIT-transport binding protein, derivative or analog of the invention acts advantageously to facilitate transport of the therapeutic active agent through the lumen of the GIT into the systemic circulation.

The present invention also provides therapeutic compositions/formulations. In a specific embodiment of the invention, a GIT transport receptor-binding peptide or motif of interest is associated with a therapeutically or prophylactically active agent, preferably a drug or drug-containing nano- or microparticle. More preferably, the active agent is a drug encapsulating or drug loaded nano- or microparticle, such as a biodegradable nano- or microparticle, in which the peptide is physically adsorbed or coated or covalently bonded, such as directly linked or linked via a linking moiety, onto the surface of the nano- or microparticle. Alternatively, the peptide can form the nano- or microparticle itself or can be directly conjugated to the active agent. Such conjugations include fusion proteins in which a DNA sequence coding for the peptide is fused in-frame to the gene or cDNA coding for a therapeutic peptide or protein, such that the modified gene codes for a recombinant fusion protein in which the "targeting" peptide is fused to the therapeutic peptide or protein and where the "targeting" peptide increases the absorption of the fusion protein from the GIT. Preferably the particles range in size from 200–600 nm.

Thus, in a specific embodiment, a GIT transport-binding protein is bound to a slow-release (controlled release) device containing a drug. In a specific embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)).

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances.

6. EXAMPLES

6.1. Selection of GIT Receptor Targets

The HPT1, hPEPT1, D2H, and hSI receptors were selected for cloning as GIT receptor targets based on several criteria, including: (1) expression on surface of epithelial cells in gastrointestinal tract (GIT); (2) expression along the length of small intestine (HPT1, hPEPT1, D2H); (3) expression locally at high concentration (hSI); (4) large putative extracellular domains facing into the lumen of the GIT; and (5) extracellular domains that permit easy access and bioadhesion by targeting particles.

The four recombinant receptor sites screened with the peptide libraries additionally have the following characteristics:

TABLE XC

Genetic Studies of A129 X IMC 01

| Genotype | Ratio | Frequency | |
|---|---|---|---|
| | | Observed | Expected |
| od − od − ld − ld − | 1 | 11 | 12 |
| od − od − ld − ld + | 2 | 30 | 24 |
| od − od − ld + ld + | 1 | 10 | 12 |
| od − od + ld − ld − | 2 | 25 | 24 |
| od − od + ld − ld + | 4 | 54 | 47 |
| od − od + ld + ld + | 2 | 18 | 24 |
| od + od + ld − ld − | 1 | 7 | 12 |
| od + od + ld − ld + | 2 | 25 | 24 |
| od + od + ld + ld + | 1 | 8 | 12 |

FIGS. 1–4 (SEQ ID NOS:176, 178, 179, and 181, respectively) show the predicted amino acid sequences for hPEPT1, HPT1, hSI and D2H, respectively.

6.2. Cloning of Extracellular Domain of Selected Receptor Site

The following receptor domains were cloned and expressed as His-tag fusion proteins by standard techniques:

| Receptor | Domain (amino acid residues) |
|---|---|
| hPEPT1[a] | 391–571 |
| HPT1[b] | 29–273 |
| hSI[c] | 272–667 |
| D2H[d] | 387–685 |

[a]Liang et al., 1995, J. Biol. Chem. 270:6456–6463
[b]Dantzig et al., 1994, Association of Intestinal Peptide Transport with a Protein Related to the Cadherin Superfamily
[c]Chantret et al., Biochem. J. 285:915–923
[d]Bertran et al., J. Biol. Chem. 268:14842–14949

The receptor proteins were expressed as His-tag fusion proteins and affinity purified under denaturing conditions, using urea or guanidine HCl, utilizing the pET His-tag metal chelate affinity for Ni-NTA Agarose (Hochuli, E., Purification of recombinant proteins with metal chelate adsorbent, Genetic Engineering, Principals and Methods (J. K. Setlow, ed.), Plenum Press, NY, Vol. 12 (1990), pp. 87–98).

6.3. Phage Libraries

Three phage DC8, D38, and DC43 libraries expressing N-terminal pIII fusions in M13 were used to identify peptides that bind to the GIT receptors. The D38 and DC43 libraries which are composed of 37 and 43 random amino acid domains, respectively, have been described previously (McConnell et al., 1995, Molecular Diversity, 1:165–176). The DC8 library is similar to the other two except that the random insert is 8 amino acids long flanked on each side by a cysteine residue (i.e., $CX_8C$).

6.4. Biopanning

Three rounds of biopanning on the GIT receptors were performed generally by standard methods (McConnell et al., 1995, Molecular Diversity, 1:165–176), using a mixture of the DC8 ($1 \times 10^{10}$ pfu), D38 and DC43 ($1 \times 10^{11}$ pfu) phage libraries. After each round of panning the percentage of phage recovered was determined. Following the first two rounds of panning, the eluted phage were amplified overnight. Phage from the third pan were plated out and 100 plaques were picked, amplified overnight and screened in an ELISA assay for binding to the relevant receptor and BSA. After data analysis, phage clones were identified which had high absorbance in the ELISA assay and/or a good ratio of binding to target compared to binding to BSA. The Insulin Degrading Enzyme (IDE) and recombinant human tissue factor (hTF) were used as irrelevant controls. Several variations of the standard panning technique, discussed below, were used. Selection or panning methods followed one of two strategies. The first strategy involved panning the mixed libraries on the specific GIT receptor adsorbed to a solid surface. The second strategy panned the libraries twice against the GIT receptor and then against Caco-2 cells (Peterson and Mooseker, 1992, J. Cell Science 102:581–600), Selection methods are reflected in the clone nomenclature as described below:

S designates the clone was identified by binding to the hS1 receptor domain.

D designates the clone was identified by binding to the D2H receptor domain.

P designates the clone was identified by binding to the PEPT1 receptor domain.

H designates the clone was identified by binding to the HPT-1 receptor domain.

Phage designated Ni are from a solid phase band GIT receptor pan that used the standard procedure with the addition of Ni-NTA Agarose (Qiagen, Chatsworth, Calif.). Receptor coated plates were blocked with 0.5% BSA/PBS containing 160 μl Ni-NTA agarose and libraries were panned in the presence of 50 μl Ni-NTA agarose. The receptor proteins were expressed as His-tag fusions. The His-tag has a high affinity for Ni-NTA Agarose. Blocking the plate and panning in the presence of Ni-NTA agarose minimized phage binding to the His-tag portion of the recombinant receptor.

Phage with the designation AX were eluted with acid and Factor Xa. Phage were first eluted by standard acid elution then Factor Xa (New England Biolabs, Beverly, Mass.: 1 μg protease in 300 μl of 20 mM Tris-HCL, 100 mM NaCl, 2 mM $CaCl_2$) was added to the panning plate and incubated 2 hours. Phage from both elution methods were pooled together then plated.

Phage with the designation AB were eluted with acid and base. Phage were eluted first by standard acid elution then 100 mM triethylamine pH 12.1 was added to the panning plate for 10 minutes. Phage from both elution methods were pooled together then plated.

C designates panning on receptor followed by Caco-2 cells. First and second round pans were performed on the receptor and the third round pan was on snapwells of Caco-2 cells. DCX11, DCX8 and DCX33 were identified by two pans on D2H receptor, third pan on Caco-2 cells. The third round Factor Xa eluate from the Caco-2 cells was screened by ELISA on D2H, BSA and fixed Caco-2 cells. For HCA3 the first two rounds of panning were performed on the HPT-1 receptor and the third pan was on monolayers cultured on snapwells of Caco-2 cells.

Phage designated 5PAX were carried through five rounds of panning after which a number of phage were sequenced prior to screening by ELISA.

6.5. Sequencing of Selected Phage

The amino acid-sequence of phage inserts demonstrating a good ratio of binding to receptor domains and/or Caco-2 cells over background BSA binding were deduced from the nucleotide sequence obtained by sequencing (Sequenase®, U.S. Biochemical Corp., Cleveland, Ohio) both DNA strands of the appropriate region in the viral genome. The third round acid eluate was screened by ELISA on HPT-1, BSA and Caco-2 fixed cells. Phage designated 5PAX were carried through five rounds of panning after which a number of phages were sequenced prior to screening by ELISA.

One well of a 24 well plate was coated with 10 μg/ml of GIT receptor and the plate was incubated overnight at 4° C. The plate was blocked with 0.5 BSA-PBS for one hour. A mixture of the DC8, D38 and DC43 phage libraries was added to the plate and the plate was incubated for 2 to 3 hours at room temperature on a rotator. After washing the well 10 times with 1% BSA plus 0.05% Tween 20 in PBS, the well was eluted with 0.05 m glycine, pH2. The phage was then eluted with 0.2M $NaPO_4$. The eluted phage was titered on agar plates; the remaining phage was amplified overnight. The next day the amplified phage was added to a second coated plate and the panning procedure was repeated as described above. The eluted phage from the second pan as well as the amplified phage from the first pan was titered on agar plates. Following amplification overnight of the phage from the second pan, the panning procedure was repeated as described above. The phage eluted from the third pan and the amplified phage from the second pan were then titered overnight on agar plates. Isolated phage colonies were amplified overnight prior to use in an ELISA assay.

6.6. Receptor ELISA Procedure 96 well plates were coated overnight with GIT receptor, BSA and, optionally, IDE (insulin degrading enzyme, an irrelevant His-fusion protein) or hTF. The plates were blocked for one hour with 0.5% BSA-PBS. After clarification, the amplified phage were diluted 1:100 in 1% BSA plus 0.05% Tween 20 in PBS and added to the plates. Following incubation of the plates on a rotator for 1 to 2 hours, the plates were washed 5 times with 1% BSA plus 0.05% Tween 20 in PBS. Dilute anti-M13-HRP conjugate (anti-M13 antibody linked to horse radish peroxidase (HRP)) was added to all the wells and the plate was incubated for one hour on a rotator. After the plates were washed 5 times, as described above, TMB substrate was added to the wells. The plates were read at 650 nm absorbance.

Receptor ELISA Results:

Below are the results of ELISA assays which assessed the binding of phage panned on the hSI receptor to microtiter plates coated with hSI and BSA. Table 1 shows the OD results as well as the ratio of hSI to BSA binding.

TABLE XIII

| Fatty Acid Composition of Advanced Breeding Generation with High Oleic Acid Trait (IMC 129 X Legend) | | | | | |
|---|---|---|---|---|---|
| $F_7$ Selections | Fatty Acid Composition (%) | | | | |
| of 89B60303 | $C_{16:0}$ | $C_{18:0}$ | $C_{18:1}$ | $C_{18:2}$ | $C_{18:3}$ |
| 93.06194 | 3.8 | 1.6 | 78.3 | 7.7 | 4.4 |
| 93.06196 | 4.0 | 2.8 | 77.3 | 6.8 | 3.4 |
| 93.06198 | 3.7 | 2.2 | 78.0 | 7.4 | 4.2 |

Below are the results of an ELISA which assessed the binding of phage panned on the D2H receptor to microtiter plates coated with D2H and BSA. Table 2 shows the OD results as well as the ratio of D2H to BSA binding.

TABLE 2

| Phage | D2H | BSA | D2H/BSA |
|---|---|---|---|
| DAB3 | 0.406 | 0.072 | 6 |
| DAB7 | 0.702 | 0.09 | 8 |
| DAB10 | 0.644 | 0.153 | 4 |
| DAB18 | 0.467 | 0.085 | 5 |
| DAB24 | 1.801 | 0.441 | 4 |
| DAB30 | 0.704 | 0.121 | 6 |
| DAX15 | 0.391 | 0.101 | 4 |
| DAX23 | 0.698 | 0.153 | 5 |
| DAX24 | 0.591 | 0.118 | 5 |
| DAX27 | 1.577 | 0.424 | 4 |
| BLANK | 0.038 | 0.037 | 1 |

Below are the results of an ELISA which assessed the binding of phage panned for two rounds on the D2H receptor followed by a third round pan on Caco-2 snapwells. Binding to fixed Caco-2 cells, D2H and BSA was examined. Table 3 shows the OD results as well as the ratio of D2H to BSA binding.

TABLE 3

| PHAGE | Caco-2 | D2H | BSA | D2H/BSA |
|---|---|---|---|---|
| DCX8 | 0.498 | 0.163 | 0.063 | 3 |
| DCX11 | 0.224 | 0.222 | 0.071 | 3 |
| DCX26 | 0.114 | 0.956 | 0.213 | 4 |
| DCX33 | 0.164 | 0.616 | 0.103 | 6 |
| DCX36 | 0.149 | 0.293 | 0.064 | 5 |
| DCX39 | 0.121 | 0.299 | 0.066 | 5 |
| DCX42 | 0.308 | 0.158 | 0.065 | 2 |

TABLE 3-continued

| PHAGE | Caco-2 | D2H | BSA | D2H/BSA |
|---|---|---|---|---|
| DCX45 | 0.147 | 0.336 | 0.075 | 4 |
| Blank | 0.065 | 0.043 | 0.04 | 1 |

Below are the results of an ELISA which assessed the binding of phage panned on the hPEPT1 receptor to hPEPT1 and BSA. Table 4 shows the OD results as well as the ratio of hPEPT1 to BSA binding.

TABLE 4

| PHAGE | hPEPT1 | BSA | PEPT1/BSA |
|---|---|---|---|
| PAX9 | 0.312 | 0.079 | 4 |
| PAX14 | 1.102 | 0.139 | 8 |
| PAX15 | 0.301 | 0.079 | 4 |
| PAX16 | 0.648 | 0.171 | 4 |
| PAX17 | 0.514 | 0.095 | 5 |
| PAX18 | 0.416 | 0.087 | 5 |
| PAX35 | 0.474 | 0.065 | 7 |
| PAX38 | 0.292 | 0.064 | 5 |
| PAX40 | 0.461 | 0.076 | 6 |
| PAX43 | 0.345 | 0.069 | 5 |
| PAX45 | 0.419 | 0.081 | 5 |
| PAX46 | 0.429 | 0.077 | 6 |
| P31 | 0.807 | 0.075 | 11 |
| P90 | 1.117 | 0.107 | 9 |
| 5PAX3 | 0.173 | 0.04 | 4 |
| 5PAX5 | 0.15 | 0.036 | 4 |
| 5PAX7 | 0.171 | 0.037 | 5 |
| 5PAX12 | 0.227 | 0.04 | 6 |
| Blank | 0.102 | 0.039 | 3 |

Table 5 shows the results of an ELISA which assessed the binding of phage panned on the HPT-1 receptor to HPT-1 and BSA. The table shows the OD results as well as the ratio of HPT-1 to BSA binding.

TABLE XIV

Fatty Acid Composition of Advanced Dihaploid Breeding Generation with High Oleic Acid Trait (IMC 129 X Hyola 41)

| DH5 of 90DU.146 at | Fatty Acid Composition (%) | | | | |
|---|---|---|---|---|---|
| Multiple Locations | $C_{16:0}$ | $C_{18:0}$ | $C_{18:1}$ | $C_{18:2}$ | $C_{18:3}$ |
| Aberdeen | 3.7 | 2.6 | 75.4 | 8.1 | 7.2 |
| Blackfoot | 3.3 | 2.4 | 75.5 | 8.8 | 7.5 |
| Idaho Falls | 3.7 | 3.1 | 75.0 | 7.5 | 8.1 |
| Rexberg | 3.9 | 3.7 | 75.3 | 7.0 | 6.5 |
| Swan Valley | 3.5 | 3.4 | 74.5 | 7.0 | 7.3 |
| Lamont | 3.9 | 2.8 | 72.0 | 10.1 | 8.4 |

Table 6 shows the results of an ELISA which assessed the binding of phage panned for two rounds on the HPT-1 receptor followed by a third round pan on Caco-2 snapwells. Binding to fixed Caco-2 cells, HPT-1 and BSA was examined. The table shows the OD results as well as the ratio of HPT-1 to BSA binding.

TABLE 6

| PHAGE | Caco-2 | HPT1 | BSA | HPT1/BSA |
|---|---|---|---|---|
| HCA3 | 0.406 | 0.048 | 0.038 | 1 |

Cell ELISA Procedure

Phage ELISA was used as described above with the following changes. Diluent and wash buffer was PBS containing 1% BSA and 0.05% Tween 20 and plates were washed five times at each wash step. Supernatant of infected bacterial cultures was diluted 1:100 and incubated with protein coated plates for 2–3 hours with mild agitation. Anti-M13 Horseradish peroxidase (HRP) conjugate (Pharmacia, Piscataway, N.J.) was diluted 1:8000.

Fixed Caco-2, C2BBe1, and A431 cell plates were prepared by growing cells on tissue culture treated microtiter plates. When cells were confluent, plates were fixed with 10% formaldehyde, washed twice with PBS and stored with 0.5% BSA-PBS at −20° C. On the day of the assay, thawed plates were treated with PBS containing 0.1% phenylhydrazine for one hour at 37° C. followed by two PBS washes and blocking for one hour with 0.5% BSA-PBS. The standard ELISA procedure was followed at this point.

Phage which showed specificity to a GIT receptor was further characterized by ELISA on a variety of recombinant proteins. Phage which continued to exhibit GIT receptor specificity was sequenced.

TABLE 7

TARGET BINDING PHAGE INSERT SEQUENCES:

| | SEQ. ID. NO. | |
|---|---|---|
| hSI | | |
| S15 | 1 | RSGAYESPDGRGGRSYVGGGGGCGNIGRKHNLWGLRTASPACWD |
| S21 | 2 | SPRSFWPVVSRHESFGISNYLGCGYRTCISGTMTKSSPIYPRHS |
| S22 | 3 | SSSSDWGGVPGKVVRERFKGRGCGISITSVLTGKPNPCPEPKAA |
| SNi10 | 4 | RVGQCTDSDVRRPWARSCAHQGCGAGTRNSHGCITRPLRQASAH |
| SNi28 | 5 | SHSGGMNRAYGDVFRELRDRWNATSHHTRPTPQLPRGPN |
| SNi34 | 6 | SPCGGSWGRFMQGGLFGGRTDGCGAHRNRTSASLEPPSSDY |
| SNi38 | 7 | RGAADQRRGWSENLGLPRVGWDAIAHNSYTFTSRRPRPP |
| SNi45 | 8 | SGGEVSSWGRVNDLCARVSWTGCGTARSARTDNKGFLPKHSSLR |
| SNiAX2 | 9 | SDSDGDHYGLRGGVRCSLRDRGCGLALSTVHAGPPSFYPKLSSP |
| SNiAX4 | 10 | RSLGNYGVTGTVDVTVLPMPGHANHLGVSSASSSDPPRR |
| SNiAX6 | 11 | RTTTAKGCLLGSFGVLSGCSFTPTSPPPHLGYPPHSVN |
| SNiAX8 | 12 | SPKLSSVGVMTKVTELPTEGPNAISIPISATLGPRNPLR |

TABLE 7-continued

TARGET BINDING PHAGE INSERT SEQUENCES:

| | SEQ. ID. NO. | |
|---|---|---|
| D2H | | |
| DAB3 | 13 | RWCGAELCNSVTKKFRPGWRDHANPSTHHRTPPPSQSSP |
| DAB7 | 14 | RWCGADDPCGASRWRGGNSLFGCGLRCSAAQSTPSGRIHSTSTS |
| DAB10 | 15 | SKSGEGGDSSRGETGWARVRSHAMTAGRFRWYNQLPSDR |
| DAB18 | 16 | RSSANNCEWKSDWRRRACIARYANSSGPARAVDTKAAP |
| DAB24 | 17 | SKWSWSSRWGSPQDKVEKTRAGCGGSPSSTNCHPYTFAPPPQAG |
| DAB30 | 18 | SGFWEFSRGLWDGENRKSVRSGCGFRGSSAQGPCPVTPATIDKH |
| DAX15 | 19 | SESGRCRSVSRWMTTWQTQKGGCGSNVSRGSPLDPSHQTGHATT |
| DAX23 | 20 | REWRFAGPPLDLWAGPSLPSFNASSHPRALRTYWSQRPR |
| DAX24 | 21 | RMEDIKNSGWRDSCRWGDLRPGCGSRQWYPSNMRSSRDYPAGGH |
| DAX27 | 22 | SHPWYRHWNHGDFSGSGQSRHTPPESPHPGRPNATI |
| DCX8 | 23 | RYKHDIGCDAGVDKKSSSVRGGCGAHSSPPRAGRGPRGTMVSRL |
| DCX11 | 24 | SQGSKQCMQYRTGRLTVGSEYGCGMNPARHATPAYPARLLPRYR |
| DCX26 | 25 | SGRTTSEISGLWGWGDDRSGYGWGNTLRPNYIPYRQATNRHRYT |
| DCX33 | 26 | RWNWTVLPATGGHYWTRSTDYHAINNHRPSIPHQHPTPI |
| DCX36 | 27 | SWSSWNWSSKTTRLGDRATREGCGPSQSDGCPVNGRLTTVKPRT |
| DCX39 | 28 | SGSLNAWQPRSWVGGAFRSHANNNLNPKPTMVTRHPT |
| DCX42 | 29 | RYSGLSPRDNGPACSQEATLEGCGAQRLMSTRRKGRNSRPGWTL |
| DCX45 | 30 | SVGNDKTSRPVSFYGRVSDLWNASLMPKRTPSSKRHDDG |
| hPEPT1 | | |
| PAX9 | 31 | RWPSVGYKGNGSDTIDVHSNDASTKRSLIYNHRRPLFP |
| PAX14 | 32 | RTFENDGLGVGRSIQKKSDRWYASHNIRSHFASMSPAGK |
| PAX15 | 33 | SYCRVKGGGEGGHTDSNLARSGCGKVARTSRLQHINPRATPPSR |
| PAX16 | 34 | SWTRWGKHTHGGFVNKSPPGKNATSPYTDAQLPSDQGPP |
| PAX17 | 35 | SQVDSFRNSFRWYEPSRALCHGCGKRDTSTTRIHNSPSDSYPTR |
| PAX18 | 36 | SFLRFQSPRFEDYSRTISRLRNATNPSNVSDAHNNRALA |
| PAX35 | 37 | RSITDGGINEVDLSSVSNVLENANSHRAYRKHRPTLKRP |
| PAX38 | 38 | SSKVSSPRDPTVPRKGGNVDYGCGHRSSAPMPTSALSSITKCYT |
| PAX40 | 39 | RASTQGGRGVAPEFGASVLGRGCGSATYYTNSTSCKDAMGHNYS |
| PAX43 | 40 | RWCEKHKFTAARCSAGAGFERDASRPPQPAHRDNTNRNA |
| PAX45 | 41 | SFQVYPDHGLERHALDGTGPLYAMPGRWIRARPQNRDRQ |
| PAX46 | 42 | SRCTDNEQCPDTGTRSRSVSNARYFSSRLLKTHAPHRP |
| P31 | 43 | SARDSGPAEDGSRAVRLNGVENANTRKSSRSNPRGRRHP |
| P90 | 44 | SSADAEKCAGSLLWWGRQNNSGCGSPTKKHLKHRNRSQTSSSSH |
| 5PAX3 | 45 | RPKNVADAYSSQDGAAAEETSHASNARRKSPKHKPLRRP |
| 5PAX5 | 46 | RGSTGTAGGERSGVLNLHTRDNASGSGFKPWYPSNRGHK |
| 5PAX7 | 47 | RWGWERSPSDYDSDMDLGARRYATRTHRAPPRVLKAPLP |
| 5PAX12 | 48 | RGWKCEGSQAAYGDKDIGRSRGCGSITKNNTNHAHPSHGAVAKI |
| HPT-1 | | |
| HAX9 | 49 | SREEANWDGYKREMSHRSRFWDATHLSRPRRPANSGDPN |
| HAX35 | 50 | EWYSWKRSSKSTGLGDTATREGCGPSQSDGCPYNGRLTTVKPRK |
| HAX40 | 51 | REFAERRLWGCDDLSWRLDAEGCGPTPSNRAVKHRKPRPRSPAL |
| HAX42 | 52 | SDHALGTNLRSDNAKEPGDYNCCGNSTGRKVFNRRRPSAIPT |
| HCA3 | 53 | RHISEYSFANSHLMGGESKRKGCGINGSFSPTCPRSPTPAFRRT |
| H40 | 54 | SRESGMWGSWWRGHRLNSTGGNANMNASLPPDPPVSTP |
| PAX2 | 55 | STPPSREAYSRPYSVDSDSDTNAKHSSHNRRLRTRSRPN |

TABLE XVII

| LOCATION | SITE CHARACTERISTICS |
|---|---|
| BURLEY | Irrigated. Long season. High temperatures during flowering. |
| TETONIA | Dryland. Short season. Cool temperatures. |
| LAMONT | Dryland. Short season. Cool temperatures. |
| SHELLEY | Irrigated. Medium season. High temperatures during flowering. |

Peptide Motifs

By comparison of the amino acid sequences of the clones binding GIT receptors, certain sequence similarities or "motifs" were recognized. These motifs can often represent the part of the sequence that is important for binding to the target. Table 9 identifies regions of sequence similarity or sequence motifs (in boldface) that were identified among GIT binding peptides (corresponding SEQ ID NOS. are shown in Table 7).

TABLE XX

Alignment of Amino Acid Sequences of Cloned Canola Membrane Bound-Desaturases

| Desaturase Gene | Sequence[a] | Position[b] |
|---|---|---|
| Canola-fad2-D(129) | AHKCGH | 109 |
| Canola-FAd2-D | AHECGH | 109 |
| Canola-FAd2-F | AHECGH | 109 |
| Canola FadC | GHDCAH | 170 |

TABLE XX-continued

Alignment of Amino Acid Sequences
of Cloned Canola Membrane Bound-Desaturases

| Desaturase Gene | Sequence[a] | Position[b] |
|---|---|---|
| Canola-Fad3 | GH<u>D</u>CGH | 96 |
| Canola-FadD | GH<u>D</u>CGH | 125 |

(FadD = Plastid delta 15, Fad3 = Microsomal delta-15),
(FadC = Plastid delta-12, Fad2 = Microsomal delta-12)
[a]One letter amino acid code; conservative substitutions are underlined; non-conservative substitutions are in bold.
[b]position of first amino acid in gene product.

Phage Binding to Caco-2 Cells

Phage expressing presumed GIT binding peptide inserts were also assayed by ELISA on fixed Caco-2 or C2BBe1 cells as follows. Cells were plated at $1 \times 10^5$ cells/well on 100 µl culture media and incubated at 30° C. in 5% $CO_2$ overnight. 100 µl 25% formaldehyde was added to each well for 15 minutes. Contents of the wells were removed by inverting the plate. The plate was then washed 3 times with DPBS. 0.1% phenylhydrazine DPBS solution was added to each well and incubated for 1 hr at 37° C. The plate was inverted and washed 3 times. The plate was blocked with 0.5% BSA-DPBS for 1 hr at room temperature. The plate was inverted and washed 3 times with 1% BPT (PBS containing 1% BSA and 0.05% Tween20). Phage diluted with 1% BPT was added to wells containing fixed cells. Wells without phage added were used to determine background binding of the HRP conjugate. The plates were incubated 2–3 hours on a rotor at room temperature. Plates were washed as before. Plates were incubated with dilute anti-M13-HRP antibody in 1% BPT for 1 hour at room temperature. Following washing, TMB substrate was added and absorbance of the plates were read at 650 nm. Table 10 shows the relative binding of phage encoding peptides to fixed Caco-2 cells.

TABLE 10

Relative binding of phage encoding peptides to fixed Caco-2 cells

| Phage | Fixed Caco-2 cell binding |
|---|---|
| SNi10 | ++ |
| SNi34 | + |
| P31 | ++ |
| 5PAX5 | ++ |
| PAX2 | + |
| HAX42 | + |
| DCX8 | +++ |
| DCX11 | + |
| H1 | + |
| M13mp118 | − |

In vivo Phase Selection:

Further selection of phage expressing peptides capable of binding to the GIT or transporting the GIT was done as follows. The purified library was resuspended in a buffer, such as TBS or PBS, and introduced onto one side of a tissue barrier, e.g., injected into the duodenum, jejunum, ileum, colon or other in vivo animal site using, for instance, a closed loop model or open loop model. Following injection, samples of bodily fluids located across the tissue barrier, e.g., samples of the portal circulation and/or systemic circulation, were withdrawn at predetermined time points, such as 0 to 90 minutes and/or 2 to 6 hours or more. An aliquot of the withdrawn sample (e.g., blood) was used to directly infect a host, e.g., E. coli, in order to confirm the presence of phage. The remaining sample was incubated, e.g., overnight incubation with E. coli at 37° C. with shaking. The amplified phage present in the culture can be sequenced individually to determine the identity of peptides coded by the phage or, if further enrichment is desired, can be precipitated using PEG, and resuspended in PBS. The phage can then be further precipitated using PEG or used directly for administration to another animal using a closed or open GIT loop model system. Portal or systemic blood samples are collected and the phage transported into such circulation systems is subsequently amplified. In this manner, administration of the phage display library with, if desired, repeat administration of the amplified phage to the GIT of the animal, permitted the selection of phage which was transported from the GIT to the portal and/or systemic circulation of the animal.

If desired, following administration of the phage display library to the tissue barrier (e.g., GIT) of the animal model, the corresponding region of the tissue barrier can be recovered at the end of the procedures given above. This recovered tissue can be washed repeatedly in suitable buffers, e.g., PBS containing protease inhibitors and homogenized in, for example, PBS containing protease inhibitors. The homogenate can be used to infect a host, such as E. coli, thus permitting amplification of phages which bind tightly to the tissue barrier (e.g., intestinal tissue). Alternatively, the recovered tissue can be homogenized in suitable PBS buffers, washed repeatedly and the phage present in the final tissue homogenate can be amplified in E. coli. This approach permits amplification (and subsequent identification of the associated peptides) of phages which either bind tightly to the tissue barrier (e.g., intestinal tissue) or which are internalized by the cells of the tissue barrier (e.g., epithelial cells of the intestinal tissue). This selection approach of phage which bind to tissues or which are internalized by tissues can be repeated.

Treatment of Animal Tissue Barriers in vivo With Phage Display Populations

The purified phage display library (random or preselected) was diluted to 500 µl in PBS buffer and injected into the closed (or open) intestinal loop model (e.g., rat, rabbit or other species). At time 0 and at successive time points after injection, a sample of either the portal circulation or systemic circulation was withdrawn. An aliquot of the withdrawn blood was incubated with E. coli, followed by plating for phage plaques or for transduction units or for colonies where the phage codes for resistance to antibiotics such as tetracycline. The remainder of the withdrawn blood sample (up to 150 µl) was incubated with 250 µl of E. coli and 5 ml of LB medium or other suitable growth medium. The E. coli cultures were incubated overnight by incubation at 37° C. on a shaking platform. Blood samples taken at other time points (such as 15 min, 30 min, 45 min, 60 min, up to 6 hours) were processed in a similar manner, permitting amplification of phages present in the portal or systemic circulation in E. coli at these times. Following amplification, the amplified phage was recovered by PEG precipitation and resuspended in PBS buffer or TBS buffer. The titer of the amplified phage, before and after PEG precipitation, was determined. The amplified, PEG precipitated phage was diluted to a known phage titer (generally between $10^8$ and $10^{10}$ phage or plaque forming units (p.f.u.) per ml) and was injected into the GIT of the animal closed (or open) loop model. Blood samples were collected from portal and/or systemic circulation at various time points and the phage transported into the blood samples were amplified in *E. coli* as given above for the first cycle. Subsequently, the phage was PEG-precipitated, resuspended, titered, diluted and injected into the GIT of the animal closed (or open) loop model. This procedure of phage injection followed by collection of portal and/or systemic blood samples and amplification of phage transported into these blood samples can be repeated, for example, up to 10 times, to permit the selection of phages which are preferentially transported from the GIT into the portal and/or systemic circulation.

6.7. Transport of Phage From Rat Lumen Into the Portal and Systemic Circulation Phage from random phage display libraries as well as control phage were injected into the lumen of the rat gastro-intestinal tract (in situ rat closed loop model). Blood was collected over time from either the systemic circulation or portal circulation and the number of phage which were transported to the circulation was determined by titering blood samples in *E. coli*.

The phage display libraries used in this study were D38 and DC43 in which gene III codes for random 38-mer and 43-mer peptides, respectively. As a negative control, the identical phage M13mp18, in which gene III does not code for a "random" peptide sequence, was used. Both the library phages D38 and DC43 were prepared from *E. coli*, mixed together, dialyzed against PBS, precipitated using PEG/NaCl and were resuspended in PBS buffer. The M13mp18 control was processed in a similar manner. The titer of each phage sample was determined and the phage samples were diluted in PBS to approximately the same titers prior to injection into the rat closed loop model.

For sampling from the systemic circulation, approximately 15 cm of the duodenum of Wistar rats was tied off (closed loop model), approximately 0.5 ml of phage solution was injected into the closed loop and blood (0.4 ml) was sampled from the tail vein at various times. The time points used (in min) were: 0, 15, 30, 45, 60, 90, 120, 180, 240 and 300 minutes. For sampling from the portal circulation, the portal vein was catheterized, approximately 15 cm of the duodenum was tied off (closed loop model), 0.5 ml of phage solution was injected into the closed loop and blood was sampled from the portal vein catheter at various times. As the portal sampling is delicate, sampling times were restricted to 15, 30, 45 and 60 minutes, where possible. The volume of phage injected into each animal was as follows:

| ANIMALS (15) | VOLUME OF PHAGE INJECTED |
|---|---|
| R1–R3 | 0.50 ml |
| R4 | 0.43 ml |
| R5–R15 | 0.45 ml |

The estimated number of transported phage has been adjusted to account for differences in volume injected into each animal (using 0.5 ml as the standard volume).

To investigate transport into the systemic circulation, animals R1, R2 and R3 received the control phage M13mp18 and animals R4, R5, R6 and R7 received the test phage D38/DC43 mix. To investigate transport into the portal circulation, animals R8, R9 and R10 received the control phage M13mp18 and animals R11, R12, R13 and R14 received the test phage D38/DC43 mix. Animal R15* received the combined phage samples from animals R4–R7 (see Table 11) which were sampled from the systemic circulation on day one, followed by amplification in *E. coli*, PEG precipitation and resuspension in PBS. On subsequent analysis, the titer of this phage was found to be 100 times greater than the other phage samples used for animals R8–R14. Thus, the data presented for animal R15* is adjusted down.

Approximately 0.4 ml of the blood was collected at each time point in each model system. 30 µl of the collected blood (systemic) was mixed with 100 µl of the prepared *E. coli* strain K91Kan, incubated at 37° C. for 30 min, and plated out for plaque formation using Top Agarose on LB plates. Various negative controls were included in the titering experiments. The following day, the number of plaque forming units was determined. Similarly, 30 µl of the collected blood (portal) and serial dilutions (1:100, 1:1000) thereof was mixed with 100 µl of the prepared *E. coli* strain K91Kan, incubated at 37° C. for 30 min, and plated out for plaque formation using Top Agarose on LB plates. The following day, the number of plaque forming units was determined.

In addition, approximately 300 µl of the collected blood from each time point (systemic and portal) was incubated with 5 ml of prepared *E. coli* strain K91Kan in modified growth media containing 5 mM $MgCl_2/MgSO4$ at 37° C. overnight with shaking (to permit phage amplification). The samples were centrifuged and the cell pellet was discarded. Samples of the phage supernatant were collected, serially diluted ($10^{-2}$, $10^{-4}$, $10^{-6}$, $10^{-8}$) in TBS buffer, and plated for plaques in order to determine the number of plaque forming units present in the amplified phage samples.

Furthermore, an aliquot of phage was removed from the "amplified" supernatants obtained from test animals R4–R7 (samples from each time point were used), combined, and precipitated using PEG for two hours. The precipitated phage was resuspended in PBS buffer and was injected into closed loop model of animal R15*, followed by portal sampling.

The number of phage transported from the closed loop model into the systemic circulation is presented in Table 11 hereafter. The number of phage transported from the closed loop model into the portal circulation is presented in Table 12 hereafter. These numbers are corrected for phage input difference and for volume input differences. Clearly, more phage are present in the portal samples than in the systemic samples, indicative of either hepatic or RES clearance and/or phage instability in the systemic circulation. In addition, the uptake of phage from the GIT into the portal circulation is quite rapid, with substantial number of phages detected within 15 minutes. The results from the portal sampling experiments would also indicate that the kinetics of uptake of phage from the D38/DC43 libraries is quicker than that of the control phage. Thus, there may be preferential uptake of phage coding for random peptide sequences from the GIT into the portal circulation. In the case of animals R13, R14 and R15*, the % of the phage transported into the titered blood sample within the limited time frame (30, 45 and 15 mins, respectively) was estimated as 0.13%, 1.1% and 0.013%, respectively.

TABLE 11

NUMBER OF PHAGE TRANSPORTED FROM THE CLOSED LOOP MODEL INTO THE SYSTEMIC CIRCULATION

| Time (min) | R1 | R2 | R3 | R4 | R5 | R6 | R7 |
|---|---|---|---|---|---|---|---|
| 0 | 0 | 0 | 0 | 0 | 0 | 0 | 0 |
| 15 | 0 | 1 | 9 | 0 | 0 | 1 | 7 |
| 30 | 2 | 1 | 0 | 0 | 46 | 1 | 11 |
| 45 | 10 | 4 | 2 | 1 | 32 | 0 | 20 |
| 60 | 63 | 19 | 21 | 1 | 114 | 0 | 21 |
| 90 | 104 | 20 | 18 | 3 | 115 | 0 | 22 |
| 120 | 94 | 24 | 27 | 0 | 64 | 0 | 6 |
| 180 | 94 | 12 | 23 | 1 | 413 | 0 | 0 |
| 240 | 14 | 1 | 20 | 0 | 36 | 0 | 0 |
| 300 | 1 | 1 | 4 | 2 | 0 | 0 | 0 |
| Total number of transported phage | 382 | 83 | 124 | 8 | 820 | 2 | 87 |

Animals R1, R2 and R3 received the control phage M13mP18.
Animals R4, R5, R6 and R7 received the test phage D38/DC43 mix.

TABLE 12

NUMBER OF PHAGE TRANSPORTED FROM THE CLOSED LOOP MODEL INTO THE PORTAL CIRCULATION

| Time (min) | R8 | R9 | R10 | R11 | R12 | R13 | R14 | R15* |
|---|---|---|---|---|---|---|---|---|
| 15 | 15 | 6 | 3 | 1 | — | 19 | 231,000 | 1,000,000 | 20,000 |
| 30 | 1 | 5 | 26 | — | 0 | 60,000 | 272,000 | — |
| 45 | — | 1 | 555 | — | 1 | — | 1,240,000 | — |
| 60 | — | — | — | — | 420,000 | — | — | — |

Animals R8, R9 and R10 received the control phage M13mp18.
Animals R11, R12, R13 and R14 received the test phage D38/DC43 mix.
Animal R15* received the combined phage samples from animals R4–R7 (see Table 11) which were sampled from the systemic circulation on day one, followed by PEG precipitation and resuspension in PBS. On subsequent analysis, the titer of this phage was found to be 100 times greater than the other phage samples used for animals R8–R14. Thus, the data measuring phage transport into the portal circulation for animal R15* is adjusted down.

These studies demonstrated that both the control phage and the D38/DC43 phages are transported over time from the lumen of the GIT into the portal and systemic circulation, as demonstrated by titering the phage transported to the blood in *E. coli*. More phage were transported from the test phage samples into the portal circulation than the corresponding control phage sample. In addition, the kinetics of transport of the test phage into the portal circulation appeared to exceed that of the control phage. Phage from the D38/DC43 libraries which appeared in the systemic circulation of different animals (R4–R7) were pooled, amplified in *E. coli*, precipitated, and re-applied to the lumen of the GIT, followed by collection in the portal circulation and titering in *E. coli*. These selected phage were also transported from the lumen of the GIT into the portal circulation. This in situ loop model may represent an attractive screening model in which to identify peptide sequences which facilitate transport of phage and particles from the GIT into the circulation.

Using this screening model system, a number of preselected phage libraries now exist, including a one pass systemic phage library from animals R4–R7, a one-pass portal library from animals R11–R14, and a two pass, rapid transport, systemic-portal phage library SP-2 from animal R15*.

6.8. Transport of Phage From Preselected Phage Libraries From the Rat Lumen Into the Portal and Systemic Circulation Four preselected phage libraries, GI-D2H, GI-hSI, GI-HPT1 and GI-hPEPT1, were constructed by pooling phage previously selected by screening random phage display libraries D38 and DC43 using the HPT1, HPEPT1, D2H and hSI receptor or binding sites located in the GIT. The phage pools, preselected phage libraries are shown in Table 13. Note that the sequences for PAX2, HAX1, HAX5, HAX6, HAX10, H10 and HAX44 are the same. Also, the sequence for HAX40 is the same as that for H44. The corresponding SEQ ID NOS. are shown in Table 7.

Examples of asset types and their constituent parts.

| | Asset Type | Algorithmic Logic & Data | Extended Environment | Base Environment |
|---|---|---|---|---|
| Base | CDS Adapter | Adapter Class Files | Version Information Licensing Information | CDS Client Agent JVM |
| Java | Static Content | HTML Page | Web Server Aliases | Web Server |
| | Static Content | GIF Image | | Web Server |
| | JSP | JSP Page | JNDI Entries | JVM Servlet Engine |
| | Java Class File | Class File | JNDI Entries | JVM |
| | Session Bean | EJB Implementation | EJB Stub and Skeleton Deployment Descriptor JNDI Entries | JVM EJB Application Server |
| | Entity Bean | EJB Implementation Data based on query | EJB Stub and Skeleton Deployment Descriptor JNDI Entries Table Schema | JVM EJB Application Server DBMS |
| | Reference Data | Data based on query | Table Schema | DBMS |

*-continued*

Examples of asset types and their constituent parts.

| Asset Type | | Algorithmic Logic & Data | Extended Environment | Base Environment |
|---|---|---|---|---|
| | Entity Data | Data based on query | Table Schema | DBMS |
| Non-Java | SmallTalk C++ | Image Executable, or Dynamic Library | Image Registry Entries Environment Variables | SmallTalk VM Operating System or Platform Emulator |
| | Perl | Perl Script | Environment Variables | Perl Interpreter |
| Non-Language | Music | MP3 File | Album and track information. | MP3 Player |
| | Video Documents | MPEG File PDF File | Production Notes Authentication Certificate | MPEG Player PDF Viewer |

Similar to methods described herein above, these preselected phage libraries together with the negative control phage M13mp18 were injected into the rat closed loop model (6 animals per preselected phage library), blood was collected over time from the portal circulation via the portal vein and, at the termination of the experiment, a systemic blood sample was collected from the tail vein and the intestinal tissue region from the closed loop was collected.

In particular, phages selected in vitro to each receptor or binding site located in the GIT were amplified in *E. coli*, PEG-precipitated, resuspended in TBS and the titer of each phage sample was determined by plaquing in *E. coli* as described above. Subsequently, an equal number of each phage ($8 \times 10^8$ phage) for each receptor site was pooled into a preselected phage library together with the negative control phage M13mp18 and each preselected phage library was administered to 6 Wistar rats per library (rats 1–6; GI-D2H, rats 7–12; GI-hSI, rats 13–18; GI-hPEPT1, and rats 19–24; GI-HPT1). Using the in situ loop model described above, 0.5 ml of preselected phage library solution was injected into the tied-off portion of the duodenum/jejunum. Blood was collected into heparinized tubes from the portal vein at 0, 15, 30, 45 and 60 minutes. A blood sample was taken from the systemic circulation at the end of the experiment. Similarly, the portion of the duodenum/jejunum used for phage injection was taken at the end of the experiment.

Thirty microliters of the collected portal blood (neat and $10^{-2}$, $10^{-4}$, $10^{-6}$ dilutions) was added to 30 µl *E. coli* K91Kan cells (overnight culture) and incubated at 37° C. for 10 min. Subsequently, 3 ml of top agarose was added and the samples were plated for plaques. One hundred microliters of the collected portal blood was added to 100 µl of *E. coli* K91Kan. Five milliliters of LB medium was then added and the samples were incubated at 37° C. overnight in a rotating microbial incubator. The *E. coli* was removed by centrifugation and the amplified phage supernatant samples were either titered directly or were PEG-precipitated, resuspended in TBS and titered. Following titration of the amplified phage, samples containing phage from each set of animals were combined, adjusting the titer of each sample to the same titer, and were plated for plaques on LB agar plates (22 cm² square plates). Either 12,000 or 24,000 phage were plated for plaques.

Thirty microliters of the collected systemic blood (neat and $10^{-2}$, $10^{-4}$, $10^{-6}$ dilutions) was added to *E. coli* K91Kan cells, incubated at 37° C. for 10 min. Three ml of top agarose was then added and the samples were plated for plaques.

One hundred microliters of the collected systemic blood was added to 100 µl of *E. coli* K91Kan, incubated at 37° C. for 10 min. Five milliliters of LB medium was then added and the samples were incubated at 37° C. overnight in a rotating microbial incubator. The *E. coli* was removed by centrifugation and the amplified phage supernatant samples were either titered directly or were PEG-precipitated, resuspended in TBS and titered. Following titration of the amplified phage, samples containing phage from each set of animals were combined, adjusting the titer of each sample to the same titer, and were plated for plaques on LB agar plates (22 cm² square plates). Either 12,000 or 24,000 phage were plated for plaques. The intestinal tissue portion used in each closed loop was excised. The tissue was cut into small segments, followed by 3 washings in sterile PBS containing protease inhibitors, and homogenized in an Ultra thorex homogeniser (Int-D samples). Alternatively, the tissue (in PBS supplemented with protease inhibitors) was homogenized in an Ultra Thorex homogenizer, washed 3 times in PBS containing protease inhibitors and resuspended in PBS containing protease inhibitors (Int-G samples). In each case, serial dilutions (neat and $10^{-2}$, $10^{-4}$, $10^{-6}$ dilutions) of the tissue homogenate was titered in *E. coli*. In addition, an aliquot (100 µl) of the tissue homogenate was added to 100 µl of *E. coli* K91Kan, incubated at 37° C. for 10 min, followed by addition of 5 ml of LB medium and incubation overnight at 37° C. in a rotating microbial incubator.

The phage amplified from the portal blood, systemic blood and intestinal tissue was plated for plaques. The plaques were transferred to Hybond-N Nylon filters, followed by denaturation (1.5M NaCl, 0.5M NaOH), neutralization (0.5M TRIS-HCl, pH7.4, 1.5M NaCl), and washing in 2×SSC buffer. The filters were air-dried, and the DNA was cross-linked to the filter (UV crosslinking: 2 min, high setting). The filters were incubated in pre-hybridization buffer (6×SSC, 5×Denhardt's solution, 0.1% SDS, 20 µg/ml yeast tRNA) at 40° C.–45° C. for at least 60 min.

Synthetic oligonucleotides, (22-mers), complimentary to regions coding for the receptor or binding sites used to create the preselected phage library, were synthesized (see Table 14 below).

TABLE 14

OLIGONUCLEOTIDES USED IN IN VIVO SCREEN

| CLONE NAME | OLIGO | SEQ. ID. NO. |
|---|---|---|
| S15 | 5'TCCGGACTCTCATAAGCGCCGG3' | 111 |
| S21 | 5'ACAACGGGCCAGAAAGAGCGAG3' | 112 |
| S22 | 5'ACACCACCCCAATCGGAGCTAC3' | 113 |
| SNi10 | 5'TCAGAATCCGTGCACTGGCCAA3' | 114 |
| SNi28 | 5'GCCCTATTCATACCACCGGAGT3' | 115 |
| SNi34 | 5'CATCAGTCCTACCGCCGAAAAG3' | 116 |
| SNi38 | 5'CGTATAGCTATTGTGAGCGATG3' | 117 |
| SNi45 | 5'ACGCGCGGAACGAGCAGTACCA3' | 118 |
| SNiAX2 | 5'CCATAATGATCCCCGTCACTAT3' | 119 |
| SNiAX6 | 5'AGACACCCCTTAGCCGTCGTAG3' | 120 |
| SNiAX8 | 5'AGCTCCGTGACCTTAGTCATAA3' | 121 |
| DAB3 | 5'TGCACAGCTCAGCGCCGCACCA3' | 122 |
| DAB7 | 5'ACGGGTCATCAGCGCCGCACCA3' | 123 |
| DAB10 | 5'TGTCACCCCCCTCCCCGGACTT3' | 124 |
| DAB18 | 5'ACTCGCAATTATTGGCGCTCGA3' | 125 |
| DAB24 | 5'GTCTTCTCAACCTTATCCTGCG3' | 126 |
| DAB30 | 5'AAAGCCCCCTGCTAAACTCCCA3' | 127 |
| DAX15 | 5'CTGCGTCTGCCACGTCGTCATC3' | 128 |
| DAX23 | 5'GTTAAAAGAGGGCAAGCTCGGA3' | 129 |
| DAX24 | 5'CCGAGTTCTTGATGTCCTCCAT3' | 130 |
| DAX27 | 5'TCCAATGCCTGTACCACGGATG3' | 131 |
| DCX8 | 5'TCGCAACCGATATCGTGCTTAT3' | 132 |
| DCX11 | 5'TGCATACACTGCTTGGAGCCCT3' | 133 |
| DCX26 | 5'GAAATCTCACTAGTAGTCCGCC3' | 134 |
| DCX33 | 5'GCGGGCAAGACAGTCCAATTCC3' | 135 |
| DCX36 | 5'GAGCTCCAATTCCACGACGACC3' | 136 |
| DCX39 | 5'GGTTGCCATGCGTTCAAACTAC3' | 137 |
| DCX42 | 5'TCCCGCGGGGACAAACCCGAAT3' | 138 |
| DCX45 | 5'CTGCTAGTCTTATCATTCCCCA3' | 139 |
| PAX2 | 5'CTATCGACACTATAGGGCCTAC3' | 140 |
| PAX9 | 5'TACCCTTGTAACCCACACTAGG3' | 141 |
| PAX14 | 5'TTCTTCTGAATAGACCGGCCGA3' | 142 |
| PAX15 | 5'CCACCACCCTTAACCCGACAAT3' | 143 |
| PAX16 | 5'AGGGGGAGACTTGTTCACAAAC3' | 144 |
| PAX17 | 5'CGGCTCATACCACCGAAAGCTA3' | 145 |
| PAX18 | 5'ATCGTCCTACTGTAATCCTCGA3' | 146 |
| PAX35 | 5'GACACACTACTCAGGTCCACCT3' | 147 |
| PAX38 | 5'CCATAATCAACATTGCCGCCCT3' | 148 |
| PAX40 | 5'CAAAACGCTCGCCCCAAACTCA3' | 149 |
| PAX43 | 5'GTAAACTTGTGCTTCTCGCACC3' | 150 |
| PAX45 | 5'CCATGGTCCGGGTACACCTGAA3' | 151 |
| PAX46 | 5'GTTACTAACGGAACGAGACCTA3' | 152 |
| P31 | 5'TGTTGGCGTTCTCAACCCCGTT3' | 153 |
| P90 | 5'ACAACCGGAGTTGTTCTGCCTA3' | 154 |
| 5PAX3 | 5'TAAGCATCGGCCACGTTCTTCG3' | 155 |
| 5PAX5 | 5'TTATCCCTGGTGTGCAGGTTGA3' | 156 |
| 5PAX7 | 5'TATCAGAATCGTAGTCGGACGG3' | 157 |
| 5PAX12 | 5'CTTTGTAATGGAACCACAACCC3' | 158 |
| HAX9 | 5'CGGTGGCTCATCTCCCTCTTAT3' | 159 |
| HAX35 | 5'ATCAGACTGGCTGGGACCACAA3' | 160 |
| HAX40 | 5'CACAACCTCCTCTCCGCGAACT3' | 161 |
| HAX42 | 5'AGATTCGTCCCCAACGCGTGAT3' | 162 |
| HCA3 | 5'GGGAATTCGCAAAGCTATACTC3' | 163 |
| H40 | 5'CCCCGTGGAATTCAACCTGTGA3' | 164 |
| M13 (positive) | 5'GTCGTCTTTCCAGACGT3' | 165 |
| M13 (negative) | 5'CTTGCATGCCTGCAGGTCGAC3' | 166 |

The oligonucleotides (5 pmol) were 5' end labelled with $^{32}$P-ATP and T4 polynucleotide kinase and approximately 2.5 pmol of labelled oligonucleotide was used in hybridization studies. Hybridizations were performed at 40–45° C. overnight in buffer containing 6×SSC, 5×Denhardt's solution, 0.1% SDS, 20 µg/ml yeast tRNA and the radiolabeled synthetic oligonucleotide, followed by washings (20–30 min at 40–45° C.) in the following buffers: (i) 2×SSC/0.1% SDS, (ii) 1×SSC/0.1% SDS, (iii) 0.1×SSC/0.1% SDS. The filters were air-dried and exposed for autoradiography for 15 hours, 24 hours or 72 hours.

Hybridization data indicated that all the oligonucleotide probes bound specifically to their phage target except for the HAX9 probe which apparently was not labeled. A negative control probe that hybridized only to M13mp18 DNA showed a weak to negative signal in all samples tested (data not shown).

Hybridization data for pools from each receptor group of rats was compiled. Tables 15, 16, 17 and 18 show a representative compilation of autoradiograph signals of the HSI, D2H, HPT1 and hPEPT1 receptor groups. These Tables show the phage absorption and uptake from the closed loop GIT model to portal and systemic circulation and phage absorption/internalization to intestinal tissue. In these Tables, Int-G refers to intestinal tissue homogenized prior to washing and recovery while Int-D refers to intestinal tissue washed prior to homogenization and phage recovery. In all cases, leading phage candidates were present in more than one animal.

TABLE 15

SUMMARY OF AUTORADIOGRAPH SIGNALS OF HSI ANIMAL STUDY

| Phage | Portal | Int.-G | Int.-D |
|---|---|---|---|
| S15 | ++ | +/− | +/− |
| S21 | − | − | − |
| S22 | − | −/+ | − |
| SNi-10 | +++/+ | ++ | ++ |
| SNi-28 | − | − | − |
| SNi-34 | ++ | − | − |
| SNi-38 | ++ | − | − |
| SNi-45 | − | − | − |
| SNiAX-2 | − | − | − |
| SNiAX-6 | − | − | − |
| SNiAX-8 | − | − | − |
| M13 | ++++++ | ++++++ | ++++++ |
| M13 | nd* | + | − |

*not detected

TABLE 16

SUMMARY OF AUTORADIOGRAPH SIGNALS OF D2H ANIMAL STUDY

| Phage | Portal | Int.-G | Int.-D |
|---|---|---|---|
| DAB3 | +++ | +/− | −/+ |
| DAB7 | ++ | ++ | −/+ |
| DAB10 | ++++++ | +/− | −/+ |
| DAB18 | − | − | − |
| DAB24 | − | − | − |
| DAB30 | ++++ | ++ | +++ |
| DAX15 | − | − | − |
| DAX23 | −/+ | + | −/+ |
| DAX24 | − | − | − |
| DAX27 | − | + | − |
| DCX8 | +++++ | +/− | − |
| DCX11 | ++++++ | ++ | −/+ |
| DCX26 | − | − | − |
| DCX33 | +++ | ++ | ++ |
| DCX36 | − | − | − |
| DCX39 | − | −/+ | − |
| DCX42 | − | − | −/+ |
| DCX45 | − | ++ | − |
| M13 (+) | +++++ | +++++ | +++++ |
| M13 (−) | +/− | −/+ | − |

TABLE 17

SUMMARY OF AUTORADIOGRAPH SIGNALS OF HPT1 ANIMAL STUDY

| Phage | Int.-G | Portal | Systemic |
|---|---|---|---|
| H40 | − | − | ++++ |
| HAX9 | ND | ND | ND |
| HAX35 | − | + | − |
| HAX40 | − | − | − |
| HAX42 | − | ++ | ++ |
| HCA3 | − | − | − |
| PAX2 | − | +++ | ++++ |
| M13(+) | ++++++ | ++++++ | ++++++ |
| M13(−) | − | −−/+ | − |

TABLE 18

SUMMARY OF AUTORADIOGRAPH SIGNALS OF hPEPT1 ANIMAL STUDY

| Phage | Int.-G | Portal | Systemic |
|---|---|---|---|
| PAX2 | − | ++ | − |
| PAX9 | ++ | +++ | − |
| PAX14 | − | ++ | − |
| PAX15 | −/+ | − | − |
| PAX16 | − | − | − |
| PAX17 | + | ++/+ | − |
| PAX18 | − | − | − |
| PAX35 | − | − | − |
| PAX38 | −/+ | − | − |
| PAX40 | + | +++ | − |
| PAX43 | + | − | − |
| PAX45 | − | − | − |
| PAX46 | − | +++ | − |
| P31 | ++ | ++++ | ++ |
| 5PAX3 | ++/+ | ++ | − |
| 5PAX5 | − | − | ++ |
| 5PAX7 | +++ | − | − |
| 5PAX12 | ++++ | ++ | − |
| H40 | ++ | ++ | − |
| M13(+) | ++++++ | ++++++ | ++++++ |
| M13(−) | − | − | − |

Apart from the synthetic oligonucleotide to HAX9, all oligonucleotides were initially confirmed to be radiolabeled, as determined by hybridization to the corresponding phage target (eg., phage S15 hybridized to the oligonucleotide S15). In addition, under the experimental conditions used, the oligonucleotides essentially did not hybridize to the negative control phage template M13mp18. Two oligonucleotides were synthesized to the phage M13mp18: (1) a positive oligonucleotide which hybridizes to a conserved sequence in both M13mp18 and each of the GIT receptor or GIT binding site selected phages [designated M13 (positive)]; and (2) a negative oligonucleotide which only hybridizes to a sequence unique to the multiple cloning site of phage M13mp18 and which does not hybridize to any of the GIT receptor or GIT binding site selected phages.

In the case of the hSI pool of phages, only four phages were transported from the closed loop model into the portal circulation: phages S15, SNi-10, SNi-34 and SNi-38. The other phages, S21, S22, SNi-28, SNi-45, SNiAX-2, SNiAX-6 and SNiAX-8, were not transported from the GIT into the portal circulation. In addition, phages SNi-10 and to a lesser extent phages S15 and S22 were found in the intestine samples or fractions, whereas the other phages were not. There was a very low presence (<0.1%) of the phage M13mp18 in the Int-G samples. These results show that phages can be further selected from pre-selected libraries, permitting the identification of phages which are transported from the GIT closed loop into the portal circulation or phages which bind to or are internalized by intestinal tissue.

In the case of the D2H pool of phages, there was a rank order by which phages were transported from the GIT closed loop model into the portal circulation, with phages DCX11 and DAB10 preferably transported, followed by phages DCX8, DAB30, DAB3 and DAB7. A number of phages from this pool were not transported into the portal circulation, including phages DAB18, DAB24, DAX15, DAX24, DAX27, DCX26, DCX36, DCX39, DCX42, DCX45. There is a very low level of transport of phage DAX23 from the GIT into the portal circulation. Similarly, only some of the phages were found in the intestinal samples fractions, including phages DAB30, DCX33, DAB7, DCX11, DCX45 and to a much lesser extent phages DAB3, DAB10, DCX8, DCX39, DCX42. Some phages were not found in the intestinal samples, including phages DAB18, DAB24, DAX15, DAX24, DCX26, and DCX36. There was a very low presence (<0.1%) of the phage M13mp18 in the Int-G samples. These results showed that phages can be further selected from pre-selected libraries, permitting the identification of phages which are transported from the GIT closed loop into the portal circulation or phages which bind to or are internalized by intestinal tissue.

In the case of the HPT1 pool of phages, there was a rank order by which phages were transported from the GIT closed loop model into the portal or systemic circulation. Phage PAX2 (which was used at a 4× concentration relative to the other phages in this pool) followed by phage HAX42 was found in the portal and systemic circulation; phage H40 was found in the systemic circulation only. None of the phages in this pool were found in the intestine samples or fractions. Phage M13mp18 was not found in the intestine fractions or systemic circulation, with very low incidence (<0.001%) in the portal circulation. These results show that phages can be further selected from pre-selected libraries, permitting the identification of phages which are transported from the GIT closed loop into the portal and/or systemic circulation or phages which bind to or are internalized by intestinal tissue.

In the case of the hPEPT1 pool of phages, the phages PAX2 and H40 were also included in this pool. A number of phages from this pool were found in the portal circulation, including phages P31 (SEQ ID NO:43), PAX46, PAX9, H40, PAX17, PAX40, PAX2, PAX14, 5PAX3 and 5PAX12. A number of phages were not found in the portal blood including the negative control phage M13mp18, PAX15, PAX16, PAX18, PAX35, PAX38, PAX43, PAX45, P90, 5PAX5 and 5PAX7. The only phage found in the systemic circulation were phages 5PAX5 and P31 (SEQ ID NO:43). In addition, there was preferential binding of some phages to the intestine, including phages 5PAX12, 5PAX7, 5PAX3, H40, P31 (SEQ ID NO:43), PAX9, and to a lesser extent phages PAX38 and PAX15. Some phages were not found in the intestine samples, including the negative control phage M13mp18 and the phages PAX2, PAX14, PAX16, PAX18, PAX35, PAX45, PAX46, P90 and 5PAX5. These results show that phages can be further selected from pre-selected libraries, permitting the identification of phages which are transported from the GIT closed loop into the portal and/or systemic circulation or phages which bind to or are internalized by intestinal tissue.

Further Characterization of Select Sequences

Following initial screening of the four recombinant receptor sites (hPEPT1, HPT1, D2H, hSI) of the gastrointestinal tissue, with the phage display libraries, a series of phage were isolated which showed preferential binding to the respective target receptor sites in comparison to negative control protein BSA protein and the recombinant protein recombinant human tissue factor (hTF) (which, like the recombinant receptors of the gastrointestinal tissue, contained a poly-histidine tag at its $NH_2$-terminal end). In subsequent experiments same titers of the selected phage which bound to each target receptor site were combined into a single pool (i.e., one pool of HPT1 binding phage, one pool of hPEPT1 binding phage, one pool of D2H binding phage, and one pool of hSI binding phage). Each pool was supplemented with an equivalent titer of the negative control phage M13mp18. These phage pools were injected into a closed duodenal loop region of rat intestinal tissue and subsequently phage was harvested and recovered which was bound to and retained by the intestinal tissue and/or was absorbed from the intestinal loop into the portal and/or systemic circulation. In addition, a selection of the initial phages which bound to the target recombinant receptor site were analyzed for binding to either fixed Caco-2 cells and/or to fixed C2BBe1 cells. The selection of the final lead peptide sequences was based on the ability of the phage, coding for that peptide sequence (1) to bind to the target recombinant receptor site in vitro in preference to its binding to the negative control proteins BSA and/or hTFs, (2) to bind to rat intestinal tissue following injection into a closed duodenal loop of rat intestinal tissue in preference to the negative control phage M13mp18, (3) to be absorbed from rat intestinal tissue into either the portal and/or systemic circulation following injection into a closed duodenal loop of rat intestinal tissue in preference to the negative control phage M13mp18, and (4) to bind to either fixed Caco-2 cells or fixed C2BBe1 cells in phage binding studies in preference to the negative control phage M13mp18. Peptides were also selected with consideration to the ease of chemical synthesis.

6.9. GST Fusion Proteins of GIT Targeting Peptides Construction of GST Fusion Proteins of GI Targeting Peptides Glutathione S-transferase (GST) vectors encoding fusion proteins of GI targeting peptides were constructed in the vector pGEX4T-2 (source, Pharmacia Biotech, Piscataway, N.J.). Briefly, single-strand DNA from the clones of interest were amplified by the polymerase chain reaction. The amplified DNA was then cleaved with the restriction enzymes XhoI and NotI and then ligated into SalI/NotI cleaved pGEX4T-2. Following transformation, the DNA sequence for each construct was verified by sequencing.

For construction of the truncated versions of the GST fusion proteins, where the inserted sequence was less than 45 base pairs, overlapping oligonucleotides containing cohesive SalI and NotI termini, and encoding the sequence of interest, were annealed and then ligated directly into SalI/NotI cleaved pGEX4T-2. Following transformation, the DNA sequence for each construct was verified.

A diagrammatic representation of the various GST fusion protein constructs that have been synthesized is indicated in FIGS. 5A–5C.

Expression and Purification of GST Fusion Proteins

*Escherichia coli* BL21 cells containing GST fusion protein constructs were grown overnight in 2× YT media containing 100 µg/ml ampicillin (2× YT/amp). Overnight cultures were diluted 1:100 in 2× YT broth (100 ml), and cells were grown to an $A_{600}$ of 0.5 at 30° C., induced with 1 mM isopropyl-1-thio-B-D-galactopyranoside, and grown for an additional 3 h. Cells were harvested by centrifugation and resuspended in 5 ml of PBS containing a mixture of the proteinase inhibitors (Boehringer/Mannheim). Cells were sonicated on ice, and the cell lysates were centrifuged at 12,000×g for 10 minutes at 4° C. Supernatant fractions were reacted for 30 minutes at room temperature with 2 ml of a 50% slurry of glutathione-Sepharose® 4B, washed 3 times with 1.5 ml of PBS (at room temperature), and the bound GST fusion proteins were eluted by reaction for 10 minutes at room temperature with 3×1 ml of 10 mM reduced glutathionein 50 mM Tris HCl pH 8.0. Protein was quantified by the Bio-Rad protein assay followed by characterization by SDS-polyacrylamide gel electrophoresis.

ELISA of GST Fusion Peptides

The standard ELISA procedure was modified as follows. GST proteins were diluted to an appropriate concentration in PBS containing 1% BSA and 0.05% Tween20 (1% BPT), titered and incubated one hour at room temperature. Following five washes an anti-GST monoclonal antibody was added (Sigma, St. Louis Clone GST-2 diluted 1:10,000 in 1% BPT) and incubated one hour. After five more washes goat anti-mouse IgG2b-HRP was added (Southern Biotechnology Associates Inc., Birmingham, Ala., diluted 1:4000 in 1% BPT) and incubated one hour. After five washes plates were developed with TMB peroxidase substrate (Kirkegard and Perry, Gaithersburg, Md.). All data is presented with background binding subtracted.

FIG. 6 shows the binding of GST-SNi10, GST-SNi34 and GST alone to the hSI receptor and to fixed C2BBe1 cells.

GST Fusion Proteins of Selected GIT Targeting Peptides

Results show that GST-DXB8, GST-PAX2, GST-P31, GST-SNi10 and GST-SNi34 bound fixed Caco-2 or C2BBe1 cells (FIGS. 7 and 8) relative to GST control binding. GST-HAX42, GST-5PAX5, all showed weak to moderate binding relative to GST control.

Interestingly, P31 truncation 103-GST fusion protein bound almost as well as full-length P31 (SEQ ID NO:43) to fixed Caco-2 cells (A). This suggests the portion of the P31 sequence (SEQ ID NO:43) responsible for binding resides in this portion. PAX2.107 bound similarly to full-length PAX2; therefore, this portion most likely contains the amino acid sequence responsible for binding (B). In preliminary assays, none of the DCX8 truncations bound similarly to full-length DCX8 to Caco-2 cells suggesting the binding region spans more than one of these pieces.

Inhibition of Binding by Synthetic Peptides Binding of GST-P31 to Fixed C2BBe1 Cells The standard ELISA procedure was modified as follows. GST fusion proteins and peptides were diluted to an appropriate concentration in PBS containing 1% BSA and 0.05% Tween 20. Peptides were titered, a constant concentration of diluted GST protein was added to titered peptides and the mixture was incubated one hour at room temperature. Following five washes, an anti-GST monoclonal antibody was added (Sigma, St. Louis Clone GST-2 diluted 1:10,000 in 1% BPT) and incubated one hour. After five more washes goat anti-mouse IgG2b-HRP was added (Southern Biotechnology Associates Inc., Birmingham, Ala., diluted 1:4000 in 1% BPT) and incubated one hour. After five washes plates were developed with TMB peroxidase substrate (Kirkegard and Perry, Gaithersburg, Md.). All data is presented with background binding subtracted.

FIGS. 9A and 9B show the inhibition of GST-P31 binding to C2BBe1 fixed cells. The peptide competitors are ZElan024 which is the dansylated peptide version of P31 (SEQ ID NO:43) and ZElan044, ZElan049 and ZElan050 which are truncated, dansylated pieces of P31 (SEQ ID NO:43). Data is presented as O.D. vs. peptide concentration and as percent inhibition of GST-P31 binding vs. peptide concentration. Uncompeted GST-P31 binding was considered as 100% binding. $IC_{50}$ values are estimates using the 50% line on the percent inhibition graph.

GST-P31 and GST-PAX2 exhibited no crossreactive binding to ZElan024 (P31) (SEQ ID NO:43) and ZElan018 (PAX2) at the 0.5 μg/ml concentration used in competition assays. GST-HAX42 exhibited crossreactivity to ZElan018 (PAX2) and ZElan021 (HAX42) at the 5 μg/ml concentration used in competition assays.

FIGS. 10A–10C present a compilation of data generated by competition ELISA of GST-P31, GST-PAX2, GST-SNi10 and GST-HAX42 versus various dansylated peptides on fixed C2BBe1 cells. $IC_{50}$ values are in MM and include ranges determined from multiple assays. The GST/C2BBe1 column is a summary of GST protein binding to fixed C2BBe1 cells.

Binding to Fixed Caco-2 Cells

Caco-2 cells were fixed, treated with phenylhydrazine and blocked as described above. Synthetic peptides (100 μg/ml) were applied in duplicate to Caco-2 cells and serially diluted down the 96-well plate. The corresponding GST-peptide fusion protein (10 μg) was added to each well and the plates were incubated for 2 h at room temperature with agitation. Binding of the GST-peptide fusion proteins to the cells was assayed using the ELISA technique described above. GST-P31 binding was inhibited by ZElan024, ZElan028 and ZElan031 as well as the two D forms ZElan053 and ZElan054. GST-PAX2 binding was inhibited by ZElan032, ZElan033, and ZElan035. GST-HAX42 binding was not inhibited by ZElan021 (full length HAX42) but it was inhibited by ZElan018 (PAX2) and ZElan026 and ZElan038 (scrambled PAX2 peptides).

Transport and Uptake of GST-Peptide Fusions Into Live Caco-2 Cells

Transport and uptake of GST-peptide fusions and deletion derivatives across cultured polarized Caco-2 monolayers over 4 hours in HBSS buffer was examined using an anti-GST ELISA assay. In another experiment, transport and uptake of GST-peptide fusions and deletion derivatives across cultured polarized Caco-2 monolayers over 24 hours in serum-free medium (SFM) was examined using an anti-GST ELISA assay.

Materials

Buffered Hank's balanced salt solution (bHBSS)=1× HBSS (Gibco CN.14065-031) supplemented with 0.011M glucose (1 g/l), 25 mM Hepes (15 mM acid (3.575 g/l; Sigma CN.H3375); 10 mM base (2.603 g/l; Sigma CN.H1016)].

Chloroquine: Made up as 10 mM solution in water [Sigma CN C6628].

Lysate buffer: 30 mM Tris-HCl pH8.0; 1 mM EDTA.

Serum-free medium (SFM) is normal medium without serum.

Method a) 4 h HBSS study: Transepithelial electrical flux (TER) across the Caco-2 monolayers grown on snapwells (passage 33; 23 days old) was measured to confirm monolayer integrity before beginning the experiment. The medium was removed and the cells were washed once with bHBSS. bHBSS containing 100 μM chloroquine was added and the cells were incubated for 2 h at 37° C. The bHBSS+ chloroquine was replaced with 0.5 ml bHBSS containing GST-peptide fusions (100 μg/ml) and the cells were incubated as before. Basolateral samples were removed at the following times: 0, 0.5 h, 2 h, and 4 h. At 4 h, TER was measured, the apical medium was sampled and the apical reservoir was washed 6 times with HBSS. The cells were allowed to lyse for 1 h on ice in lysate buffer, after which, lysate sample was collected. All samples were stored at −70° C. until assay by anti-GST ELISA. Before analysis, samples were normalized for protein content relative to each other using a BioRad protein assay.

b) 24 h SFM study: Transepithelial electrical flux (TER) across the Caco-2 monolayers grown on snapwells (passage 33; 23 days old) was measured to confirm monolayer integrity before beginning the experiment. The medium was removed and the cells were washed once with SFM. SFM containing GST-peptide fusions (100 μg/ml) was added to the cells which were incubated at 37° C. for 24 h at 5% $CO_2$. After 24 hours, TER readings were taken, and samples from the basolateral and apical reservoirs were removed. The apical reservoir was washed 6 times with PBS. The cells were allowed to lyse for 1 h on ice in lysate buffer, after which lysate sample was collected. All samples were stored at −70° until assay by anti-GST ELISA. Before analysis, samples were normalized for protein content relative to each other using a BioRad protein assay.

Results

All of the GST-peptide fusions and controls examined were transported across live Caco-2 monolayers. Full-length GST-P31 and GST-DCX8, but not truncations of these molecules had a higher flux than GST alone.

Internalization of GST-peptide fusions into polarized Caco-2 cells was investigated in two experiments. In experiment 1, 15 μg of GST-peptide fusion was applied in bHBSS and internalized GST-peptide was recovered by lysing the cells after 4 h. In experiment 2, 10 μg of GST-peptide was applied in either a) bHBSS (lysate recovered after 4 h), or b) serum-free medium (lysate recovered after 24 h).

FIG. 11A describes complete transport of GST-peptide across a polarized Caco-2 monolayer and does not necessarily refer to internalization, i.e., the GST-peptide was recovered from the basolateral reservoir of a snapwell but the proteins could have crossed the barrier by the paracellular route.

Effect of Thrombin Cleavage on Binding of GST-Peptide Fusions to Fixed Caco-2 Cells Binding of intact and thrombin-cleaved GST-peptide fusions to fixed Caco-2 cells was compared. Reduced binding of the thrombin-cleaved GST-peptide fusions relative to intact fusions indicates that the peptide component of the fusion, and not the GST domain, mediates binding.

Method

Confluent Caco-2 monolayers grown in 96-well plates (p38) were fixed and treated with 0.1% phenylhydrazine before blocking with 0.1% BSA in PBS. Thirty micrograms of each GST-peptide was treated with bovine thrombin (1μ/ml; 0.4 NIH units; Sigma CN.T9681) for 18 h at room temperature in 20 mM Tris-HCl pH8.0, 150 mM NaCl, 2.5 mM $CaCl_2$. Controls were similarly treated without addition of thrombin. Ten micrograms of each GST-peptide fusion was removed for PAGE analysis, and 10 μg of fusions were added in duplicate to the fixed Caco-2 cells before 5-fold serial dilutions (1% BPT diluent). The fusions were allowed to bind for 1 h at room temperature. Following 6 washes with 1% BPT, binding was assayed by ELISA.

Results

Results are shown in FIG. 12.

Conclusions

PAGE analysis confirmed that the GST-peptide fusions were effectively cleaved with thrombin. Cleavage with thrombin significantly reduced detection of binding of GST-P31.103, GST-PAX2.106, GST-DCX8, GST-SNi10 to fixed Caco-2 cells, indicating that the peptide component, and not the GST domain, mediates binding.

6.10. Synthesis of Peptides 6.10.1. Procedure for Solid Phase Synthesis

Peptides may be prepared by methods that are known in the art. For example, in brief, solid phase peptide synthesis consists of coupling the carboxyl group of the C-terminal amino acid to a resin and successively adding N-alpha protected amino acids. The protecting groups may be any known in the art. Before each new amino acid is added to the growing chain, the protecting group of the previous amino acid added to the chain is removed. The coupling of amino acids to appropriate resins is described by Rivier et al., U.S. Pat. No. 4,244,946. Such solid phase syntheses have been described, for example, by Merrifield, 1964, J. Am. Chem. Soc. 85:2149; Vale et al., 1981, Science 213:1394–1397; Marki et al., 1981, J. Am. Chem. Soc. 103:3178 and in U.S. Pat. Nos. 4,305,872 and 4,316,891. In a preferred aspect, an automated peptide synthesizer is employed.

By way of example but not limitation, peptides can be synthesized on an Applied Biosystems Inc. ("ABI") model 431A automated peptide synthesizer using the "Fastmoc" synthesis protocol supplied by ABI, which uses 2-(1H-Benzotriazol-1-yl)-1,1,3,3,-tetramethyluronium hexafluorophosphate ("HBTU") (R. Knorr et al., 1989, Tet. Lett., 30:1927) as coupling agent. Syntheses can be carried out on 0.25 mmol of commercially available 4-(2',4'-dimethoxyphenyl-(9-fluorenylmethoxycarbonyl)-aminomethyl)-phenoxy polystyrene resin ("Rink resin" from Advanced ChemTech) (H. Rink, 1987, Tet. Lett. 28:3787). Fmoc amino acids (1 mmol) are coupled according to the Fastmoc protocol. The following side chain protected Fmoc amino acid derivatives are used: FmocArg (Pmc)OH; FmocAsn(Mbh)OH; FmocAsp($^t$Bu)OH; FmocCys(Acm)OH; FmocGlu($^t$Bu)OH; FmocGln(Mbh)OH; FmocHis(Tr)OH; FmocLys(Boc)OH; FmocSer($^t$Bu)OH; FmocThr($^t$Bu)OH; FmocTyr($^t$Bu)OH. [Abbreviations: Acm, acetamidomethyl; Boc, tert-butoxycarbonyl; $^t$Bu, tert-butyl; Fmoc, 9-fluorenylmethoxycarbonyl; Mbh, 4,4'-dimethoxybenzhydryl; Pmc, 2,2,5,7,8-pentamethylchroman-6-sulfonyl; Tr, trityl].

Synthesis is carried out using N-methylpyrrolidone (NMP) as solvent, with HBTU dissolved in N,N-dimethylformamide (DMF). Deprotection of the Fmoc group is effected using approximately 20% piperidine in NMP. At the end of each synthesis the amount of peptide present is assayed by ultraviolet spectroscopy. A sample of dry peptide resin (about 3–10 mg) is weighed, then 20% piperidine in DMA (10 ml) is added. After 30 min sonication, the UV (ultraviolet) absorbance of the dibenzofulvene-piperidine adduct (formed by cleavage of the N-terminal Fmoc group) is recorded at 301 nm. Peptide substitution (in mmol $g^{-1}$) can be calculated according to the equation:

TABLE 5

| Example | Polymer (wt. %) | Cornstarch (wt. %) | rice starch (wt. %) | Rucoflex ® (wt. %) |
|---------|-----------------|--------------------|--------------------|--------------------|
| 70 | 80 | 20 | | |
| 71 | 60 | 40 | | |
| 72 | 55 | 40 | | 5 |
| 73 | 45 | 35 | | 20 |
| 74 | 60 | | 40 | |
| 75 | 45 | | 35 | 20 | where A is the absorbance at 301 nm, v is the volume of 20% piperidine in DMA (in ml), 7800 is the extinction coefficient (in $mol^{-1} dm^3 cm^{-1}$) of the dibenzofulvene-piperidine adduct, and w is the weight of the peptide-resin sample (in mg).

Finally, the N-terminal Fmoc group is cleaved using 20% piperidine in DMA, then acetylated using acetic anhydride and pyridine in DMA. The peptide resin is thoroughly washed with DMA, $CH_2Cl_2$ and finally diethyl ether.

6.10.2. Cleavage and Deprotection

By way of example but not limitation, cleavage and deprotection can be carried out as follows: The air-dried peptide resin is treated with ethylmethyl-sulfide (EtSMe), ethanedithiol (EDT), and thioanisole (PhSMe) for approximately 20 min. prior to addition of 95% aqueous trifluoracetic acid (TFA). A total volume of approximately 50 ml of these reagents are used per gram of peptide-resin. The following ratio is used: TFA:EtSMe:EDT:PhSme (10:0.5:0.5:0.5). The mixture is stirred for 3 h at room temperature under an atmosphere of $N_2$. The mixture is filtered and the resin washed with TFA (2×3 ml). The combined filtrate is evaporated in vacuo, and anhydrous diethyl ether added to the yellow/orange residue. The resulting white precipitate is isolated by filtration. See King et al., 1990, Int. J. Peptide Protein Res. 36:255–266 regarding various cleavage methods.

6.10.3. Purification of the Peptides

Purification of the synthesized peptides can be carried out by standard methods including chromatography (e.g., ion exchange, affinity, and sizing column chromatography, high performance liquid chromatography (HPLC)), centrifugation, differential solubility, or by any other standard technique.

6.10.4. Conjugation of Peptides to Other Molecules

The peptides of the present invention may be linked to other molecules (e.g., a detectable label, a molecule facilitating adsorption to a solid substratum, or a toxin, according to various embodiments of the invention) by methods that are well known in the art. Such methods include the use of homobifunctional and heterobifunctional cross-linking molecules.

The homobifunctional molecules have at least two reactive functional groups, which are the same. The reactive functional groups on a homobifunctional molecule include, for example, aldehyde groups and active ester groups. Homobifunctional molecules having aldehyde groups include, for example, glutaraldehyde and subaraldehyde. The use of glutaraldehyde as a cross-linking agent was disclosed by Poznansky et al., 1984, Science 223:1304–1306.

Homobifunctional molecules having at least two active ester units include esters of dicarboxylic acids and N-hydroxysuccinimide. Some examples of such N-succinimidyl esters include disuccinimidyl suberate and dithio-bis-(succinimidyl propionate), and their soluble bis-sulfonic acid and bis-sulfonate salts such as their sodium and potassium salts. These homobifunctional reagents are available from Pierce, Rockford, Ill.

The heterobifunctional molecules have at least two different reactive groups. Some examples of heterobifunctional reagents containing reactive disulfide bonds include N-succinimidyl 3-(2-pyridyl-dithio)propionate (Carlsson et al., 1978, Biochem J. 173:723–737), sodium S-4-succinimidyloxycarbonyl-alpha-methylbenzylthiosulfate, and 4-succinimidyloxycarbonyl-alpha-methyl-(2-pyridyldithio)toluene. N-succinimidyl 3-(2-pyridyldithio) propionate is preferred. Some examples of heterobifunctional reagents comprising reactive groups having a double bond that reacts with a thiol group include succinimidyl 4-(N-maleimidomethyl)cyclohexahe-1-carboxylate and succinimidyl m-maleimidobenzoate.

Other heterobifunctional molecules include succinimidyl 3-(maleimido)propionate, sulfosuccinimidyl 4-(p-maleimido-phenyl)butyrate, sulfosuccinimidyl 4-(N-maleimidomethyl-cyclohexane)-1-carboxylate, maleimidobenzoyl-N-hydroxy-succinimide ester. The sodium sulfonate salt of succinimidyl m-maleimidobenzoate is preferred. Many of the above-mentioned heterobifunctional reagents and their sulfonate salts are available from Pierce.

Additional information regarding how to make and use these as well as other polyfunctional reagents may be obtained from the following publications or others available in the art: Carlsson et al., 1978, Biochem. J. 173:723–737; Cumber et al., 1985, Methods in Enzymology 112:207–224; Jue et al., 1978, Biochem 17:5399–5405; Sun et al., 1974, Biochem. 13:2334–2340; Blattler et al., 1985, Biochem. 24:1517–152; Liu et al., 1979, Biochem. 18:690–697; Youle and Neville, 1980, Proc. Natl. Acad. Sci. USA 77:5483–5486; Lerner et al., 1981, Proc. Natl. Acad. Sci. USA 78:3403–3407; Jung and Moroi, 1983, Biochem. Biophys. Acta 761:162; Caulfield et al., 1984, Biochem. 81:7772–7776; Staros, 1982, Biochem. 21:3950–3955; Yoshitake et al., 1979, Eur. J. Biochem. 101:395–399; Yoshitake et al., 1982, J. Biochem. 92:1413–1424; Pilch and Czech, 1979, J. Biol. Chem. 254:3375–3381; Novick et al., 1987, J. Biol. Chem. 262:8483–8487; Lomant and Fairbanks, 1976, J. Mol. Biol. 104:243–261; Hamada and Tsuruo, 1987, Anal. Biochem. 160:483–488; Hashida et al., 1984, J. Applied Biochem. 6:56–63.

Additionally, methods of cross-linking are reviewed by Means and Feeney, 1990, Bioconjugate Chem. 1:2–12.

6.10.4.1. Biotinylation of Peptides

Methods of biotinylating peptides are well known in the art. Any convenient method may be employed in the practice of the invention. For example, the following procedure was used. Ten micrograms of peptide was dissolved in 100 μl of 0.1% acetic acid. PBS (900 μl) and 3.3 mg of biotin-LC-NHS (Pierce, Rockford, Ill.) was added. Following incubation for 30 minutes at room temperature the biotinylated peptides were purified over a Superose 12 column (Pharmacia, Piscataway, N.J.).

6.10.5. Synthetic Peptides

Tables 19, 20 and 21 provide the primary structure for various synthetic peptides manufactured in the practice of the present invention.

TABLE 9

| Example Number | Feed Rate (pph) | Screw Torque (% max.) | Die Pressure (psig) | Melt Temperature (° C.) | Vacuum (Inches Hg) |
|---|---|---|---|---|---|
| 82 | 34 | 52 | 800 | 205 | 13 |
| 83 | 30 | 70 | 800 | 220 | 13 |
| 84 | 31 | 70 | 800 | 220 | 12 |
| 85 | 32 | 80 | 800 | 230 | 12 |
| 86 | 33 | 50 | 600 | 205 | 13 |
| 87 | 32 | 50 | 600 | 205 | 13 |
| 88 | 30 | 70 | 800 | 220 | 12 |

TABLE 16

| Example | Layer A (wt. %) | Layer B (wt. %) |
|---|---|---|
| 109 | 25 | 75 |
| 110 | 50 | 50 |
| 111 | 75 | 25 |

GST fusion proteins of GIT peptides are shown in Table 21.

TABLE 18

| Ex. | Polymer Ex. | Extruder Temp. (° C.) | Paper/Paperboard Stock |
|---|---|---|---|
| CE 14 | CE 3 | 230 | Parchment |
| 112 | 4 | 240 | Parchment |
| 113 | 9 | 225 | 15 pound basis weight Kraft paper |
| 114 | 12 | 205 | 18 pound basis weight natural paper |
| 115 | 15 | 180 | 18 pound basis weight bleached paper |
| 116 | 16 | 150 | 25 pound basis weight bleached Kraft paper |
| 117 | 18 | 210 | 35 pound basis weight natural Kraft paper |
| 118 | 19 | 210 | Parchment |
| 119 | 69 | 240 | 15 pound basis weight Kraft paper |
| 120 | 75 | 180 | 18 pound basis weight bleached paper |
| 121 | 82 | 210 | 18 pound basis weight natural paper |
| CE 15 | CE 3 | 230 | Trilayered cup paperboard (210 g/m² weight) |
| 122 | 5 | 240 | Trilayered cup paperboard (210 g/m² weight) |
| 123 | 10 | 225 | Trilayered cup paperboard (210 g/m² weight) |
| 124 | 13 | 195 | Trilayered cup paperboard (210 g/m² weight) |
| 125 | 15 | 180 | Trilayered cup paperboard (210 g/m² weight) |
| 126 | 16 | 150 | Trilayered cup paperboard (210 g/m² weight) |
| 127 | 18 | 210 | Trilayered cup paperboard (210 g/m² weight) |
| 128 | 19 | 210 | Trilayered cup paperboard (210 g/m² weight) |
| 129 | 66 | 240 | Trilayered cup paperboard (210 g/m² weight) |
| 130 | 71 | 180 | Trilayered cup paperboard (210 g/m² weight) |
| 131 | 83 | 210 | Trilayered cup paperboard (210 g/m² weight) |
| CE 16 | CE 3 | 230 | 18 point paperboard |
| 132 | 6 | 230 | 18 point paperboard |
| 133 | 11 | 215 | 12 point paperboard |
| 134 | 14 | 205 | 18 point paperboard |
| 135 | 15 | 180 | 12 point paperboard |
| 136 | 16 | 150 | 18 point paperboard |
| 137 | 18 | 210 | 12 point paperboard |
| 138 | 19 | 210 | 18 point paperboard |
| 139 | 67 | 240 | 12 point paperboard |
| 140 | 72 | 180 | 18 point paperboard |
| 141 | 84 | 210 | 12 point paperboard |

6.10.6. Peptide Stability

The relative stability for ZElan031, ZElan053 and ZElan054 was determined in simulated intestinal fluid (SIF) SIF was made by dissolving 100 mg of pancreatin (Sigma cat# P-5 1625, lot# 122H0812) in 8.4 ml of phosphate stock solution, adjusting the pH to 7.5 with 0.2N NaOH and adjusting the volume to 10 ml with water.

Peptide (3.25 mg) was dissolved in 3.25 ml of 10,000 fold diluted SIF solution at 37° C. Aliquots (0.7 ml) of the digestion solution were then withdrawn at <1 min, 1 h, 3 h, and 21 h or 24 h. The samples were quickly passed through a syringe filter (Millipore Millex-GV 0.22 μm, part# SLGV025LS, lot# H2BM95250) and 300 μL of the filtered solution was immediately injected onto a Hewlett-Packard HPLC system equipped with a C-8 column (Applied Biosystems column and guard column: column-p/n 0711-0023 Spheri-5 ODS 5 μm, 220×4.6 mm). The products were eluted at 1.5 ml/min using an acetonitrile-water gradient. The major fluorescent peaks were collected, lyopholized and identified by MS analysis.

The HPLC gradient used was:

| Time (min) | Solvent Mixture |
|---|---|
| 0 | 95% $H_2O$-5% acetonitrile (0.1% TFA) |
| 5 | 95% $H_2O$-5% acetonitrile (0.1% TFA) |
| 35 | 85% $H_2O$-15% acetonitrile (0.1% TFA) linear solvent change |
| 40 | 0% $H_2O$-100% acetonitrile (0.1% TFA) linear solvent change |
| 45 | 95% $H_2O$-5% acetonitrile (0.1% TFA) linear solvent change |
| 52 | 95% $H_2O$-5% acetonitrile (0.1% TFA) linear solvent change |

As shown in Table 22, the relative stability (to SIF) for the three peptides was found to be ZElan053>ZElan054>ZElan031. Enzymatic cleavage of the peptide was found to occur at arginine and/or lysine as expected. The replacement of l-amino acids with their D-amino acid analogs significantly reduced the rate of proteolysis at these residues.

TABLE 19

| Example | Film Example | Paper Substrate | Paper Basis Wt./ Thickness (oz/yd$^2$/mils) |
|---|---|---|---|
| 144 | 22 | Towel, (Scott, Viva) | 1.2/6 |
| 145 | 36 | Towel, (G.P., Sparkle) | 1.3/10 |
| 146 | 53 | Toilet Tissue, (Charmin) | 0.9/6 |
| 147 | 57 | Wrapping Tissue, (white) | 0.5/2 |
| 148 | 78 | Newsprint | 1.5/4 |
| 149 | 90 | Kraft, recycled | 2.8/6 |

7. CHARACTERIZATION OF PEPTIDE-COATED PARTICLES

Binding of Peptide-coated PLGA Nanoparticles to Fixed Caco-2 Cells

Binding of nanoparticles coated with targeting peptides to fixed Caco-2 cells was investigated using an ELISA assay based on reaction of antibody with the dansyl moiety present on the peptides. Isoelectric points of selected synthetic peptides are shown in Table 23 (corresponding SEQ ID NOS. are shown in Table 7). Corresponding dansylated synthetic GIT binding peptides are given in Table 24.

TABLE 23

| Peptide | Sequence | pI |
|---|---|---|
| P31 | SARDSGPAEDGSRAVRLNGVENANTRKSSRSNPRGRRHP | 12.26 |
| 5PAX5 | RGSTGTAGGERSGVLNLHTRDNASGSGFKPWYPSNRGHK | 11.49 |
| SNi10 | RVGQCTDSDVRRPWARSCAHQGCGAGTRNSHGCITRPLRQASAH | 10.45 |
| SNi34 | SPCGGSWGRFMQGGLFGGRTDGCGAHRNRTSASLEPPSSDY | 8.25 |
| DCX11 | SQGSKQCMQYRTGRLTVGSEYGCGMNPARHATPAYPARLLPRYR | 10.44 |
| DCX8 | RYKHDIGCDAGVDKKSSSVRGGCGAHSSPPRAGRGPRGTMVSRL | 11.03 |
| HAX42 | SDHALGTNLRSDNAKEPGDYNCCGNGNSTGRKVFNRRRPSAIPT | 9.62 |
| PAX2 | STPPSREAYSRPYSVDSDSDTNAKHSSHNRRLRTRSRPN | 11.26 |

TABLE 24

| Peptide | Sequence |
|---|---|
| P31 | $H_2N$-K(dns)SARDSGPAEDGSRAVRLNGVENANTRKSSRSNPRGRRHPGG-$CONH_2$ |
| 5PAX5 | $H_2N$-K(dns)RGSTGTAGGERSGVLNLHTRDNASGSGFKPWYPSNRGHK-$CONH_2$ |
| SNi10 | $H_2N$-K(dns)RVGQCTDSDVRRPWARSCAHQGCGAGTRNSHGCITRPLRQASAH-$CONH_2$ |
| SNi34 | $H_2N$-K(dns)SPCGGSWGRFMQGGLFGGRTDGCGAHRNRTSASLEPPSSDY-$CONH_2$ |
| DCX11 | $H_2N$-K(dns)SQGSKQCMQYRTGRLTVGSEYGCGMNPARHATPAYPARLLPRYR-$CONH_2$ |
| DCX8 | $H_2N$-K(dns)RYKHDIGCDAGVDKKSSSVRGGCGAHSSPPRAGRGPRGTMVSRL-$CONH_2$ |
| HAX42 | $H_2N$-K(dns)SDHALGTNLRSDNAKEPGDYNCCGNGNSTGRKVFNRRRPSAIPT-$CONH_2$ |
| PAX2 | $H_2N$-K(dns)STPPSREAYSRPYSVDSDSDTNAKHSSHNRRLRTRSRPNG-$CONH_2$ |
| DAB10 | $H_2N$-K(dns)SKSGEGGDSSRGETGWARVRSHAMTAGRFRWYNQLPSDR-$CONH_2$ |

Method

Confluent Caco-2 monolayers grown in 96-well plates (p38) were fixed and treated with 0.1% phenylhydrazine before blocking with 0.1% BSA in PBS. Control and dansyl peptide-coated nanoparticles were resuspended in sterile water at 10 mg/ml and stirred with a magnet for 1 h at room temperature. Samples consisted of: (1) blank nanoparticle control, (2) scrambled PAX2-coated nanoparticles, (3) PAX2-coated nanoparticles, (4) HAX42-coated nanoparticles, (5) PAX2/HAX42-coated nanoparticles, and (6) 8 peptide-coated nanoparticles.

Nanoparticles were added to the cells at 10 mg/ml in 100 μl 1% BSA-PBS (no Tween80 is used in this assay) and 2-fold serially-diluted. The 96-well plates were incubated for 1 h at room temperature. The plates were washed 5 times with 1% BSA-PBS and 100 μl of anti-dansyl antibody (Cytogen DB3-226.3; 0.5 μg/ml; batch May 1997) was added per well and the plates incubated 1 h at room temperature. The wells were washed 5 times with 1% BSA-PBS; 100 μl of goat anti-mouse λ:HRP antibody (Southern Biotechnology CN. 1060-05; 1:10,000) was added per well, and the plates incubated 1 h at room temperature. After washing 5 times with 1% BSA-PBS, 100 μl of TMB peroxidase substrate (KPL CN. 50-76-00) was added to the wells and the optical density at 650 nm was measured after 15 minutes.

As shown in FIGS. 13A–B, a decreasing anti-dansyl ELISA response was observed for nanoparticles coated with PAX2, HAX2, PAX2+HAX2, and a mixture of 8 targeting peptides, when decreasing amounts of the nanoparticles were applied to fixed Caco-2 cells. No concentration effect was observed for blank nanoparticles or nanoparticles coated with a scrambled version of PAX2 peptide. Nanoparticles coated with PAX2, HAX2, PAX2+HAX2, and the 8 peptide mix, showed increased response relative to blank nanoparticles or nanoparticles coated with a scrambled version of PAX2 peptide. The OD values were low relative to those normally observed for GST-peptide fusion binding to fixed Caco-2 cells.

Table 25 below shows the insulin potency and level of peptides coated onto the particles (measured by fluorescense) for formulation 1 particles (formulation by the coacervation method given below).

TABLE 25

| Peptide | Blend | |
|---|---|---|
| | Insulin mg/g | Peptide μl/mg |
| PAX2 | 60.7 | 3.51 |
| HAX42 | 55.9 | 2.93 |
| PAX2 SCRAMBLED | 57.7 | 1.26 |
| P31 | 67.0 | 1.22 |
| 5PAX5 | 52.7 | 2.83 |
| SNi10 | 59.5 | 1.75 |
| SNi34 | 61.5 | 4.03 |
| DCX8 | 59.1 | 1.87 |
| DAB10 | 55.9 | 1.99 |

ELISA of Dansylated Peptides and Insulin Coated PLGA Particles

The standard ELISA procedure was modified as follows. Peptides and particles were diluted to an appropriate concentration in PBS containing 1% BSA (particles were sonicated to achieve a homogenous solution), titered and incubated one hour at room temperature. Following five washes with PBS containing 1% BSA, an in-house IgG1λ anti-dansyl monoclonal antibody was added (diluted to 1 μg/ml in 1% BSA-PBS) and the plates were incubated for one hour. After five more washes goat anti-mouse λ-HRP was added (Southern Biotechnology Associates Inc., Birmingham, Ala., diluted 1:10,000 in 1% BSA-PBS) and the plates were incubated one hour. After five washes, plates were developed with TMB peroxidase substrate (Kirkegard and Perry, Gaithersburg, Md.). All data is presented with background binding subtracted. Tween 20 was not added to the diluent or the washes when insulin coated PLGA particles were included in the assay.

FIGS. 14A–14B show the binding of the dansylated peptide SNi10 to hSI and BSA.

8. BINDING OF SYNTHETIC PEPTIDES AND PEPTIDE-COATED PARTICLES TO S100 AND P100 FRACTIONS DERIVED FROM CACO-2 CELLS

8.1. Detection of Binding to Membrane (P100) and Cytosolic (S100) Fractions

Caco-2 cell membrane (P100) and cytosolic (S100) fractions were prepared using a modification of the method described in Kinsella, B. T., O'Mahony, D. J. and G. A. FitzGerald, 1994, J. Biol. Chem. 269(47): 29914–29919. Confluent Caco-2 cell monolayers (grown in 75 cm$^2$ flasks for up to 1 week at 37° C. and 5% $CO_2$) were washed twice in Dulbecco's PBS (DPBS) and the cells were harvested by centrifugation at 1000 rpm after treatment with 10 mM EDTA-DPBS. The cells were washed 3 times in DPBS and the final cell pellet was resuspended in 3 volumes of ice cold HED buffer (20 mM HEPES (pH 7.67), 1 mM EGTA, 0.5 mM dithioreitol, 1 mM phenylmethylsulphonyl fluoride (PMSF)). The cells were allowed to swell for 5 min on ice prior to homogenization for 30 sec. The homogenates were centrifuged at 40,000 rpm for 45 min at 4° C. The supernatant (S100) was removed and the pellet (P100) was resuspended in HEDG buffer (20 mM HEPES (pH 7.67), 1 mM EGTA, 0.5 mM dithiothreitol, 100 mM NaCl, 10% glycerol, 1 mM PMSF). Protein concentrations were determined using the Bradford assay (Bradford, M. M., 1976, Anal. Biochem. 72: 248–254).

Binding of peptide and/or peptide-coated PLGA particles to membrane (P100) and cytosolic (S100) fractions was assessed by detection of the dansyl moiety incorporated in the peptide. Costar ninety six well ELISA plates were coated with S100 and P100 fractions (100 μg/ml in 0.05 M $NaHCO_3$) overnight at 4° C. The plates were blocked with 0.5% bovine serum albumin in DPBS for 1 h at room temperature and washed 3 times in 1% BSA-DPBS. Peptide-coated particles or peptides were dispersed in the same buffer and added to the plates at concentrations in the range 0.0325–0.5 mg/well. After 1 h at room temperature the plates were washed 5 times in 1% BSA-DPBS and 100 μl of anti-dansyl antibody (Cytogen DB3-226.3; 0.5 μg/ml) was added per well. The plates were incubated for 1 h at room temperature. The wells were washed 3 times in 1% BSA-DPBS and 100 μl of goat anti-mouse IgGλ:HRP antibody (Southern Biotechnology 1060-05; 1:10,000) was added per well. The plates were incubated for 1 h at room temperature. After washing 3 times in 1% BSA-DPBS 100 μl of TMB substrate (3,3',5',5-tetramethylbenzidine; Microwell Peroxidase Substrate System (Kirkegaard and Perry Laboratories 50-76-00)) was added and the optical density was measured at 650 nm at various time intervals.

8.2. Binding of Peptide-coated PLGA Particles

A novel assay system is provided by the instant invention for detection of binding of peptide-coated PLGA particles to membrane (P100) and cytosolic (S100) fractions derived from live Caco-2 cells. The absorbance readings obtained using this assay system were substantially higher than those obtained using similar peptide-coated PLGA particle concentrations on fixed Caco-2 cells. This greater sensitivity together with the derivation of the S100 and P100 fractions from live Caco-2 cells suggests that this assay may be the assay system of choice for detection of peptide-coated PLGA particle binding. The assay was concentration dependent and peptide/particle correlation permitted differentiation between specific and non-specific binding interactions.

Binding of peptide-coated PLGA particles was assessed using S100 and P100 fractions derived from live Caco-2 cells as described above. The fractions were coated onto 96-well plates at 10 μg/well in 0.05 M NaHCO$_3$ and peptide-coated PLGA particles were assayed by ELISA at concentrations in the range 0.0325–0.5 mg/well.

FIGS. 15A and 15B illustrate the data obtained on S100 and P100 fractions respectively for particles coated with no peptide, scrambled PAX2 (control), P31 D-Arg 16-mer (ZElan053), HAX42, PAX2 and HAX42/PAX2. Using particle concentrations of 0.0325–0.5 mg/well all test peptide-coated PLGA particles exhibited greater binding to both the S100 and P100 fractions than the scrambled PAX2 coated control particles. All particles except P31 D-Arg 16-mer (ZElan053) exhibited greater binding to the P100 fraction than the S100 fraction. Greater binding of the P31 D-Arg 16-mer (ZElan053) coated particles to the S100 fraction may be indicative of non-specific binding due to the D-Arg modification of the P31 peptide (SEQ ID NO:43).

Binding of PLGA particles coated with varying concentrations of PAX2 peptide ranging from 0.05–5.0 mg/g was assessed using a) fixed Caco-2 cells (P35) and b) S100 and P100 fractions (Caco-2 P33). The particles were assayed at concentrations in the range 0.03125–0.0625 mg/well.

Using a particle concentration of 0.0625 mg/well, all PAX2 coated particles except those coated at 0.05 mg/g exhibited greater binding to fixed Caco-2 cells than the scrambled PAX2 coated control particles. There appeared to be a concentration effect with increasing PAX2 peptide concentration resulting in improved Caco-2 cell binding (in the range 0.05–1.0 mg/g). However all absorbance readings were low and binding of the PAX2 (5 mg/g) was not consistent with this pattern.

Using particle concentrations of 0.03125–0.0625 mg/well all test peptide coated particles except PAX2 (0.05 mg/g) exhibited comparable or greater binding to both the S100 and P100 fractions than the scrambled PAX2 coated control particles. All particles exhibited greater binding to the P100 fraction than the S100 fraction. Binding to both the S100 and P100 fractions was directly proportional to the concentration of the PAX2 peptide on the particle. The absorbance readings obtained using this assay system were substantially higher than those obtained on the fixed Caco-2 cells.

The effect of blocking solution on binding of peptide-coated PLGA particles to P100 fractions (Caco-2 P35) was assessed using 1% bovine serum albumin (BSA) and 1% milk powder blocking solutions to assess background binding. The following particles were assayed at concentrations in the range 0.03125–0.0625 mg/well: no peptide; scrambled PAX2; and a range of PAX2 coated particles having peptide concentrations from 5–0.05 mg/g. As previously observed using 1% BSA, all test peptide coated particles except PAX2 coated at 0.05 mg/g exhibited comparable or greater binding to the P100 fractions than the scrambled PAX2 coated control particles. Binding to P100 fractions was directly proportional to the concentration of the PAX2 peptide on the particle (although in this instance PAX2 (5 mg/g) exhibited slightly lower binding than PAX2 (1 mg/g)). A similar trend was observed using 1% milk powder and a particle concentration of 0.0625 mg/well. However all absorbance readings were low when 1% milk powder was used and the binding pattern was not detectable using particles at a concentration of 0.0625 mg/well.

Non-specific binding of peptide-coated PLGA particles to plastic was also assessed using 1% BSA and 1% milk powder blocking solutions. The binding pattern observed above could be detected when BSA was used; however, absorbance readings were substantially lower and binding of particles PAX2 (0.1 and 0.05 mg/g respectively) was not detectable. When 1% milk powder was used, all absorbance readings were low and no binding pattern was detectable. BSA was chosen for blocking in subsequent assays.

8.3. Comparison of Peptide-coated Particle and Synthetic Peptide Binding to P100 Fractions Binding of dansylated peptides to P100 fractions was assessed to determine if peptide binding was predictive of peptide-coated particle binding. FIG. 16 illustrates the data obtained for the dansylated peptides A) HAX42, P31 D-form and scrambled PAX2 and B) PAX2, HAX42 and scrambled PAX2.

Two consecutive assays produced substantial variations in absorbance readings. Initially, the HAX42 peptide exhibited strong binding when compared to the scrambled PAX2 control. The P31 D-form peptide (ZElan053) exhibited binding at the highest dilution only. In the repeat assay, HAX42 also exhibited significant binding compared to the scrambled PAX2 control. However, the scrambled PAX2 control and HAX42 produced relatively high absorbance values compared to those obtained in the previous assay. The PAX2 peptide was indistinguishable from the scrambled PAX2 control. Peptide/particle binding correlation is summarized as follows in Table 26:

TABLE 26

| Peptide/particle assay correlation | |
|---|---|
| Peptide | Assay correlation |
| HAX42 | + |
| PAX2 | +/− |
| P31 D-form | − |
| Scrambled PAX2 | +/− |

+ positive; +/− equivocal; − negative

Peptide/particle binding correlated well for the HAX42 peptide. In contrast, no correlation could be detected for the P31 D-form (ZElan053) peptide. Since the P31 D-form peptide-coated particles exhibited greater binding to the S100 fraction than the P100 fraction (unlike the other test peptides) it appears that the particle binding interaction was non-specific or that some other molecule was competing for binding to the P100 fraction but not to the S100 fraction. Thus the peptide/particle assay correlation may be useful for distinguishing between specific and non-specific binding interactions. The scrambled PAX2 control produced variable results so that it was difficult to assess the PAX2 binding correlation.

8.4. Determination of HAX42 and PAX2 Binding Motif Sequences

Peptides and GST fusion proteins of HAX42, PAX2 and various derivatives were assayed using peptide ELISA to P100 membrane fractions derived from Caco-2 cells. The GST-PAX2 protein and PAX2 peptide data indicate that a core binding motif lies in the amino acid sequence TNA-KHSSHNRRLRTR (SEQ ID NO: 237) otherwise named GST-106 and ZElan033. Similarly, the HAX42 peptide data suggest that a core binding motif for HAX42 lies in the amino acid sequence PGDYNCCGNCNSTG (SEQ ID NO: 52), otherwise named ZElan091.

The peptides and proteins were analyzed by a dansylated peptide ELISA method in which 96 well plates were coated overnight at 4° C. with 100 μl/well coating protein (normally 100 μg/ml P100 membrane fraction) in 0.05M carbonate buffer pH9.6. Nonspecific binding was blocked using 200 μl/well, 2% Marvel/PBS for 2 hours at 37° C. prior to incubation with dansylated peptides. The plates were washed three times with PBS/0.05% Tween 20 and after each subsequent incubation step. The peptides were diluted in blocking solution at a starting concentration of 100 μg/ml and diluted 1:2 downwards, 100 μl/well, followed by incubation at room temperature for 1 hour, exactly. A buffer blank control was included to ensure that background binding to plastic was not due to the antibodies used in the assay system. To detect the dansylated peptides, a mouse anti-dansyl antibody (DB3, Cytogen Corp.) at 1:1340 dilution in blocking buffer and 100 μl/well was added followed by incubation at room temperature for 1 hour. The plates were then incubated with an anti-mouse λ-HRP conjugated antibody (Southern Biotech 1060-05) at a 1:10,000 dilution in blocking solution, 100 μl/well for 1 hour at room temperature. Plates were developed using 75 μl/well Bionostics TMB substrate and incubated for approximately 10 minutes. The developing reaction was stopped using Bionostics Red Stop solution (25 μl/well), and the optical density of the plates was read at 650 nm.

GST-PAX2 Peptides—Relative Binding to P100 Fractions

After subtraction of the GST-peptide binding to plastic from P100 binding values, the binding of GST-PAX2 peptides were represented as a ratio of GST-HAX42 binding to P100, which was given the arbitrary value of 1.00. The following ratios were determined from binding to P100 of GST-peptides at a peptide concentration of 20 μg/ml. Bold denotes positive binding to the P100 membrane fraction.

TABLE 27

| GST-peptide | Value |
|---|---|
| GST-HAX42 | 1.00 |
| GST-PAX2 | 1.79 |
| GST-104 | 0.01 |
| GST-105 | −0.08 |
| GST-106 | 2.71 |
| GST-113 | 0.26 |
| GST-114 | 0.17 |
| GST-115 | 0.36 |
| GST | 0.48 |

TABLE 28

GST-peptide Amino Acid Sequence

| | |
|---|---|
| GST-PAX2 | STPPSREAYSRPYSVDSDSDTNAKHSSHNRRLRTRSRPN |
| GST-104 | STPPSREAYSRPYSVDSDSD |
| GST-105 | STPPSREAYSRPYSVDSDSDTNAKHSSHN |
| GST-106 | TNAKHSSHNRRLRTRSRPN |
| GST-113 | TNAKHSSHN |
| GST-114 | SSHNRRLRTRSRPN |
| GST-115 | RRLRTRSRPN |

PAX2 Peptides—Relative Binding to P100 Fractions

ZElan021, full length HAX42, was given the arbitrary value of 1.00 for binding to P100 at a given peptide concentration determined from the signal-to-noise ratio, data. PAX2 and its derivatives are given as a ratio of HAX42 value to reflect their binding abilities to P100 membrane fractions derived from a Caco-2 cell line as shown in Table 29. Table 30 provides a line-up of the PAX2 peptides showing the positive binding peptides in boldface. The GST-PAX2 peptide and PAX2 peptide data agree, demonstrating that a binding motif is in the amino acid sequence TNAKHSSHNRRLRTR (GST-106 and ZElan033).

```
CREATE TABLE PACKAGEDESCRIPTOR (                                1400
    PACKAGE_ID         VARCHAR(32)      NOT NULL,              1410
    IMMEDIATE          CHAR(1)          NOT NULL,              1452
    URL                VARCHAR(200)     NOT NULL,              1420
    REFRESH_RATE       INTEGER,                                1462
    START_DT           TIMESTAMP        NOT NULL,              1454
    STOP_DT            TIMESTAMP,                              1456
    EXPIRED_DT         TIMESTAMP,                              1458
    REMOVE_DT          TIMESTAMP,                              1460
    PRIMARY KEY (PACKAG_ID)
CREATE TABLE PACKAGEASSETS (                                    600
    PACKAGE_ID         VARCHAR(32)      NOT NULL,               630
    ASSET_ID           BIGINT           NOT NULL,               620
    PRIMARY KEY (PACKAGE_ID,ASSET_ID)
CREATE TABLE ASSETDESCRIPTOR (                                  700
    ASSET_ID           BIGINT           NOT NULL,               720
    ASSET_TYPE         VARCHAR(3)       NOT NULL,               750
    ASSET_NAME         VARCHAR(100)     NOT NULL,               740
    TIMESTAMP          TIMESTAMP,
    PRIMARY KEY (ASSET_ID)
```

TABLE 30

| PAX2 Peptide | Amino acid sequence | SEQ ID NO: |
|---|---|---|
| ZElan018 | H₂N-K(dns)STPPSREAYSRPYSVDSDSDTNAKHSSHNRRLRTRSRPNG-CONH₂ | |
| ZElan032 | H₂N-K(dns)TNAKHSSHNRRLRTRSRPN-CONH₂ | |

TABLE 30-continued

| PAX2 Peptide | Amino acid sequence | SEQ ID NO: |
|---|---|---|
| ZElan033 | H₂N-K(dns)TNAKHSSHNRRLRTR-CONH₂ | |
| ZElan034 | H₂N-K(dns)SSHNRRLRTRSRPN-CONH₂ | |
| ZElan035 | H₂N-K(dns)SSHNRRLRTR-CONH₂ | |
| ZElan055 | H₂N-K(dns)TNAKHSSHN-CONH₂ | |
| ZElan056 | H₂N-K(dns)RRLRTRSRPN-CONH₂ | |
| ZElan057 | H₂N-K(dns)RRLRTRSR-CONH₂ | |
| ZElan058 | H₂N-K(dns)RRLRTR-CONH₂ | |
| ZElan059 | H₂N-K(dns)rrLrTrSrPN-CONH₂ | |
| ZElan073 | H₂N-K(dns)ASHNRRLRTR-CONH₂ | |
| ZElan074 | H₂N-K(dns)SAHNRRLRTR-CONH₂ | |
| ZElan075 | H₂N-K(dns)SSANRRLRTR-CONH₂ | |
| ZElan076 | H₂N-K(dns)SSHARRLRTR-CONH₂ | |
| ZElan077 | H₂N-K(dns)SSHNARLRTR-CONH₂ | |
| ZElan078 | H₂N-K(dns)SSHNRALRTR-CONH₂ | |
| ZElan079 | H₂N-K(dns)SSHNRRARTR-CONH₂ | |
| ZElan080 | H₂N-K(dns)SSHNRRLATR-CONH₂ | |
| ZElan081 | H₂N-K(dns)SSHNRRLRAR-CONH₂ | |
| ZElan082 | H₂N-K(dns)SSHNRRLRTA-CONH₂ | |
| SCRAMBLED PAX2 PEPTIDES: | | |
| ZElan083 | H₂N-K(dns)GRNHDVVSSNTHKSYRSPRSASYPRLSNDRTDRTEPAPSS-CONH₂ | |
| ZElan084 | H₂N-K(dns)RNTRNKTSRLSANPHRSHR-CONH₂ | |

HAX42 Peptides—Relative Binding to P100 Fractions

ZElan021, full length HAX42, was given the arbitrary value of 1.00 for binding to P100 at a given peptide concentration determined from the signal-to-noise ratio data. HAX42 and its derivatives are given as a ratio of HAX42 value to reflect their binding abilities to P100 membrane fractions derived from a Caco-2 cell line as shown in Table 31. Table 32 provides a line-up of the HAX42 peptides showing the positive binding peptides in boldface. A core binding-motif appears to lie in the amino acid sequence PGDYNCCGNCNSTG (ZElan091).

TABLE 31

| HAX42 peptide | Binding value at 20 µg/ml | Binding value at 50 µg/ml | Binding value at 50 µg/ml | Binding value at 25 µg/ml | Binding value at 25 µg/ml | Binding value at 25 µg/ml |
|---|---|---|---|---|---|---|
| ZElan021 | 1.00 | 1.00 | 1.00 | 1.00 | 1.00 | 1.00 |
| ZElan060 | 0.44 | 0.56 | 0.43 | | | |
| ZElan061 | 0.20 | 0.60 | 0.38 | | | |
| ZElan062 | 0.11 | 0.42 | 0.34 | | | |
| ZElan065 | 0.00 | 0.54 | 0.30 | | | |
| ZElan067 | 0.08 | 0.52 | 0.40 | | | |
| ZElan070 | 0.59 | 0.97 | 0.39 | | | |
| ZElan071 | 1.22 | 0.89 | 0.75 | | | |
| ZElan072 | 0.83 | 0.61 | 0.88 | | | |
| ZElan087 | | | | 0.46 | 0.44 | |
| ZElan088 | | | | 2.21 | 1.41 | 1.63 |
| ZElan089 | | | | 0.55 | 0.44 | 0.49 |
| ZElan090 | | | | 2.06 | 1.54 | 2.16 |
| ZElan091 | | | | 2.02 | 1.37 | 1.20 |
| ZElan092 | | | | 1.41 | 1.90 | 0.91 |
| ZElan093 | | | | 1.88 | 1.37 | 1.33 |

TABLE 32

| HAX42 Peptide | Amino acid sequence |
|---|---|
| ZElan021 | H₂N-K(dns)SDHALGTNLRSDNAKEPGDYNCCGNGNSTGRKVFNRRRPSAIPT-CONH₂ |
| ZElan060 | H₂N-K(dns)SDHALGTNLRSDNAKEPGDYNCCGNG-CONH₂ |
| ZElan061 | H₂N-K(dns)GNGNSTGRKVFNRRRPSAIPT-CONH₂ |
| ZElan062 | H₂N-K(dns)SDHALGTNLRSDNAKEPG-CONH₂ |
| ZElan065 | H₂N-K(dns)RKVFNRRRPS-CONH₂ |
| ZElan067 | H₂N-K(dns)NRRRPS-CONH₂ |
| ZElan070 | H₂N-K(dns)SDHALGTNLRSDNAKEPGDYNCCGNGNST-CONH₂ |
| ZElan071 | H₂N-K(dns)NLRSDNAKEPGDYNCCGNGNSTGRKVFNR-CONH₂ |
| ZElan072 | H₂N-K(dns)PGDYNCCGNGNSTGRKVFNRRRPSAIPT-CONH₂ |
| ZElan087 | H₂N-K(dns)SDHALGTNLRSDNAKEPGDY-CONH₂ |
| ZElan088 | H₂N-K(dns)SDNAKEPGDYNCCGNGNSTG-CONH₂ |
| ZElan089 | H₂N-K(dns)SDHALGTNLRSDNAK-CONH₂-CONH₂ |
| ZElan090 | H₂N-K(dns)EPGDYNCCGNGNSTG |
| ZElan091 | H₂N-K(dns)PGDYNCCGNGNSTG-CONH₂ |
| ZElan092 | H₂N-K(dns)PGDYNCCGNG-CONH₂ |
| ZElan093 | H₂N-K(dns)NCCGNGNSTG-CONH₂ |

9. FORMULATIONS

General Method for Preparation of Coacervated Particles

Solid particles containing a Therapeutic as defined herein are prepared using a coacervation method. The are particles are formed from a polymer and have a particle size of between about 10 nm and 500 µm, most preferably 50 to 800 nm. In addition the particles contain targeting ligands which are incorporated into the particles using a number of methods.

The organic phase (B) polymer of the general method given above may be soluble, permeable, impermeable, biodegradable or gastroretentive. The polymer may consist of a mixture of polymer or copolymers and may be a natural or synthetic polymer. Representative biodegradable polymers include without limitation polyglycolides; polylactides; poly (lactide-co-glycolides), including DL, L and D forms; copolyoxalates; polycaprolactone; polyesteramides; polyorthoesters; polyanhydrides; polyalkylcyanoacrylates; polyhydroxybutyrates; polyurethanes; albumin; casein; citosan derivatives; gelatin; acacia; celluloses; polysaccharides; alginic acid; polypeptides; and the like, copolymers thereof, mixtures thereof and stereoisomers thereof. Representative synthetic polymers include alkyl celluloses; hydroxyalkyl celluloses; cellulose ethers; cellulose esters; nitrocelluloses; polymers of acrylic and methacrylic acids and esters thereof; dextrans; polyamides; polycarbonates; polyalkylenes; polyalkylene glycols; polyalkylene oxides; polyalkylene terephthalates; polyvinyl alcohols; polyvinyl ethers; polyvinyl esters; polyvinyl halides; poyvinylpyrrolidone; polysiloxanes and polyurethanes and co-polymers thereof.

Typically, particles are formed using the following general method:

An aqueous solution (A) of a polymer, surface active agent, surface stabilising or modifying agent or salt, or surfactant preferably a polyvinyl alcohol (PVA) or derivative with a % hydrolysis 50–100% and a molecular weight range 500–500,000, most preferably 80–100% hydrolysis and 10,000–150,000 molecular weight, is introduced into a vessel. The mixture (A) is stirred under low shear conditions at 10–2000 rpm, preferably 100–600 rpm. The pH and/or ionic strength of this solution may be modified using salts, buffers or other modifying agents. The viscosity of this solution may be modified using polymers, salts, or other viscosity enhancing or modifying agents.

A polymer, preferably poly(lacide-co-glycolide), polylactide, polyglycolide or a combination thereof or in any enantiomeric form or a covalent conjugate of the these polymers with a targeting ligand is dissolved in water miscible organic solvents to form organic phase (B). Most preferably, a combination of acetone and ethanol is used in a range of ratios from 0:100 acetone:ethanol to 100:0 acetone:ethanol depending upon the polymer used.

Additional polymer(s), peptide(s) sugars, salts, natural/biological polymers or other agents may also be added to the organic phase (B) to modify the physical and chemical properties of the resultant particle product.

A drug or bioactive substance may be introduced into either the aqueous phase (A) or the organic phase (B). A targeting ligand may also be introduced into either the aqueous phase (A) or the organic phase (B) at this point.

The organic phase (B) is added into the stirred aqueous phase (A) at a continuous rate. The solvent is evaporated, preferably by a rise in temperature over ambient and/or the use of a vacuum pump. The particles are now present as a suspension (C). A targeting ligand may be introduced into the stirred suspension at this point.

A secondary layer of polymer(s), peptide(s) sugars, salts, natural/biological polymers or other agents may be deposited on to the pre-formed particulate core by any suitable method at this stage.

The particles (D) are then separated from the suspension (C) using standard colloidal separation techniques, preferably by centrifugation at high 'g' force, filtration, gel permeation chromatography, affinity chromatography or charge separation techniques. The supernatant is discarded and the particles (D) re-suspended in a washing solution (E) preferably water, salt solution, buffer or organic solvent(s). The particles (D) are separated from the washing liquid in a similar manner as previously described and re-washed, commonly twice. A targeting ligand may be dissolved in washing solution (E) at the final washing stage and may be used to wash the particles (D).

The particles may then be dried. Particles may then be further processed for example, tabletted, encapsulated or spray dried.

The release profile of the particles formed above may be varied from immediate to controlled or delayed release dependent upon the formulation used and/or desired.

Drug loading may be in the range 0–90% w/w. Targeting ligand loading may be in the range 0–90% w/w.

Specific examples include the following examples:

EXAMPLE 1

Peptide Added at the Final Washing Stage

Product: Bovine Insulin loaded nanoparticles

Aim: To prepare a 2 g batch of insulin loaded nanoparticles at a theoretical loading of 50 mg/g and with the peptide ZElan018 added.

| Formulation Details | |
|---|---|
| RG504H (Lot no. 250583) | 2.0 g |
| Acetone | 45 ml |
| Ethanol: | 5 ml |
| PVA (aq. 5% w/v) | 400 ml |
| Bovine Insulin (Lot no. 86H0674) | 100 mg |
| Peptide: PAX2 (ZElan018) | 10 mg/50 ml dH$_2$O |

Experimental Details:

The 5% w/v PVA solution was prepared by heating water until near boiling point, adding PVA and stirring until cool. The organic phase was prepared by adding acetone, 45 ml, and ethanol, 5 ml, together. The polymer solution was prepared by adding RG504H, 2 g, to the organic phase and stirring until dissolved. The IKA™ reactor vessel was set up, all seals greased and the temperature was set at 25° C. The PVA solution, 400 ml, was added into the reactor vessel and stirred at 400 rpm.

Bovine insulin, 100 mg, was added into the stirring PVA solution. Using clean tubing and a green needle, the polymer solution was slowly dripped in the stirring PVA solution with the peristaltic pump set at 40. The solvent was allowed to evaporate by opening the ports and allowing the dispersion to stir overnight at 400 rpm.

The suspension was centrifuged in a Beckman Utracentrifuge™ with swing-out rotor at 12,500 rpm, 4° C. The supernatant was decanted and discarded. The "cake" of particles was broken up and dH$_2$O (200 mls) was added to wash the particles. The centrifugation and washing steps were repeated twice.

The peptide solution, (ZElan018, 10 mg in 50 ml dH$_2$O) was prepared and added to the particles for a final washing stage. The suspended particles were centrifuged as before. The supernatant liquid was decanted, the 'cake' broken up, and the particles were dried in the vacuum oven.

The particles were ground, placed in a securitainer and sent for analysis. The weight of particles recovered was 1.45 g. A SEM showed discrete, reasonably spherical particles in the 300–500 nm size range. The potency was 49.2 mg/g (98.0% of label claim). Peptide loading was 2.42 μg/mg (48.4% of label claim).

EXAMPLE 2

Peptide Added at the Beginning of Manufacture

Product: Bovine Insulin loaded nanoparticles

Aim: To prepare a 2 g batch of insulin loaded nanoparticles at a theoretical loading of 50 mg/g and with the peptide ZElan018 added at the beginning of manufacture.

| Formulation Details | |
| --- | --- |
| RG504H (Lot no. 250583) | 2.0 g |
| Acetone | 45 ml |
| Ethanol: | 5 ml |
| PVA(aq. 5% w/v) | 400 ml |
| Bovine Insulin (Lot no. 65H0640) | 100 mg |
| Peptide: PAX2 (ZElan018ii) | 10 mg |

Experimental Details:

The 5% w/v PVA solution was prepared by heating water until near boiling point, adding PVA and stirring until cool. The organic phase was prepared by adding acetone, 45 ml, and ethanol, 5 ml, together. The polymer solution was prepared by adding RG504H (polyactide-co-glycolide, Boehringer Ingelheim), 2 g, to the organic phase prepared in step above and stirring until dissolved. The IKA™ reactor vessel was set up, all seals greased and the temperature was set at 25° C. The PVA solution, 400 ml, was added into the reactor vessel and stirred at 400 rpm.

Bovine insulin, 100 mg, was added into the stirring PVA solution. PAX2 (ZElan018ii, 10 mg) was added to the stirring PVA solution. Using clean tubing and a green needle, the polymer solution was slowly dripped into the stirring PVA solution with the peristaltic pump set at 40. The solvent was allowed to evaporate by opening the ports and allowing the dispersion to stir overnight at 400 rpm. The suspension was centrifuged in a Beckman Ultracentrifuge™ with swing-out rotor at 12,500 rpm, 4° C. The supernatant was decanted and discarded.

The "cake" of particles was broken up and dH$_2$O (200 ml) was added to wash the particles. The centrifugation and washing steps were repeated twice. The 'cake' was broken up and the particles were dried in the vacuum oven.

The particles were ground, placed in a securitainer and sent for analysis. The weight of the particles recovered was 1.6 g. The potency was 47.3 mg/g (94.6% of label claim). Peptide loading was 1.6894 g/mg (33.8% of label claim).

EXAMPLE 3

Peptide Added 1 Hour Before Centrifugation

Product: Bovine Insulin loaded nanoparticles

Aim: To prepare a 1 g batch of insulin loaded nanoparticles at a theoretical loading of 50 mg/g and with the peptide ZElan018 added 1 hour before centrifugation.

| Formulation Details | |
| --- | --- |
| RG504H (Lot no. 250583) | 1.0 g |
| Acetone | 22.5 ml |
| Ethanol: | 2.5 ml |
| PVA (aq. 5% w/v) | 200 ml |
| Bovine Insulin (Lot no. 65H0640) | 50 mg |
| Peptide: PAX2 (ZElan018) | 5 mg |

Experimental Details:

The 5% w/v PVA solution was prepared by heating water until near boiling point, adding PVA and stirring until cool. The organic phase was prepared by adding acetone, 22.5 ml, and ethanol, 2.5 ml, together. The polymer solution was prepared by adding RG504H, 1 g, to the organic phase prepared above and stirring until dissolved. The IKA™ reactor vessel was set up, all seals greased and the temperature was set at 25° C. The PVA solution, 200 ml, was added into the reactor vessel and stirred at 400 rpm.

Bovine insulin, 50 mg, was added into the stirring PVA solution. Using clean tubing and a green needle, the polymer solution was slowly dripped in the stirring PVA solution with the peristaltic pump set at 40. The solvent was allowed to evaporate by opening the ports and allowing the dispersion to stir overnight at 400 rpm.

PAX2 (ZElan018 5mg) was added to the stirring particle suspension. After 1 hr, the suspension was centrifuged in a Beckman Ultracentrifuge™ with swing-out rotor at 12,500 rpm, 4° C. The supernatant was decanted and discarded. The "cake" of particles was broken up and dH$_2$O (200 ml) was added to wash the particles. The centrifugation and washing steps were repeated twice.

The 'cake' was broken up and the particles were dried in the vacuum oven. The particles were ground, placed in a securitainer and sent for analysis. Potency was 20.75 mg/g (41.5% of label claim). Peptide loading was 1.256 μg/mg (25.12% of label claim).

EXAMPLE 4

Leuprolide Acetate Loaded Nanoparticles

Aim: To prepare a 3 g batch of leuprolide-acetate loaded nanoparticles at a theoretical loading of 20 mg/g and with the peptide ZElan024 added.

| Formulation Details | |
| --- | --- |
| RG504H (Lot no. 271077) | 3.0 g |
| Acetone | 67.5 ml |
| Ethanol: | 7.5 ml |
| PVA (aq. 5% w/v) | 600 ml |
| Leuprolide acetate (Lot no. V14094) | 60 mg |
| Peptide: P31 (ZElan024) | 15 mg/50 ml dH$_2$O |

Experimental Details:

The PVA solution was prepared and the organic phase as prepared by adding acetone, 67.5 ml, and ethanol, 7.5 ml, together. The polymer solution was prepared by adding RG504H, 3 g, to the organic phase prepared above and stirring until dissolved. The IKA™ reactor vessel was set up, all seals greased and the temperature was set at 25° C. The PVA solution, 600 ml, was added into the reactor vessel and stirred at 400 rpm.

Leuprolide acetate, 60 mg, was added into the stirring PVA solution. Using clean tubing and a green needle, the polymer solution, was slowly dripped in the stirring PVA solution with the peristaltic pump set at 40. The solvent was allowed to evaporate by opening the ports and allowing the dispersion to stir overnight at 400 rpm. The suspension was centrifuged in a Beckman Ultracentrifuge™ with swing-out rotor at 15,000 rpm, 4° C. The supernatant was decanted and retained for analysis.

The "cake" of particles was broken up and dH$_2$O 200 ml) was added to wash the particles. The centrifugation and washing steps were repeated twice.

The peptide solution (P31 (SEQ ID NO:43), 15 mg in 50 ml dH$_2$O) was prepared and added to the particles for a final washing stage. The suspended particles were centrifuged as before. The supernatant liquid was decanted, and the particles were dried in the vacuum oven.

The particles were ground, placed in a securitainer and sent for analysis. The weight of particles recovered was 1.87 g. SEM showed discrete, reasonably spherical particles in the 300–500 nm size range. The potency was 4.7 mg/g (23.4% of label claim). Peptide loading was 1.76 µg/mg.

EXAMPLE 5

Peptide Added by 'Spiking' Polymer Phase With Polymer-peptide Conjugate

Product: Bovine Insulin loaded nanoparticles

Aim: To prepare a 3 g batch of insulin loaded nanoparticles at a theoretical loading of 50 mg/g and with the polymer-peptide conjugate PLGA-ZElan019 added.

```
CREATE VIEW VIEW_S9 ( CLIENT_ID, ASSET_ID, JAR ) AS
    SELECT VIEW_S7.CLIENT_ID, VIEW_S7.ASSET_ID,
ASSETCACHE.JAR FROM
        ASSETCACHE, VIEW_S7 WHERE ASSETCACHE.ASSET_ID =
VIEW_S7.ASSET_ID
    CREATE VIEW VIEW_S7 ( CLIENT_ID, ASSET_ID, ACTION ) AS
        SELECT CLIENT_ID, ASSET_ID, 'ADD' ACTION
        FROM VIEW_S6
            WHERE
            ASSET_ID NOT IN
            (SELECT ASSET_ID
                FROM VIEW_S3
                WHERE VIEW_S3.CLIENT_ID =
                    VIEW_S6.CLIENT_ID)
            AND                     ASSET_ID IN
            (SELECT ASSET_ID
                FROM VIEW_S5A)
    CREATE VIEW VIEW_S5A ( ASSET_ID, TIMESTAMP ) AS
        SELECT ASSET_ID, TIMESTAMP FROM
        DEPLOYABLEASSETS WHERE ASSET_ID NOT IN
        (SELECT ASSET_ID FROM VIEW_S4)
    CREATE VIEW VIEW_S3 ( CLIENT_ID, ASSET_ID, TIMESTAMP ) AS
        SELECT CLIENTASSETS.CLIENT_ID, CLIENTASSETS.ASSET_ID,
        CLIENTASSETS.TIMESTAMP FROM DEPLOYABLEASSETS
        JOIN CLIENTASSETS ON
        CLIENTASSETS.ASSET_ID = DEPLOYABLEASSETS.ASSET_ID
        WHERE CLIENTASSETS.TIMESTAMP =
DEPLOYABLEASSETS.TIMESTAMP
            AND CLIENTASSETS.ASSET_ID IN
                (SELECT ASSET_ID FROM VIEW_S6 WHERE
                    CLIENTASSETS.ASSET_ID = VIEW_S6.ASSET_ID)
    CREATE VIEW VIEW_S6 ( ASSET_ID, CLIENT_ID ) AS
        SELECT DISTINCT ASSET_ID, CLIENT_ID FROM
PACKAGEASSETS JOIN
        CLIENTREGISTRY ON
        PACKAGEASSETS.PACKAGE_ID =
CLIENTREGISTRY.PACKAGE_ID
    CREATE VIEW VIEW_S4 ( ASSET_ID, TIMESTAMP ) AS
        SELECT ASSET_ID, TIMESTAMP FROM VIEW_S3
        GROUP BY ASSET_ID, TIMESTAMP
        HAVING COUNT( ASSET_ID ) =
        ( SELECT COUNT( DISTINCT CLIENT_ID ) FROM VIEW_S6
            WHERE view_s6.asset_id = view_s3.asset_id)
```

Experimental Details:

The 5% w/v PVA solution was prepared by heating water until near boiling point, adding PVA and stirring until cool. The organic phase was prepared by adding acetone, 67.5 ml, and ethanol, 7.5 ml, together. The polymer solution was prepared by adding RG504H and the polymer-peptide conjugate to the organic phase and stirring until dissolved.

The IKA™ reactor vessel was set up, all seals greased and the temperature was set at 25° C. The PVA solution, 400 ml, was added into the reactor vessel and stirred at 400 rpm.

Bovine insulin, 100 mg, was added into the stirring PVA solution. Using clean tubing and a green needle, the polymer solution, was slowly dripped in the stirring PVA solution with the peristaltic pump set at 40. The solvent was allowed to evaporate by opening the ports and allowing the dispersion to stir overnight at 400 rpm.

The suspension was centrifuged in a Beckman Ultracentrifuge™ with swing-out rotor at 12,500 rpm, 4° C. The supernatant was decanted and discarded. The "cake" of particles was broken up and dH$_2$O (200 ml) was added to wash the particles. The centrifugation washing step was repeated twice.

The 'cake' was broken up and the particles were dried in the vacuum oven. The particles were ground, placed in a securitainer and sent for analysis. The weight of particles recovered was 2.8 g. The potency was 53.1 mg/g 106.2% of label claim). Peptide loading was 4.02 µg/mg (80.4% of label claim).

10. ANIMAL STUDIES

Study 1

An open-loop study in which the test solution was injected directly into the ileum was done Wistar rats (300–350 g) were fasted for 4 hours and anaesthetized by intramuscular administration 15 to 20 minutes prior to administration of the test solution with a solution of ketamine [0.525 ml of ketamine (100 mg/ml) and 0.875 ml of acepromazine maleate-BP ACP (2 mg/ml)]. The rats were then injected with a test solution (injection volume: 1.5 ml PBS) intra-duodenally at 2–3 cm below the pylorus. The test solution contained either PLGA particles manufactured according to the coacervation procedure given above with or without targeting peptides or by the "spiked" method given above. Insulin (fast-acting bovine; 28.1 iu/mg) was incorporated in the particles at 5% drug loading for a total of 100 iu insulin (70 mg particles) or 300 iu insulin (210 mg particles). Blood glucose values for the rats were measured using a Glucometer™ (Bayer; 0.1 to 33.3 m/mol/L); plasma insulin values were measured using a Phadeseph RIA Kit™ (Upjohn Pharmacia; 3 to 240 µU/ml-assayed in duplicate). Systemic and portal blood was sampled.

Study groups included animals receiving test solutions containing particles coated with the following peptides shown in Table 33.

TABLE 33

| Study Group | Receptor | Peptide |
|---|---|---|
| I | hSI | SNi10 |
| | | SNi34 |
| II | hPEPT1 | P31 |
| | | 5PAX5 |
| III | HPT1 | PAX2 |
| | | HAX42 |
| IV | D2H | DCX8 |
| | | DCX11 |
| V ("spiked") | hPEPT1 | P31-PLGA conjugate |
| | | 5PAX5-PLGA conjugate |

Control groups included: 1) PBS control (1.5 ml) Open-Loop; 2) Insulin solution (1 iu/0.2 ml) subcutaneous; 3) Insulin particles—no peptide (1 iu/0.2 ml) subcutaneous; 4) Insulin particles/all 8 peptides mix (1 iu/0.2 ml) subcutaneous; 5) Insulin loaded particles/peptide control (scrambled 5PAX5) (100 iu/1.5 ml) Open-Loop; 6) Insulin loaded particles/peptide control (scrambled 5PAX5) (300 iu/1.5 ml) Open-Loop; 7) Control particles (insulin-free)/all 8 peptide mix (equivalent 100 iu/1.5 ml) Open-Loop; and 8) Control particles (insulin-free)/all 8 peptide mix (equivalent 300 iu/1.5 ml) Open-Loop.

The following describes the pharmacokinetics for 300 iu-loading:

| Target Receptor | F%* | Fold-increase** | Stat. Sig.** |
|---|---|---|---|
| HPT1 | 10.37 | 17.0 | <0.001 |
| Spiked hPEPT1 | 4.94 | 7.5 | 0.005 |
| PAX2 scrambled | 3.50 | 3.6 | NS |
| Mix-8 | 2.00 | 2.0 | NS |
| hPEPT1 | 1.60 | 1.5 | NS |
| D2H | 1.57 | 1.4 | NS |
| hSI | 0.54 | 0.9 | NS |

*based on area under the curve (AUC) (1–4 h), base-line adjusted, relative to subcutaneous insulin solution liu
**Fold increase in AUC compared to insulin particles: 300 iu FIGS. 17A and 17B show the systemic blood glucose and insulin levels following intestinal administration of control (PBS); insulin solution; insulin particles; all 8 peptides mix particles and study group peptide-particles (100 iu). FIGS. 18A and 18B show the systemic blood glucose and insulin levels following intestinal administration of control (PBS); insulin solution; insulin particles and study group peptide-particles (300 iu).

HPT1 targeted peptide coated particles provided the most potent enhancement of the delivery of insulin over subcutaneous injection of insulin followed by hPEPT1 spiked>PAX2 scrambled>mix-8>hPEPT1>D2H>uncoated particles>hSI>solution. In a repeat study, the uncoated particles containing insulin gave similar profiles but the HPT1-peptide targeted particles gave a reduced profile (3-fold). The insulin-free PLGA particles and the all-8 mix particles did not show an effect on the basal insulin or glucose levels. The HPT1 targeting particles, the PEPT1 spiked, targeting particles, and the PEPT1 targeting particles also reduced blood glucose levels indicative that the insulin delivered was bioactive. The other targeting particles were also shown to reduce blood glucose levels although not to the same extent as the HPT1 and PEPT1 spiked particles. No histological differences were observed in the small intestine for any of the formulations evaluated.

Study 2

A second open-loop study, similar to study 1 above, as undertaken with the following treatment groups as shown in Table 34.

```
CREATE TABLE CLIENTREGISTRY (1522
    CLIENT_ID         VARCHAR(32)   NOT NULL, 1524J
    PACKAGE_ID        VARCHAR(32)   NOT NULL, 1526J
    PACKAGE_STATUS    VARCHAR(32)   NOT NULL,
    PRIMARY KEY (CLIENT_ID PACKAGE_ID)
```

Availability of insulin following administration was assessed relative to a 1 and 20 iu subcutaneous dose because the response to increasing subcutaneous doses of bovine insulin does not increase linearly over the range of 1 to 20 iu. Data up to three hours post-dosing was available for most animals. Therefore, availability was first assessed using individual AUC(0–3 h) data estimated from baseline-subtracted data for which data up to 3 hours was available. This approach may lead to an underestimation of the availability as some animals that gave a high response often did not survive for 3 hours and, therefore, were excluded from the analyses. In an attempt to capture as much of these high responses observed at the earlier timepoints as possible, the mean baseline-subtracted plasma concentration data was used to estimate an AUC for each group. Table 35 shows the results based on this second approach (AUC(0–3 h) calculated from the mean plasma concentration data).

TABLE 35

| Group | Dose iu | Mean AUC$_{(0-3\ h)}$ | F vs. 1 iu | F vs. 20 iu |
|---|---|---|---|---|
| 1 | 0 | 2.14 | | |
| 2a | 1 | 875.27 | 100.00 | 28.86 |
| 2b | 2 | 2439.36 | 139.35 | 40.22 |
| 2c | 3 | 3671.44 | 139.82 | 40.36 |
| 2d | 4 | 6912.18 | 197.43 | 56.98 |
| 2e | 10 | 27224.41 | 311.04 | 89.77 |
| 2f | 20 | 60651.28 | 346.47 | 100.00 |
| 2g | 4 | 14255.49 | 407.17 | 117.52 |
| 3 | 300 | 10677.78 | 4.07 | 1.17 |
| 3-Rat43 | 300 | 4645.06 | 1.77 | 0.51 |
| 4 | 100 | 3527.18 | 4.03 | 1.16 |
| 5 | 300 | 27112.26 | 10.33 | 2.98 |
| 6 | 300 | 33091.68 | 12.60 | 3.64 |
| 7 | 300 | 9303.09 | 3.54 | 1.02 |
| 8 | 300 | 34241.83 | 13.04 | 3.76 |
| 9 | 300 | 10968.83 | 4.18 | 1.21 |
| 10 | 300 | 27692.78 | 10.55 | 3.04 |
| 11 | 300 | 3004.29 | 1.14 | 0.33 |
| 12 | 300 | 18852.61 | 7.18 | 2.07 |
| 13 | 300 | 20278.43 | 7.72 | 2.23 |
| 14 | 300 | 17400.38 | 6.63 | 1.91 |
| 15 | 300 | 16775.69 | 6.39 | 1.84 |
| 16 | 300 | 14217.47 | 5.41 | 1.56 |
| 17 | 300 | 8197.97 | 3.12 | 0.90 |
| 18 | 300 | 25050.59 | 9.54 | 2.75 |
| 19 | 300 | 7927.96 | 3.02 | 0.87 |
| 20 | 300 | 21519.57 | 8.20 | 2.37 |
| 21 | 300 | 6322.41 | 2.41 | 0.69 |
| 22 | 300 | 12553.01 | 4.78 | 1.38 |

The data for group 3 (uncoated insulin particles) are expressed with and without Rat 43. This animal had an atypically high response to these uncoated particles and, therefore, may have biased the data for this group.

This data shows that a combination of peptide-coated particles (HAX42/PAX2 or 5PAX5/P31) shows no greater availability than particles coated with the individual peptides. Further, peptide-coated particles have a greater availability than uncoated peptides. Scrambling the 40mer PAX2 peptide did not result in a loss of bioavailability. Scrambling the PAX2 peptide and reducing the size to 19 mer resulted in a loss of bioavailability although this loss may be attributed in part to the reduction in peptide size. Reducing peptide size resulted in loss of bioavailability. The D-form of P31 (ZElan053) had increased bioavailability possibly due to greater resistance to peptide breakdown. A competitive excess of peptide resulted in a loss of bioavailability, and freeze drying caused a loss in bioavailability. By way of example, measurement of blood glucose levels showed that the HPT1 and hPEPT1 targeting particles incorporating HAX42, PAX2, P31 (SEQ ID NO:43), and P31 D-form (ZElan053) reduced blood glucose levels indicating that the insulin delivered was bioactive.

In further studies, insulin was recovered from the targeting particles following particle formation by dissolution and analyzed by electrophoresis in non-denaturing sodium dodecyl sulfate (SDS) polyacrylamide gel electrophoresis (PAGE). The analysis of the insulin by non-denaturing SDS-PAGE and also by western blot transferred to membranes and subsequent screening with an antibody to insulin, indicated that the insulin was intact, with no evidence of degradation, dimerization, or aggregation during the process of particle formation.

Study 3

An intraduodenal open loop model study was carried out on Wistar rats (300–350 g). Group 1 was administered leuprolide acetate (12.5 µg) subcutaneously. Group 2 was administered intraduodenally uncoated leuprolide acetate particles (600 µg, 1.5 ml). Group 3 was intraduodenally administered leuprolide acetate particles coated with PAX2 (600 µg; 1.5 ml). Group 4 was administered intraduodenally leuprolide acetate particles coated with P31 (SEQ ID NO:43) (600 µg, 1.5 ml). FIG. 19 shows the leuprolide plasma concentration following administration to these four groups. Both the P31 (SEQ ID NO:43) and the PAX2 coated leuprolide particles administered intraduodenally provided enhanced plasma levels of leuprolide relative to subcutaneous injection.

Homologies of GIT transport-binding peptides to known proteins are shown in FIGS. 20, 21A–F, and 22A–D.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A composition comprising a purified protein which specifically binds to the gastro-intestinal tract receptor HPT1 (SEQ ID NO:178), wherein the purified protein is bound to a material comprising an active agent selected from the group consisting of an imaging agent, a drug, and an antigen, and wherein the protein comprises the amino acid sequence of SEQ ID NO:50 or a portion thereof of at least 6 contiguous amino acids that mediates binding to HPT1.

2. The composition of claim 1 wherein the protein comprises the amino acid sequence of SEQ ID NO:50.

3. The composition of claim 1 wherein the material is a particle containing the active agent.

4. The composition of claim 1 wherein the material is a slow-release device containing the active agent.

5. The composition of claim 1 wherein the active agent is a drug.

6. The composition of any one of claims 1 and 3–5 wherein the purified protein is not more than 40 amino acids in length.

7. The composition of any one of claims 1 and 3–5 wherein the purified protein is not more than 30 amino acids in length.

8. The composition of any one of claims 1 and 3–5 wherein the purified protein is not more than 20 amino acids in length.

9. The composition of any one of claims 1, 2 and 3–5 wherein said protein facilitates the transport of the active agent through human or animal gastro-intestinal tissue.

10. A pharmaceutical composition comprising a therapeutically effective amount of the composition of any one of claims 1, 2 and 3–5, and a pharmaceutically acceptable carrier.

11. A composition comprising a chimeric protein wherein the chimeric protein is bound to a material comprising an active agent selected from the group consisting of an imaging agent, a drug, and an antigen, and wherein the chimeric protein comprises (i) an amino acid sequence fused via a covalent bond to (ii) a second amino acid sequence which specifically binds to the gastro-intestinal tract receptor, HPT1 (SEQ ID NO:178), and wherein the second amino acid sequence comprises SEQ ID NO:50 or a portion thereof at least 6 contiguous amino acids that mediates binding to HPT1.

12. The composition of claim 11 wherein the protein comprises the amino acid sequence of SEQ ID NO:50.

13. The composition of claim 11 wherein the material is a particle containing the active agent.

14. The composition of claim 11 wherein the material is a slow-release device containing the active agent.

15. The composition of claim 11 wherein the active agent is a drug.

16. The composition of any one of claims 11 and 13–15 wherein the purified protein is not more than 40 amino acids in length.

17. The composition of any one of claims 11 and 13–15 wherein the purified protein is not more than 30 amino acids in length.

18. The composition of any one of claims 11 and 13–15 wherein the purified protein is not more than 20 amino acids in length.

19. The composition of any one of claims 11, 12 and 13–15 wherein said chimeric protein facilitates the transport of the active agent through human or animal gastrointestinal tissue.

20. A pharmaceutical composition comprising a therapeutically effective amount of the composition of any one of claims 11, 12 and 13–15, and a pharmaceutically acceptable carrier.

21. A composition comprising a purified protein which specifically binds to the gastro-intestinal tract receptor HPT1 (SEQ ID NO:178), wherein the purified protein is bound to a drug, said drug being of value in the treatment of a mammalian disease or disorder, and wherein the protein comprises the amino acid sequence of SEQ ID NO:50 or portion thereof of at least 6 contiguous amino acids that mediates binding to HPT1.

22. The composition of claim 21 wherein the protein comprises the amino acid sequence of SEQ ID NO:50.

23. The composition of claim 21 wherein the purified protein is not more than 40 amino acids in length.

24. The composition of claim 21 wherein the purified protein is not more than 30 amino acids in length.

25. The composition of claim 21 wherein the purified protein is not more than 20 amino acids in length.

26. The composition of claim 21 or 22 wherein said protein facilitates the transport of the active agent through human or animal gastro-intestinal tissue.

27. A pharmaceutical composition comprising a therapeutically effective amount of the composition of claims 21 or 22 and a pharmaceutically acceptable carrier.

28. A composition comprising a purified protein which specifically binds to the gastro-intestinal tract receptor HPT1

(SEQ ID NO:178), wherein the purified protein is coated onto or absorbed onto or covalently bonded to the surface of a nanoparticle or microparticle, and wherein the protein comprises the amino acid sequence of SEQ ID NO:50 or a portion thereof of at least 6 contiguous amino acids that mediates binding to HPT1.

29. The composition of claim 28 wherein the protein comprises the amino acid sequence of SEQ ID NO:50.

30. The composition of claim 28 wherein the nanoparticle or microparticle contains a drug.

31. The composition of claim 28 wherein the nanoparticle or microparticle is a slow-release device.

32. The composition of any one of claims 28, 30, and 31 wherein the purified protein is not more than 40 amino acids in length.

33. The composition of any one of claims 28, 30, and 31 wherein the purified protein is not more than 30 amino acids in length.

34. The composition of any one of claims 28, 30, and 31 wherein the purified protein is not more than 20 amino acids in length.

35. The composition of any one of claims 28, 30, and 31 wherein said protein facilitates the transport of the active agent through human or animal gastro-intestinal tissue.

36. A pharmaceutical composition comprising a therapeutically effective amount of the composition of any one of claims 28, 29, 30 and 31, and a pharmaceutically acceptable carrier.

37. A nanoparticle or a microparticle comprising a purified protein which specifically binds to the gastro-intestinal tract receptor, HPT1 (SEQ ID NO:178), wherein the purified protein comprises the amino acid sequence of SEQ ID NO:50 or a portion thereof of at least 6 contiguous amino acids that mediates binding to HPT1.

38. The composition of claim 37 wherein the protein comprises the amino acid sequence of SEQ ID NO:50.

39. The composition of claim 37 wherein the purified protein is not more than 40 amino acids in length.

40. The composition of claim 37 wherein the purified protein is not more than 30 amino acids in length.

41. The composition of claim 37 wherein the purified protein is not more than 20 amino acids in length.

42. The composition of claim 37 or 38 wherein said protein facilitates the transport of the active agent through human or animal gastro-intestinal tissue.

43. A pharmaceutical composition comprising a therapeutically effective amount of the composition of claim 37 or 38, and a pharmaceutically acceptable carrier.

44. A pharmaceutical composition comprising a therapeutically effective amount of a chimeric protein comprising (i) a first protein comprising at least 6 contiguous amino acids of an amino acid sequence comprising SEQ ID NO:50, said contiguous amino acids being capable of specifically binding to the gastro-intestinal tract receptor HPT1 (SEQ ID NO:178), said first protein being fused via a covalent bond to (ii) a second protein, said second protein being a drug; and a pharmaceutically acceptable carrier.

45. A pharmaceutical composition comprising a therapeutically effective amount of a nucleic acid encoding a chimeric protein comprising (i) a first protein comprising at least 6 contiguous amino acids of an amino acid sequence comprising SEQ ID NO:50, said contiguous amino acids capable of specifically binding to the gastrointestinal tract receptor HPT1 (SEQ ID NO:178), said first protein being fused via a covalent bond to (ii) a second protein, said second protein being a drug; and a pharmaceutically acceptable carrier.

\* \* \* \* \*